United States Patent
Ascenzi et al.

(10) Patent No.: US 7,353,153 B2
(45) Date of Patent: Apr. 1, 2008

(54) METHOD AND SYSTEM FOR MODELING BONE STRUCTURE

(76) Inventors: Maria-Grazia Ascenzi, 1713 Bryn Mawr Ave., Los Angeles, CA (US) 90405; John M. Kabo, 17048 Jeanine Pl., Los Angeles, CA (US) 91344

( * ) Notice: Subject to any disclaimer, the term of this patent is extended or adjusted under 35 U.S.C. 154(b) by 460 days.

(21) Appl. No.: 10/844,051

(22) Filed: May 11, 2004

(65) Prior Publication Data

US 2005/0131662 A1 Jun. 16, 2005

Related U.S. Application Data

(63) Continuation-in-part of application No. 10/429,491, filed on May 5, 2003, now Pat. No. 7,212,958, which is a continuation-in-part of application No. 10/357,090, filed on Feb. 3, 2003, now Pat. No. 7,283,940, which is a continuation-in-part of application No. 10/066,293, filed on Jan. 31, 2002, now Pat. No. 7,127,383, which is a continuation-in-part of application No. 09/981,684, filed on Oct. 17, 2001, now Pat. No. 7,124,067.

(60) Provisional application No. 60/380,174, filed on May 6, 2002, provisional application No. 60/353,768, filed on Feb. 1, 2002.

(51) Int. Cl.
*G06F 9/455* (2006.01)

(52) U.S. Cl. .............................. 703/11; 703/2; 700/98; 700/182; 424/9.2; 424/49; 382/128; 600/586; 600/36; 600/449

(58) Field of Classification Search .................... 703/2; 424/9.2, 49; 382/128; 600/586, 36, 449, 600/407; 514/12; 623/23.56, 23.61; 29/896.6; 700/98, 182

See application file for complete search history.

(56) References Cited

U.S. PATENT DOCUMENTS

| | | | |
|---|---|---|---|
| 3,929,971 A | 12/1975 | Roy et al. | |
| 5,150,304 A * | 9/1992 | Berchem et al. | 700/182 |
| 5,172,695 A * | 12/1992 | Cann et al. | 600/407 |
| 5,728,510 A | 3/1998 | White | |
| 5,732,469 A * | 3/1998 | Hamamoto et al. | 29/896.6 |
| 5,947,893 A * | 9/1999 | Agrawal et al. | 600/36 |
| 6,083,264 A * | 7/2000 | Wood et al. | 623/23.56 |
| 6,213,958 B1 * | 4/2001 | Winder | 600/586 |
| 6,293,970 B1 * | 9/2001 | Wolfinbarger et al. | 623/23.61 |
| 6,333,313 B1 * | 12/2001 | Copland et al. | 514/12 |
| 6,414,320 B1 | 7/2002 | Ishikawa et al. | |

(Continued)

OTHER PUBLICATIONS

R. Lakes, "Materials with structural hierarchy", Nature 361, Feb. 1993.*

(Continued)

*Primary Examiner*—K. Thangavelu
(74) *Attorney, Agent, or Firm*—Darby & Darby

(57) ABSTRACT

The present invention discloses a structural and mechanical model and modeling methods for human bone based on bone's hierarchical structure and on its hierarchical mechanical behavior. The model allows for the assessment of bone deformations, computation of strains and stresses due to the specific forces acting on bone during function, and contemplates forces that do or do not cause viscous effects and forces that cause either elastic or plastic bone deformation.

59 Claims, 63 Drawing Sheets

U.S. PATENT DOCUMENTS

| | | | |
|---|---|---|---|
| 6,416,737 B1* | 7/2002 | Manolagas et al. | 424/9.2 |
| 6,442,287 B1* | 8/2002 | Jiang et al. | 382/128 |
| 6,517,487 B1* | 2/2003 | Mazess et al. | 600/449 |
| 6,692,532 B1* | 2/2004 | Healy et al. | 623/23.51 |
| 2002/0042663 A1* | 4/2002 | St. Ville | 700/98 |
| 2002/0136696 A1* | 9/2002 | Lee et al. | 424/49 |

OTHER PUBLICATIONS

Mann et al., "Pre-yield and Post-yield shear behavior of cement-bone inetrface", Journal of orthopedic Research, 1998.*

Giraud-Guille, "Twisted plywood architecture of collagen fibrils in human compact bone osteons", Calcified Tissue International, 1988.*

Ascenzi et al., "Orientation of Apatite in single osteon samples as studied by pole Figures", Calcified Tissue International, 1979.*

Riggs et al., "Functional Association between collagen fibre orientation and locomotor strain direction in cortical bone of the equine radius", Anatomy and Embryology, 1993.*

Kim et al., "Scaffolds for Engineering smooth muscle under cyclic mechanical strain conditions", Transactions of ASME, Jun. 2000.*

MacKenna et al., "Microstructural model of perimysial collagan fibres for resting myocardial mechanics during ventricular filling", American Jornal of Physiology, 1997.*

R.Lakes, "Materials with structural Hierarchy", Nature 361, Feb. 1993.

Kotha et al., "*Tensile damage and its effects on cortical bone*", Journal of Biomechanics, 36 (2003) 1683-1689.

Kotha et al., "*Modeling the Tensile Mechanical Behavior of Bone along the Longitudinal Direction*", J. theor. Biol. (2002) 219, 269-279.

Van Lenthe et al., G.H., "Stress Shielding After total Knee Replacement May Cause Bone Resorption In The Distal Femur", The Journal of Bone and Joint Surgery, Jan. 1997, pp. 117-122, vol. 79-B, No. 1, British Editorial Society of Bone and Joint Surgery © 1997.

Carter, Dennis R., et al., "Mechanical Properties and Composition of Cortical Bone", Basic Science and Pathology, Section III, J.B. Nippincott Company, No. 135, Sep. 1978, pp. 192-217.

Ascenzi, A., et al., "Pinching in Longitudinal and Alternate Osteons During Cyclic Loading", J. Biomechanics, 1997, vol. 30, No. 7, pp. 689-695.

Ascenzi, Antonio, et al., "The Torsional Properties of Single Selected Osteons", J. Biomechanics, 1994, vol. 27, No. 7, pp. 875-884.

Ascenzi, Antonio, et al., "The Shearing Properties of Single Osteons", Anat. Rec., vol. 172, pp. 499-510, Sep. 1971.

Ascenzi, Antonio, et al., "X-Ray Diffraction on Cyclically Loaded Osteons", Calcif. Tissue Int., 1998, vol. 62, pp. 266-273.

Ascenzi, Maria-Grazia, "A first estimation of prestress in so-called circularly fibered osteonic lamellae", Journal of Biochemanics, 1999, vol. 32, pp. 935-942.

Crolet, J.M., et al., "Compact Bone: Numerical Situation of Mechanical Characteristics", J. Biomechanics, 1993, vol. 26, No. 6, pp. 677-687.

* cited by examiner

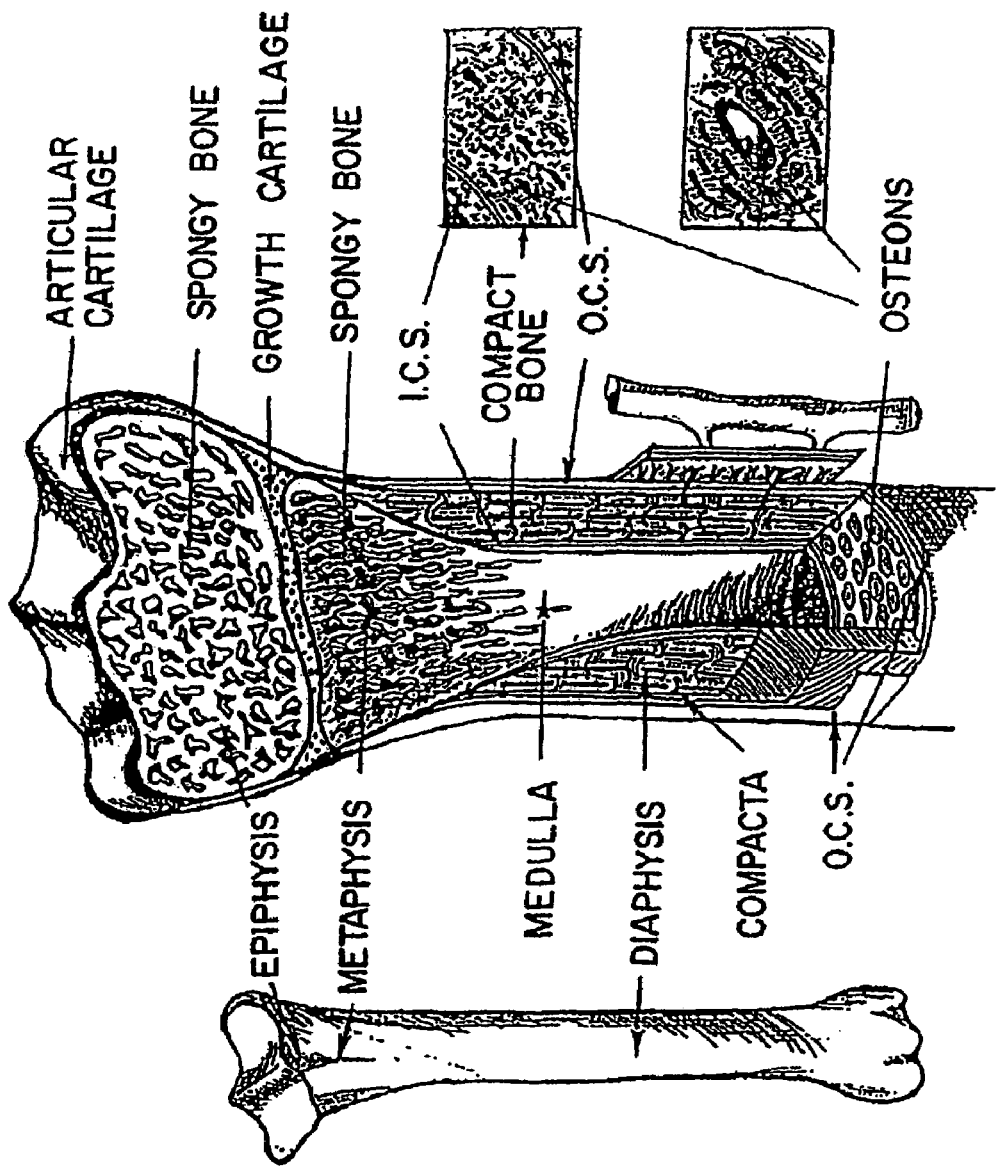

FIG. 7A
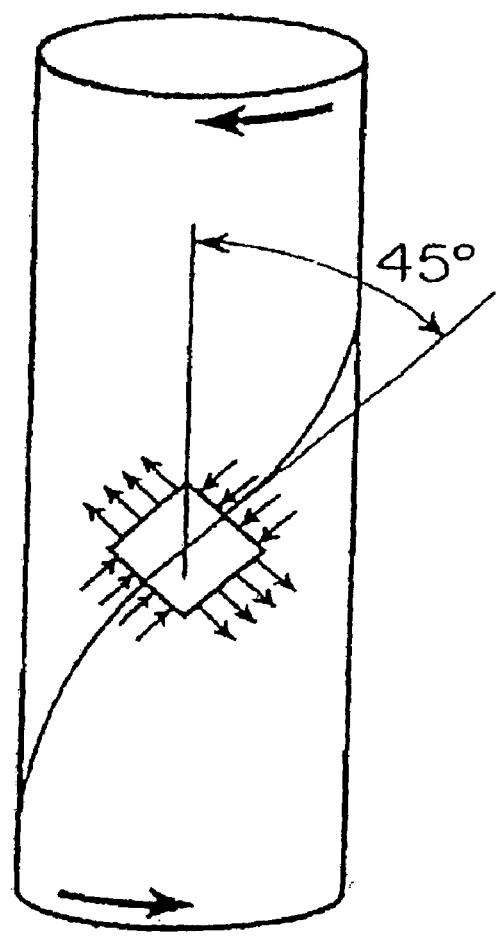
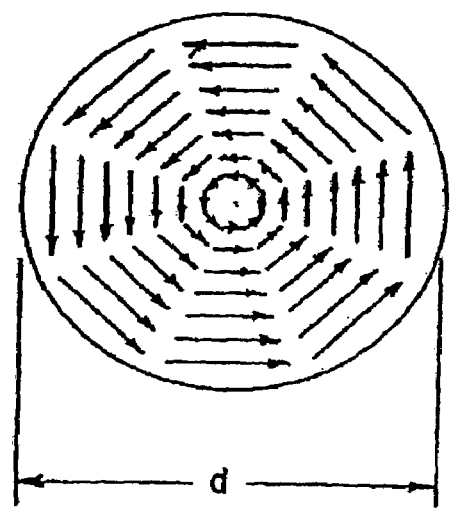
FIG. 7B

FIG. 16

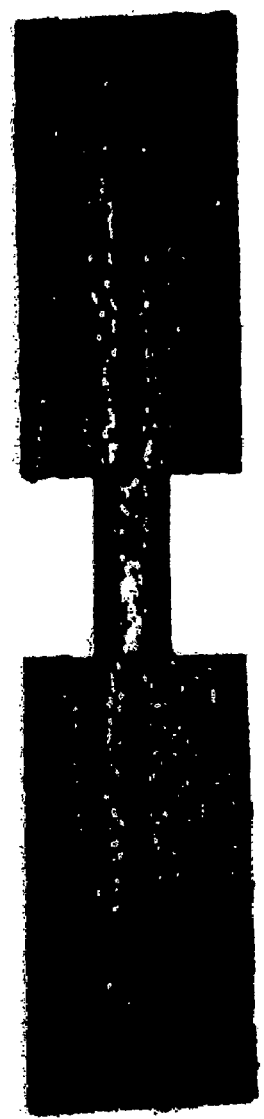
FIGURE 28B
FIGURE 28A

FIGURE 33A 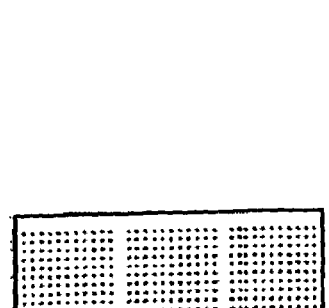 FIGURE 33B 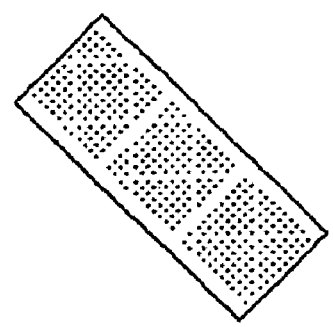
A  B 
FIGURE 34
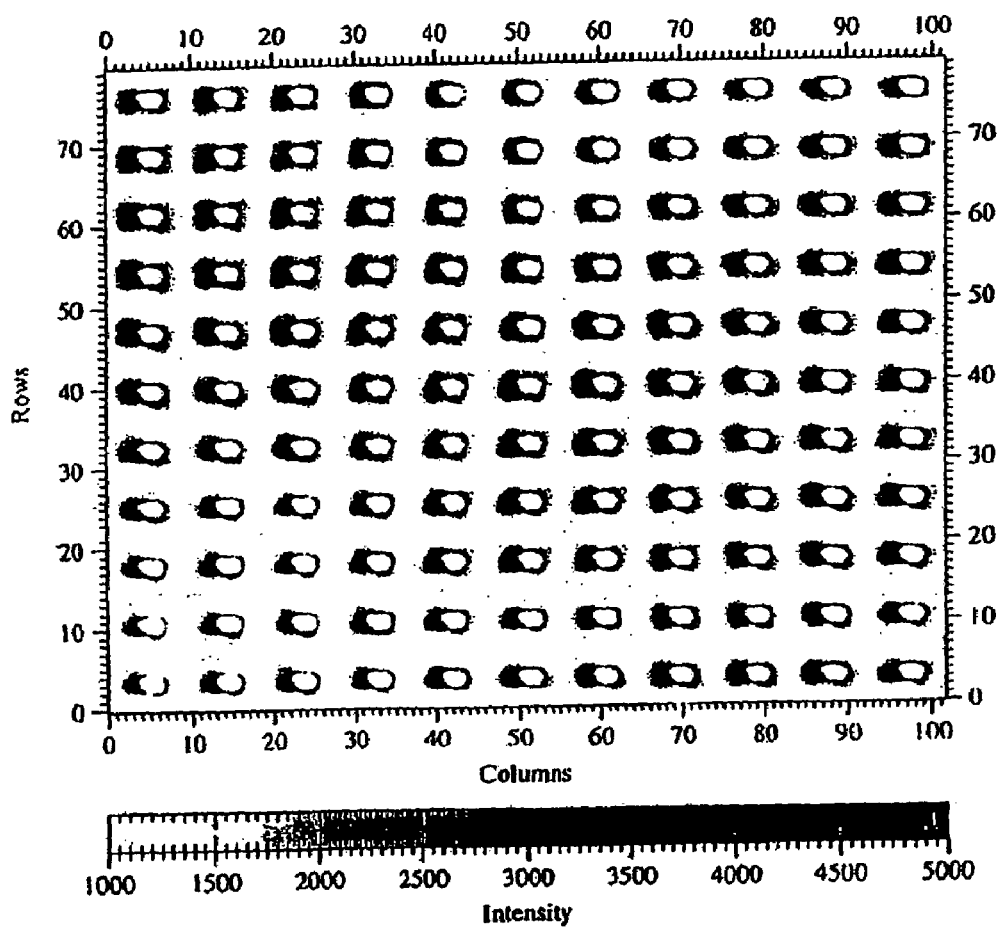

FIGURE 37
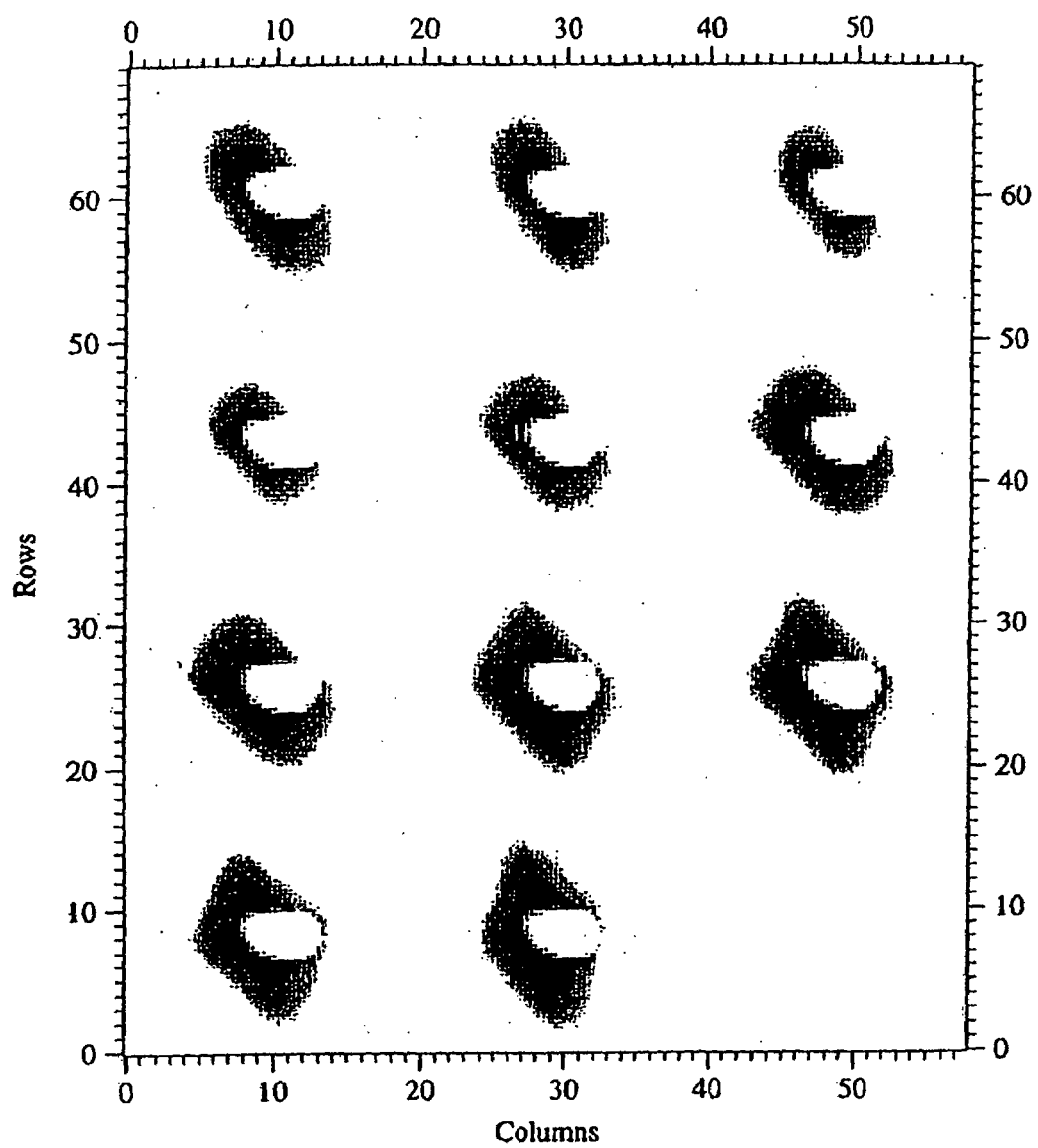
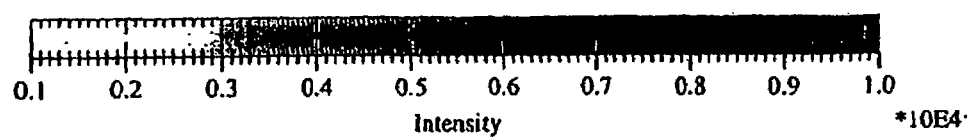

Diagram showing the trapezoid cut from a thin transverse femoral section of bone that contains a chosen alternate osteon.

Dark lamellar specimen oriented at 0° (top) and 45° (bottom) with respect to the plane of polarization.

From top to bottom: the orientation of the bright lamellar specimen changes in discrete steps of 0°, 39°, 45°, 80°, 84°, 90° relative to the plane of polarization.

Confocal microscopy detail of isolated and flattened dark lamella. Opposed arrows show the orientation of a collagen bundle arrangement ⊥ to the lamella edges. Cut radial collagen bundles appear as dots within the circle.

Detail of isolated and flattened bright lamellar sample as viewed by confocal microscopy. Arrows indicate oblique collagen bundles extending across the lamella thickness.

Diagram of relative inclination of dark (a) and bright (b) lamellae with respect to the incident beam. Dots indicate chosen locations of scanning.

SAXS images of dark lamella. The images are unchanged across the scanned area.

Enlargement of one SAXS image from FIGURE 45. Clear arching and maximum intensity orientations show single preferential collagen bundle direction perpendicular to bright lamellar width.

WAXS image of the scanned location of the Figure 48 SAXS Image. Clear preferential orientation of the 002 reflection parallel to the dark lamellar width shows single preferential collagen bundle direction perpendicular to bright lamellar width.

SAXS images of dark lamella from a scanned area.
The images change across the scanned locations.

Photograph of lamella specimen attached to SEM grid sections as prepared for the tensile test.

On a small and thin laminar element, the principal material axes are labeled 1, 2, and 3. Direction 1 is parallel, and direction 2 perpendicular, to the fibers. Direction 3 is the radial direction, perpendicular to the plane of the diagram. Circumferential and axial directions are labeled θ and z. The angle between the circumferential direction and direction 1 is denoted by γ.

Isolated flattened lamellar specimen. The breadth of this figure corresponds to the "length" of the lamellae.

(A) SAXS of dark lamella; (B) WAXS of dark lamella.

SAXS of bright lamella

SAXS of bright lamella

SAXS of bright lamella

Collagen and hydroxyapatite dominant directions of dark and bright lamella

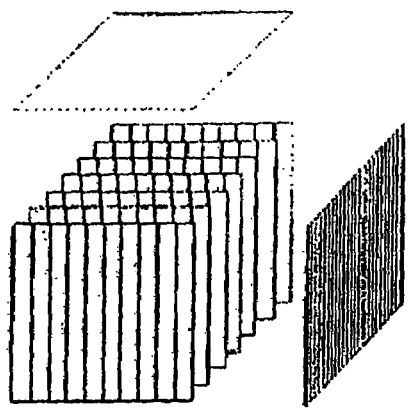 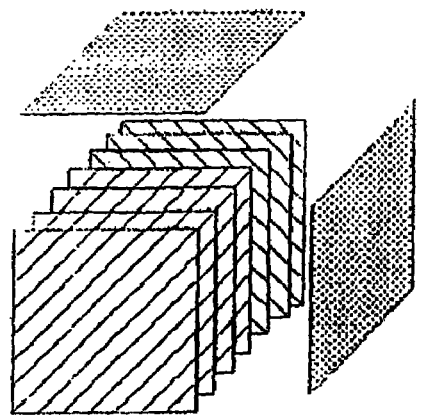
FIGURE 57A  FIGURE 57B
X-ray diffraction results of (A) dark lamella and (B) bright lanmella Twisted plywood model of osteon

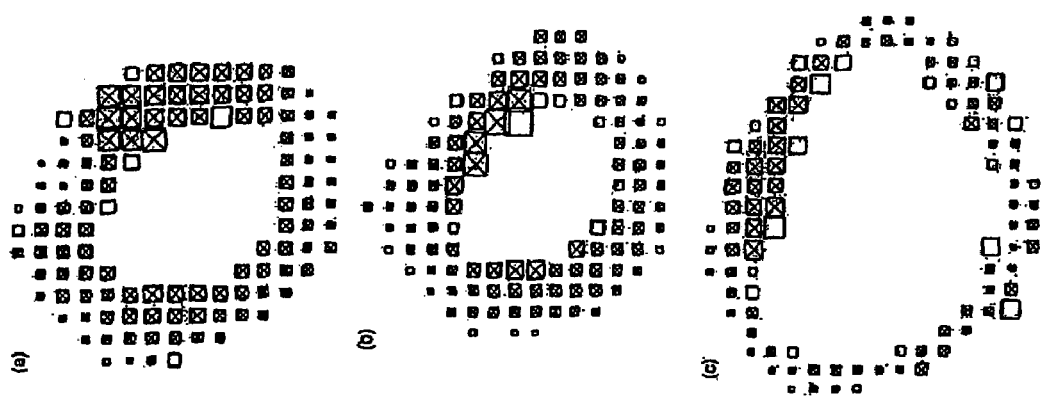
FIGURE 59
Dark and bright lamellar distribution correlates to cyclic forces and geometry

FIGURE 63
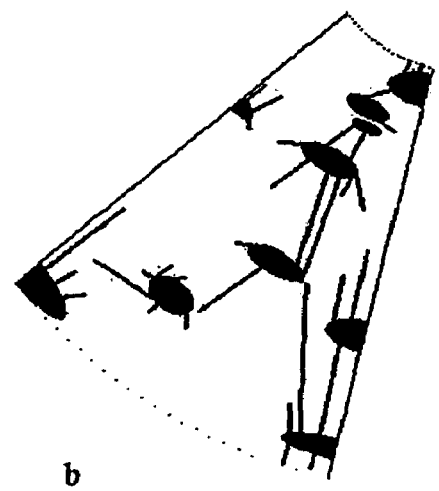
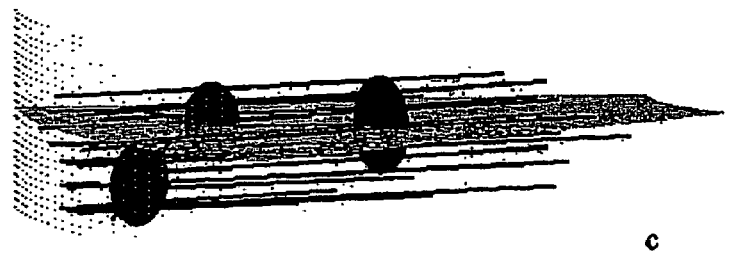

METHOD AND SYSTEM FOR MODELING BONE STRUCTURE

This application is a continuation-in-part of U.S. patent application Ser. No. 10/429,491 (now U.S. Pat. No. 7,212,958), filed May 5, 2003, which is a continuation-in-part of U.S. patent application Ser. No. 10/357,090 (now U.S. Pat. No. 7,283,940), filed Feb. 3, 2003, which claims priority under 35 U.S.C. §119 from U.S. Provisional Patent Application Ser. No. 60/353,768, filed Feb. 1, 2002, and U.S. Provisional Patent Application Ser. No. 60/380,174, filed May 6, 2002; each of which is hereby incorporated by reference in its entirety; and which is also a continuation-in-part of U.S. patent application Ser. No. 10/066,293 (now U.S. Pat. No. 7,127,383), filed Jan. 31, 2002, which is a continuation in part of U.S. patent application Ser. No. 09/981,684 (now U.S. Pat. No. 7,124,067), filed Oct. 17, 2001. Each of these applications is hereby incorporated by reference in its entirety.

FIELD OF THE INVENTION

The present invention discloses a structural and mechanical model and modeling methods for human bone based on bone's hierarchical structure and on its hierarchical mechanical behavior. The model allows for the assessment of bone deformations and the computation of strains and stresses due to the specific forces acting on bone during function. The model further contemplates forces that do or do not cause viscous effects and forces that cause either elastic or plastic bone deformations characterized by fractures. In preferred embodiments the model is computerized, for example using computer simulation, imaging and rendering techniques.

This invention also relates to the viscoelastic behavior of human compact bone's hierarchical structure. Specifically, the present invention relates to modeling of viscoelastic osteon behavior under torsional loading. This invention further relates to morphological and mechanical properties of isolated osteonic lamellae, which represent the microstructural building blocks of individual secodnary osteons and hence of adult human compact bone tissue. Morphology and mechanical function is related to the properties of the collagen bundle orientation and density distribution, and the behavior under quasi-static tensional loading such bone behavior is also incorporated into the computerized model.

BACKGROUND OF THE INVENTION

Material science defines the structural properties of an object as the properties that describe the object's makeup independent from its shape. Adult human bone has a complex structure and can be described as a four-order hierarchy, arranged in decreasing size (Petersen, 1930). The first order, macrostructure (FIG. 1), comprises the structures corresponding to gross shape and differentiation between compact (or cortical) bone (FIG. 2) and spongy (cancellous or trabecular) bone (FIG. 3). Compact bone is present in the long bone shaft (or diaphysis). Spongy bone is present in the lower jaw (mandible), in the epiphysis of long bone shaft, and in flat and short bones. The second order (or microstructure) of compact bone includes lamellar systems (lamellae). Organized lamellae around vascular canals are referred to as osteons (harvesian systems) and disorganized lamellae among osteons are referred to as the interstitial bone. The second order also is comprised of related structures such as bone marrow (see e.g. Bloom and Fawcetts, 1986). The third order (or ultrastructure) of compact bone consists mainly of collagen bundles and hydroxyapatite crystallites; mucopolysaccarides amount to a small amout but may have a significant role. The fourth order of compact bone consists of molecular arrangements between organic and inorganic substances. For cancellous bone, the second order includes trabeculae, which comprise lamellar systems and related structures, e.g. bone marrow. The third and forth orders of cancellous bone are the same those described for compact bone.

The osteon comprises a haversian canal with concentrically arranged lamellae. Osteons of long bone are generally directed along the long bone axis. Osteonic lamellae are organized as consisting of an organic framework (mostly a collagen bundle) embedded in ground substances, such as proteins and water, and hydroxyapatite crystallites. The hydroxyapatite crystallites are oriented in directions analogous to those of the bundles. Osteons measure a few centimeters in length and are between 200 and 300 μm in diameter. The degree of osteon calcification (relative amount of hydroxyapatite crystallites) is variable from osteon to osteon as well as within osteons. These differences are proposed to be due to the process of bone renewal or remodeling. In this process, osteons are renewed continuously. Consequently, osteons at different degrees of calcification are always present in adult compact bone.

There is a spectrum of osteon types that refer to the arrangements of fiber bundle direction in the lamellae. Two osteon types, "longitudinal" and "alternate", are representative of the two ends of the spectrum. Longitudinal osteons consist of bundles with a marked longitudinal spiral course. Alternate osteons consist of bundles with a marked longitudinal, oblique, and transversal course in successive lamellae (Frasca et al., 1977, Giraud-Guille, 1988, Ascenzi M.-G. et al., 2003). There are two types of lamellae, termed extinct (or longitudinal) and bright (or transverse or circularly-fibered) lamellae. Extinct (or dark) lamellae appear extinct whereas bright lamellae appear bright under a polarizing microscope when the microscope and osteon axes are aligned.

Compact bone consists of about 40% minerals, 40% collagen, and 20% fluids. The major internal spaces or discontinuities of compact bone include the vascular system, pits and cavities (lacunae), narrow channels (canaliculae), fine porosity, and spaces between the mineral phases. The major internal material discontinuities of compact bone (FIG. 5), in order of decreasing size, are:

| | |
|---|---|
| Vascular system | 20-50 μm |
| Lacunae | 4-6 μm |
| Canaliculae | 0.5-2 μm |
| Fine porosity | 600-800 Å |
| Spaces between mineral phases | 50-100 Å |

Cancellous bone consists of trabeculae, i.e. osseous structures with either a sheet-like or a rod-like configuration. These structures interlace to form a lattice-like or spongy biological structure (FIG. 3). For example, both types of trabeculae are present in the calcaneous; however, up to 3% of the rod-like configurations are tubular due to the vascular canal running through them. Therefore, they are similar to the harvesian system. In general, tubular trabeculae appear to have a relatively simple structure. Collagen fibrils run mostly parallel to the long axis of tubular trabeculae in the trabeculae outer portion and perpendicular in the inner portion. Although the true density of fully calcified cancellous bone is a little lower and the proteoglycan content a little greater than those of the fully calcified compact bone, the substantial difference between compact and cancellous bone resides in the porosity. The cancellous bone porosity, which ranges from 30% to more than 90%, is mainly due to the wide vascular and bone marrow intrabecular spaces. As is seen in compact bone, levels of calcification vary from trabecula to trabecula and within trabeculae.

The connections and orientations of trabeculae are found to have precise patterns, which are believed to relate to specific mechanical properties. The structure of the cancellous bone in the head and in the neck of the femur is usually given as an example of the correlation between the orientation of the trabeculae and the linear distribution of the principal forces during load bearing (stress trajectoral theory (Bell, 1956)). In general, such correlation between the orientation of the trabeculae and the linear distribution of the principal forces during load bearing is still under study because while in line with the mathematical calculations, the possible effect of muscle traction is complex (Koch, 1917; Rybicki et al., 1972). Nevertheless, there is a close relationship between the number and arrangement of trabeculae and the strength of cancellous bone (see e.g. Kleerekoper et al., 1985). This is evidenced by the age-induced loss of trabeculae (see e.g. Birkenhäger-Frenkel et al., 1988). Since this loss is rather selective (i.e. transverse trabeculae disappear more frequently than vertical ones in the central zone of the osteoporotic vertebral body; entire trabeculae totally disappear in elderly women; sharp fall in trabecular number is seen in elderly men), it is possible that cancellous bone contains some bundles of trabeculae whose main function is to resist mechanical forces while others have mainly a metabolic role.

The mechanical behavior of an object, or the response of an object to forces, of an object depends on the structure of the object. If the object is comprised of a hierarchical structure, the mechanical behavior of the object varies from order to order. That is, each order or level of the hierarchy responds to forces according to the structures and relationships within that order. Overall mechanical behavior of the object is ultimately determined by the mechanical properties of the different orders. Therefore, the mechanical properties of an object will vary with the hierarchical structure of the object. Bone is an example of an object where the mechanical behavior and mechanical properties are dependent upon this kind of hierarchical structure.

Mechanical properties of bone have been and are being investigated at various hierarchical levels through invasive (specimen isolation) and non-invasive testing. Osteonic trabecular lamellae, osteons, trabeculae, and macroscopic compact and cancellous bone samples have been and are the objects of such studies. Micromechanical results include Ascenzi A. and Bonucci, 1964, 1967; Ascenzi A. and Bonucci, 1968, 1972; Currey, 1969; Ascenzi A. et al., 1985, 1997, 1998; Hohling et al., 1990; Ascenzi A. et al., 1990, 1994; Marotti et al., 1994; Ziv et al., 1996; Ascenzi M.-G., 1999a, 1999b; Huja et al., 1999; Zysset et al., 1999; Ascenzi M.-G. et al., 2000. Macromechanical results include Hazama, 1956; Cook and Gordon, 1964; Carter and Hayes, 1976 and 1977; Carter et al., 1976 and 1981; Carter and Spengler, 1978; Hayes and Carter, 1979; Burr et al., 1988; Cater and Carter 1989; Jepsen and Davy, 1997.

Viscoelasticity

Material science regards viscoelasticity as a characteristic feature of polymer containing materials. Bone, like most biological materials, contains polymers. Viscoelastic properties depend on temperature and moisture content, which the work will hold constant at physiological level. In viscoelastic materials, some of the elastic energy generated by application of external forces is dissipated as heat. Such dissipated energy may contribute to the force driving the bone remodeling process (Levenston and Carter, 1998).

Studies of the mechanisms that generate bone viscoelasticity, that can shed light on the physico-chemical origin of Wolff's law and the properties of osteons, have not yet been conducted. However, osteon viscoelastic behavior could differ between longitudinal osteons and alternate osteons at the same degree of calcification (initial and final) and within each osteon type between initial and final stages of calcification. The only reported mechanical testing of whole osteons, isolated at their natural boundaries, is a preliminary non-systematic monotonic dynamic torsional loading (Frasca et al., 1981). It indicates structure and strain dependence of shear storage modulus in osteons of unspecified type and degree of calcification, and a linear viscous behavior up to strain values of $10^{-4}$. However, this model does not explain the behavior of the osteon structural components.

Even though numerous publications have addressed bone micromechanics in recent years, many biomechanical issues relating to bone are still not understood due to the lack of reliable or predictive models. The lack of inclusion of such micromechanical properties in current models of bone functions and behavior have severely limited their usefulness in predicting macromechanical properties. These properties include the bone behavior in response to external forces or identifying the requirements of bone reconstruction and prosthesis. However, the inclusion of these factors requires the development of methods and studies that may provide reliable and reproducible results.

There is a need in the art for realistic and meaningful models of bone behavior. To meet this need, the above-discussed parameters need to be investigated and resolved. The studies described herein provide surprising insights into the role of the underlying organizational arrangement of osteonic lamellar specimens in resisting applied loads. These findings are integrated into a novel and meaningful hierarchically based model of the mechanical behavior of macroscopic bone.

Such a model could provide clinicians with a tool to fundamentally improve the precision of their interventions.

The present invention describes a method to understand and predict the behavior of bone. The method includes a model of macroscopic bone which is constructed in terms of bone's hierarchical structural and mechanical properties and their interaction with forces acting on the macroscopic bone, including forces associated with the ordinary functioning of the body and forces applied clinically. The method can be applied to any bone structures, including human bone and the bones of vertebrates in general. The model applies to normal bone, and to pathological bone, when the pathology either does not alter the structural hierarchy, or when the alterations are characterized. The model is also applicable to fossilized bone.

SUMMARY OF THE INVENTION

The present invention contemplates a model of macrostructural properties of bone. The model comprises hierarchical structural and hierarchical mechanical properties of microstructure of the bone and includes interactions of the bone with internal and external forces. In a preferred embodiment, the bone that is modeled is either compact bone, particularly osteons and their lamellar layers, or cancellous bone. In an additional preferred embodiment, the mechanical properties used in the model are selected from the group consisting of tension, compression, shear, bending, torsion, prestress, pinching, and cement line slippage.

The present invention also contemplates methods of predicting deformation and fractures of bone and for identifying the requirements of bone reconstruction and prosthesis using the model of the present invention.

The present invention further provides a geometric/material model of hierarchical bone based on the mechanical properties and relative components of osteons. The model is based upon experimental studies of the microstructural viscoelastic properties (in terms of ultra-structural properties) of the osteon, the predominant microstructural component of adult bone. In one embodiment, the model comprises one or more elements selected from the following group: osteon mechanical properties; collagen-bundle orientation; the relative content of collagen and mucopolysaccharides in osteons; hydroxyapatite content; lacunae, canaliculae, and other porosity fluids within the pores; amounts of osteocytes and osteoblasts, and relative contents of other proteins.

The invention also provides a method of predicting deformation and fractures of bone using a model based on the viscoelastic properties of bone or osteons. According to this method, the effect of torsional loading in terms of microcracking, debonding, breakage, and void growth can be predicted from a model based on collagen-bundle orientation and/or the relative contents of collagen and mucopolysaccharides in osteons.

In addition, the invention provides a method of identifying the requirements of bone reconstruction and prosthesis using a model of the viscoelastic properties of compact bone. This method could, for example, utilize simultaneous computer simulation, based on the model of the invention, of the interaction of a patient's bone and the bone used for reconstruction or prosthesis.

The invention further provides a mechanical method for studying osteon specimens of prescribed shape, dimensions, lamellar type arrangement, lamellar thickness and degree of calcification for viscoelastic behavior. This method is preferably based on structural and dimensional analysis of individual lamellae and controlled dynamic torsional tests.

The invention also provides a model for the properties of bone based on the relative percentages of collagen and mucopolysaccharides in osteons. Preferably, the model also comprises results from mechanical testing, for example, torsional loading, of osteon specimens of the same specifications as those subjected to biochemical analysis for collagen and mucopolysaccharide content. In one embodiment, the model takes into account the influence of collagen orientation versus percentage contents of collagen and mucopolysaccharides to assess the influence of these constituents on the viscoelastic response of the osteon specimens. In another embodiment, there is a correlation between the distribution of the percentages of collagen, mucopolysaccharides with the orientation of collagen bundles at both initial and final degree of calcification.

Furthermore, the invention provides a Finite Element Model (FEM). This model reflects the geometry, distribution and orientation of the identified osteon component elements. In one embodiment, FEM incorporates known structural porosity (canaliculae and lacunae) to properly reflect the microscopic structure of the single osteon. Preferably, a three-dimensional model containing a large number of elements is prepared to represent the constituents in sufficient detail so that the results converge. The model can be parametrically exercised, within the limits of known property variation, to allow for biological variations and to study biological effects. This can include variation of the porosity distribution and of the bulk modulus in the porosity to assess the effect of fluid in the structure. Finally, the effects of these parametric manipulations on fracture and failure characteristics can be investigated.

Lamella

The present invention is further based on examinations of the structure of lamellar specimens and their behavior under quasi-static loading under tension. These studies provide surprising information on the role that the ultrastructural constituents play in the mechanical behavior of a single lamella.

By describing the limits and extent of the role that the lamellar ultrastructure plays in determining lamellar mechanical behavior, the invention provides an improved understanding of how bone tissue absorbs energy during quasi-static loading is gained, thereby enabling novel computer models of bone behaviour.

The invention also provides important insights into the differences in the processes of tissue formation for dark and bright lamellae, and points to different stimulation of the osteocytes responsible for dark and bright lamellar formation.

In addition, the invention provides a method of identifying the requirements of bone reconstruction and prostheses using a model based upon the surprising findings regarding the ultrastructural constituents of lamellae. This method could, for example, utilize simultaneous computer simulation, based on the model of the invention, of the interaction of a patient's bone and the bone used for reconstruction or prosthesis.

The above features and many other advantages of the invention will become better understood by reference to the following detailed description when taken in conjunction with the accompanying drawings.

BRIEF DESCRIPTION OF DRAWINGS

FIG. 1. A schematic representation of the upper third of the tibia; i.c.s. and o.c.s. stand for inner and outer circumferential systems, respectively. Both compact and cancellous bone are represented (from Bonucci, 2000, Basic composition and structure of bone. In: Mechanical Testing of Bone (An Y. and Draughn R. eds.) pp. 3-21, CRC Press, Boca Raton, Fla.).

FIGS. 7(*a*) and (*b*). (a) Tensile and compressive stress distribution during torsion in a material, such as macroscopic bone, which is weaker in tension than in shear; (b) Shearing stress on the cross section of a specimen subjected to torsion. The arrows' length indicates the magnitude of the shearing stress, which progressively increases from the center to the periphery of the specimen (from Evans, 1973).

FIGS. 8B, 8C, and 8D display the distribution of transverse and longitudinal lamellae in the sections prepared from the upper, middle and lower shaft, respectively. The posterior, anterior, medial and lateral regions correspond to the top, bottom, left and right regions, respectively, on the page. The distance between the centers of two adjacent square symbols measures 1.86 mm. The size of the square symbol is proportional to the ratio of the bright area in circularly polarized light to bright area in a dark field illumination. The regions with dominant transverse lamellae correspond to the regions with concentration of larger squares in the upper medial, middle medial-posterior and lower posterior shaft, which correspond to the areas of compression in FIG. 8A. The regions with dominant longitudinal lamellae correspond to the regions with concentration of smaller squares in the upper lateral, middle lateral-anterior, and lower anterior shaft, which correspond to the areas of tension in FIG. 8A.

FIG. 16. Shows a lamella after tensional testing (from Ascenzi, 1982).

FIGS. 28A and 28B. (A) Cross section of two isolated osteons: longitudinal (above) and alternate (below), ×110. (B) Osteon specimen (inner diameter: 40 µm; outer diameter: 210 µm; length: 500 µm) with its lugs, ×30.

FIG. 33 A Diagram of relative inclination of dark lamellae with respect to incident beam. FIG. 33B Diagram of relative inclination of bright lamellae with respect to incident beam. Dots indicate chosen locations for scanning.

FIG. 34. SAXS images of dark lamella. The images are unchanged across the scanned area.

FIG. 37. SAXS image of dark lamella from a scanned area. The images change across the scanned locations.

FIGS. 57A and 57B. X-ray diffraction results of (A) dark lamella and (B) bright lamella.

FIG. 59 Dark and bright lamellar distribution correlates to cyclic forces and geometry.

FIG. 63(a)-(c). Details of the lacunar-canalicular network in the model of bright osteon #381: (a) transverse view (×281); (b) 3-dimensional view; (c) a three-dimensional detail of the sector model with a plane indicating the section represented in (b). The (two) lacunae and their canaliculae that intersect the plane appear also in (b) while the rest of the structure is randomly generated.

DETAILED DESCRIPTION OF THE INVENTION

Figure 2B:
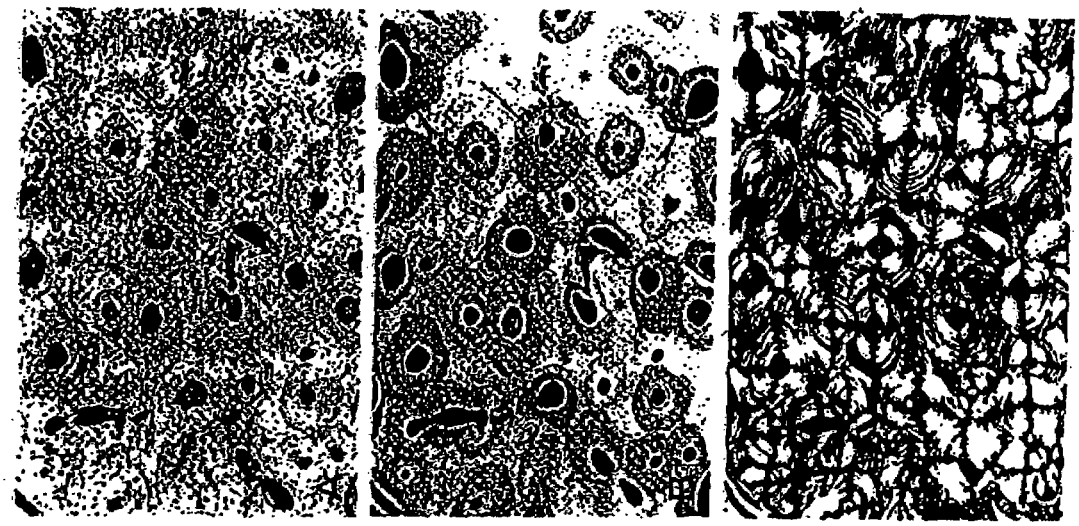
FIGS. 2 (a) and (b). (a) Diagram of a diaphysis sector of cortical long bone. The osteons or haversian system (HA) are located between the outer OL and inner IL circumferential lamellae. The osteonic lamellae are disposed cylindrically around the haversian canal (HC) (from Bouligand et al., (1985) Spatial organization of collagen fibrils in skeletal tissues: analogies with liquid crystals. In: Bairati A, Garrone R (eds.) Biology of invertebrate and lower vertebrate collagens. Plenum Publishing Corporation). (b) Cross-sectioned osteons as seen (A) under a light microscope; (B) in a microradiograph; and (C) under the polarizing microscope (from Bonucci, 2000).
Figure 2A:
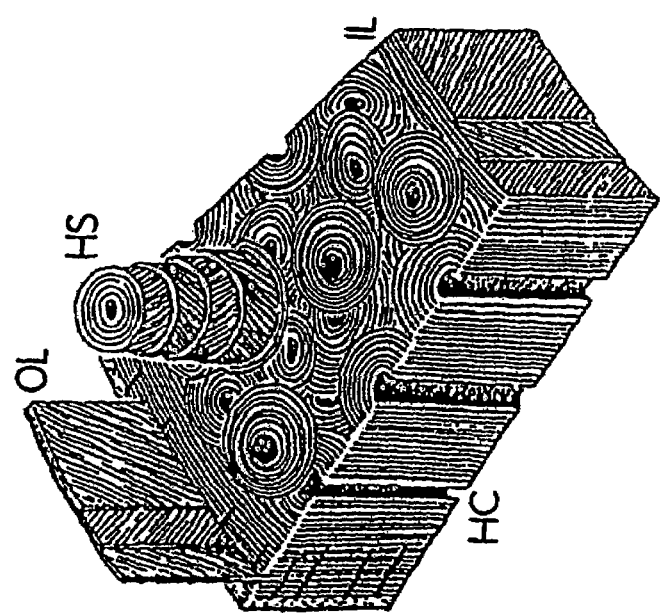
Figure 3A:
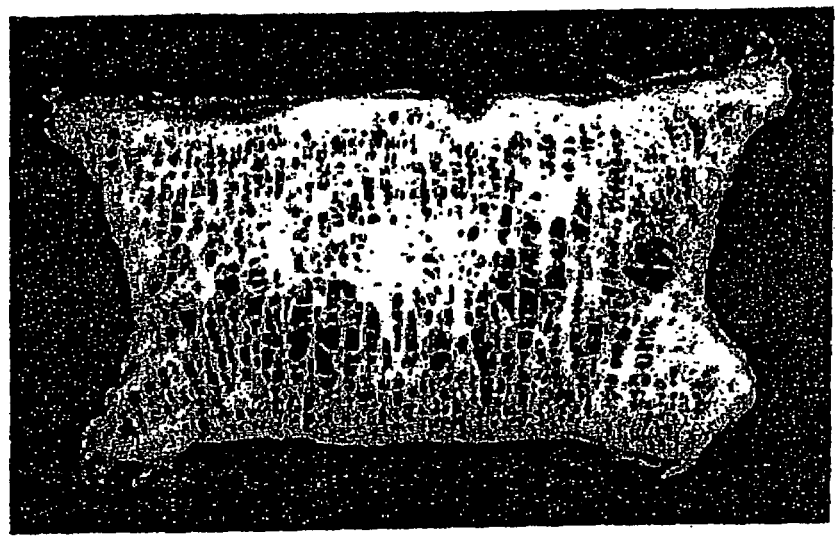
FIGS. 3 (a) and (b). (a) Section of the body of a lumbar vertebra showing vertical and horizontal trabeculae. The upper and lower surfaces correspond to articular cartilage (from Bonucci, 2000). (b) Section of half of tibia's upper third. The cancellous bone of the metaphysis consists of comparatively think vertical trabeculae connected by thin trabeculae (from Bonucci, 2000).
Figure 3B:
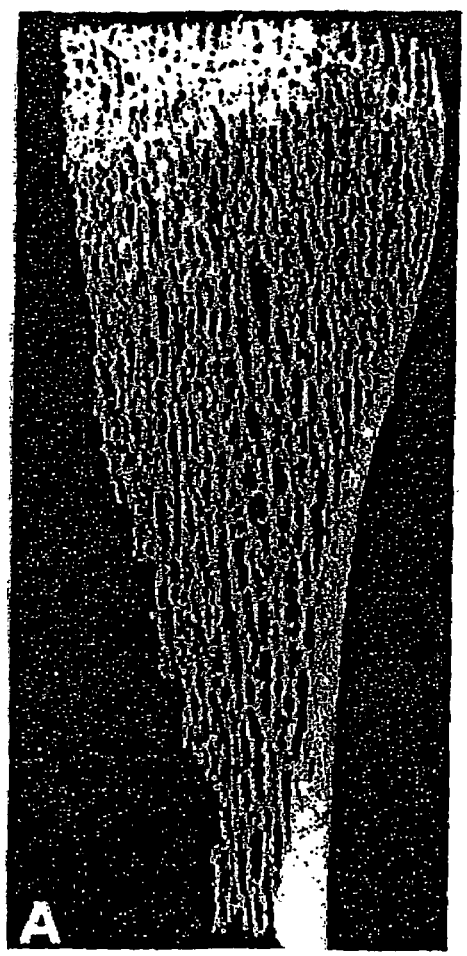

The present invention describes a method for modeling the anisotropic (direction-dependent) and non-homogeneous macrostructural properties of compact bone in terms of the microstructure. The model is based on the hierarchical structural and mechanical properties and bone interactions with internal and external forces. An example of such forces includes, but is not limited to, the ordinary functioning of the body. The model includes properties of the microstructure, in particular distributions of transverse lamellae of trabeculae and of alternate osteons, pinching of osteons, and slippage of osteons at the cement line.

Morphological and mechanical studies of bone show that at all hierarchical levels bone is anisotropic (the local mechanical properties are direction dependent), and non-homogeneous (the structure is not the same at different points). Nevertheless to simplify bone modeling, bone structure often is assumed to be homogeneous, isotropic (not direction dependent), transversely isotropic (one plane of symmetry), or orthotropic (three planes of symmetry). The simplifications of isotropy, orthotropy, and transverse isotropy give rise to unrealistic models because these simplifications assume that symmetries that do not exist. For instance, in such models stresses may be over- or underestimated. When such models are applied to practical applications, for example bone implants, poor estimates of stress may give rise to screw loosening in implants. The simplification of homogeneity gives rise to unrealistic models because it disregards the hierarchy of the bone structure. The existing hierarchical models are based on homogeneity theory, finite element analysis, and classic and Cosserat elasticity theories (see e.g. Katz, and Meunier, 1987; Crolet et al., 1993; Pidaparti and Burr, 1992). These models do not include important properties of the microstructure, which are included in the present invention and are described below.

The present model provides for modeling each level of the hierarchical structure of bone in terms of the structural and mechanical properties of that level. The model further provides for determining the relationships among the various levels.

In compact bone:

(1) Collagen bundles, hydroxyapatite crystallites, and mucopolysaccharides are organized in two lamellar types, bright, which are prestressed, and dark extinct lamellae. Lamellae show porosity.

(2) Lamellae are organized in osteons. Osteons show pinching under tension-compression cyclic loading.

(3) Osteons samples are organized in osteon sample groups on bone sections. Osteon groups show cement line slippage during torsion.

(4) Osteon groups are organized to complete a bone section. The collagen bundle direction distributions are used to complete this organization.

(5) Transverse sections are organized to complete the macroscopic bone.

In cancellous bone:

(1) Collagen bundles, hydroxyapatite crystallites, and mucopolysaccharides are arranged in bright and dark extinct lamellae. Bright lamellae are prestressed. Lamellae show porosity.

(2) Lamellae fill in trabeculae. Trabeculae show porosity.

(3) Trabeculae are grouped in trabecular sample groups on bone sections.

(4) Trabecular groups are organized to complete a bone section. The prevalent collagen bundle directions are used to complete this organization.

(5) Sections are organized to complete the macroscopic cancellous bone.

To produce the model, each microstructural level of the hierarchical bone structure commences with the microstructural components and proceeds through the macrostructure. Each element of the assembly is correlated with mechanical properties either determined from literature sources or that are newly estimated. Homogenization methods are used to assemble the structure at one level with the structure at the next level, and so on, to build a hierarchical model. The finite element method allows for the computation of strains and stresses throughout the model.

The invention results in a model of macroscopic compact and cancellous bone that respects the hierarchical, structural, and mechanical properties starting from the microstructural components. The model may be applied to all bones to result in a model for each bone of the skeleton.

The present invention further defines methods of predicting deformation and fractures of bone and identifying the requirements of bone reconstruction and prosthesis using the model. From the specific forces that act on bone during function, the model allows for the assessment of bone deformation, strain, stresses, and fractures. Additionally, from the fractures and stress distribution, the model allows for the computation of strain deformation and forces that cause the observed fracture and stress distributions. The model also contemplates forces that do or do not cause viscous effects. The model contemplates forces that cause either elastic or plastic bone deformations as characterized by fractures.

The model includes torsional cyclic loading functions of two representative osteon types in terms of degrading properties such as stiffness and pinching, and increasing energy absorption. These mechanical property changes are correlated to the idealized or mathematical behavior of ultrastructural components, which includes yielding, buckling, and fracturing properties. The resulting algorithms and behaviors comprise an osteon model, which simulates fracture propagation in osteons under cyclic torsional loading in terms of microcracking, debonding, void growth, and fiber breakage. Verification of the model is demonstrated by checking that the model produces the fractures observed in osteon samples that are separately submitted to tension, compression, and shear.

The model also includes simulation of microstructural fracture propagation in bone. Because of the dependence of the macrostructure's mechanical properties on microstructure, the model will provide an improved understanding of properties of long bone, such as fracture propagation, including a better understanding of how human bone macrostructure responds to forces acting on it.

The model will have application in many areas, including without limitation:
- the mechanics of natural composites and the manufacture of new composites, since bone is a natural composite material;
- the identification of the fundamental requirements of bone reconstruction and prostheses (which will increase design effectiveness and reduce testing and related cost); and
- the microstructure of vertebrates whose microstructure is similar to human's Definitions The present invention spans through both elastic and plastic ranges. As used herein, the term "elastic range" refers to the stress and strain values for which the material structure does not break and returns to its original shape when the force is removed. As used herein, the term "plastic range" refers to the stress and strain values for which the material structure does break and therefore does not return to its original shape when the force is removed. When an increasing force (starting from zero) is applied to a material, the material undergoes first elastic and then plastic deformation. Any bone type can undergo elastic deformation only or both elastic and plastic deformation depending on the force magnitude. Elastic and plastic deformations provide a starting point to predict strain and stress distributions and fractures of bone. The model also may be used to compute the stress distribution from the strain distribution and strain distribution from elastic and plastic deformations. It further identifies the requirements of bone reconstruction and prostheses.

As used herein, the term "boundary conditions" refers to the relative movements of the boundaries of the various hierarchical structures under loading. In a specific embodiment, the behavior of the cement line under loading is the boundary conditions for the osteon and the interstitial bone between which the cement line lies.

The term "pinching" refers to a sharp change of stiffness of bone. As used herein, the change in stiffness can be either from increasing stiffness to decreasing stiffness or from decreasing stiffness to increasing stiffness. In a preferred embodiment, the change presents itself on each half-cycle.

The term "material analog" refers to a model or reproduction produced from material, as distinguished from a mathematical or computer model.

The term "distraction device" refers to an apparatus that generates bone by stimulating growth of existing bone by application of forces to such existing bone.

As used herein, the term "strain distribution" refers to a measure of the degree of elongation at any point on a sample. In a preferred embodiment, the sample is bone.

The term "stress" refers to the force per unit area.

The term "stress distribution" refers to strain distribution and on the mechanical property distribution throughout the body.

The term "corrected break area" refers to the actual bone area, except for the lacunae and canaliculi, subjected to stress in the vicinity of a break.

The terms "viscous effect" and "viscoelastic" refer to a system that exhibits behavior that combines liquid-like and solid-like characteristics. In particular, this term herein refers to the viscoelastic properties of osteons. According to the invention, these viscoelastic properties include one or more of the following parameters: osteon mechanical properties (e.g., elastic and viscous constants for osteon specimens, torque versus angle-of-twist behavior, etc.), degree of calcification of osteons, the relative contents of collagen and mucopolysaccharides in osteons, collagen-bundle orientation in osteons, osteon hydroxyapatite content, amount of lacunae and canaliculae porosity fluids within the pores, osteon content of osteocytes and osteoblasts, as well as the contents of other proteins present in osteons. Preferably, these parameters are measured in both longitudinal and alternate osteons.

A Finite Element Model, or "FEM", is a well-known method for modeling. According to this model, the gross shape of the object, e.g., a bone, that one wishes to model is filled with homogenous elements (e.g., 3D brick-shaped) in a finite number. The mechanical analysis is conducted on the individual elements, so that elastic or viscoelastic properties are declared for each element. The loads and boundary conditions are applied to the gross shape through the distribution of loads on the element. At this point, one can compute the strain and stress for each element. A sufficient number of elements must be applied so that the strain and stress distributions are compatible along the boundaries between any two adjacent elements. The principles of FEM has been described, e.g., in Dwoyer et al., (1988), which is hereby incorporated in its entirety.

A "reference osteon" is a set of osteon data and/or parameters representative of an osteon to be used in the model of the invention.

Factors

Mechanical Properties

Various mechanical properties are included in the model of the present invention. The properties will be correlated with each hierarchical level of the bone to produce the model. A non-limiting list of such properties is disclosed and described herein.

Figure 6A:
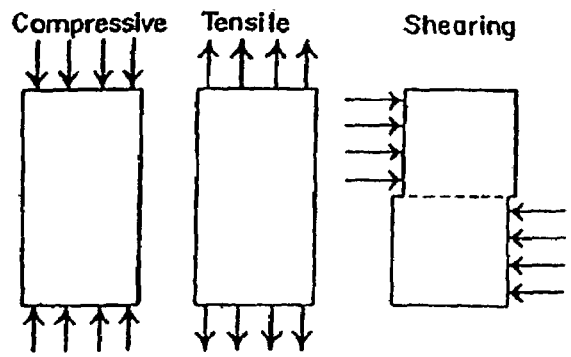
FIG. 6 (*a*)-(*c*). (a) Types of pure forces; (b) Definition of stress on an area on which the force is constant; (c) Definition of unidirectional strain for D much smaller than L (from Evans F. G., Mechanical Properties of Bone, Thomas, Springfield, 1973).
Figure 6B:
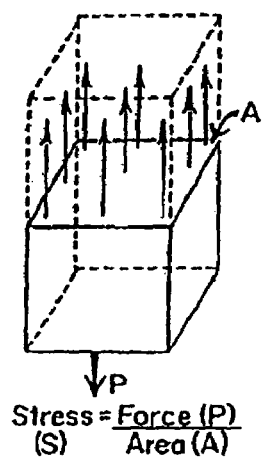
Figure 6C:
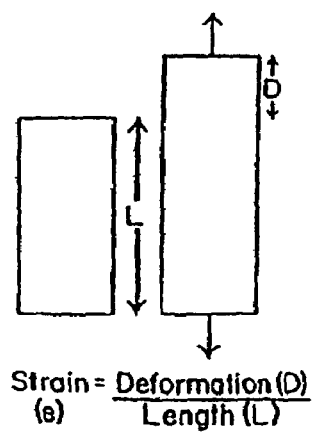

The mechanical properties of bone are quantified by parameters or coefficients that describe the response of bone to tension, compression, shear, bending and torsion. Tension, compression, and shear are termed "pure forces" because each of them is recognized by the effect (the deformation) produced in the body to which it is applied (FIG. 6). A tension (tensile) force tends to lengthen the body to which it is applied, while a compression (compressive) force has a tendency to shorten the body. A shear force tends to make one part of a body slide in a direction opposite to that of an adjacent part. Bending and torsion (FIG. 7) are a combination of tension, compression and shear.

The effect of the application of one of the above-mentioned forces to a body at a natural state is described in terms of strain and stress. Strain is the measure of dimensional changes in a body and is computed by means of the deformation (Antman, 1995). Since in general the value of strain changes from point to point throughout the body, more properly one refers to strain as the strain distribution throughout the body, which provides the value of strain at each point of the body. The tendency of a body to be deformed by the application of a force is resisted by the internal force among the molecules composing the body. Such resistance is measured by the stress, which is a force per unit area. Similar to strain, in general the value of stress changes from point to point throughout the body. More properly one refers to stress as the stress distribution throughout the body, which provides the value of stress at each point of the body. The stress distribution depends on the strain distribution and on the mechanical property distribution throughout the body. What all elastic structures have in common is that the stress distribution is a linear function of strain within the elastic range (Hooke's Law; see e.g. Jones). Beyond the elastic range the relationship between stress and strain distributions depends on the particular structures. For instance, the mechanical testing of a specimen provides a stress-strain diagram, which allows the study of the relationship between stress and strain.

Studies indicate that the mechanical behavior of longitudinal and alternate osteon samples at equal degree of calcification, as assessed by the method of Amprino and Engström (1952), differs because of their structural difference. The comparison of experimental stress-strain diagrams for longitudinal and alternate osteons shows that under monotonic tension and torsion, longitudinal osteon samples resist stresses better than alternate osteons; while under compression, shearing and bending, alternate osteon samples resist stresses better than longitudinal osteons. Under cyclic tension-compression loading, longitudinal osteon samples show a larger energy loss and lesser pinching degradation per cycle than alternate osteons; longitudinal osteon samples show a greater strain increase during compression than tension. The opposite is true for alternate osteons.

Figure 8A:
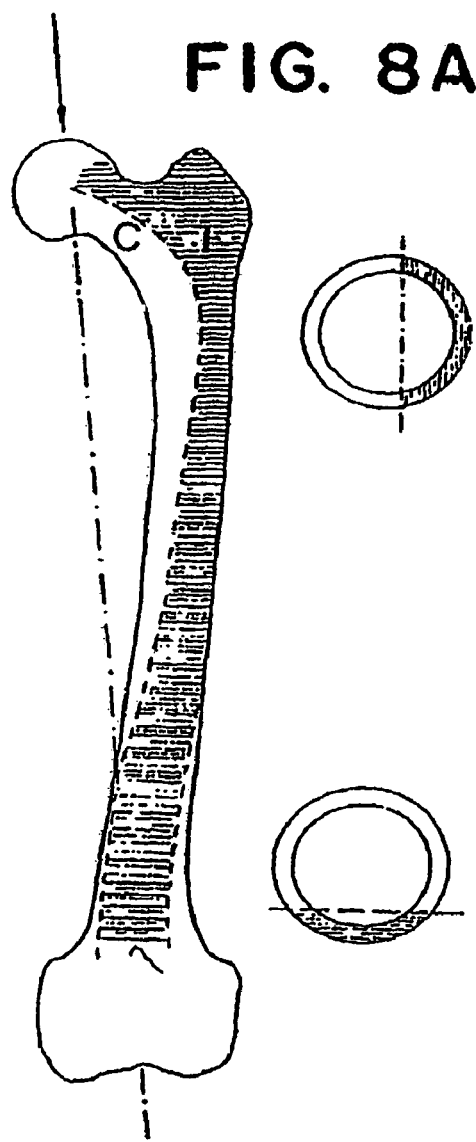
FIGS. 8(A) 8(B) 8(C) and 8(D). 8A Bending of femur due to gravity. C indicates the area under compression and T indicates the area under tension.
Figure 8B:
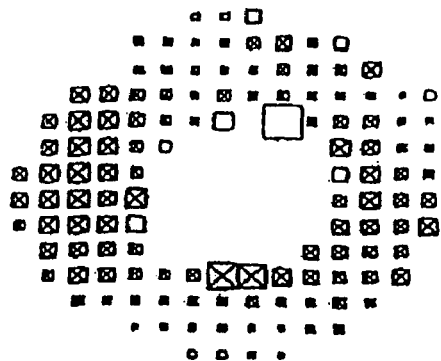
Figure 8C:
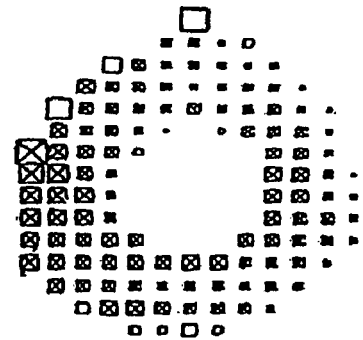
Figure 8D:
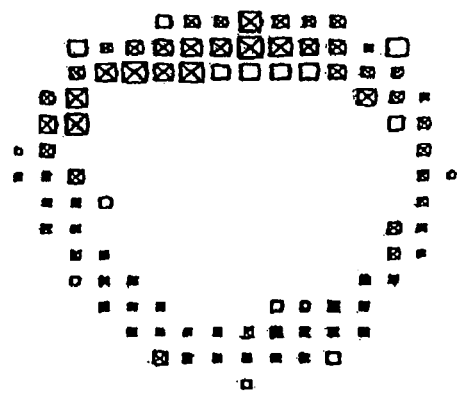

The macroscopic mechanical properties have been found to depend on and to be explained by the microstructure. In particular, they have been found to depend on the numerical presence of osteons, the size and percentage volume of osteons, and collagen fiber orientation (Currey, 1959; Evans and Vincentelli, 1969). As early as 1873, Rauber considered the correspondence between bone micro- and macro-structure. He hypothesized that the structure of osteons and interstitial bone in the long bone shaft relates both to their distribution in the shaft under normal conditions, and also under pathological conditions that do not alter the bone's hierarchical configuration. This hypothesis was later confirmed (Portigliatti-Barbos, 1983, 1984, and 1987; Boyde et al., 1984; Ascenzi A. et al., 1987a and 1987b; Ascenzi A., 1988; Carando et al., 1989 and 1991). Specifically, the distribution of dark lamellae (whose bundles have a transverse and oblique course) and of bright lamellae (whose bundles have a longitudinal course) in osteonic and interstitial bone follows a characteristic non-random pattern. Studies indicate that this distribution is consistent with the distribution of bending forces usually operative on this bone (Ascenzi M.-G., 1999a). For example, the femoral dominant distribution of dark and bright lamellae displays a clockwise rotation of approximately 90° in sequential sections from upper, middle, and lower third of the shaft (Portigliatti-Barbos, 1983, 1984). In fact, because of the femoral overall shape which includes two curvatures (an anterior-posterior curvature and a lateral-medial curvature), gravity on the body results in the bending of the femur. Because bending always includes an area of tension and an area in compression, the femur presents an area in tension and an area in compression (FIG. 8a). It turns out that the femoral dominant distribution of dark (bright, respectively) lamellae coincides with the area in tension (compression, respectively) (FIG. 8b). Recent work also has found that the above-mentioned transverse/longitudinal lamellar distribution is consistent with the distribution of alternate osteons (Hert et al., 1994). Neither the transverse/longitudinal lamellar distribution nor the alternate osteon distribution have been included in prior models of bone structure. Transverse/longitudinal lamellar distribution and the alternate osteon distribution are included in exemplary models of the present invention.

Additional Factors

The following provides a non-limiting list of factors that may be included in the models of the present invention, and which are used in exemplary embodiments.

(1) Fracture of macroscopic bone. The invention incorporates fracture dynamics into the bone model and modeling methods, including mechanisms by which a fracture starts and spreads. Unlike other models of bone, fracture propagation is modeled in terms of ultrastructural components. The literature indicates that the fracture mechanism of bone depends on bone structural and composition properties such as collagen architecture and collagen content (e.g., Jepsen et al., 1999). In 1969, Evans and Vincentelli showed significant differences among osteons of various bones (fibula, tibia, and femur) in the "corrected break area", which is the actual bone area, except for the lacunae and canaliculi, subjected to stress in the vicinity of a break. Characteristic differences were found between the means of the corrected break area for groups of longitudinal and transverse (i.e., consisting of transverse lamellae) osteons and of osteon fragments of the femoral and tibia sections and for groups of the transverse osteons and fragments of the tibia and fibula sections. The percentage of the "corrected break area" of transverse osteons and their fragments in the tibia and fibula sections was also statistically different. Another study (Vincentelli and Evans, 1971) established a relationship among macromechanical properties, collagen bundles, and calcification in the shaft of long bones. Furthermore, fracture lines appear to follow the cement lines between osteons and lamellar boundaries within osteons (Simkin and Robin, 1974) where the bone is weaker. According to the invention, inclusion of the differences between the means of the corrected break area for groups of osteons would increase the predictability of the present model compared to prior art models.

(2) The prestress distribution in bone. The models and methods of the invention incorporate computations of the stress distribution in long bone so as to include pre-stress (Currey 1964, Ascenzi A. and Benvenuti, 1980). Stress distribution in long bone depends on structural and composition properties such as collagen architecture and collagen content. Bone areas where collagen bundles are transverse and oblique to the long bone axis are prestressed. Such prestress, estimated on the order of 0.1 GPa, is too large to be disregarded. It locally impacts the stress produced by forces acting on bone (see Ascenzi M.-G., 1999a). Newly estimated prestress variables are included in the present invention (Ascenzi M.-G., 1998a and 1999b). The newly estimated prestress was evaluated through the structural and mechanical modeling of isolated lamellar samples, and has been shown to be a realistic approach. See e.g., A. Meunier, 1999. Inclusion of this prestress into the model of the present invention allows one to more accurately model bone in terms of computation of stresses.

(3) The phenomenon of "pinching". The invention for the first time incorporates pinching into bone models and modeling methods. Pinching is the mechanism of yielding and buckling of collagen bundles under loading beyond the elastic phase. It is an important step in the formation and propagation of fractures. The understanding of pinching requires detailed analysis of osteon mechanical behavior. In fact, while the stress-strain curves for monotonic loading under tension, compression, and torsion show trends no different from those recorded from macroscopic bone samples, the tension-compression hysteretic loops showed a new behavior for osteon samples not observed in macroscopic samples (Ascenzi et al., 1985 and 1997). The new behavior observed is that tension-compression hysteretic loops of osteons demonstrate S-shaped half-cycles. This phenomenon has been observed and studied only relative to earthquake-resisting structures. In such context the behavior is usually called "pinching" (see, e.g. Narayanan and Roberts, 1991). Pinched hysteretic loops are typical of structures that incorporate a matrix that cracks and reinforcements that yield or whose members buckle when subjected to compressive loads. In osteons, the shape and dimensions of hydroxyapatite crystallites and the relationship of these parameters to the organic components of the matrix are only partially known. Not all collagen bundles are completely calcified. Those that are not calcified take up crystallites only on 400 Å bands (Ascenzi A. et al., 1965). Hence such bundles may be comprised of relatively more stiff 400 Å bands separated by relatively more flexible non-calcified collagen segments.

Pinching in osteons is hypothesized to be mainly localized at the partially calcified bundles. Therefore, in osteons, either bundles yield in tension and buckle in compression while crystallites fracture and detach from collagen, or crystallites fracture and detach from collagen in tension while collagen yields in compression. Thus, cyclic tension-compression loading shows pinching. Since cyclic torsional loading involves tension and compression, cyclic torsional loading is expected to show pinching. Nevertheless, it may be that the disruption created by torsional loading is too disordered, in comparison to that due to tension-compression, to allow closing of lesions and resolution of members as controlled as under tension-compression. In any event, if cyclic torsional loading of osteons shows pinching, pinching is included in the invention applied to macroscopic compact bone torsional loading.

(4) Macrostructure and mechanical loading studies of whole bone or macrosamples. The invention takes account the influence of bone microstructure in evaluating mechanical loading of whole bone and of bone macrosamples. In the literature, for example the torsional loading in bone has been analyzed using finite element analyses (see e.g. Hazama, 1956; Pfafrod et al., 1972 and 1975; Knets et al., 1973; Miller and Piotrowski, 1974; Evans, 1978; Martens et al., 1980; Moreland, 1980). However, models presently do not completely reflect the changing properties of bone at the microstructural level. Similarly, cancellous bone has been described as continuous and isotropic, which does not reflect the high porosity and the changing details (such as collagen bundles direction and lamellar structure) at the microstructural level. The elastic and plastic moduli change locally in relation to the microstructural properties.

Such studies ignore most of the mechanical properties of the microstructure (because macroscopic samples do not always have the same mechanical properties as the microstructure that comprises them) and therefore do not provide a realistic understanding of bone mechanics. For instance, pinching is present in longitudinal and alternate osteons but not in macroscopic compact bone samples during tension-compression cyclic loading; also the torsional stiffness varies from osteon samples to osteon groups and relative to that of larger compact bone samples (Lakes, 1995). Lakes shows that the torsional shear moduli of osteons are much larger than shear moduli obtained for macroscopic samples. That is, slender specimens are stiffer than thick ones; the lower stiffness in thick specimens is attributed to slippage of osteons at the cement lines during torsion of macrosamples. Such slippage is described well by Cosserat elasticity theory since it allows a moment per unit area in addition to the usual force per unit area of classic elasticity theory. The inclusion of this factor into the model impacts, for example, the simulation of fracture propagation. The fracture propagation model is able to simulate the slippage of osteons at the cement lines during torsion and therefore the experimentally obtained results regarding fractures spreading along the cement line.

Local Properties and Bone Modeling

The knowledge of the mechanical properties and of the strain and stress distributions of compact and cancellous bone under specific loading is necessary in all contexts where the local behavior of bone is in question. For example, stability is the crucial characteristic of an osteotomy fixation device. When a tibia requires an osteotomy, the device that holds in place the two bone edges created by the cut (osteotomy) can only allow for micro-movements of one edge with respect to the other during function, such as walking, to be successful. The stability of device depends on its shape, and material, and on the number, position and inclination of the pins that secure the device to the tibia. The best position and inclination of pins for the stability of the device depends on the spot chosen, that is on the local property of the tibia. The anisotropy and non-homogeneity of the tibia make a difference with respect to the screw loosening while walking. In fact, the screw may or may not get loose if the chosen spot is more or less resistant to the force that it takes for the pin to get into place, if one inclination is chosen instead of another one, if the spot is prestressed in one direction or another. The question of osteotomy fixation stability cannot be fully studied with a computer bone model that does not take into account the hierarchical structure of bone that renders bone anisotropic and non-homogeneous. Because if the model assumes less than that, the local information is lost and the bone shows the same properties where it should not.

Another example refers to cemented implants. The local bone conditions affect the bone-implant interface. The loosening rates in cemented implants, especially in younger, active persons, is partially due to the local bone mechanical properties. This problem has led many investigators to pursue methods of cementless fixation. In the meantime a great deal of attention is being focused on the bone-implant interface and the factors affecting its strength. A thorough solution to the problems involves the knowledge of the local bone mechanics.

Simulation of Fracture Propagation

The fracture propagation model of either compact or cancellous bone under specific loading follows the same steps as the fracture propagation model of single osteon samples under torsion (See, Example 2, Steps 1-19). The computer program may be based on any suitable simulation program, for example, a Monte Carlo simulation. The fracture propagation steps are applied to the finite element mesh for the compact or cancellous bone in question, instead of to the finite element mesh of single osteon samples.

The purpose of the fracture model is to show that cumulative micro-cracking, de-bonding, void growth and fiber breakage associated with repeated loading of osteons causes a progressive loss of stiffness and pinching, and increase of energy absorption.

The fracture model reflects the following hystological/physiological observations. Fluids occupy vascular canals, canaliculae and lacunae, which are interconnected. The flow of liquids under stress can absorb large amounts of energy, increasing the toughness of bone. Large strains may be accommodated by the organic phase (e.g. collagen, mucopolysaccarides). When a strain is sufficient to cause cracking, the organic phase may also contribute to the dissipation of energy at the front of a propagating crack. Crack propagation also appears to be arrested in the presence of canaliculae and lacunae. In fact, when the crack gets to a hollow space, it just stops because at the hollow space there is no more resistance, no more material to rip. Therefore, discontinuities to some extent increase the robustness of bone rather than increase its tendency for brittle fracture (Currey, 1962). In the case where a crack enters a discontinuity, the front tends to be blunted, hence reducing the stress concentration factor (i.e. the level of stress necessary to create a crack) and slowing crack propagation. When a crack is forced to enter a vascular canal, the radius at the tip of the crack becomes larger. Lacunae are probably more likely to act as stress concentrators than canaliculae because of their generally ellipsoidal cross-section and because they are generally oriented normal to the long axis. Stress concentrators are define as entities that raise the stress concentration factor. However, their much smaller size precludes them from acting as fracture initiators (i.e. causes for the structure to begin fracturing) until or unless plastic deformation has created cracks at the tip. Fractures spread along cement lines and lamellar interfaces.

Additional Applications

The model also can be used with complimentary applications and technologies. An example includes, but is not limited, to combination with software to model soft tissue (such as the one developed by the company Infocus, Sylicon Valley, Calif.). Material analogs of bone can be obtained by means of 3D printers (see, e.g. the printers manufactured by Stratasys-3D printing in Eden Prairie, Minn.). Implants and distraction devices will be manufactured by computer guided robots. See, e.g., Mah and Hatcher, 2000. The present model will provide the model of the bone structure to be distracted and during distraction.

The application of modeling to imaging (e.g., clinical MRI and CAT scan x-ray imaging) of human bone offers the prospect of a qualitative leap in the predictability, effectiveness, and convenience of surgical, orthodontic, orthopedic and other medical interventions. Embodiments of the model can enable medical professionals, based on patient specific data, to visualize how bone in various parts of the body will grow and heal in response to medical interventions. First, the current lack of bone local mechanical properties impairs the comparison between natural and synthetic bones. Second, the current lack of knowledge of mechanical properties, strain and stress distributions throughout the bone, impairs the research for new synthetic bones to move towards the same properties. For instance, the latest synthetic long bone is made out of fiber-reinforced glass (Szivek, 2000) of unknown local mechanical properties. There are no reports of synthetic porous structures with the interconnecting pores having the same stiffness and strength characteristic of human trabecular bone. Even the most popular synthetic closed-cell polyurethane foams (such as Daro, Butler, Wis.) which have a structure that shows similarities with human trabecular bone are homogeneous in theory and with inhomogeneities difficult to control in practice. In any event the non-homogeneous hierarchical structure of human bone is not even close to being imitated. Third, the current lack of knowledge of mechanical properties and of strain and stress distributions throughout the bone, impairs bone reconstruction, bone grafting, placement of screws, insertion of prostheses.

The invention is applicable to the bones of other vertebrates whose bone structure somewhat differs from that of humans. For instance, the invention would give valuable results on the prevention and healing of fracture in equine bone. Currently, the micromechanical bone studies of vertebrates are scarce, often limited to a few small animals, such as mouse, dog, and sheep. Because of that, the results on human bone microstructure are erroneously used in studies of vertebrates to which they do not apply (Riggs et al., 1993a, 1993b).

The present invention provides a more realistic prediction of the macroscopic bone mechanical properties, strain, and stress distribution than computer models based on omission of either anisotropy or non-homogeneity of bone. Moreover, this invention provides more realistic prediction than purely mathematical models, that is models based on hypotheses, which are not based on experimentation. The literature is full of research on bone microstructure, which employs purely mathematical models of osteon behavior (Pidaparti and Burr, 1992). Such approach is limited, often unrealistic and does not always predict biological phenomena. The invention is flexible so as to include new experimental findings of bone structural and mechanical properties. This ensures the invention's realistic characteristic insertion of prostheses, etc.

The present invention will be better understood by reference to the following Examples, which are provided by way of exemplification and not by way of limitation.

EXAMPLE 1

To produce a model of the present invention, compact bone is subjected to any method that may produce non-invasive slices of biological structures that are known in the art (i.e., μCT-scan or micro computerized tomography). Images then are stored in a computer and a 3-dimensional-reconstruction is applied using a standard method known in the art (see e.g. Materialise, XYZ Scientific Applications, Inc. Livermore, Calif.). The high resolution of a μCT-scan (about 30 μm) allows for determination of the outline of osteons, of osteons' vascular canals and interstitial bone. Also the 3D-reconstruction shows varying shades of gray, which represent the degree of calcification. Osteons are filled with structure by means of the two lamellar types (bright and extinct lamellae), which have been previously assembled. The criteria by which the lamellar structure is drawn into each osteon follows the distribution of alternate osteons (Hert, et al. 1994) and the distribution of dominant collagen fibril directions (Portigliatti-Barbos, 1983, 1984, and 1987; Boyde et al., 1984; Ascenzi A. et al., 1987a and 1987b; Ascenzi A., 1988; Carando et al., 1989 and 1991).

Figure 9A:
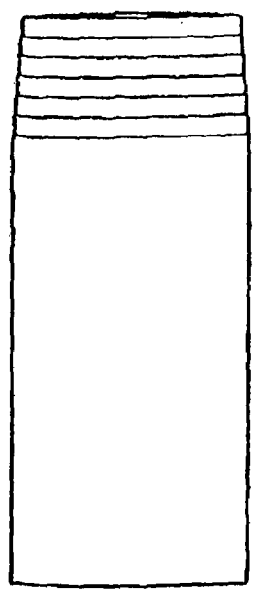
FIG. 9 (*a*)-(*c*). (a) The osteonic lamellar model is a laminate, which consists of fiber-reinforced unidirectional laminae. (b) The interstitial lamellar model is a portion of the osteonic lamellar model. The figure shows three thin laminae (lamellae) and a thick lamina (portion of cement line) (from Crolet, J. M., Aoubiza, B., and Meunier, A., Compact bone: numerical simulation of mechanical characteristics. J. Biomechanics, (26):677-687, 1993). (c) On a small laminar element of constant thickness, the principal material axes are labeled 1, 2, and 3. Direction 1 is parallel and direction 2 is perpendicular to the fibers. Direction 3 is the radial direction perpendicular to the page. Circumferential and axial directions are labeled Θ and z. The angle between the circumferential direction and direction 1 is called γ (from Ascenzi, M.-G. (1999) A first estimation of prestress in so-called circularly fibered osteonic lamellae, J. Biomechanics, (32): 935-942).

The structure of the osteonic lamellar model consists of a laminate whose length, width and height correspond to a cylindrical shell circumference, thickness, and height (FIG. 9a). The structure of the lamella within the interstitial bone is modeled as a portion of the osteonic lamellar model (FIG.

Figure 9B:
Figure 9C:
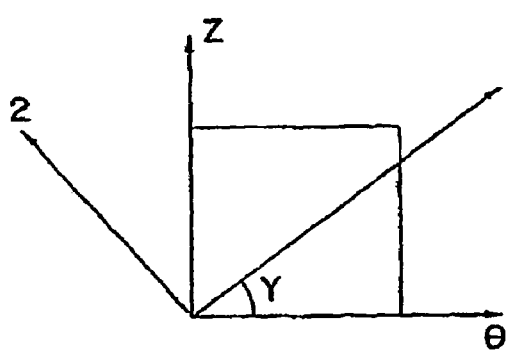

9b). The layers are unidirectional fiber-reinforced laminae (FIG. 9c) of the same matrix and fibers. The matrix and fibers, i.e. individual components of the hierarchical structure, and not the microstructure as a whole, are each treated as homogeneous and isotropic.

All fibers, of which there are two types, are assumed to be circular in cross-section, randomly distributed in the transverse plane. The fibers of the first type have a diameter of about 800 Å and fibers of the second type have a diameter of about 200 Å. The fibers of the first type are proposed to be perfectly embedded in matrix (they are idealized to have essentially no gaps between them and do not move relative to each other). The fibers of the second type are proposed to be perfectly embedded in matrix only when bone undergoes physiological static loading. When bone undergoes physiological dynamic loading the fibers of the second type are given the option to move with respect to matrix in which they are embedded. Such displacement is specified following experimentation, such as boundary condition or de-bonding experiments. The experimentation may also dictate further conditions for the relative position of the two fiber types. Examples of such experiments are discussed below.

In the present model, the lamina with fiber inclination $\gamma$ is named $\gamma$-lamina. The thickness of the dark lamella ranges between 4 and 12 $\mu$m (Ascenzi M.-G. et al., 2003). It is described by the sequence [82, −82] (Frasca et al., 1977). The notation [82, −82] refers to two $\gamma$-laminae where $\gamma$=82, −82. The thickness of the bright lamella ranges between 2 and 7 $\mu$m (Ascenzi A., et al., 2000). It is described by the sequence [−61.5, −41, −20.5, 0, 20.5, 41, 61.5] (Ascenzi M.-G., 1999b).

For the matrix, Young's modulus of 114 GPa, Poisson's ratio of 0.27, and ultimate strength of 0.59 GPa are assumed for hydroxyapatite (Katz and Ukraincik, 1971). For the fibers of the first type, Young's modulus of 1.2 GPa, Poisson's ratio of 0.35, yield strength of 0.002 GPa are used for collagen (Currey, 1969). For the fibers of the second type, Young's modulus of 1.1 GPa, Poisson's ratio of 0.23, are used for mucopolisaccarydes (Boume, 1971). Depending on the degree of calcification, the matrix occupies up to 40% of the lamina volume without voids (Bonfield and Li, 1967). The cement line is modeled as homogeneous and isotropic: the Young's modulus of 70 GPa and Poisson's ratio of 0.27 (Philipson, 1965; Schaffler et al., 1987).

Since osteons vary with respect to the distribution of dark and bright lamellae, the model of an osteon with a specific distribution of dark and bright lamellae is obtained by assembling the model of dark and bright lamellae so as to follow the osteon's particular distribution. For instance, a model of the longitudinal osteon, which consists of dark lamellae, is made of 12 laminae. The fiber inclination angle changes from 82° and −82° six consecutive times. A model of the alternate osteon, which consists of alternating dark and bright lamellae, is made of 36 laminae. The fiber inclination angle increases by 20.5° from −82° to 82° and then decreases by 20.5° from 82° and −82° four consecutive times.

Information included for the present model may not be currently available for all bones that are evaluated. Any information that is needed for the practice of this invention may be obtained by experimentation using methods that are standard in the art. Additionally, methods that may be used to evaluate bone in one species may be used to evaluate a similar bone structure in another species. For example, the distribution of dominant collagen bundle directions is available for the shaft of the human long bone but not for other vertebrates nor for the mandible. For any compact bone the distribution of dominant collagen fibril directions can be obtained by applying the method of Boyde et al. (1984).

For cancellous bone the same method can be applied after embedding (soaking and letting dry) the bone in a conventional resin used for the specimens examined under the electron microscope. Such resin should not change the microscopic characteristics (birefringence) of the specimens, so that the image of the collagen bundle and hydroxyapatite needle directions under the polarizing microscope is not altered by artifacts. Examples of such resins include, but are not limited to epoxy. Note that application of the invention to cancellous bone will model lamellae that form trabeculae, as compared with the osteons of compact bone, however trabeculae and osteons can both be modeled in terms of lamellae.

From the above-mentioned mechanical properties of matrix and fibers (e.g., Young's modulus and Poisson's ratio) the same types of mechanical properties for lamellae under various load types (such as tension, compression, shear, and torsion) will be deduced by means of standard fiber-reinforced laminate methods known in the art (see e.g., Jones, 1975; Vinson, 1993; Antman, 1995).

Based on mechanical properties of the lamellae, homogenization theory will allow for the deduction of the osteon, osteon group, and interstitial bone mechanical properties for compact bone and trabecular mechanical properties for cancellous bone. The mathematically computed mechanical properties of lamellae, osteons, osteon groups, interstitial bone, and trabeculae are compared to the experimental results. If the experimental results are not available for the particular bone to which the invention needs to be applied, the properties may be determined using the methods for mechanical testing as described herein. The mechanical properties of lamellae, osteons, osteon groups, interstitial bone, and trabeculae are used as input for the homogenization methods to deduce the mechanical properties of the desired macroscopic bone.

Results are included of a finite element model, which allows for the assessment of the mechanical properties of the sample. The sample dimensions before and after testing allow for the formulation of an equation that describes the deformation from the shape before testing to the shape after testing. The deformation equation allows for the computation of the strain distribution throughout the sample. For example equations see Antman, 1995. The combination of such strain distribution with the experimental diagrams, the known sample structure before testing, and the fracture patterns after testing allow for the computation of the elastic properties through standard finite element methods. Statistical student t-test (Moore and McCabe, 1989) is run across the sample's results to allow for comparison of mechanical properties across the samples and to allow statistical conclusions.

These studies provide the mechanical properties of all the hierarchical orders. Therefore, the mechanical property distribution throughout the bone in terms of the microstructural components is known. The finite element method is applied (see e.g. the software package Abaqus) to compute the bone response to any given force acting on it. Boundary conditions are entered as assumptions into the finite element method. The first step is to create a 3-dimensional mesh (see e.g. Couteau et al., 2000).

The bone overall shape is filled with "elements". These elements are used to represent the osteons present in the bone. For example, a hollow cylindrical portion of an osteon with an inner and diameter of 40 $\mu$m, an outer diameter of 220 $\mu$m, and height of 500 $\mu$m, is filled with about 600,000 elements. Mechanical properties and boundary conditions are the method's input. Boundary conditions express the movements of the boundaries of the various hierarchical structures under loading. For example, dynamic loading evidences bone's viscous behavior. The literature points to mucopolysaccharides or perhaps collagen as the microstructural component responsible for the viscosity. In the structural part of the invention the second type of fibers models the mucopolysaccharides. The fibers of the second type are free to move. Such movement at the interface between the fibers of the second type and the matrix is expressed by a boundary condition (to be determined experimentally). Another example, the behavior of the cement line under loading is the boundary conditions for the osteon and the interstitial bone between which it lies. If the boundary conditions of a specific bone, to which one wants to apply the invention, are not available in the literature; they can be assessed experimentally by applying methods described herein or that are well known in the art. The software application gives as output the strain and stress distributions throughout the bone.

The mechanical properties of compact bone microstructure (lamellae, single osteons, osteon groups, single trabeculae) can all be experimentally found with the following method (other acceptable methods, including non-invasive methods are available in the literature). Human cadaveric bone aged between 20-50 is obtained according to the US regulations. The cadaveric bones are chosen either free of pathology to apply the invention to normal bone or with a specific pathology to apply the invention to a specific pathology. The bone marrow is removed by standard anatomical techniques (Wickramasinghe, 1975). At least 15 samples of any of such structures (lamellae, single osteons, osteon groups, single trabeculae) are isolated from the surrounding bone. The samples have about the same size and shape. The shape is a parallelepiped, a cylinder, or a hollow cylinder (depending on the chosen structure) with lugs (see e.g. FIG. 4c) for mechanical testing. Sample preparation and selection of compact bone microstructure is achieved by the methods of Ascenzi A. et al. (1994, 2000). For example, although any technique can be used, the method of Ascenzi A. et al. (1994) is preferably used to isolate osteons. The preferred form chosen for isolation of osteon samples is a cylindrical shape around the vascular canal. In general, the shape and location of a structural sample are chosen in such a way so that all the properties of the structure are preserved. Mechanical testing of osteon samples (Ascenzi M.-G. et al., 2000) may include, but is not limited to, monotonic and cyclic testing in tension, compression, shear, bending and torsion. The methods conducted as described in Ascenzi A. and Bonucci, 1967; Ascenzi A. and Bonucci, 1968, 1972; Ascenzi A. et al., 1990, 1994; Ascenzi A. et al., 1985, 1997, 1998 have proven themselves successful. The testing is conducted within the elastic range and beyond the elastic range to study fractures. Sample preparation and selection of cancellous bone (single trabecula and trabecular groups) is achieved by any of the methods whose bibliography is listed in Mente, 2000. Each sample is measured (the three dimensions for the parallelepiped; base radius and height for the cylinder base inner and outer radii and height for the hollow cylinder) before and after isolation and before mechanical test. Change in dimensions before and after isolation and before mechanical test shows existence of prestress. The structure of the sample is assessed before or after the mechanical testing (Ascenzi M.-G. et al., 2000). The samples are tested mechanically under physiological conditions, that is wet at 21° C. Since both compact and cancellous bone are viscoelastic, the results of mechanical testing are time-dependent (Sasaki, 2000). Consequently the strain rate and testing frequency need to be prechosen and the computer modeling depends on such choices. The stress-strain experimental curves (either monotonic or cyclic) through the elastic and plastic ranges are evaluated and recorded. After the mechanical test, the bone samples are measured and observed under the optical microscope for fracture patterns.

Figure 13:
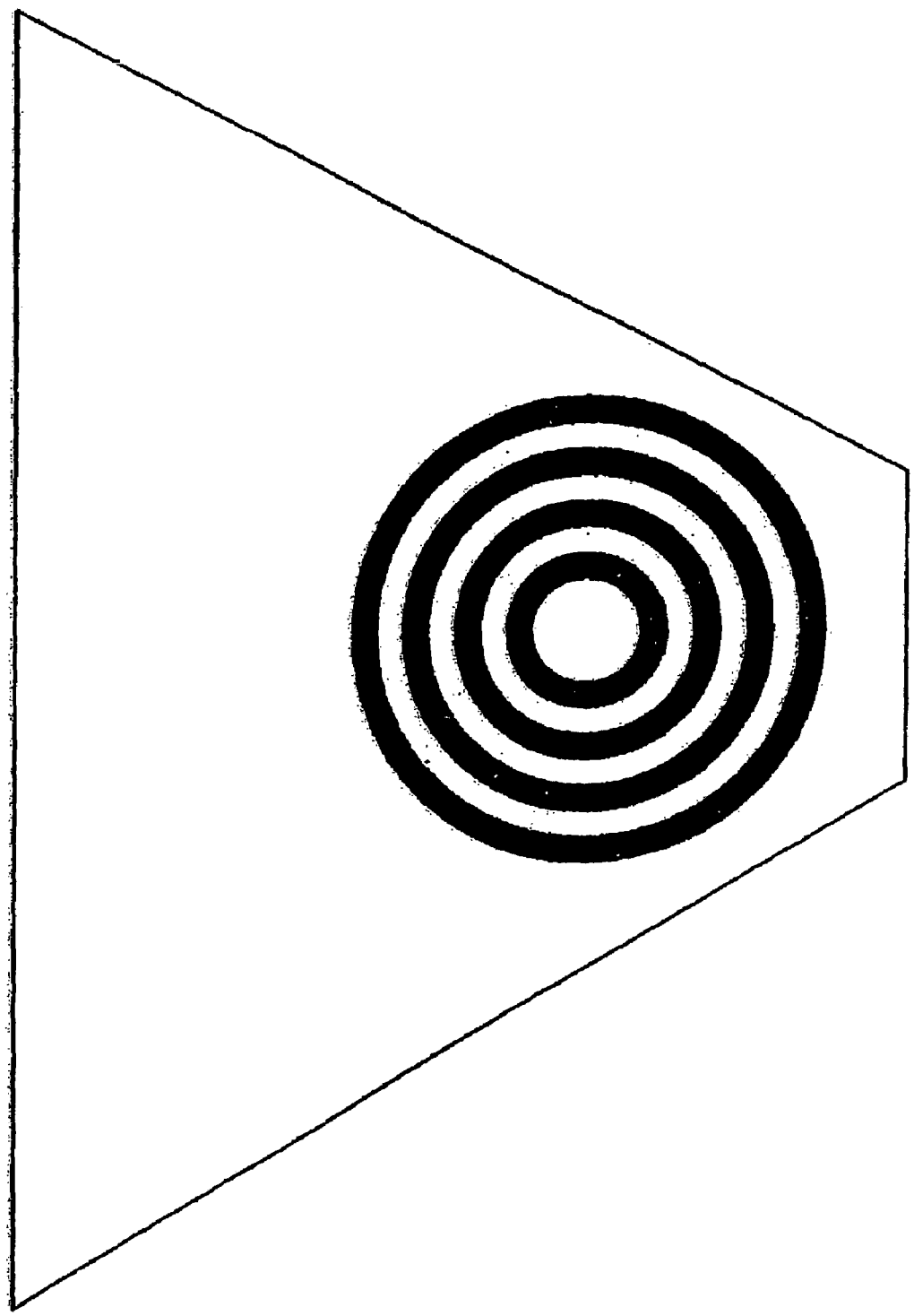
FIG. 13. Shows that around each osteon sample, a trapezoid was cut with a blade under a stereo microscope (from Ascenzi, M.-G, Ascenzi, A., Burghammer, M., Panzavolta, S., Benvenuti, A. and Bigi, A. (2003) Structural differences between "dark" and "bright" isolated human osteonic lamellae. J. Structural Biology, 141, 22-33).
Figure 14:
FIG. 14. Shows that after isolation, each lamellar sample was carefully straightened to a ribbon-like shape (from Ascenzi, A, Benvenuti, A, Bonucci, E. (1982) The tensile Properties of single osteonic lamellae: technical problems and preliminary results. J. Biomechanics, 15(1): 29-37).
Figure 15:
FIG. 15. Represents a larger view of the lamella described in FIG. 14 (from Ascenzi, 1982).
Figure 17:
FIG. 17. Shows collagen bundles of bright lamella under polarized microscope.
Figure 18:
FIG. 18. Shows collagen bundles of bright lamella under polarized microscope.
Figure 19:
FIG. 19. Shows collagen bundles of extinct lamella under polarized microscope. Bundles are parallel to the osteon axis when embedded in bone.
Figure 20A:
FIG. 20 (*a*)-(*h*). Shows isolated and flattened bright lamella under the confocal microscope. From border to center, the collagen bundles go from oblique to vertical (from Ascenzi, M.-G, Ascenzi, A., Burghammer, M., Panzavolta, S., Benvenuti, A. and Bigi, A. (2003) Structural differences between "dark" and "bright" isolated human osteonic lamellae. J. Structural Biology, 141, 22-33).
Figure 20B:
Figure 20C:
Figure 20D:
Figure 20E:
Figure 20F:
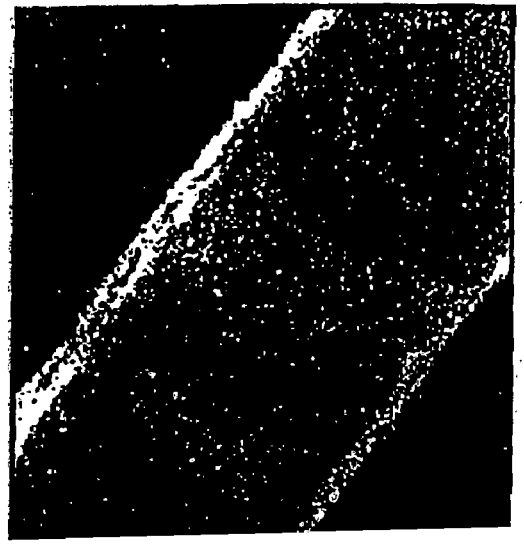
Figure 20G:
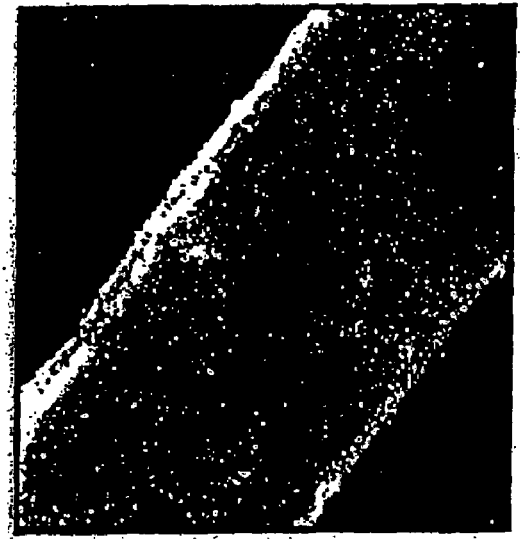
Figure 20H:
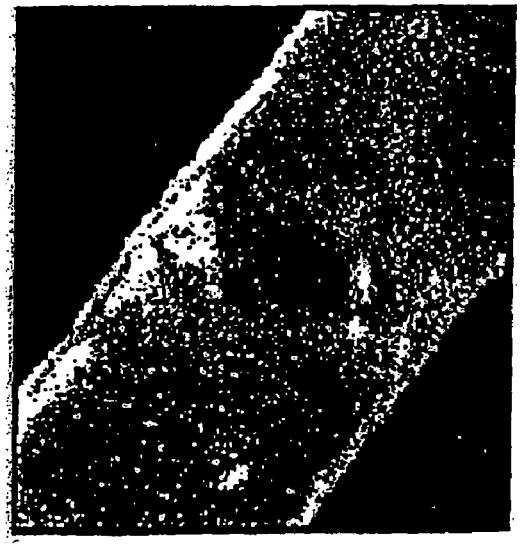
Figure 21A:
FIG. 21 (*a*)-(*g*). Shows isolated and flattened extinct lamella under the confocal microscope. From one border to the other, the collagen bundles are parallel to the osteonal axis (from Ascenzi, 2003).
Figure 21B:
Figure 21C:
Figure 21D:
Figure 21E:
Figure 21F:
Figure 21G:

A trapezoid is cut around each osteon sample (see FIG. 13). For osteon immobilization during lamellar isolation, a portion of the bone material inside the trapezoid around the osteon is glued with Kemi®Cyak adhesive to a slide. The bright and the extinct lamella at the periphery of each osteon are dissected with a razor-sharp microscopic blade, obtained by filing a steel needle. To avoid fracture formation during straightening of each lamellar sample, such operation is performed gently on wet samples while checking under an optical microscope. The selection of external lamellae, of lesser curvature than internal lamellae, decreases the risk of fracture formation during flattening. The ends of each flattened sample are secured to two supports. The samples are measured as previously described and examined under an optical microscope to assess defects.

The mechanical loading on lamella on wet samples is conducted statically at 21° C. to complete rupture, with current model of the microwave extensimeter. Flattened bright lamellar sample is expected to resist tension along its length better than extinct lamellar sample. Indeed, the bright lamella is hypothesized to contain collagen bundles transverse to the longitudinal lamellar axis when enclosed in bone. Therefore, the enclosed lamella's transverse bundles strengthen the flattened lamellar sample in the direction of its length. The extinct lamella is hypothesized to contain collagen bundles parallel to the longitudinal lamellar axis when enclosed in bone. Hence, the enclosed lamella's longitudinal bundles after flattening are a source of sample weakness in the direction of its length because they are transverse to the loading direction. Fracture patterns of ruptured samples are studied under an optical microscope. Observation of fractures in ruptured samples will allow formulation of hypotheses on fracture nucleation and growth.

Since the interest is to test the isolated and flatten lamellar samples mechanically, the stresses present in the flatten lamellar samples before testing are assessed. To compute the stresses in the wet flattened lamellar samples, a computerized geometric-material model of a bright wet lamellar sample and of an extinct wet lamellar sample will be constructed, separately before and after isolation and flattening. The bright lamella includes prestress. It is hypothesized that the the stresses in the flat bright lamella are larger than the ones in the extinct lamella. Additionally, by taking into account that the periosteous is prestressed in tension, it may very well be that the outer circumferential system is prestressed in tension, too.

The geometry of the model is based on (1) dimensions (inner and outer radii, height, and dimension variations) of wet lamellar samples before isolation from surrounding alternate osteon and after isolation and flattening (width and length, and dimension variations) and (2) structure of lamellar sample. Therefore, dimensional measurements are needed. The structure model also is based on the lamellar structural components' arrangement. Therefore, lamellar structure under a confocal microscope will be assessed.

EXAMPLE 2

A. Sample Preparation, Measurements, and Experimentation

Figure 4A:
FIG. 4(a)-(c). (a) Cross section of an isolated longitudinal osteon, magnified 270 times. (b) Cross section of an isolated alternate osteon, magnified 270 times. (c) An isolated osteonic sample with lugs, magnified 20 times. Lugs are used to grab the sample during mechanical testing. Dimensions: inner diameter 52 µm, outer diameter 225 µm, length 500 µm.
Figure 4B:
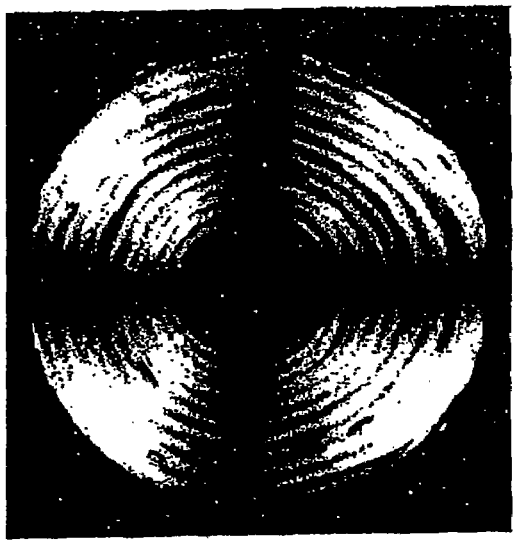

Sample preparation and selection in this example will be achieved by applying the Ascenzi A. et al. (1994) methodology. Accurate sample preparation is important, and the Ascenzi method is preferred. The femoral shafts of human corpses free from evident skeletal faults will provide the bone material for the study. Longitudinal shaft segments about 30 mm long will be first sawn off, and longitudinal sections slightly thicker than an osteon (350 µm) will then be prepared using a Leitz rotating-saw microtome. A continuous water-spout will be incorporated to prevent any overheating of the material. Osteon samples will then be isolated from the sections. The features determining sample selection will be the degree of calcification and the orientation of the collagen bundles and crystallites. Microradiographic examination, preferably according to Amprino and Engström (1952), will allow the selection of fully calcified osteon samples. Two types of osteons will be selected. They correspond to two different collagen bundle patterns in fiber orientation in successive lamellae. Under the polarizing microscope, one type, the longitudinal osteon, has a predominantly dark appearance in cross section (FIG. 4a); whereas the other type, the alternate osteon, reveals alternately bright and dark lamellae (FIG. 4b).

When bone sections are cut longitudinally, the two osteon types are easy to recognize provided that the thickness of the sections is much less than the diameter of an osteon. Longitudinal osteons appear to be almost uniformly bright under the polarizing microscope, while alternate osteons show alternatively bright and dark lamellae. When the thickness of the bone section differs little from the mean diameter of the osteon, concentric lamellae overlap, thereby reducing or precluding the visibility of dark lamellae, and leaving open the possibility that an alternate osteon may have a bright appearance. As a result, identification only becomes certain once a cross section has been cut from the osteon using a microscopic drill (Ascenzi A. et al., 1994). Hence, cyclic loading must be performed before undertaking positive identification of the osteon type.

With reference to the position and orientation of the haversian canal, it is necessary that the canal lie midway between the surface of the cylindrical sample and parallel to it, so that torsion is applied around the osteon axis. This calls for the preliminary separation of the osteon sample, e.g. by application of a technique described below. This technique allows the position and orientation of the canal to be calculated by measuring its distance from the outer surface of the sample at various levels and rotational angles.

The samples are isolated in two stages. During the first stage the sample, consisting of the central portion of an osteon, 500 µm in length, with the ends penetrating into two rectangular lugs, is separated from the bone section using a device as described in Ascenzi A. and Bonucci (1968) and Ascenzi A. (1990). As isolation of the central portion of the osteon is achieved by drilling, its section has a coarse, square shape. During the second stage, a micro-grinding lathe is used to give the central portion a cylindrical form, with the haversian canal running through it axially. The lathe to be used was designed and developed by the CECOM Company and is described by Ascenzi A. et al. (1994). The device grinds the sample by a minute steel blade whose edge, 500 µm long, is equal to the length of a coarsely isolated sample. The forward and backward movements of the blade are monitored by a micrometer. The length and other dimensions of the various samples were kept virtually constant; one criterion for the choice of the samples is that their haversian canal measures 40±3 µm in diameter. Additionally, a stopper controls the forward and backward movement of the steel blade on the micro-grinding lathe to provide a series of samples whose external diameter equals 210±3 µm. This provides a precise comparison of samples' torsional properties (Ascenzi A. et al., 1990). Osteons are not uniform in dimensions. With the dimensions carefully controlled and standardized to exclude defects and other structures, the material rather than structural properties are determined for the osteons. This information can then be applied to osteonal structures of varying dimensions under the assumption of homogeneity at the level of the osteon rather than for the macroscopic specimen.

The relative dimensions of the osteon samples may not appear to conform to those conventionally suggested for material testing. They reflect conditions made necessary by the distinctive nature of bone microstructure. In particular, 500 µm is the maximum length compatible with the avoidance of Volkmann's canals in the wall of the specimen. An external diameter of 210 µm is the maximum dimension possible that ensures that portions of the neighboring structures are not included in the sample as a result of irregularities in the thickness of an osteon. The internal diameter of fully calcified osteons averages 40 µm.

Figure 4C:
Figure 5:
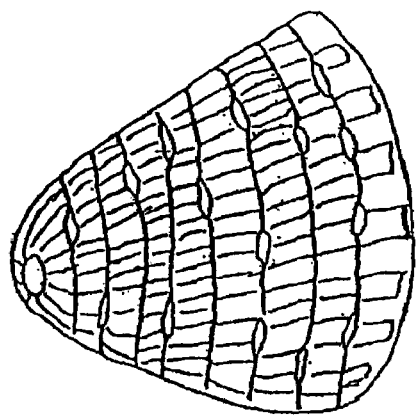
FIG. 5. Cross-section diagram of an osteon sample illustrating the arrangement of canaliculae and lacunae relative to lamellae.

FIG. 4c shows a completely isolated osteon sample held within rectangular lugs. The lugs allow the sample to be firmly attached to the device while hysteretic loops are recorded. The central portion of each sample will be only 500 µm long; consequently, the sample will not include Volkmann's canals which would behave as discontinuities. In addition, the osteon sample selection criteria includes that the vascular canal should run strictly parallel to and equidistant from the surface of the cylindrical sample and that there should not be small surface defects. The canal's position and orientation are assessed by checking the distance between vascular canal and external surface of sample at various rotational angles and levels. To exclude the presence of small surface defects that could alter the shear modulus values in torsional testing, each sample is subjected to careful optical microscope examination. Severe criteria are set for osteon sample selection. Osteon types can only be identified from a prepared cross section only after a sample has been tested. This means that to obtain 60 samples divided between those containing longitudinal and alternate osteons, which satisfactorily complete the procedures adopted for the recording of the hysteretic loops under torsion, it will be necessary to prepare between 800 and 1,000 samples.

Figure 10:
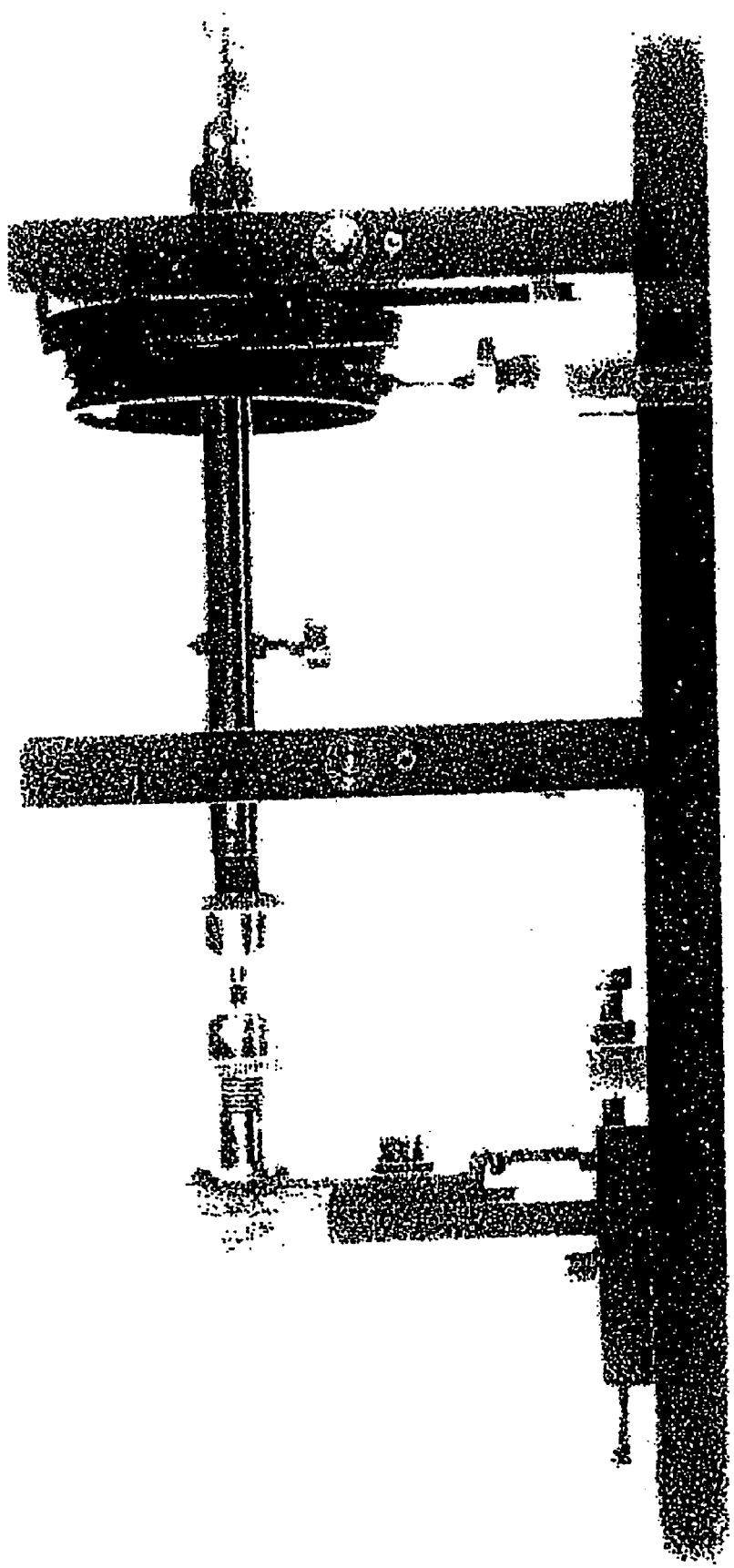
FIG. 10. Shows a device for subjecting bone to torsional cyclical loading (from Ascenzi, A, Baschieri, P. Benvenuti, A. (1994) The torsional properties of single selected osteons. J. Biomechanics, 27(7): 875-884).
Figure 11:
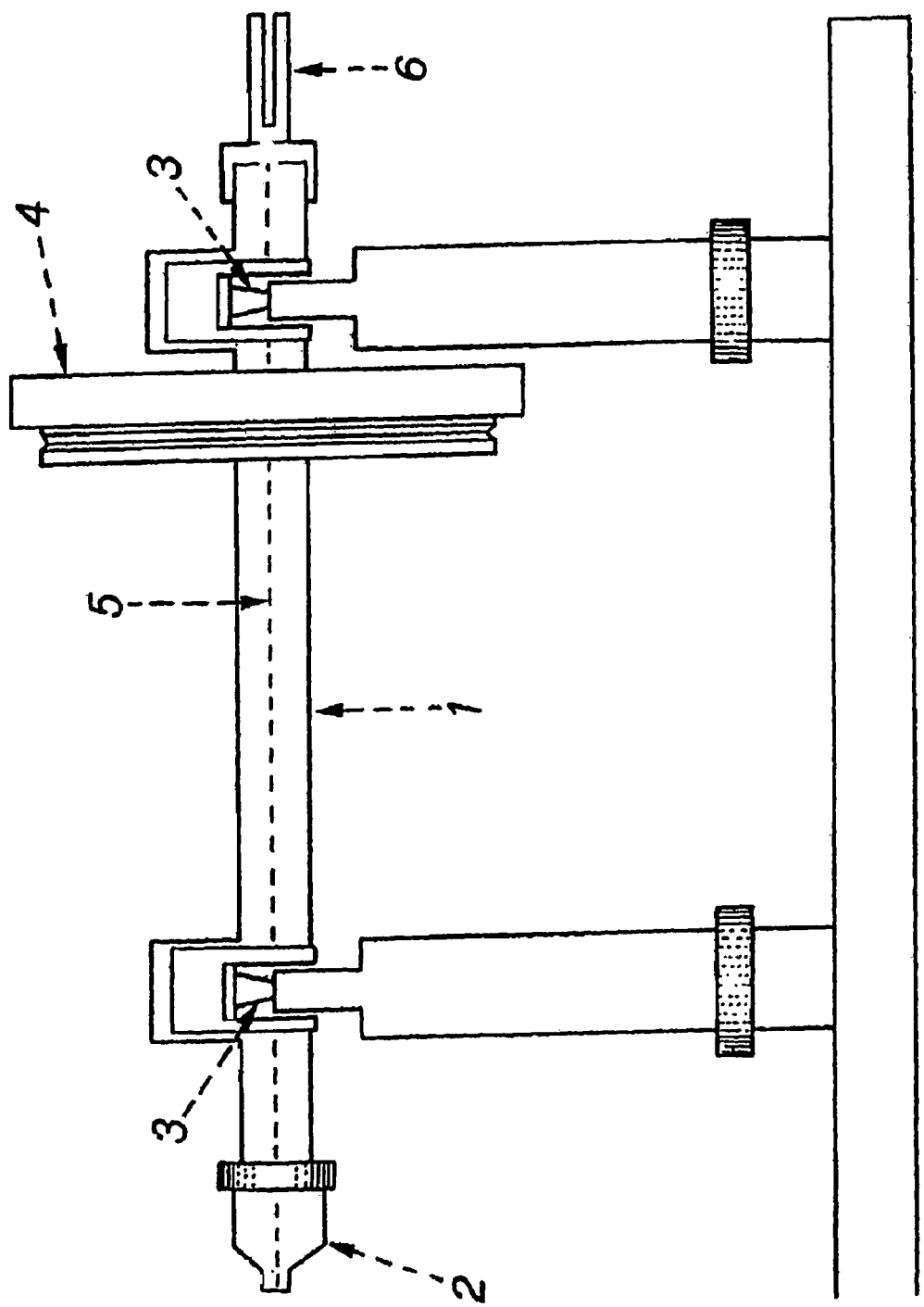
FIG. 11. Is a schematic diagram of a device for subjecting bone to torsional cyclical loading, where (1) is a rotational axis with jaws; (2) and (3) are hard metal wedges of a pendulum loading system; (4) is a wheel around which a tungsten thread loaded with weights is attached; (5) is the axis of the pendulum; and (6) is a mirror (from Ascenzi, 1994).

The apparatus is an adaptation of the device for testing osteons under torsion to failure described in Ascenzi A. et al., 1994), and further described in FIGS. 10 and 11. This device consists of a rotational axis, point (1) in FIG. 11, with two sets of jaws, point (2) in FIG. 11, which grip the specimen during testing. The jaws are oriented along the same axis but none of them are free to move axially. This sets up an axial loading effect, which could influence absolute measurements but may be neglected when, as in this investigation, comparative measurements are considered.

One set of jaws is fixed, while the other turns in synchrony with a wheel, point (4) in FIG. 11, measuring 61 mm in diameter. In order to minimize the rotating friction of the turning jaw, a pendulum loading system is adopted. The axis of the pendulum loading system is indicated as point (5) in FIG. 11. The frictionless fulcrum of the pendulum loading system is the tip of a hard metal wedge, point (3) in FIG. 11.

The maximum oscillation of the pendulum is fixed at 55°. A tungsten thread, whose section measures 20 μm in diameter, winds around the rim of the wheel as a series of 0.1 gram weights is attached incrementally at one end of the tungsten thread. Weights are added one by one until failure occurs for monotonic torsional loading. The load limit is chosen so that the corresponding torque is approximately equal to the middle value between the maximum possible elastic torque and fully plastic torque. Preliminary trials indicate a load limit of 0.9-1.0 gram for fully calcified longitudinal osteons and of 0.8-0.9 gram from fully calcified alternate osteons and of 0.6-0.7 gram for decalcified longitudinal osteons and of 0.5-0.6 gram from decalcified alternate osteons. Once the load limit is reached, the weights will be detached one by one. The procedure will then be repeated at the other end of the tungsten thread. In this way, the osteon specimen rigidly clamped at one end is progressively twisted at the other end by a torque in counterclockwise and clockwise directions alternatively, so as to achieving cyclic loading. The interval between the application of two consecutive weights will be kept constant at 4 sec. A stereoscopic microscope will be used to verify that the axis around which torsion occurs coincides with the osteon axis. The aim of this operation is to check that the center of each jaw corresponds to one end of the osteon sample canal. The angle through which one end of the specimen twists relative to the other during testing is measured by applying an optical method based on the reflection of a laser beam from a small mirror attached to the rotating set of jaws. The variations in the angle of twist are read on a graduated scale placed 160 cm from the device. The precision and accuracy of the graduated scale coincide with those of the apparatus, as checked by applying experimental procedures. Because the diagrams obtained when testing begins in the counterclockwise (or positive) direction should look essentially like the diagrams obtained when testing begins in the clockwise (or negative) direction, all the diagrams will be recorded starting in the counterclockwise direction, according to the standard practice reported in the literature.

The cycles applied to each specimen will vary in number and they will be interrupted before the spontaneous sample rupture. Preliminary specimen testing taken to rupture gives an indication of the angle-of-twist values at rupture and therefore give an indication to stop cycling when angle-of-twist values get close to the preliminary rupture values. The final cycle will therefore be interpreted as the cycle preceding the interruption of the experiment; in consequence, it has no physical meaning. Issues related to osteon fatigue-life will not be part of this study because they require the ultimate destruction of the specimen which would prevent the ability to properly identify the sample after cyclic loading. Interruption of the experiment prior to rupture is necessary because, as previously noted, the osteon type can only be identified with certainty by preparation of a cross-section before rupture, but after testing. Before preparation of the cross-section for identification, samples will be examined under the optical microscope to analyze the nature and size of lesions. Osteon samples are examined under an optical microscope as whole, even though to do so samples need to be removed from the torsion device; such removal can cause structural changes, e.g. partial closure of cracks. The nature of fatigue-damage cannot be verified directly under microscope. In fact, fractures due to cycling and those due to osteon sawing to produce the section are not distinguishable. There is no universally accepted technique available to allow qualitative observation of fatigue-damage. The only experimental alternative is x-ray diffraction, which provides only quantitative indication of fatigue-damage (Ascenzi A. et al., 1998).

Of 60 osteon samples, 7 longitudinal and 7 alternate osteon samples will be decalcified by treatment in a versene solution buffered to pH 7 (Ascenzi A. et al., 1967). Measuring the increase in birefringence at regular intervals of time will check the decalcification (Ascenzi A. and Bonucci, 1964). After hydration of the material with saline solution, 20 longitudinal and 20 alternate fully calcified osteon samples, and the 7 longitudinal and 7 alternate decalcified osteon samples will be tested wet as described above. The remaining 6 osteons will be tested on the first and second cycles only and their dimensions will be measured (by means of a micrometer under an optical microscope) after cycling and before the sectional cutting for osteon type determination. The mechanical testing will be conducted at 20° C. The specimens will be maintained wet during testing by continuous use of a micropipette.

Upon completion of the experimental portion of the research, hysteretic values of torque vs. angle of twist will be plotted for each osteon sample.

The proposed mechanical testing is performed quasi-statically so rate dependencies not expected in the material response. To confirm this, a series of twist and hold experiments will be performed as a preliminary test to see if significant strain relaxation (creep) occurs in the time frame that it takes to complete an experimental cycle. The presence of creep would manifest itself by maintenance of the shape of the curve but with a clear translation of the entire hysteresis loop. If creep is not present, the area under the hysteresis loop is the energy absorption. If creep is present, it will be accounted for by the addition of viscoelastic terms.

B. Mathematical Analysis of Hysteretic Curves

To establish analogies and differences among plots, the characteristics of torque vs. angle of twist plots are quantified by means of a polynomial approximation for each half-cycle. (Shiga et al., 1970; Ascenzi A. et al., 1997).

Measurements and Plots (a) Least-square regression will be applied to the data for each half-cycle to identify the best polynomial approximation of at least second order. The degree cannot be 1 because the half-cycle involves the inelastic range which is characteristically nonlinear.

(b) The goodness of the approximation will be determined through analysis of the residuals and computation of the percent variation in torque explained by the regression. A lower bound for r2 is set to 0.98. The degree of the polynomial approximation at (a) will be increased in a stepwise fashion until a good-approximation is found for all half-cycles.

(c) Let n be the smallest integer for which there is a good-approximating polynomial for all half-cycles. Let the polynomial equation be $y(x)=\Sigma a_i x^i$. Note that such an equation does not include symbolism that denotes the half-cycle; this is done to add clarity and does not lead to confusion. A literature search suggests that n might equal 3 or 4 (Shiga et al., 1970 and Ascenzi et al., 1997a). Each coefficient $a_i$ for any given cycle will be plotted with respect to the maximum angle-of-twist on that cycle, for negative and positive torque half-cycles separately for each osteon type, to visualize the value's variation as the number of cycles increases.

(d) The first derivative of the polynomial, $y'(x)=\Sigma i a_i x^{(i-1)}$, will be taken to represent the stiffness of each individual half cycle.

(e) Compute relative extrema of $y'(x)$ on each half-cycle. Because of increasing structural damage, stiffness is generally either always decreasing on both negative and positive torque half-cycles or it shows a sharp change from decreasing to increasing only once on each half-cycle. Therefore, y'(x) should show no relative maximum and a marked relative minimum. If such relative minimum exists, the graph of y(x) shows an inflection point, i.e. pinching is present. Let $h_m$ and $k_m$ denote twist and torque values at the stiffness relative minimum of the half-cycle. In these notations, $y'(h_m)$ denotes the minimum value of stiffness.

(f) Compute $y'(x_b)$ and $y'(x_e)$, the stiffness at the begin and at the end of each cycle.

(g) Compute the absolute maximum of the function $|y''(x)|/(1+(y'(x))2)3/2$ on any given half-cycle. This is the maximum curvature per half-cycle and will be denoted by mc.

(h) Compute the difference between the integral of y(x) over the first half-cycle and the integral of y(x) over the second half-cycle. Such value approximates the area of the region bounded by the first cycle. This is the energy absorption during the first cycle and will be denoted el.

Differences in hysteretic behavior between longitudinal and alternate osteons will be established by studying the distributions of maximum twist, $h_m$, $k_m$, $y'(h_m)$, $y'(x_b)-y'(x_e)$, $m_c$, and el computed above. The statistical t-test, paired or unpaired, will be applied on means of distribution or on the mean of the distribution's $logarith_m$ if the distribution is not normal.

The mean of the differences of twist limits between the last and first cycle obtained from the experimental diagram will be computed. It will be compared between negative and positive torque half-cycles for longitudinal and for alternate osteons, separately. The magnitude of such value should be smaller for longitudinal osteons than alternating osteons because longitudinal osteons resist torsion better than alternate osteons.

The signs of $h_m$ (and $k_m$, respectively) at the first and last cycle will be analyzed. $h_m$ (and $k_m$, respectively) should have the same sign for the two osteon type separately, up to possibly a few samples. This would indicate that the twist at minimum stiffness should not change much at all within all negative and positive torque half-cycles separately, for both osteon types. This would be in agreement with the tight and well organized osteon structure.

A paired two-sample t-test will be applied to the means of the values of $h_m$ (and $k_m$, respectively) at each of the cycles in any given set of corresponding cycles of the two osteon types. This compares the values of minimum twist (and torque, respectively) for negative and positive torque half-cycles.

A paired two-sample t-test will be applied to the means of $y'(h_m)$ and the coefficients of y'(x) for the two osteon types, separately at each of the cycles in any given set of corresponding cycles of hysteretic diagrams. This compares the minimum value of the stiffness between the negative and positive torque half-cycles.

An unpaired two-sample t-test will be applied to the means of $h_m$ (and $k_m$, respectively) for the two osteon types at each of the cycles in any given set of corresponding cycles of hysteretic diagrams. This will compare the values of twist (and torque, respectively) at the inflection point for the two osteon types.

A unpaired two-sample t-test will be applied to the means of $y'(h_b)-y'(h_e)$ for the two osteon types at each of the cycles. This will compare the stiffness decrease within a given cycle between the two osteon types.

A paired t-test will be used on the mean of the difference of $m_c$ for negative and positive torque half-cycles at each of the cycles in any given set of corresponding cycles of hysteretic diagrams. This will compare the maximum value of the curvature of the stress-twist diagram between negative and positive torque half-cycles, for the two osteon types, separately. The maximum value of curvature of the torque-twist diagram is expected to be larger on the positive than negative torque half-cycle for longitudinal osteons; whereas, the maximum values of the curvature of the torque-twist diagram under negative and positive torque half-cycle for alternate osteons should show no difference. As a consequence of the reduced stiffness the energy absorption should be larger for longitudinal than for alternate osteons.

A paired t-test will be used on the difference of the means of each coefficient $a_i$ of y' at last and first cycles, on both negative and positive torque half-cycles, separately. For both osteon types, the value of y' is expected to decrease from the first to the last cycle on both negative and positive torque half-cycles for any value of the twist x. This test will measure stiffness degradation here defined as the decreasing of stiffness at any given twist value on either a negative or positive torque half-cycle as the number of cycles increases.

The existence of the value $h_m$ shows the S-shape of the half-cycles that identifies pinching. Pinching is expected to be present for each cycle for both types of osteon. If pinching is present, pinching degradation will be computed.

A paired two-sample t-test will be applied to the means of $y'(h_m)$ for the two half-cycles of any given cycle. This compares pinching degradation for the two osteon types separately. Pinching degradation at any cycle is the reduction in stiffness from its value at the deflection point of the negative torque half-cycle to a lesser value at the deflection point of the positive torque half-cycle.

An unpaired two-sample t-test on the means of the value of minimum stiffness $y'(h_m)$ for longitudinal and alternate osteons at any given half cycle. This compares pinching degradation between the two osteon types.

An unpaired two-sample t-test will be applied to the means of el for longitudinal and alternate osteons. This compares energy absorption between the two osteon types at each of the cycles in any given set of corresponding cycles of hysteretic diagrams.

The mechanical meaning of some of the parameters used in the above analysis of experimental diagrams (e.g. stiffness, energy absorption) will be made clear as such parameters will be correlated to ultrastructural behavior during fracture propagation in the model described at section IV. Up to this point they are comparative measures of behavior between longitudinal and alternate osteons under torsional loading.

C. Interpretation

A structural and biological interpretation of the shape of torsional hysteretic loops in osteons through the results of the previous steps uses a segment representation of each cycle of the curvilinear recorded diagram.

If, as it is anticipated, pinching exists, the bilinear model of FIG. 12 is appropriate. Here points B and E approximate endpoints of the negative torque half-cycle, while points E and H approximate endpoints of the positive torque half-cycle; segments DC and FG approximate tangent lines to the curves at the inflection points. The three segments modeling the twist decreasing branch show that stiffness decreases (along segments BC and CU) to a minimum value and then increases (along segments UD and DE). Similarly, the three segments modeling the positive torque half-cycle show that stiffness decreases (along segments EF and FL) to a minimum value and then increases (along segments LG and GH).

The slope of segment DC on the negative (FG on the positive, respectively) torque side of the bilinear model is smaller than both the slopes of segments ED and CB (EF and GH, respectively) and therefore responsible for a contraction of the cycle that constitutes pinching. The existence of pinching resides in the torque-angle-of-twist branch AB of the primary curve, where lesions appear as a result of yielding of components of the bone matrix under load as the angle-of twist increases to the right. Reversal of loading is required to close the lesions; this will occur once the minimum angle-of-twist of the unloading portion BC of the curve is exceeded. Once point C is passed, stiffness, as negative torque is decreasing, shows a progressive, slight, unsteady increase to point D. The lesions are then repaired and stiffness rises steadily to point E.

The opposite will occur at the diagram portions marked EF, FG, and GH. After passing the minimum angle-of-twist of the unloading portion (EF), progressive resolution of the damaged structural components will occur, leading to a slight, unsteady increase in stiffness as negative torque increases (FG). After point G, stiffness will increase steadily to point H, as negative torque increases. In particular, pinching would correspond to segment CD on the negative torque side, where repair of the lesions occurs, and to segment FG on the positive torque side, where resolution of the lesions occurs. This explanation, in which lesions form on the negative torque half-cycle and reinforcements yield on the positive torque half-cycle, does not take into account buckling. If buckling occurs, the situation is reversed: lesions form on the positive torque half-cycle and reinforcements yield on the negative torque half-cycle.

If pinching does not exist, there is no contraction along the cycle. In this case, the slope of segment DC on the negative (FG on the positive, respectively) torque side of the model lies in between the values of the slopes of ED and CB (EF and GH, respectively), as depicted in FIG. 12b. The slope of the segments modeling the cycle shows that stiffness decreases along all of them; which might mean that lesions do not repair and do not resolve as they would with pinching. In this scenario it is reasonable to assume that torsional loading creates lesions distributed in a more disorderly fashion in the osteon than in tensile-compressive loading (aligned with longitudinal bundles and where pinching is present). Before load reversal, the hydroxyapatite crystallites might have detached and cracked in a way that the original alignment is destroyed. In this case a partial realignment does not occur later along the first half-cycle as to bring an increase in stiffness. Consequently, there are no lesions to resolve during the successive half-cycle and stiffness would keep decreasing. This explanation, in which lesions form on the negative torque half-cycle and reinforcements yield on the positive torque half-cycle, does not take into account buckling. If buckling occurs, the situation is reversed. Before load reversal, collagen bundles might yield in a way that loses track of the original alignment. Similarly this does not allow even a partial realignment to take place later along the first half-cycle, after lesions involving the cracking of hydroxyapatite have occurred, so as to increase stiffness. Consequently, no partial alignment of bundles could be restored before bundles start yielding during the successive half-cycle and stiffness would keep decreasing. Such interpretation, where lack of hydroxyapatite crystallite alignment is greater under torsional cyclic loading than tension-compression cyclic loading, could be verified additionally by means of X-ray diffraction (Ascenzi A. et al., 1998).

Figure 12A:
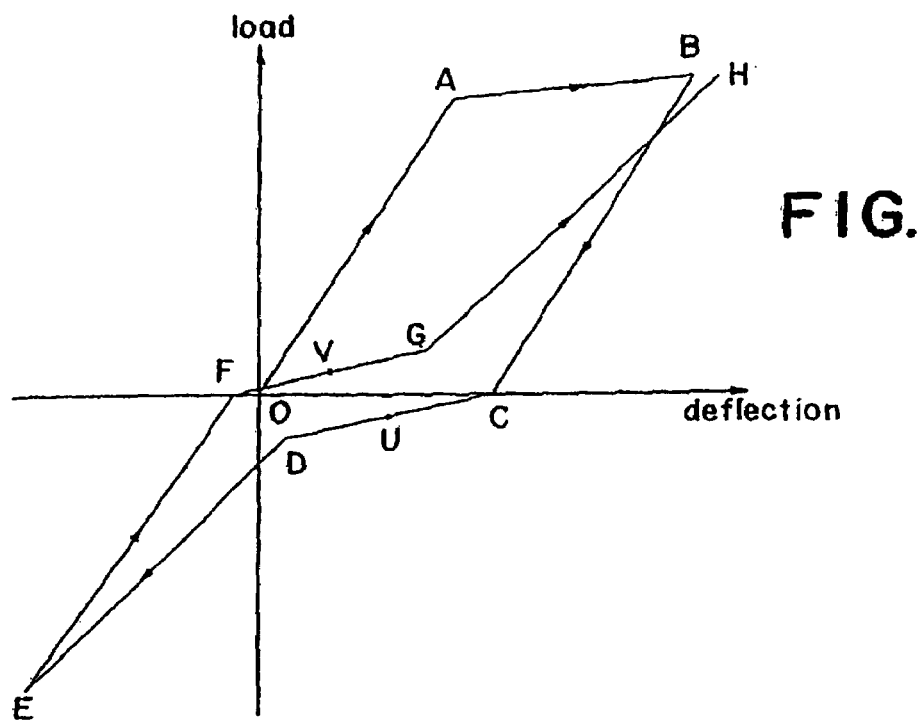
FIG. 12A is an idealized bilinear hysteresis model of curve prior to cycling and a first cycling loop where pinching is present.
Figure 12B:
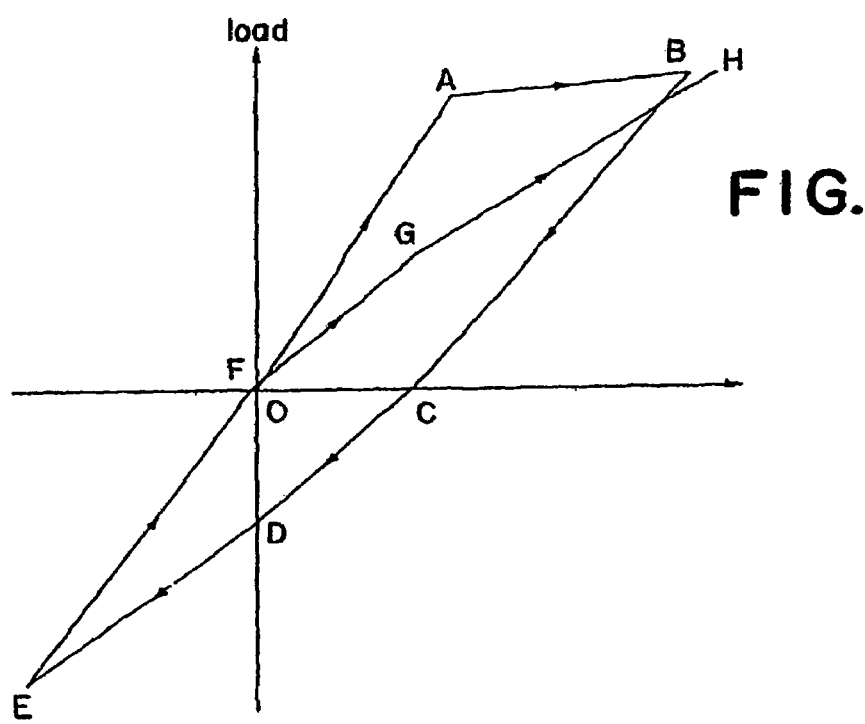
FIG. 12B is an idealized bilinear hysteresis model of curve prior to cycling and a first cycling loop where pinching is not present.

The results of the measurements and plots above will give the positions and inclinations of the segments in FIG. 12. For instance, the t-test on the means of $k_m$ along the first half-cycle for longitudinal and alternate osteons is expected to indicate that $k_m$ is significantly higher for alternate osteon. This means that point U in FIG. 12a is higher for alternate osteons, that is, cracks close and stiffness switches start increasing for a smaller torque value. This is consistent with the more complex structure of alternate osteons.

D. Fracture Model

The purpose of the fracture model is to show that cumulative micro-cracking, de-bonding, void growth and fiber breakage associated with repeated loading of osteons causes a progressive loss of stiffness and pinching, and increase of energy absorption. The lesions observed under an optical microscope in osteon samples subjected to cyclic torsional loading will serve to develop osteon models and to formulate biological hypotheses on propagation of fractures. The fracture model will be based on:

hypotheses on ultrastructural components' behavior under cyclic torsional loading formulated from the experimental hysteretic plots;

ultrastructural components' mechanical properties;

fractures observed in osteons during monotonic torsional loading; and fractures observed in macroscopic bone specimens.

This aspect of the model is an adaptation and extension of the approach of Gupta and Bergstrom (1998). The fracture propagation model is a micromechanical bone model that allows prediction of the progressive growth of faulting zones, by considering the increased stress experienced in the vicinity of an already highly cracked region. The nucleation of initial damage is determined by the assessment of the points more susceptible to fracture. The progressive growth of the fault nucleus is considered in a statistical manner by the use of stress enhancement factors, which address the increased probability of failure in the vicinity of regions that are already cracked.

The geometric model of each of the longitudinal and alternate osteon samples before mechanical testing consists of a hollow cylinder with coaxial lateral surfaces. Its internal diameter, external diameter, and height equal 40 μm, 210 μm, and 500 μm, respectively. Each such hollow cylinder presents voids, and about 20% of each such hollow cylinder consists of voids (Piekarski, 1970) which model canaliculae and lacunae.

The material model of each of the longitudinal and alternate osteon samples before mechanical testing consists of a laminate whose length, width, and height correspond to cylindrical shell circumference, thickness, and height, respectively (FIG. 9a). The layers are unidirectional fiber-reinforced laminae (FIG. 9b) of the same matrix and fibers. The matrix and fibers are each treated as homogeneous and isotropic. The fibers are assumed to be circular in cross-section with a diameter of 800 Å, randomly distributed in the transverse plane and perfectly embedded in matrix. The lamina with fiber inclination γ is named γ-lamina. The elastic properties of matrix and fibers model the elastic properties of hydroxyapatite (Katz and Ukraincik, 1971) and collagen (Currey, 1969). The matrix occupies 40% of the lamina volume without voids (Bonfield and Li, 1967). The matrix (fiber, respectively) volume decreases (increases, respectively) slightly from inner to outer lamina (Amprino and Engstrom, 1952; Rho et al., 1999).

The longitudinal osteon model consists of 9 longitudinal lamellae of the same thickness. Longitudinal lamellae are modeled by alternating +82-laminae and −82-laminae (Frasca et al., 1977). The alternate osteon model consists of 7 transverse lamellae with 5 longitudinal lamellae layered between them (Giraude-Gille, 1988). The transverse lamella is modeled by the laminar sequence [−61.5, −41, −20.5, 0, 20.5, 41, 61.5] (Ascenzi M.-G., 1999b). This sequence is subjected to prestress as described in Ascenzi M.-G., 1998a and 1999b. A longitudinal lamellar model is 9.45 μm thick and a transverse lamellar model is 5.40 μm thick (e.g. Gebhardt, 1906; Ziv et al., 1996). The matrix volume is 10% higher in the longitudinal lamellar model than it is in the the transverse lamellar model (Marotti et al., 1994).

E. Bone Structure Simulation

To model fracture propagation in osteons, each of the longitudinal and alternate osteon models is divided into a discrete number of elements, e.g. 618,317. The element mesh will be refined to achieve a convergent solution. A computer simulation program, such as a Monte Carlo simulation, will be used to do the following tasks.

1. For any given value of torque applied to experimental samples, the distribution of stress in the osteon model is computed. Such computation will take into account voids.
2. Such stress distribution will be added to the distribution of prestress.
3. The strain associated to the resulting stress will be computed on each phase within each element.
4. From the strain associated to the resulting stress, the overall deformation of the hollow cylindrical shell will be computed.
5. From the strain in each phase within each element, the phase deformation will be computed.
6. The strain in each phase within each element is compared to the yield strain.
7. The strain is chosen as the criterion for osteon failure (Piekarski, 1970). The maximum strain, called critical strain, after which fracture occurs within each phase is provided by the literature. Perfect bonding at the interface between phases is assumed unless experimentally observed cracks appear to initiate at this interface. If that is the case, a failure criterion (e.g. Von Mises) will be included.
8. The elastic properties of fractured phases will be computed by means of formulas of the type $E_i=E_e/(1+(1+v_e)(k_e\lambda)/2)$ (Gupta and Bergstrom, 1998).
9. The element is declared broken if all phases in that element have failed.
10. The elements are assumed to be aligned in independent rows such that the problem of fracture propagation becomes one dimensional.
11. To model the progressive growth of damage, the torque will be increased incrementally, and using the fracture criterion above, the number of failure elements will be established.
12. The increased probability of fracture in the neighborhood of an already fractured element will be considered using the concept of stress enhancement factors.
13. If all elements on one row are broken, the strain level at which all elements on one row are broken is taken as the failure strain for that row. The process is repeated for each row in the model. Once the maximum torque is reached, the program stops.
14. At this point, the simulation of fracture propagation before the first hysteretic half-cycle is completed.
15. The program incrementally applies a clockwise torque decreasingly to the maximum torque applied experimentally to samples, and at each increment it repeats steps 2 and 3 above, so as to complete the failure simulation during the first half-cycle of the first cycle.
16. Step 15 is repeated for the corresponding counterclockwise torque so as to complete the fracture simulation during the second half cycle of the first cycle.
17. The fractures obtained according to the model should be comparable with those observed in osteon samples submitted to one cycle only.
18. The fracture simulation sequence is repeated through the last cycle.
19. Fracture simulation is repeated further, as desired. Fractures obtained in this way, according to the model, should be compatible with those observed in cycled osteon samples at the last cycle.

F. Results

Entities computed from the experimental hysteretic diagrams, such as stiffness degradation, pinching degradation and increase in energy absorption, up to the second cycle, correlate with the fracture propagation of the fracture model.

The same geometric/material models and computer program will be used to simulate fracture propagation under tension, compression, and shear, separately. The resulting fractures will match the fractures observed in osteon propagation under tension, compression, and shear respectively (Ascenzi A. and Bonucci, 1967 and 1968; Ascenzi A. et al., 1972).

Predictions and phenomena simulated according to the model of the invention include that in both osteon types, a fracture starts at a weaker point of the bone structure (Carter et al., 1981), at the weak interfaces between two outer lamellae (e.g. Piekarski, 1970), presumably because of the hydroxyapatite decrease in osteons from vascular canal to outer wall (Rho et al., 1999).

In longitudinal osteons, the fracture starts somewhat longitudinally, between collagen bundles. It then deviates once or twice at the beginning of the fracture and is soon followed by a smooth crack advancing rapidly across the osteon to possibly end in the vascular canal. As cycling continues, collagen bundles between cracks break, and cracks join to create one or more long almost vertical cracks.

In alternate osteons, cracks are expected to spread obliquely by following the weak interfaces of lamellae. The transverse and oblique collagen bundles may break before the longitudinal ones as the osteon section enlarges. Cracks spread through lamellae less rapidly than in longitudinal osteons as explained by the crack propagation control, characteristic of composite materials (Cook and Gordon, 1964). Once the crack breaks through transverse and oblique bundles, it will propagate faster straight through the vascular canal. A long crack should show an oblique orientation between upper and lower extremities.

It follows, unexpectedly, that the longitudinal osteon is weaker in longitudinal than in transverse shearing, while expectedly the alternate osteon is weaker in tension than in shear (Ascenzi et al., 1967 and 1972). This is because when a torque is applied to a body, tensile and compressive stresses are produced on the lateral surface and torsional shearing stresses are produced on the cross-section of the body. The tensile and compressive stresses act approximately at a 45° angle to the long axis of the body. The direction of the shearing stress on the cross-section of the body is the same as that of the force producing torsion. If a material is weaker in longitudinal than in transverse shearing, the first cracks arise from axial shearing stresses and appear in a longitudinal direction. However, if the material is weaker in tension than in shear, it usually cracks along a spiral course inclined at a 45° angle to the long axis of the body. The reason for this is that a state of pure shear is equivalent to a state of tension in one direction and of compression in the opposite direction (Timoshenko and Young, 1940). The tension stress produces a spiral crack in the body.

For both osteon types 3 to 4 small cracks form in the hydroxyapatite and collagen, which yields and pulls and/or buckles and makes the cracks spread within lamellae. Microcracks form ahead of the advancing fracture line. Afterwards, during torque reversal, width of cracks and deformation decrease. Collagen may buckle and some resisting strength may appear at zero torque. As cycling continues, cracks extend through the lamellae and join.

The slow propagation of cracks in the areas containing transverse and oblique collagen bundles allows for the area to absorb a large amount of energy. Slow propagation is essentially a pull-out type mechanism, that is, hydroxyapatite crystallites are pulled out of the collagen by shear failure at the fiber-matrix interface. The rapid propagation of cracks in areas containing approximately vertical collagen bundles allows very low energy absorption. This should be compatible with larger areas enclosed by cycles of experimental plots of alternate osteons (see last t-test in Sec. A above).

Hydroxyapatite crystallites are pulled out from collagen around canaliculae.

At low strain rates in compression distortion of the lamellar structures occurs (McElhaney and Byars, 1965).

The propagating crack generally has the tendency to avoid discontinuities (Piekarsly, 1970), hence increasing its length. Discontinuities act as crack arresters by blunting the tip of the crack which enters them.

The fracture model is expected to agree with fractures observed in osteons cycled only for first and second complete cycle. The dimensions of the hollow cylindrical model after one cycle, two cycles, and the last cycle of torsional loading should match the means of the osteon samples' dimensions measured experimentally. Furthermore, the role of the models' fibers is expected to check with the cyclic behavior of decalcified osteons.

The sudden shift of the osteon shape (FIG. 4) from a circular to a square cross-section suggests a stress concentration at the lugs. Therefore, fractures may begin at the end of some samples earlier during loading than would otherwise be expected.

Lamellar thickness and width were measured on 20 bright and 20 extinct peripheral lamellar samples in quintuplicate in dry osteon samples by Delta Sistemi IAS 2000 image analysis system, and again after wetting with a micropipette. This table shows means and standard deviations. Thinner extinct lamellae were used for comparison with bright lamellae. It is known that extinct lamellae are thicker than bright ones, whether dry or wet. The Student t-test is run on the data to determine statistical differences between dry and wet lamellar dimensions.

| Sample | Thickness Dry | Thickness Wet | Width dry | Width wet |
| --- | --- | --- | --- | --- |
| Bright | 3.30 ± 0.88 | 3.56 ± 0.93 | 70.30 ± 9.28 | 72.45 ± 9.58 |
| Extinct | 4.13 ± 1.23 | 4.10 ± 1.10 | 70.30 ± 9.28 | 72.45 ± 9.58 |

Whether dry or wet, bright lamellae are significantly thinner than extinct lamellae when enclosed in alternate osteons (this agrees with previous results, e.g. J. Y. Rho, P. Zioupos, J. D. Currey and G. M. Pharr (1999) Bone 25: 295-300). Additionally, wet and dry conditions affect bright and extinct lamella thickness differently. Bright lamellae are significantly less thick when dry than wet. In contrast, extinct lamellae thickness remains constant whether wet or dry.

The bright lamella thickness increases from dry to wet which may be due to the higher quota of mucopolysaccarides, which expand with water, and to the transverse collagen bundles in the bright lamella tightly encircling extinct lamella, thereby impeding expansion. Height of both bright and extinct lamellae is significantly smaller when dry. In addition, the thickness along lower and upper borders shows variations up to 50-60%. This will be included in the model. Width variation is very low.

The model provides an advantageously simplified simulation or representation of osteon structure. For example, partially calcified collagen bundles are excluded from the model. The model provides a useful and improved description of bone structure and mechanics, even though the shape and dimensions of hydroxyapatite crystallites and the relationship of these parameters to the organic components of the matrix are only partially known. Not all collagen bundles are completely calcified. Those, which are note calcified take up crystallites only on 400 A bands (Ascenzi, A. et al., 1965). Such bundles may be comprised of relative more stiff 400 A bands separated by relatively more flexible decalcified collagen segments. In a preferred embodiment of the invention, partially calcified collagen bundles are not modeled, in favor of modeling fibers in uncalcified collagen bundles. The matrix, which models the hydroxyapatite crystals, lies outside the fibers. Pinching is incorporated into the model is related to the yielding and bucking of fibers, and provides an approximation of the yielding and buckling of partially calcified collagen bundles. In preferred embodiments, fracture propagation is modeled and cracks will tend to propagate before buckling is likely to occur, because the model in most cases assumes that individual fibers are perfectly bonded to and are uniformly supported by the matrix. The model also excludes complex consideration of pore fluids in preferred embodiments which balance relative simplicity with achieving a reliable and accurate bone model.

EXPERIMENTAL DESIGN OF EXAMPLES 3-6

The experiments conducted as described in Examples 3-6 examine the behavior of elementary components of adult human compact bone tissue during dynamic loading of its microstructure. The link between biological composition and mechanical function are investigated through several sets of experiments. For example, one set addresses properties of the ultrastructure, and another addresses the behavior of the microstructure under dynamic torsion.

In particular, these experiments examine secondary osteons to evaluate whether collagen bundle arrangements and degree of calcification indicate or determine the relative percentages of collagen and mucopolysaccharides and characteristics of dynamic loading behavior. "Secondary osteons" are present in adult bone, as opposed to "primary osteons", which are present at earlier stages of development. These experimental data can be used to further create the numerical model for bone viscoelastic behavior according to the invention.

The present invention also provides experimental designs to assemble data for the model of the invention. For example, osteon samples of varying hydroxyapatite crystallite density and collagen bundle arrangements can be mechanically tested under dynamic torsional loading at low and high strain rates. The viscoelastic properties identified can be related to the biochemically obtained relative percentages of collagen and mucopolysaccharides. A computerized geometric-material model, based on the experimental findings and observations of sample fracture, is then created to describe viscoelastic osteon behavior under torsional loading in terms of microcracking, debonding, breakage, and void growth.

The model of the invention is founded on the recognized dependency of bone's macrostructural properties on osteon properties established by osteon ultrastructure (Rauber, 1873; Evans, 1958; Currey, 1959; Evans and Vincentelli, 1969; Vincentelli and Evans, 1971; Portigliatti-Barbos, 1983, 1984, and 1987; Boyde et al., 1984; Ascenzi A. et al., 1987a and 1987b; Katz, and Meunier, 1987; Ascenzi A., 1988; Carando et al., 1989 and 1991; Boyde and Riggs, 1990; Crolet et al., 1993; Hert et al., 1994; Ascenzi M.-G., 1999a). The model is also based on observed mechanical properties of osteons, using methods of the invention, which can neither be inferred from macroscopic samples nor derived by purely mathematical models.

Indeed, some microstructural properties are absent at the macrostructural level and are not susceptible to inference by purely mathematical models (Pidaparti and Burr, 1992). For instance, osteon samples under monotonic torsional loading display a shear modulus larger than that of macroscopic samples. This unanticipated result arises through localized slippage at cement lines in larger macroscopic samples. Also, tension-compression hysteretic loops of osteon samples (Ascenzi A. et al., 1985, 1997) are S-shaped, in contrast to the monotonically increasing behavior of macroscopic specimens. This result was not anticipated due to incomplete knowledge of the ultrastructure as well as the absence of such phenomena in macrostructural samples, possibly due to the mechanical role of cement lines. Close linkage of mathematical models to micromechanical empirical results such as these has led to prediction of lamellar stiffness (Ascenzi M.-G., 1999b) subsequently confirmed empirically (Meunier, 1999; Rho et al., 1999).

Examples 3-6 will elucidate three specific elements towards the long-term goal of understanding how human bone macro-structure responds to function. These elements are as follows.

Viscoelastic Properties of Macroscopic Compact Bone Need Clarification (Sasaki, 2000). Starting in 1965 with Currey, and with Smith and Keiper, viscoelasticity has long been recognized as one of the important properties of bone. However, divergent experimental conditions and parameters impede meaningful comparison of the various time-dependent tensional and compressional studies on macroscopic compact bone samples, e.g. Smith and Keiper, 1965; McElhaney, 1966; Lugassy, 1968; Sammarco, 1971; Black, 1972. Comparison under the hypothesis of linear-viscosity (Lakes and Katz, 1974) found conflicting results and pointed to a macroscopic nonlinear-viscoelastic behavior. This conflict may arise from the lack of consideration of the heterogeneity of the macrosamples' ultrastructural composition, i.e. collagen bundles and hydroxyapatite densities and their arrangements. Time-dependent torsional studies on macroscopic samples show nonlinear-viscoelastic behavior (Lakes and Katz, 1979a, b, c). For osteon groups, Frasca and Katz's studies suggest a decreasing trend of strain values at the onset of plasticity with increasing number of osteons. The authors explain such decreasing trend in terms of mucopolysaccharides, the principal constituent of cement lines. None of the above-mentioned results derives from a systematic study or has been experimentally correlated to the samples' micro- and ultra-structural components. The present work relates the osteon viscoelastic properties to the properties of the ultrastructural components. While the mineral phase behaves purely elastically (Katz and Ukraincik, 1971), collagen and mucopolysaccharides are viscoelastic in nature. The known non-linear viscoelastic properties of collagen are limited to studies from tendon (Haut, 1983). There are no explicit data available on the viscoelastic properties of mucopolysaccharides from bone. According to the invention, the viscoelastic behavior of bone microstructure depends on the viscoelastic behavior of collagen and mucopolysaccharides and the structural organization of collagen bundle directions. Mucopolysaccharides are believed to be bonded to the surfaces of collagen and/or hydroxyapatite crystals and embedded within the ground substance (Herring, 1971; Butler, 1984).

Dynamic Torsional Loading, Used to Evidence the Viscoelastic Properties of the Macrostructure, Serves to Incorporate the Role of Microstructure in Terms of Ultrastructure. Torsional loading in bone has been analyzed using finite element analyses (e.g. Martens et al., 1980; Spears et al., 2001). These models suffer from oversimplifications that posit non-existent structural symmetries and homogeneities. Such assumptions do not reflect the heterogeneity of the micro level. Macroscopic samples do not always have the same mechanical properties as the microstructure that comprises them, and overlooking them impedes a realistic understanding of bone mechanics. For instance, experiments on quasi-static torsional loading of microstructures revealed (Ascenzi A. et al., 1994) that the torsional shear moduli of osteons are much larger than shear moduli obtained for macroscopic samples. That is, slender samples are stiffer than thick ones. Slippage of osteons at the cement lines during torsion of macrosamples may explain the lower stiffness in thick samples. Cosserat elasticity theory (Lakes, 1995) well describes such slippage because it allows a moment per unit area in addition to the usual force per unit area of classic elasticity theory.

Mechanisms for Initiation and Propagation of Viscoelastic Fracture of Macroscopic Bone. Dynamic fracture propagation has not been modeled in terms of ultrastructural components, although the fracture mechanism of bone depends on bone structural and composition properties such as collagen architecture and collagen content (e.g., Jepsen et al., 1999). Jepsen finds that fracture in macroscopic samples is ductile and that fracture alters bone's viscous mechanism; in particular, relaxation increases with the increasing extent of fractures. Consequently, viscous effects in osteon samples can increase with the increasing extent of fracture.

According to the invention, and as described in the Examples, osteon samples show a linear viscoelastic behavior, at least in the physiological strain range, explained by the Ramberg-Osgood equation. Osteons consisting of longitudinal collagen bundles (longitudinal osteons) resist torsional stresses better than osteons consisting of alternatively longitudinal, oblique, and transverse collagen fibers (alternate osteons) regardless of the relative hydroxyapatite crystallites percentage. The viscoelastic effects are less evident in longitudinal than alternate osteons because longitudinal osteons contain relatively less collagen and mucopolysaccharides, two viscosity factors. The viscoelastic effects are more evident in both osteon types at lower rather than higher levels of hydroxyapatite crystallites because lower hydroxyapatite levels correspond to higher mucopolysaccharides levels.

Elementary Components of Secondary Osteons

Knowledge of compact bone microstructure results from a variety of refined techniques and sophisticated mechanical devices focused on the behavior of the complex biological and mechanical interplay of ultrastructural components in the microstructure as a whole (for a review, see Ascenzi M.-G. et al., 2000). Such research has shown, for example, how collagen and hydroxyapatite distribution and density determine the mechanical properties of osteon and lamellar specimens.

The studies described in the Examples relative to the ultrastructure of osteons' lamellae and the viscous behavior of single osteons provide a novel perspective on the link between viscoelasticity and osteon ultrastructural parameters of collagen and hydroxyapatite crystallites. Through these experiments, the viscous behavior of the single osteon is systematically evidenced for the first time in isolated osteon specimens of the same shape and dimensions. The results confirm the non-systematic findings of Frasca et al. (1981) on single osteons of various dimensions.

Various authors, e.g. Katz and Ukraincik (1971) and Frasca et al. (1981), point to collagen and mucopolysaccharides as the components responsible for viscosity, because they are viscous in nature even though the known non-linear viscoelastic properties of collagen are limited to studies from tendon (Haut, 1983). However, up until now, explicit data have not been available on the viscoelastic properties of mucopolysaccharides from bone. Osteonic lamellae show molecular organization of a mostly collagen bundle organic framework and hydroxyapatite crystallites of orientation analogous to that of the collagen bundles. Mucopolysaccharides are embedded in the ground substance and are thought to be bonded to the collagen and/or hydroxyapatite crystal surface (e.g. Herring, 1971; Butler, 1984). When the ground substance is removed from several connective tissues, the time-dependent mechanical effects decrease (Minns et al., 1973). This result further points to the role of collagen and mucopolysaccharides in the viscous behavior of osteons. Further, the relative percentages of mucopolysaccharides and hydroxyapatite in single osteons are indicated to be inversely proportional (Pugliarello et al., 1970). In fact, the mucopolysaccharides need to decrease for the formation of a substrate on which the hydroxyapatite crystallites can deposit and continue to accumulate (Herring, 1971; Sasaki and Yoshikawa, 1993).

The present invention considers lamellar structure in these examples and in examples 1, 2, and 7-14. Thus, the invention addresses the long standing question of whether the histological and radiological differences observed in osteon lamellae are due to differences in fiber orientation (as proposed by Ebner, 1887 and elaborated by Gebhardt, 1906) or composition (as theorized by Ranvier, 1887; Ruth, 1947; Rouillier et al., 1952; Rouillier, 1956). Such theories concern particularly the osteon type consisting of an alternating series of two different lamellar types (so-called alternate osteon). While Gebhardt's theory has for a long time served as a useful model in approaching and clarifying the micromechanical behavior of isolated osteonic specimens, at present Gebhardt's theory is far from universally accepted. The experiments described in the Examples support a combination of the two types of theories. On one hand, these findings support a version of Gebhardt's model, previously supported by various authors e.g. Frasca et al. (1977); Giraud-Guille (1988); Ascenzi A. et al. (1982). That is, dark and bright lamellae differ in collagen bundle and hydroxyapatite crystallites orientation. In particular, lamellae which appear dark in cross-section under polarizing light, contain longitudinal collagen bundles and hydroxyapatite patterns. Lamellae which appear bright in cross-section under polarizing light contain transverse collagen bundles and hydroxyapatite patterns. On the other hand, the same new techniques indicate differences in composition. As described in the Examples, longitudinal collagen bundles lie closer to each other than oblique and transverse collagen bundles, leaving less space between them for the ground substance and therefore mucopolysaccharides. A striking difference is found between the hydroxyapatite pattern orientation within the two lamellar types. Lamellae which appear dark in cross-section under polarizing light are thicker than lamellae appearing bright, confirming the observations of Marotti (1993). Further, wet lamellar thickness varies in relation to collagen bundle orientation and that the different changes in lamellar thickness between dry and wet states point to a difference in mucopolysaccharide percentages and collagen bundle orientation in the two lamellar types.

This shows that the viscoelastic behavior of single osteons depends on the viscosity of collagen and mucopolysaccharides, whose relative percentages depend on collagen bundle directional arrangement and the amount of hydroxyapatite present.

Osteon Specimens

Osteons vary in diameter (200-300 µm) and length (up to a few centimeters). Osteons consist of generally coaxial cylindrical layers called lamellae that are only a few microns in thickness. Osteons vary in terms of arrangements of dark and bright lamellae in cross section under (circularly) polarized light and in degree of calcification from dark gray to white on micro-x-ray. For a meaningful systematic study, all osteon specimens need to have the same dimensions and structural characteristics while maintaining the characteristics of the gross entity from which they are selected as specimens. The four above-mentioned variables can be dealt with realistically as follows:

Shape and dimension of specimens. A central cylindrical portion of the osteon around a 40±3 µm vascular canal with an external diameter of 210±3 µm avoids the irregularities of interstitial bone and a length of 500 µm avoids the discontinuities of Volkmann's canals.

Collagen bundle make-up. The examination of compact bone sections under the polarizing microscope reveals that all osteons are composed of lamellae that appear dark and lamellae that appear bright. Examination of thousands of bone sections has revealed that osteons made up exclusively with bright lamellae are rare; that all prevalently dark osteons show a thin layer of bright lamellae around the harvesian canal; and that among all the different combinations of dark and bright lamellae in osteons, osteons made up of essentially dark lamellae (so-called longitudinal osteons) and osteons made up of alternatively dark and bright lamellae (so-called alternate osteons) represent two ends of a spectrum, biologically and mechanically. Therefore, longitudinal and alternate osteons were chosen for the investigations set forth in the Examples.

Degree of calcification. Examination of micro-X-rays of compact bone sections shows a spectrum of shades, from dark gray to white, which indicate the degree of calcification from initial to final (Amprino and Engström, 1952) of osteons, as a whole. Osteons at the initial stage of calcification comprise 5-10% of adult compact bone, and this percentage decreases with age. Osteons at the final stage of calcification constitute the majority, close to perhaps 90%. The level of hydroxyapatite in osteons at final stages of calcification is usually considered to remain constant within a 27 to 49 age group. In a preferred embodiment, osteons at initial and final stages of calcification obtained from donors in this age group are modeled by the invention.

Number and thickness of lamellae. The distribution of lamellar number and thickness varies from osteon to osteon. Lamellar thickness from lamella to lamella from the cement line to the haversian canal (Rho et al., 1999; Ardizzoni, 2001) and within the lamella along the osteon length (Ascenzi A. et al., 1982) also varies from osteon to osteon. Lamellar number can be counted and thickness measured at both ends of the cylindrical portion of the osteon specimens under polarized light. Since the lamellar boundary is wavy along the lamellar 500 µm length, the thickness values obtained under polarized light for dark (bright, respectively) lamellae may be smaller (larger, respectively) than the ones obtained on thinner (70-100 µm) sections. While this potential discrepancy can affect absolute measurements, it does not affect comparative investigations. About 15-20 osteon specimens, quite homogeneous with respect to lamellar number and thickness of lamellae, can be obtained from the mid-diaphysis of a single human femur.

EXAMPLE 3

Osteon Viscous Behavior and Mucopolysaccharide Content

This Example reports two studies which provided information on osteon viscous behavior. The results show that the mucopolysaccharide content is higher in alternate rather than longitudinal osteons. These osteons can be modeled accordingly.

The bone material came from the femoral shafts of human cadavers, aged between 18 and 55, obtained in accordance with American regulation and free from evident skeletal faults and infectious diseases such as AIDS, hepatitis A and B, and syphilis.

First Study

Six osteon samples, obtained as described below, were subjected to twist and hold testing to evidence their viscous behavior through relaxation. Osteon sample isolation was achieved by applying the methodology described in Ascenzi A. et al. (1994). By means of a rotating-saw microtome, longitudinal segments about 30 mm long were first sawn from the femoral shaft. The segments were sliced in 350 µm thick longitudinal sections (i.e. slightly thicker than an osteon). A continuous water-spout was incorporated to the saw to prevent any overheating of the material.

The samples for torsional loading (FIG. 22C) were isolated in two stages from longitudinal sections. During the first stage the sample, consisting of the central portion of an osteon, 500 µm in length, with the ends penetrating into two rectangular lugs, was separated from the bone section using a specially constructed device which includes a dental drill as described in Ascenzi A. and Bonucci (1968) and Ascenzi A. et al. (1990). As isolation of the central portion of the osteon is achieved by drilling, its section has a coarse, square shape. During the second stage, a micro-grinding lathe was used to give the central portion a cylindrical form, with the haversian canal running through it axially. The lathe to be used was designed and developed by the CECOM Company and is described by Ascenzi A. et al. (1994). The device grinds the sample by a minute steel blade whose edge, 500 µm long, is equal to the length of a coarsely isolated sample. The forward and backward movements of the blade are monitored by a micrometer. The length and other dimensions of the various samples were kept virtually constant; one criterion for the choice of the samples is that the haversian canal measure 403 µm in diameter. Additionally, a stopper controls the forward and backward movement of the steel blade on the micro-grinding lathe to provide a series of samples whose external diameter equals 210±3 µm. The relative dimensions of the osteon samples may appear not to conform to those conventionally suggested for material testing. They reflect conditions made necessary by the distinctive nature of bone microstructure. In particular, 500 µm is the maximum length compatible with the avoidance of Volkmann's canals in the wall of the specimen. An external diameter of 210 µm is the maximum dimension possible that ensures that portions of the neighboring structures are not included in the sample as a result of irregularities in the thickness of an osteon. The internal diameter of fully calcified osteons averages 40 µm.

Figure 22A:
FIGS. 22A, 22B, and 22C. (A) Cross section of isolated longitudinal osteon (outer diameter: 225 µm). (B) Cross section of isolated alternate osteon (outer diameter: 225 µm). (C) Isolated osteon sample with lugs for torsional loading (inner diameter: 52 µm; outer diameter: 225 µm; length: 500 µm).
Figure 22B:
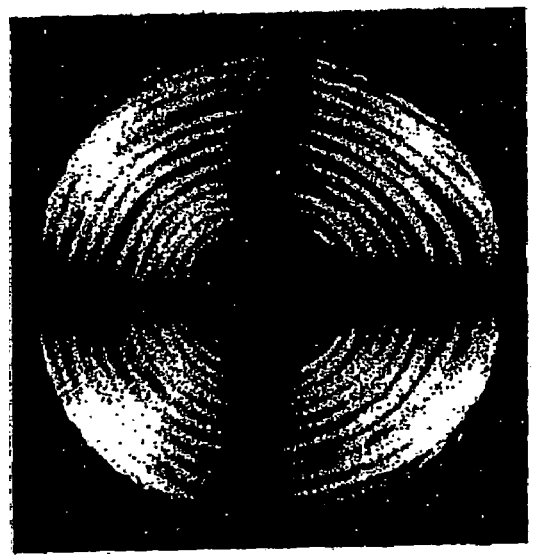
Figure 22C:

FIG. 22C shows a completely isolated osteon sample held within rectangular lugs. The lugs allow the sample to be firmly attached to the device while experimental diagrams are recorded. The central portion of each sample is only 500 µm long; consequently, the sample does not include Volkmann's canals, which would behave as discontinuities. This was determined by inspection under an optical microscope, which also checks that there are no small surface defects that could alter the shear modulus values in torsional testing. The canal's position and orientation were assessed by checking the distance between vascular canal and external surface of sample at various rotational angles and levels. Because osteon types can be identified from a prepared cross section only after a sample has been tested, between 1,600 and 2,000 samples are prepared to obtain 120 working samples (15 osteon samples per osteon type at initial and final stages of calcification), which will satisfactorily complete the procedures adopted for the recording of the experimental diagrams under torsion at low and high strain rates.

Figure 23:
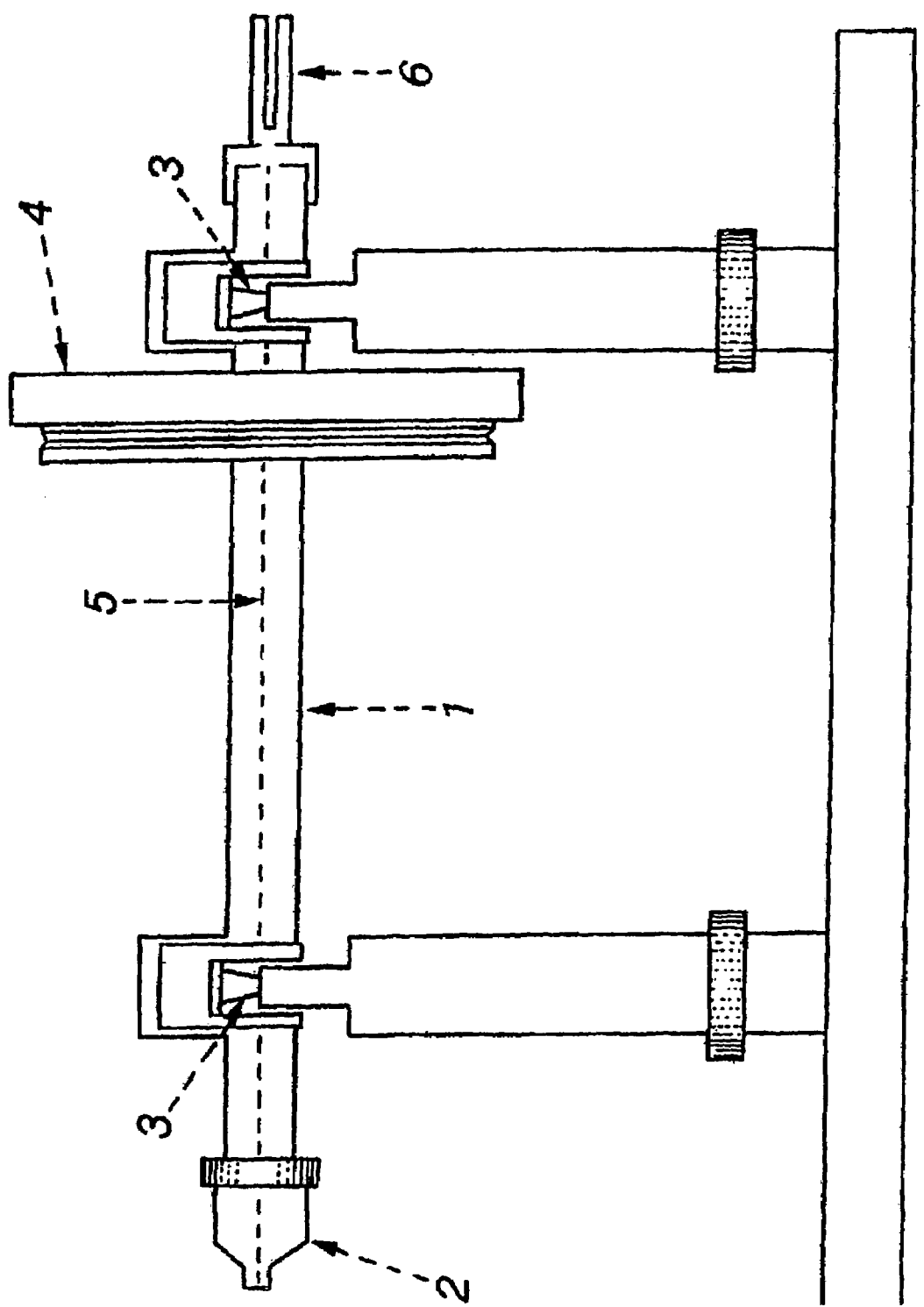
FIG. 23. Schematic drawing of torsional loading device used in the Examples. 1=Rotational axis with its jaws 2; 3=hard metal wedges of the pendulum loading system; 4=the wheel around which the thread, lodged with weights, is attached; 5=the axis of the pendulum; 6=the mirror that reflects the laser beam onto the graduated scale to detect angle-of-twist variations (from Ascenzi, 1994).

The apparatus used is the one described by Ascenzi A. et al. (1994) to test osteons under quasi-static torsion to failure. This device consists of a rotational axis, point (1) in FIG. 23, with two sets of jaws, point (2) in FIG. 23, which grip the sample during testing. The jaws are oriented along the same axis but none of them are free to move axially. This sets up an axial loading effect, which could influence absolute measurements but may be neglected when, as in this investigation, comparative measurements are considered. One set of jaws is fixed, while the other turns in synchrony with a wheel, point (4) in FIG. 23, measuring 61 mm in diameter. In order to minimize the rotating friction of the turning jaw, a pendulum counterbalance system is incorporated. The axis of the pendulum loading system is indicated as point (5) in FIG. 23. The frictionless fulcrum of the pendulum loading system is the tip of a hard metal wedge, point (3) in FIG. 23. The maximum oscillation of the pendulum is fixed at 55°. A thin light thread, whose section measures 20-60 µm in diameter, winds around the rim of the wheel. Weights may be attached to the thread to load the osteon sample. The angle through which one end of the specimen twists relative to the other during testing is measured by applying an optical method based on the reflection of a laser beam from a small mirror attached to the rotating set of jaws. The variations in the angle of twist are read on a graduated scale placed perpendicularly to the plane of the device, 40 cm higher. The precision and accuracy of the graduated scale coincide with those of the apparatus, as checked by applying experimental procedures. Because the diagrams obtained when testing begins in the counterclockwise (or positive) direction should look essentially like the diagrams obtained when testing begins in the clockwise (or negative) direction, all the diagrams were recorded starting in the counterclockwise direction, according to the standard practice reported in the literature.

This is how the torsimeter was used: Every 11 seconds a 0.1 gram weight was attached to the end of the nylon thread to a total of eight weights. The number of weights was eight because the diagrams of Ascenzi A. and Benvenuti (1994)

indicate that 0.8 gram loading with this device correspond to a torque between elastic limit and ultimate strength. The angle of twist corresponding to the 8 weights was recorded after 20 seconds and again after another 40 minutes had elapsed. All six samples showed a non zero angle-of-twist change, i.e. creep. The mean angle-of-twist change observed equals 1.6°.

Second Study

The longitudinal (alternate, respectively) osteon is constituted by longitudinal (alternatively longitudinal and alternate, respectively) lamellae (FIGS. 22A and 22B). Longitudinal and transverse lamellar samples were measured dry and wet inside the alternate osteons, were isolated and observed flat under a confocal microscope. Such examinations yield indication of a higher mucopolysaccharide content in transverse rather than longitudinal lamellae and therefore in alternate rather than longitudinal osteons.

Lamellar thickness and width were measured on 20 transverse and 20 longitudinal peripheral lamellar samples in quintuplicate in dry osteon samples by Delta Sistemi IAS 2000 image analysis system, and again after wetting with a micro-pipette. This table shows means and standard deviations. Thinner longitudinal lamellae were used for comparison with transverse lamellae. It is known that longitudinal lamellae are thicker than transverse ones (see e.g. Marotti, 1994), whether dry or wet. The student t-test is run on the data to determine statistical differences between dry and wet lamellar dimensions.

TABLE 1

| | Lamellar Thickness | | | |
|---|---|---|---|---|
| Sample | Thickness Dry(μm) | Thickness Wet (μm) | Width Dry(μm) | Width Wet (μm) |
| Transverse | 3.30 ± 0.88 | 3.56 ± 0.93 | 70.30 ± 9.28 | 72.45 ± 9.58 |
| Longitudinal | 4.13 ± 1.23 | 4.10 ± 1.10 | 70.30 ± 9.28 | 72.45 ± 9.58 |

Whether dry or wet, transverse lamellae are significantly thinner than longitudinal lamellae when enclosed in alternate osteons. Additionally, wet and dry conditions affect transverse and longitudinal lamellar thickness differently. Transverse lamellae are significantly less thick when dry than wet. In contrast, longitudinal lamellae thickness does not change significantly whether wet or dry. The transverse lamellar thickness increase from dry to wet supports the hypothesis that transverse lamellae contain a higher quota of mucopolysaccharides, which expand with water, and that the transverse collagen bundles in the transverse lamella tightly encircling longitudinal lamella impede expansion. The width of both lamellar types is significantly smaller when dry.

Figure 24:
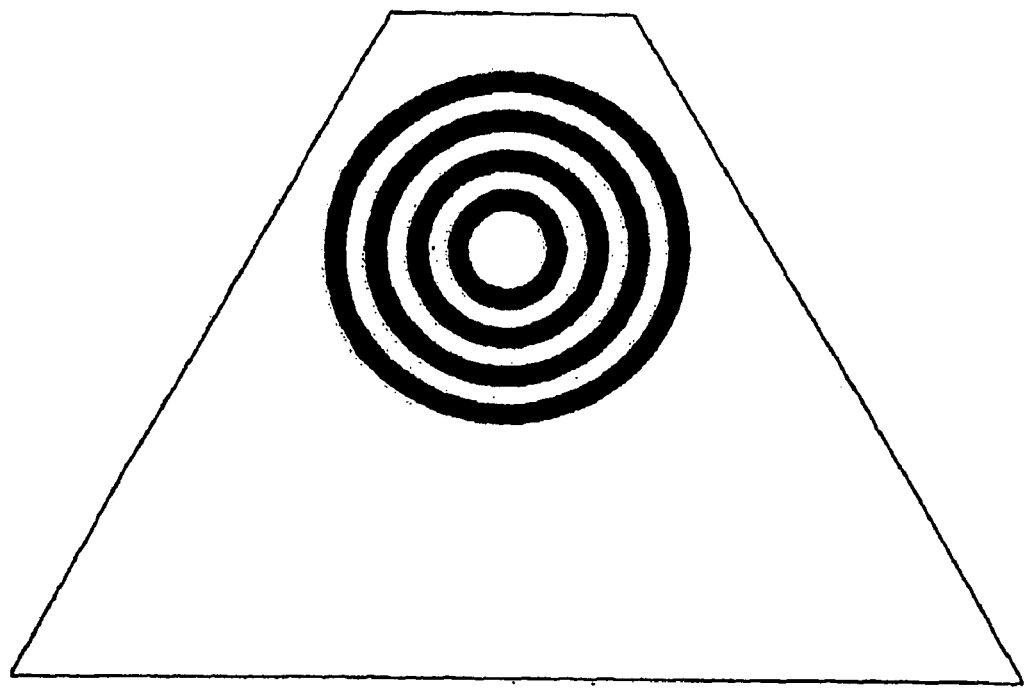
FIG. 24. Diagram showing the trapezoid cut from a thin transverse femoral section around a chosen alternate osteon (from Ascenzi, 2003).

Three longitudinal and 3 transverse lamellar samples were isolated by applying the methodology described in Ascenzi M.-G. et al. (2003). The rotating-saw microtome was employed to cut longitudinal segments about 30 mm long from the femoral shaft. The segments were then sliced in 70±6 μm thick transverse sections. The continuous waterspout prevented the material from overheating. On the thin transverse section, a trapezoid was cut around each chosen alternate osteon sample (FIG. 24). For osteon immobilization during lamellar isolation, a portion of the bone material inside the trapezoid away from the osteon was glued with Kemi®Cyak adhesive to a slide. The longitudinal and transverse lamellae at the periphery of each osteon were dissected with a razor-sharp microscopic blade, obtained by filing a steel needle. To avoid fracture formation during straightening of each lamellar sample, such operation is performed gently on wet samples while checking under an optical microscope. The selection of external lamellae, of lesser curvature than internal lamellae, decreases the risk of fracture formation during flattening. The structure of the isolated and flattened lamellar samples were observed wet under a Leitz confocal microscope. The confocal microscope worked well with the natural fluorescence of wet bone. Because the photomultipliers detect light intensity and not color, red is the color applied to the image.

The longitudinal lamellar samples show a regular arrangement of collagen bundles. From one border to the other, the collagen bundles are parallel to the osteon axis. Each dot is the cut radial collagen bundle that follows the osteocyte process. On transverse lamellar samples, collagen bundles of only one oblique inclination were evidenced for the first time. The transverse lamellar samples show ample areas of ground substance between collagen bundles, parallel and oblique to the flat lamellar borders. The larger areas of ground substance suggest a larger quota of mucopolysaccharides and a perhaps lower quota of collagen in transverse rather than longitudinal lamellae. This supports the hypothesis that, at the same degree of calcification, alternate osteons contain a larger quota of mucopolysaccharides than longitudinal osteons.

EXAMPLE 4

Viscous Osteon Model

This Example shows the experimental basis for, and subsequent mathematical modeling to create, a viscous osteon model. The study can be described by the following flow chart.

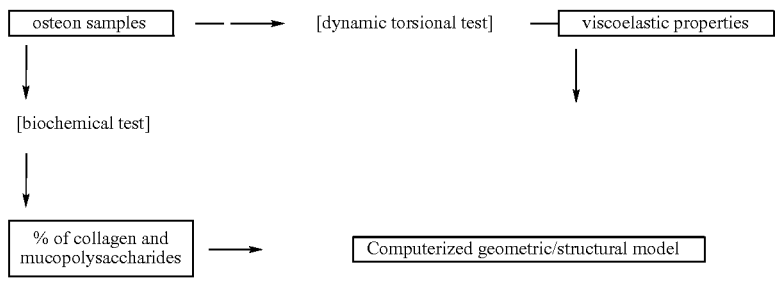

The bone material for this study conforms to the specifications described in the previous Example. Sample selection follows the specifications of Ascenzi A. et al. (1994). The features determining sample selection are their degree of calcification and their collagen bundle and crystallites orientation. Micro-X-ray, the method of Amprino and Engström (1952), provides for the selection of osteon samples at the initial and final stages of calcification. The number of osteons at initial (final, respectively) stages of calcification decreases (increases, respectively) with age. Osteons at initial stages of calcification comprise 5-10% of osteons in the above-mentioned bone age. The two osteon types, which are representative of osteon structures with respect to collagen bundle patterns in fiber orientation in successive lamellae, were selected for this study. On longitudinal bone sections, the two osteon types are easy to recognize only if the section thickness is much smaller than the diameter of an osteon. Longitudinal osteons appear to be almost uniformly bright under the polarizing microscope, while alternate osteons show alternatively bright and dark lamellae. When, as in this case, the thickness of the bone section differs little from the mean diameter of the osteon, concentric lamellae overlap, thereby reducing or precluding the visibility of dark lamellae, and leaving open the possibility that an alternate osteon may have a bright appearance. As a result, identification only becomes certain once a cross section has been cut from the osteon using a microscopic drill (Ascenzi A. et al., 1994). Hence, torsional loading must be performed before undertaking positive identification of the osteon type. On the 500 µm thick transverse bone sections, longitudinal osteons appear to be almost uniformly dark (FIG. 22A); whereas the other type, the alternate osteon, reveals alternately bright and dark lamellae (FIG. 22B).

Samples for Mechanical Testing

These samples are isolated as described above. It is necessary to isolate about 1,600-2,000 to obtain about 120 samples suitable for testing torsion at low and high strain rates (15 osteon samples per osteon type at initial and final stages of calcification).

Samples for Biochemical Analysis

Figure 25:
FIG. 25. Isolated osteon sample (under transmitted light) for the proposed biochemical analysis (length 500 µm).

The samples for biochemical analysis are isolated from 500 µm thick transverse sections using the technique of Ascenzi A. and Bonucci (1968). No lugs are necessary, and the type of each 500 µm long osteon sample can be easily recognized on transverse sections. The device used for sample isolation consists of a very thin, carefully sharpened steel needle inserted off-center in a dental drill. As the drill turns, the tip of the needle describes a circle whose diameter may be adjusted to match that of the particular sample diameter. When the rotating axis of the needle is perpendicular to bone section surfaces, i.e. coincides with the osteon axis, the tip of the needle cuts an osteon sample of cylindrical shape with walls of uniform thickness just inside its limits. To ensure that this rotating axis is perpendicular to bone section surfaces, the drill's handle is inserted in a microscope body in place of the tube and the section firmly secured onto the microscope stage. Coarse microscope adjustment controls the needle's movements into the bone section. Osteon cutting is controllable by watching the operation through a stereoscopic microscope. The length and diameter of each sample is accurately measured by means of an eyepiece micrometer. This provides a precise comparison of torsional properties. Individual osteons are not uniform in dimensions. With the dimensions carefully controlled and standardized to exclude defects and other structures, the material properties rather than variable structural properties are determined for the osteons. In the long run, this information can be applied to osteonal structures of varying dimensions under the assumption of homogeneity at the level of the osteon rather than for the macroscopic sample. The criteria of regularity for mechanical loading refer to the position and orientation of the haversian canal. It is necessary that the canal lie midway between the surface of the cylindrical sample and parallel to it, so that torsion is applied around the osteon axis. This calls for the preliminary separation of the osteon sample by application of a technique about to be outlined. This technique allows the position and orientation of the canal to be calculated by measuring its distance from the outer surface of the sample at various levels and rotational angles. After dissection, the harvesian canal is cleaned out by inserting a metal rod slightly (10 µm, approximately) thicker than the harvesian canal. FIG. 25 shows the shape of samples prepared with the above-described technique. It is necessary to isolate about 100 osteon samples per osteon type at initial and final stages of calcification to have sufficient material volume for each of the two biochemical analyses.

Mechanical Testing of Wet Osteon Samples

Mechanical testing of wet osteon samples is performed under monotonic torsional loading. Two types of testing are employed. (1) A torsimeter is used to demonstrate creep of the osteons as a function of their makeup. (2) Additional specimens are loaded under displacement control at constant strain rates of $10^{-2}$ and 10 Hz until rupture of the sample occurs. These latter measurements corresponds to low and high strain rates.

Torsimeter Tests

The torsimeter is used as follows.

1) Creep Tests

A 0.8 gram weight is attached at one end of a 20 µm thick tungsten thread, applying a static torque to the specimen. Angle of twist is recorded initially at 5 second intervals followed by longer intervals as the creep stabilizes. Preliminary work indicated that additional creep was insignificant after 40 minutes. The samples are maintained throughout the testing by a saline drip irrigation. This test yields angle of twist versus time for these quasistatic tests. Initially, Kelvin-Voigt and 3-parameter viscoelastic models are used to determine the elastic and viscous constants for the specimens. For the three parameter solid model, for example, the constitutive relation assumes the form:

$$\sigma + p_1 \sigma^\bullet = q_0 \epsilon + q_1 \epsilon^\bullet$$

where $\sigma$ is the applied stress, $\sigma^\bullet$ is the stress rate, $\epsilon$ is the strain and $\epsilon^\bullet$ is the strain rate. The coefficients $p_1$, $q_0$, and $q_1$ represent combinations of the elastic and viscous constants depending on the particular form of the model employed. These coefficients (and hence the associates elastic and viscous constants) are obtained directly from the observed angle of twist versus time diagrams obtained according to the method described by Hayes W. (1972).

2) Low and High Strain Rate Tests

For this series of tests the torsimeter is modified for attachment to an MTS 612 servohydraulic testing machine. The fixed stock of the torsimeter incorporates a reaction torque sensor (5 oz-in capacity). The drive shaft is modified to incorporate a bowstring arrangement to convert the linear actuator displacement to angle of twist. The base of the torsimeter is rigidly mounted to centralize the actuator axis with the bowstring arrangement. Ramp loadings of $10^{-2}$ mm/sec and 10 mm/sec is used to apply torque to the specimens. One output of these results is a plot of torque versus angle of twist recorded in real time. In these tests, the specimens are all taken to failure. According to the invention, there is a direct dependency of the slope of the torque versus angle of twist curves on the loading rate. This is supported by preliminary results demonstrating a significant creep effect. There is also a dependence of this slope on the actual structural material makeup of the osteon samples.

After the mechanical testing, osteon samples are examined under an optical microscope under both regular and fluorescent light (Huja et al., 1999) to assess fracture patterns; measured in terms of diameter and height; and assessed in terms of the number of bright and dark lamellae.

The experimental results include, for example, graphs of increasing functions of the angle-of-twist, which show a concave downward shape starting at the origin of the reference system, regardless of the osteon type and the degree of calcification. According to the invention, the plotted results shows a model in which the observed curves are steeper and less concave for the high (rather than low) strain rate, regardless of the osteon type and the degree of calcification. According to the model, a similar profile applies to the osteon samples at the final (rather than initial) degree of calcification, regardless of the osteon type, for any fixed strain rate. A similar profile again applies to longitudinal (rather than alternate) osteon samples, regardless of the degree of calcification, for any fixed strain rate.

Further, the experimental diagrams of fully calcified osteon samples, according to the invention, are steeper and less concave than the quasi-static experimental diagrams obtained by Ascenzi A. et al. (1994) per osteon type.

Biochemical Assessment of Collagen and Mucopolysaccharides

Biochemical assessment of collagen (as hydroxyprolines) and mucopolysaccharides (as hexosamine) is performed on 150 µg amounts of longitudinal and alternate osteons at initial and final stages of calcification. While it is difficult to quantify small quantities precisely, the uncertainty does not affect the comparative conclusions to be made (Herring, 1972).

Osteon samples are dried to constant weight in a vacuum desiccator over $P_2O_5$. Since decalcification of osteons is necessary to quantify hexosamine and hydroxyproline, acid hydrolysis is used. Residual HCl is removed before the assays are performed. Hydrolysis products are separated using refined chromatographic techniques as first described by Exley (1957).

Hexosamine is determined spectroscopically essentially according to the procedure of Elson and Morgan, (Exley 1957) and modified by Oguchi et al. (1979). The methodology is refined to eliminate the possibility of interference from amino acids and mineral salts (Pugliarello et al., 1970). Hyroxyproline is determined essentially according to the procedure of Serafini-Cessi and Cessi (1965), as refined by Teerlink et al. (1989).

The biochemical analysis has been performed successfully (Pugliarello et al., 1970) on osteon samples at initial and final stages of calcification, regardless of the osteon type. Moro et al. (2000) have employed on rat bone a technique refinement that can be applied to osteons. Collagen and mucopolysaccharides percentages are significantly lower in longitudinal rather than alternate osteons. In fact, alternate osteons contain more collagen and mucopolysaccharides than longitudinal osteons at equal degrees of calcification, because alternate osteons contain transverse lamellae, which are richer than longitudinal lamellae in collagen and mucopolysaccharides. According to the invention, the mucopolysaccharides percentage decrease, as the degree of calcification increases, is statistically significant in alternate osteons. Conversely, the mucopolysaccharide percentage decrease will not be statistically significant, as the degree of calcification increases, in longitudinal osteons. In either case, the mucopolysaccharide percentage decreases in osteons, regardless of the osteon type, when the degree of calcification increases. Here, the resulting collagen and mucopolysaccharides percentages for longitudinal (alternate, respectively) osteon samples is lower (higher, respectively) than the values found by Pugliarello et al., 1970) regardless of the osteon type. The means of collagen and mucopolysaccharide percentages are combined with the mean number of longitudinal and transverse lamellae in longitudinal and alternate osteons to yield the mean percent of collagen and mucopolysaccharides within longitudinal and transverse lamellae, at initial and final stages of calcification. These percentages are not previously reported in the literature.

According to the invention, the biochemical analysis shows a statistically significant higher percent of collagen and mucopolysaccharides in alternate rather than in longitudinal osteon samples at equal stages of calcification; a statistically significant higher percent of collagen and mucopolysaccharides in transverse rather than in longitudinal lamellae at equal stages of calcification; and a statistically significant (not significant, respectively) decreasing amount of collagen and mucopolysaccharides as the degree of calcification increases in alternate (longitudinal, respectively) osteon types.

Mathematical Modeling

Mathematical modeling will consist of analysis of the experimental diagrams to establish yield strength, ultimate strength, moduli and constitutive equations; and the realization of a computerized geometric-structural model, which will simulate the behavior of the microscopic components so as to include fracture propagation during loading.

Analysis of Experimental Diagrams

The observation of the experimental diagrams assesses the yield strength and ultimate strength. For each experimental diagram, the constitutive equation, which relates stress, strain and their time dependencies, is established in terms of the Ramberg-Osgood equation:

$$\theta = Tc(d\theta/dt)^d + aT^N(d\theta/dt)^b$$

where $\theta$ and T denote angle-of-twist and torque respectively; a, b, c, d, N denote constant values that depend on the material properties, with a, b, $c \geq 0$ and $d \leq 0$.

Such equations have accurately modeled the response set at various strain rates of a wide range of tested engineering materials (Ramberg and Osgood, 1943). This is because the geometric shape of the experimental diagrams changes only moderately as the strain rate varies; and the Ramberg-Osgood equation is a simply formulated polynomial whose coefficients are functions of the strain rate, which describes the relatively simple geometric shape of the experimental diagrams, i.e. an increasing function graph, that passes through the origin and is concave down.

The determination of the constants a, b, c, d and N will follow the procedure used by Hight and Brandeau (1983) for macroscopic compact bone samples. The Ramberg-Osgood equation is expected to suffice to produce a good fit (measured by an $r^2$ of 0.98-0.99) because the osteon viscoelastic behavior is expected to be less complex than that of macroscopic samples. If desired, increasingly more complex differential equations are employed, starting with more complex polynomials and rational functions of T whose coefficients depend on the strain rate.

Linear-viscosity is expected (Frasca et al., 1977) at least for physiological strains, which for the outer wall of the tibia (as one example) are of the order of between 0.0007 and 0.0020, at physiological strain rates, which are of the order of between 0.0135 and 0.5143 Hz. If linear-viscosity is present and the Ramberg-Osgood equation provides a good fit, the coefficients a, b, c, N equal 0, 1, 0, 0, respectively.

The approximating function of each experimental diagram will serve to compute: the viscoelastic modulus as the derivative of the diagram approximating function at zero strain and the energy absorption capacity as the area under the approximating curve.

Statistical Analysis

The Two Way Analysis of Variance is applied to the means of viscoelastic modulus, yield strength, ultimate strength and energy absorption with osteon type (longitudinal or alternate) and degree of calcification (initial or final) as factors for each strain rate. If normality is lacking, the 2-way ANOVA is applied to the means of the logarithms. Significance is set at 0.05. The Post hoc Student-Newman-Keuls test identifies the significant factors. This test yields significant differences in the following:

1. Viscoelastic modulus, yield strength, ultimate strength, and energy absorption capacity should be higher at the final stages rather than at the initial stages of calcification, regardless of the osteon type and the strain rates
2. Viscoelastic modulus, yield strength, ultimate strength, and energy absorption capacity should be higher for longitudinal rather than alternate osteon samples, regardless of the degree of calcification and the strain rate.
3. Viscoelastic modulus, yield strength, ultimate strength, and energy absorption capacity should be higher for longitudinal rather than alternate osteon samples, regardless of the degree of calcification and the strain rate;
4. Viscoelastic modulus, yield strength, ultimate strength, and energy absorption capacity should show a smaller increase in value for longitudinal rather than alternate osteon samples, as the strain rate increases, regardless of the degree of calcification.
5. Viscoelastic modulus, yield strength, ultimate strength, and energy absorption capacity should increase with increasing strain rate, regardless of the osteon type and the degree of calcification.

In certain embodiments of the model, if desired, yield strength is not determined.

Viscoelastic Osteon Model

The purpose of the viscoelastic osteon model is to relate the mechanical behavior of the osteon sample to the behavior of the ultrastructural components that causes a progressive loss of stiffness. The micromechanical behavior is described in terms of micro-cracking, de-bonding, void growth and components breakage. The lesions observed under an optical microscope in osteon samples subjected to dynamic torsional loading at various strain rates serves to develop osteon models and to formulate biological hypotheses on propagation of fractures. In a preferred embodiment, this longitudinal osteon model is an extension (so as to include components' viscoelastic properties) of the elastic model in Ascenzi M.-G. (2000); whereas the alternate osteon model is prepared ex novo. The osteon model is based on the experimental diagrams' approximating functions, angle-of twist as function of torque; the hypotheses on ultrastructural components' behavior under dynamic torsional loading formulated from the experimental diagrams; the ultrastructural components' percents, as obtained from the biochemical analysis; and the ultrastructural components' viscoelastic properties.

Figure 26:
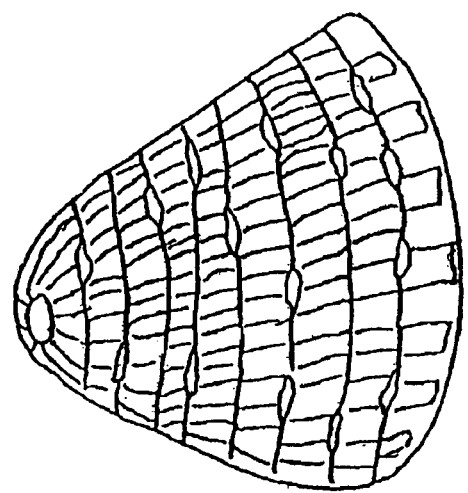
FIG. 26. Diagram of a segment of osteon in cross-linking illustrating the arrangement of canaliculae and lacunae relatively to lamellae (based on FIG. 4-11 of Leeson et al. (1985)).

The geometric model of each of the longitudinal and alternate osteon samples before mechanical testing consists of a hollow cylinder with coaxial lateral surfaces. Its internal diameter, external diameter, and height equal 40 µm, 210 µm, and 500 µm, respectively. Each such hollow cylinder presents pores, as shown in FIG. 26. Pores in the model will include the vascular canal, canaliculae and lacunae and equal 20% of the total osteon volume (Piekarski, 1970).

Figure 27A:
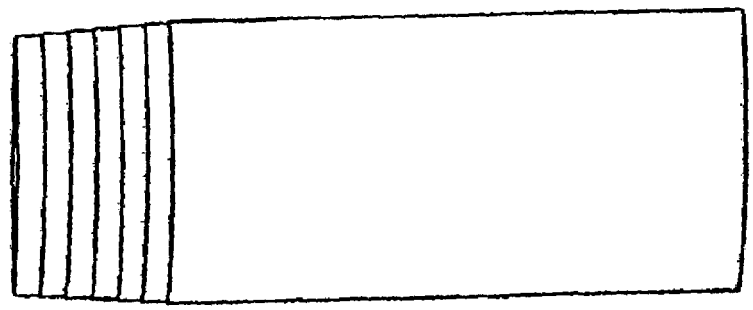
FIGS. 27A and 27B. (A) Material model consisting of fiber-reinforced unidirectional laminae. The first few external laminae are partially pulled out to show arrangement. (B) On a small laminar element of constant thickness, the principal material axes are labeled 1, 2, and 3. Direction 1 is parallel, and direction 2 perpendicular, to the fibers. Direction 3 is the radial direction, perpendicular to the plane of the diagram. Circumferential and axial directions are labeled θ and z. The angle between the circumferential direction and direction 1 is denoted y (from Ascenzi, M.-G. (1999) A first estimation of prestress in so-called circularly fibered osteonic lamellae, J. Biomechanics, (32): 935-942).
Figure 27B:
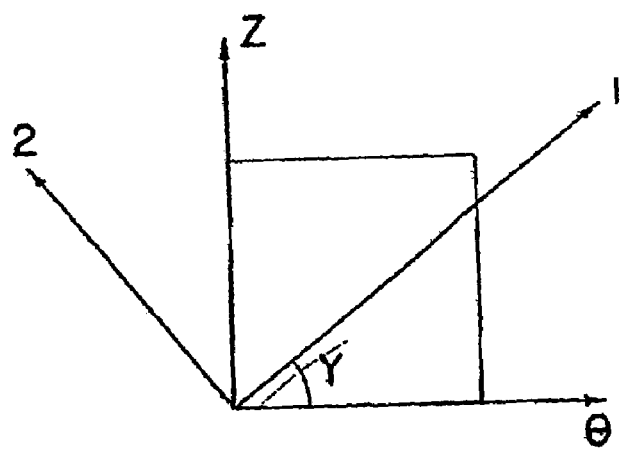
Figure 29:
FIG. 29. Isolated and flattened bright lamellar specimen rotated at 45° to the polarizing plane. Collagen bundles run parallel to its length. Lamellar width is approximately 70 microns.
Figure 30:
FIG. 30. Isolated and flattened bright lamellar specimen rotated at 0° to the polarizing plane. Collagen bundles run parallel to its length. Lamellar width is approximately 70 microns.

The material model of each of the longitudinal and alternate osteon samples before mechanical testing consists of a laminate whose length, width, and height correspond to cylindrical shell circumference, thickness, and height, respectively (FIG. 27A). The layers are unidirectional fiber-reinforced laminae of the same matrix and fibers. The matrix and fibers are each treated as homogeneous and isotropic. The matrix is considered as elastoplastic and the fibers as viscoelastoplastic. The fibers are assumed to be circular in cross-section and randomly distributed in the transverse plane. The lamina with fiber inclination $\gamma$ is named $\gamma$-lamina (FIG. 27B). There are two types of fibers. The first fiber type, with a diameter of 800 Å, represents collagen. The second fiber type, with a smaller diameter, represents mucopolysaccharides. The matrix occupies up to 40% of the lamina volume without voids (Bonfield and Li, 1967), at the highest degree of calcification. The relative percentages of matrix at the initial stages of calcification and of the two fiber types at initial and final stages of calcification, and the diameter of the second type fibers is based on the biochemical analysis.

The elastic properties of the matrix are seen to model the elastic properties of hydroxyapatite (Katz and Ukraincik, 1971). The viscoelastic properties of the fibers of the first type are seen to model the viscoelastic properties of collagen (Currey, 1959; Haut, 1983). The viscoelastic properties of the fibers of the second type are seen to model the unknown viscoelastic properties of mucopolysaccharides. Little information is available regarding the fluids within the pores incorporated in the microstructure. Initially, the proposed model simplifies or disregards the structural effects of the fluid within these pores with assignments of minimal material property values. This form of the model is exercised parametrically to include fluid within the pores, with various bulk moduli.

The longitudinal osteon model consists of 12 laminae 7.08 µm thick. It is described by the sequence (82, −82) repeated 6 times (Frasca et al., 1977). The alternate osteon model consists of 36 laminae. The fiber inclination angle increases by 20.5° from −82o to 82o and then decreases by 20.5° from 82o and −82o four consecutive times. Here the ±82-laminae are 7.08 µm thick while the other laminae are 1.01 µm thick. Because the sequence (−61.5, −41, −20.5, 0, 20.5, 41, 61.5) models a 7.08 µm thick transverse lamella, transverse and longitudinal lamellar models have the same thickness. Transverse lamella is subjected to a strain associated with prestress (Ascenzi and Benvenuti, 1980), as described in Ascenzi M.-G., 1998a and 1999b. Longitudinal lamellar model is 9.45 µm thick and transverse lamellar model is 5.40 µm thick (e.g., Gebhardt, 1906; Marotti, 1993; Ascenzi A. et al., 2001). The matrix volume is 10% higher in the longitudinal lamellar model than it is in the transverse lamellar model (Marotti et al., 1994).

Fracture Propagation Modeling

To model fracture propagation in osteons, each of the longitudinal and alternate osteon models is divided into a discrete number of elements. The starting number can be 618,137. The element mesh is refined to achieve convergence of the solution. Then a computer program, based on Montecarlo simulation, is written to perform the following tasks:

1. For any given value of torque applied to experimental samples, the distribution of stress in the osteon model is computed. Such computation will take into account voids.

2. Such stress distribution will be added to the distribution of prestress.

3. The strain associated to the resulting stress will be computed on each phase within each element.

4. From the strain associated to the resulting stress, the overall deformation of the hollow cylindrical shell will be computed.

5. From the strain in each phase within each element, the phase deformation will be computed.

6. The strain in each phase within each element is compared to the yield strain.

7. The strain is chosen as the criterion for osteon failure (Piekarski, 1970). The maximum strain, called critical strain, after which fracture occurs within each phase, is provided by the literature. A failure criterion (e.g., Von Mises) will be included if cracks appear to initiate at the matrix-fiber interface.

8. The elastic properties of fractured phases will be computed by means of formulas of type $E_i = E_e/(1+(1+v_e)(k_e\lambda)/2)$ (Gupta and Bergström, 1998).

9. The elements are assumed to be aligned in independent rows such that the problem of fracture propagation becomes one-dimensional.

10. To model the progressive growth of damage, the torque will be increased incrementally, and using the fracture criterion above, the number of failure elements will be established.

11. The increased probability of fracture in the neighborhood of an already fractured element will be considered using the concept of stress enhancement factors.

12. If all elements on one row are broken, the strain level at which all elements on one row are broken is taken as the failure strain for that row. The process is repeated for each row in the model. Once the maximum torque is reached, the program stops.

13. At this point, the simulation of fracture propagation is completed.

14. The fractures obtained in this way in the model should check with those observed in osteon samples.

Verification of the Model

Entities computed from the experimental diagrams are correlated, such as stiffness degradation and fracture propagation, to verify the osteon model. The osteon model (loaded quasi-statically) should behave like the osteon sample (loaded quasi-statically).

The influence of factor pertaining to the following ultrastructural components and voids are also considered:

Large strains, which may be accommodated by the organic phase, contribute to the dissipation of energy at the front of a propagating crack. Crack propagation appears to be arrested in the presence of canaliculae and lacunae. In the case where the crack enters a discontinuity, its front is blunted, hence reducing the stress concentration factor and slowing crack propagation. When a crack is forced to enter a vascular canal, the radius at the tip of the crack becomes larger. Lacunae are probably more likely to act as stress concentrators than canaliculae because of the ellipsoidal cross-section and because they are generally oriented normal to the long axis. However, their much smaller size precludes them from acting as fracture initiators until or unless plastic deformation has created cracks at the tip and thereby extended them to the critical length for spontaneous fracture. It seems unlikely that smaller discontinuities could act as stress concentrators. It may be that discontinuities "to some extent increase the robustness of bone" (Currey, 1962) rather than increase its tendency for brittle fracture. No cross-lamellar or cross-osteonal cracks are observed in macroscopic samples.

Examination of Model Results

In both osteon types, a fracture starts at a weaker point of the bone structure (Carter et al., 1981) at the weak interfaces between two outer lamellae (e.g. Piekarski, 1970; Simkin and Robin, 1974). That outer lamellae are involved in the fracture process is tentatively explained by the hydroxyapatite decrease in osteons from vascular canal to outer wall (Rho et al., 1999).

In longitudinal osteons, the fracture starts somewhat longitudinally, between collagen bundles. It then deviates once or twice at the beginning of the fracture and is soon followed by a smooth crack advancing rapidly across the osteon to possibly end in the vascular canal. As torque increases, collagen bundles between cracks break, and cracks join to create one or more long almost vertical cracks. Deviations causing a dentate profile may be due to the viscoelastic, strain rate sensitive mucopolysaccharides and perhaps collagen. Such dentate profile should therefore be more evident at low (rather than) high strain rate and at the initial stages of calcification when the osteons are richer in mucopolysaccharides. In alternate osteons, cracks are expected to spread obliquely by following the weak interfaces of lamellae. The transverse and oblique collagen bundles may break before the longitudinal ones as the osteon section enlarges. Cracks spread through lamellae less rapidly than in longitudinal osteons as explained by the crack propagation control, characteristic of composite materials (Cook and Gordon, 1964). Once the crack breaks through transverse and oblique bundles, it will propagate faster straight through the vascular canal. A long crack should show an oblique orientation between upper and lower extremities. In alternate osteons at initial stages of calcification the cracks may start at a higher value of torque and propagate more slowly than at the final stages of calcification if the percent of mucopolysaccharides is higher.

It follows that at the same degree of calcification, a longitudinal osteon is weaker in longitudinal than in transverse shearing while an alternate osteon is weaker in tension than in shear (confirmed by Ascenzi A. et al., 1967 and 1972). This is because when a torque is applied to a body, tensile and compressive stresses are produced on the lateral surface, and torsional shearing stresses are produced on the cross-section of the body. The tensile and compressive stresses act approximately at a 45° angle to the long axis of the body. The direction of the shearing stress on the cross-section of the body is the same as that of the force producing torsion. If a material is weaker in longitudinal than in transverse shearing, the first cracks arise from axial shearing stresses and appear in a longitudinal direction. However, if the material is weaker in tension than in shear, it usually cracks along a spiral course inclined at a 45° angle to the long axis of the body. This is because a state of pure shear is equivalent to a state of tension in one direction and of compression in the opposite direction (Timoshenko and Young, 1940). The tension stress produces a spiral crack in the body.

For both osteon types, 3 to 4 small cracks form in the hydroxyapatite and collagen, which yields and pulls and/or buckles and makes the cracks spread within lamellae. Microcracks form ahead of the advancing fracture line.

The slow propagation of cracks in the areas containing transverse and oblique collagen bundles allows for the area to absorb a large amount of energy. Slow propagation is essentially a pull-out type mechanism, that is, hydroxyapatite crystallites are pulled out of the collagen by shear failure at the fiber-matrix interface. The rapid propagation of cracks in areas containing approximately vertical collagen bundles allows very low energy absorption. This should be compatible with larger areas under the experimental graphs of alternate osteons.

Hydroxyapatite crystallites are pulled out from collagen around canaliculae.

At low strain rates in compression, distortion of the lamellar structures occurs (McElhaney and Byars, 1965).

The propagating crack generally has the tendency to avoid discontinuities (Piekarsky, 1970), hence increasing its length. Discontinuities act as crack arresters by blunting the tip of the crack, which enters them.

The osteon model agrees with fractures observed in osteon samples after loading. The dimensions of the hollow cylindrical model after dynamic torsional loading matches the means of the osteon samples' dimensions measured experimentally.

The sudden shift of the osteon shape from a circular to a square cross-section suggests a stress concentration at the lugs. Therefore, fractures can begin at the end of some samples earlier during loading than would otherwise be expected.

Advantages of the Model

The model of the invention advantageously simplifies osteon structure, in particular with respect to exclusion of partially calcified collagen bundles. The shape and dimensions of hydroxyapatite crystallites and the relationship of these parameters to the organic components of the matrix are only partially known. Not all the collagen bundles are completely calcified. Those that are not calcified take up crystallites only on 400 Å bands (Ascenzi A. et al., 1965). Hence such bundles may be comprised of relatively more stiff 400 Å bands separated by relatively more flexible decalcified collagen segments. This model does not contain fibers that model such partially calcified collagen bundles. Here the fiber of the first type model uncalcified collagen bundles, the fiber of the second type model the mucopolysaccharides and the matrix, which models the hydroxyapatite crystals, lies outside both fiber types.

EXAMPLE 5

Properties of Osteons Under Dynamic Loading

The experiments reported here examine the properties of osteons under dynamic loading. They focus on viscoelasticity, characterizing first how viscoelasticity depends on collagen bundle direction and hydroxyapatite density, and second how the relative percentages of collagen and mucopolysaccharides depend on collagen bundle direction and hydroxyapatite density. These experimental results therefore provide important information on the role that the ultrastructural constituents play in the viscoelastic behavior of the osteon. By describing the limits and extent of the role that the osteon ultrastructure plays in determining osteon viscoelasticity, a better understanding is gained of how bone tissue absorbs energy during dynamic loading and of how fractures propagate.

Furthermore, these experiments can show that longitudinal and alternate osteons show a linearly-viscous behavior in the physiological strain range. Such a showing would be of fundamental importance in the understanding of the non-linear viscous behavior hypothesized by Lakes and Katz (1979a and b) on macroscopic bone specimens. In fact, it would point to the cement lines, which are more ductile than osteons, as responsible for the non-linear effect.

Thus, the aim of these studies was three-fold: to evidence single osteon viscoelasticity, subject of the described mechanical experiments; to evidence elementary component differences in osteon lamellae, subject of the described chemical experiments; and to identify additional osteon geometric and structural variables in order to clarify long standing questions and provide a meaningful link among the proposed experimental results.

For the four experiments described below, the bone material consisted of adult human femoral shafts (27-49 years old), free from evident skeletal faults, and removed from cadavers in accordance with US regulations. The selected age range corresponds to the young age group of Kuo et al. (1998).

Mechanical Evidence of Osteon Viscous Behavior

Osteon specimens were subjected to twist and hold testing. All specimens showed viscous behavior as evidenced by relaxation. The result points to the appropriateness of dynamic loading of osteon specimens to investigate osteon viscoelasticity.

Methods. The Ascenzi A. et al. (1994) methodology was used to obtain 6 osteon specimens. A femoral shaft was first sawn into 30 mm long longitudinal segments by means of a rotating-saw microtome with a continuous watering system to provide lubrication and prevent the material from overheating. The segments were then sliced into longitudinal slabs 350 µm thick, i.e. slightly thicker than an osteon. Micro-X-rays of these longitudinal sections were prepared to allow identification (Amprino and Engström, 1952) of fully calcified osteons, as desired for this study. Both the section and the micro-X-ray were then scanned for a 500 µm long portion of fully calcified osteon around a straight haversian canal of the required diameter (in this study, averaging 40±3 µm) that was free of Volkmann's canals. The identified specimen was then isolated in a two-step procedure. During the first step, a dental drill secured to a microscope stage cut a coarse parallelepiped around the specimen. During the second step, a CECOM Company micro-grinding lathe machined the 500 µm long central portion of the coarse parallelepiped to the shape of a cylinder that contained the haversian canal. The external diameter of this cylinder is set to measure 210±3 µm. After grinding, the concentricity of the canal was assessed by checking the distance between canal and external cylindrical surface of the specimen at various rotational angles and levels. A canals that deviated more than ±10 µm at any point along its length with respect to the axis of the cylinder was deemed unacceptable for use. From a classical mechanics approach this is sufficient to ensure that the specimen's torsional stiffness (rigidity) does not vary by more than 5% due simply to structural anomalies.

The relative dimensions of the osteon specimens reflect conditions determined by the distinctive nature of bone microstructure. In particular, (i) 500 µm is the maximum length compatible with the avoidance of Volkmann's canals in the wall of the specimen that would behave as discontinuities; and (ii) an external diameter of 210 µm ensures that the central portion of the osteon is isolated and that therefore portions of the neighboring structures are not included in the specimen to avoid irregularities in the osteon specimen thickness. FIG. 28b shows a completely isolated osteon specimen with lugs, necessary to attach the specimen firmly to the loading device. Inspection under an optical microscope checks the specimen for small surface defects that could alter the shear modulus values in torsional testing.

The axisymmetric cylindrical shape of the osteon specimen lends itself well to torsional loading. At the level of a single osteon the specimen unit appears homogeneous and isotropic by observation. To determine elastic constants by mechanical testing methods, many techniques are available. The cylindrical nature of the specimens lends itself ideally to torsional testing. This loading method is used to determine the material stiffness (shear modulus in this case) and is not intended to simulate in vivo loading conditions experienced on the intact bone during activities of daily life. This method of loading is appropriate and sufficient for the determination of one of the two elastic constants that completely define the mechanical behavior of these specimens as a whole, as isotropic specimens. Extensive experience in the application of this technique for intact long bone specimens is advantageous.

The apparatus used is described in Ascenzi A. et al. (1994), to test osteon specimens under quasi-static torsional loading to failure. Weights are attached to a thin light thread (FIG. 23) to load the osteon specimen in torsion. An optical method measures the angle through which one end of the specimen twists relative to the other during testing. Although the resulting torque vs angle-of-twist diagrams are independent of the direction of loading, all the loadings were initiated in the counterclockwise direction. Every 11 seconds a 0.1 gram weight was attached to the end of the thread, up to a total of eight weights. The total number of weights was indicated by the fact that the 0.8 gram loading with this device corresponds to a torque between elastic limit and ultimate strength during quasi-static experiments (Ascenzi A. et al., 1994). For each specimen, the angle of twist corresponding to the 8 weights was recorded after 20 seconds and again after another 40 minutes had elapsed.

Results. All six specimens showed a non zero angle-of-twist change (see table below) with a mean of 1.6°. A non zero angular deflection points to tissue relaxation and reveals the viscous behavior.

TABLE 2

Osteon Angle-of Twist Change

| | Specimen No. | | | | | |
|---|---|---|---|---|---|---|
| | 1 | 2 | 3 | 4 | 5 | 6 |
| Angular Deflection (degrees) | 0.38 | 1.50 | 0.75 | 2.42 | 1.50 | 2.76 |

Thickness Variation within Dark and Bright Lamellae

The thickness of the wet outer lamellae of alternate osteons was measured along their two ends, separately, on thin transverse sections. Dark and bright lamellae show thickness variation between the two ends. The result points to the appropriateness of thickness measurements on osteon specimens for both mechanical and chemical investigations.

Methods. Transverse section thickness was set at 70 μm. Polarizing light allowed the identification of alternate osteons. Micro-X-ray allowed identification of required osteon degree of calcification (Amprino and Engström, 1952), set to final in this preliminary study. Lamellar thickness was measured at 5 points on each of the two ends of 86 dark and 66 bright peripheral lamellar specimens embedded in wet alternate osteons by Delta Sistemi IAS 2000 image analysis system. Table 3 shows means and standard deviations (in microns).

TABLE 3

Lamellar Thickness

| Specimen | Thickness On End 1 | Thickness On End 2 | Thickness Difference |
|---|---|---|---|
| Dark | 4.27 ± 1.00 | 4.85 ± 0.96 | 0.29 ± 0.26 |
| Bright | 7.62 ± 1.91 | 8.58 ± 1.99 | 0.48 ± 0.47 |

Differences between bright and dark lamellae were significant ($p<0.05$). Both dark and bright lamellar thickness varies from lamella to lamella and within any given lamella along the osteon length as previously observed by Ascenzi A. et al. (1982) on isolated bright lamellae.

Thickness Variation Between Wet and Dry Lamellar Conditions

Dry and wet lamellar thicknesses were measured within the osteon samples. Whether dry or wet, dark lamellae are thicker than bright lamellae and bright lamellae expand with water to a lesser degree than the dark lamellae. The result points to the appropriateness of biochemical analysis to quantify the mucopolysaccharides in longitudinal and alternate osteons.

Methods. The rotating-saw microtome described above was employed to cut transverse sections. A micro-X-ray of each cross section was prepared to allow identification (Amprino and Engström, 1952) of required degree of osteon calcification, set to final in this study. Lamellar thickness and width were measured at 5 points on each of 20 dark and 20 bright peripheral lamellar specimens in dry alternate osteon specimens by using a Delta Sistemi IAS 2000 image analysis system, and again after wetting with a micro-pipette. On each lamella, all measurements were taken consistently on one of the two transverse ends. Only thinner dark lamellae were used for comparison with bright lamellae because dark lamellae are in general thicker than bright ones (see e.g. Marotti et al., 1994), whether dry or wet. The mean length (±S.D.) of the whole alternate osteon equaled 70.30±9.28 μm and 72.45±9.58 μm, under dry and wet conditions, respectively. The table shows means and standard deviations (in microns) on which the student t-test was run with significance set at 0.05.

TABLE 4

Lamellar Thickness

| Specimen | Thickness Dry | Thickness Wet |
|---|---|---|
| Dark | 4.13 ± 1.23 | 4.10 ± 1.10 |
| Bright | 3.30 ± 0.88 | 3.56 ± 0.93 |

Whether dry or wet, bright lamellae are significantly thinner than dark lamellae when enclosed in alternate osteons. Additionally, wet and dry conditions affect bright and dark lamellar thickness differently. Bright lamellae are significantly less thick when dry than wet. In contrast, dark lamellae thickness does not change significantly whether wet or dry. The bright lamellar thickness increase from dry to wet supports the hypothesis that bright lamellae contain a higher quota of mucopolysaccharides, which tend to expand with moisture, and that the bright collagen bundles (see sections 4.5-4.7) in the bright lamella tightly encircling dark lamella impede expansion. The length of the whole osteon is significantly less when dry.

Isolation of Dark and Bright Lamellar Specimens

The invention provides a new technique, which allows isolation of both dark and bright lamellar specimens. Previously, Ascenzi A. et al. (1982) isolated specimens of dark lamellae by a technique that cannot be applied to bright lamellae. Here, two lamellar types are examined and compared through and across their flatten cylindrical surface. Lamellar collagen bundle orientations and hydroxyapatite patterns were observed by means of three different methodologies (Ascenzi M.-G. et al., 2003). These are: circularly polarizing microscopy, confocal microscopy, and the X-ray diffraction. Confocal microscopy and small-angle X-ray diffraction were employed for the first time on lamellar specimens. The three methodologies yield well-matched results even though the oblique collagen bundles of dark lamellae observed under polarizing light were not observed by the other two methods.

Method. The rotating-saw microtome described was employed to cut longitudinal segments approximately 30 mm long from the femoral mid-shaft. The segments were then sliced in thin (70-100 μm) transverse sections of desired thickness. A micro-X-ray of each section was prepared to allow identification (Amprino and Engström, 1952) of required osteon degree of calcification. Fully calcified osteons were selected for this study. On the section, a trapezoid was cut with the dental drill described above around each chosen alternate osteon specimen (FIG. 24). For osteon immobilization during lamellar isolation, a portion of the bone material inside the trapezoid away from the osteon was glued to a slide. The dark and bright lamellae at the periphery of each osteon were dissected wet with a razor-sharp microtome blade, obtained by filing a steel needle. Because it is necessary to hold the bone during isolation, the whole lamella with exclusion of a little tract was isolated. In some instances, to improve the microscopic examination of particular aspects of the collagen layers of the free surfaces, specimens of both lamellar types were delicately scratched with the needle for micro-dissection. To avoid fracture formation during straightening of each lamellar specimen, the operation is performed gently on wet specimens while under direct visualization with an optical microscope. The selection of external lamellae, of lesser curvature than internal lamellae, decreases the risk of fracture formation during flattening. The difficulty of applying this free-hand micro-dissection to obtain regularly dissected and discontinuity-free specimens is evidenced by the fact that approximately only 1 out 3 specimens successfully complete the procedure.

Circularly Polarizing Light Microscopy on Dark and Bright Lamellae

Dark (bright, respectively) specimens are composed of longitudinal (transverse, respectively) and oblique up to ±45° collagen bundle orientations.

Method. 102 dark and 110 bright lamellar specimens were examined with a Laborlux Leitz equipped for polarizing light. A Zeiss laser scan microscope equipped with argon ion and helium-neon lasers was used to locate the structures of interest and to obtain digital images, respectively. These last were archived on a hard disk and subsequently transferred to a film. To increase the digital image fluorescence, structures of interest were stained with a diluted solution of eosin. For result verification, a few 1-2 μm thick section were cut at a slight angle with respect to the transverse plane from decalcified bone embedded in paraffin. The lamellae appeared better separated than in the cross-section and consequently better resolved optically. After staining with eosin the sections were observed under a fluorescent microscope.

Figure 31:
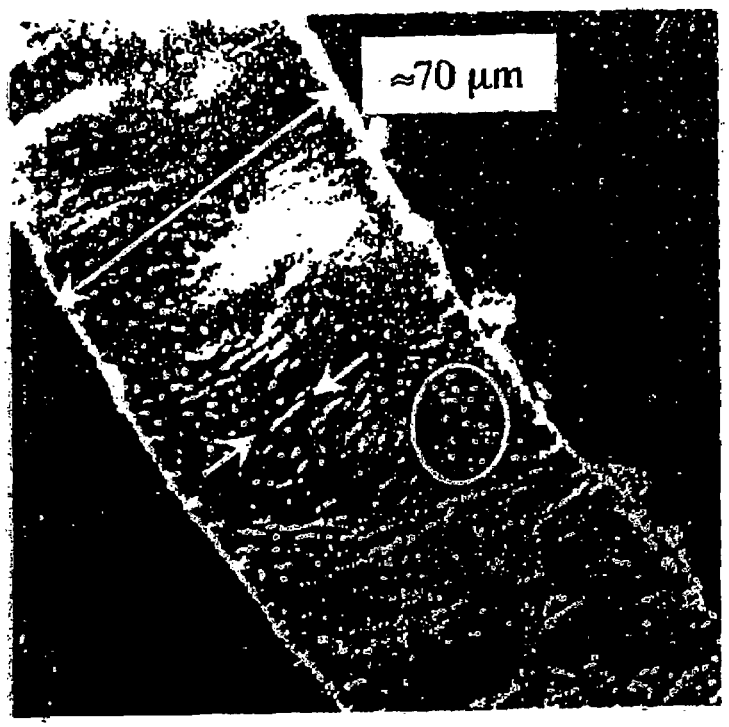
FIG. 31. Confocal microscopy detail of isolated and flattened dark lamella. Opposed arrows show the orientation of a collagen bundle arrangement perpendicular to the lamella edge. Cut radial collagen bundles appear as dots within the circle.
Figure 32:
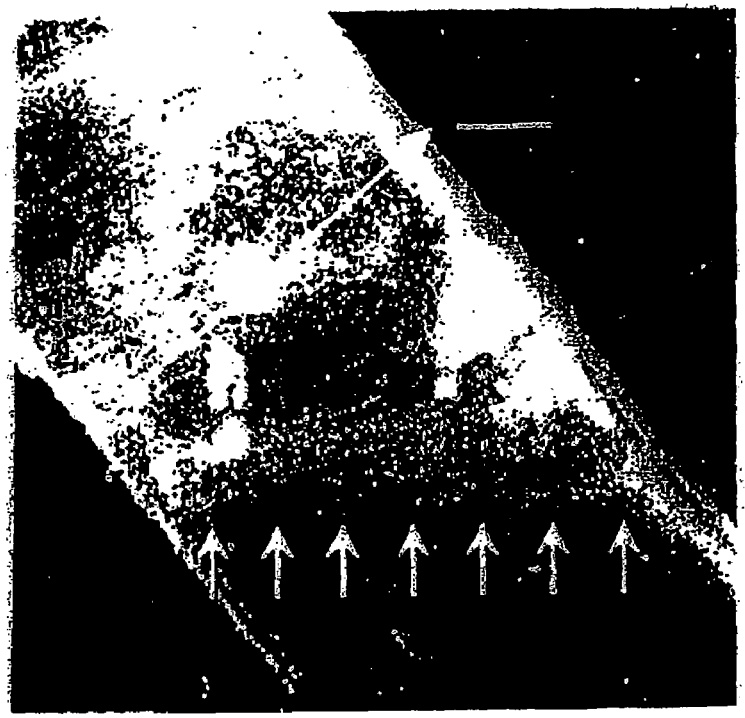
FIG. 32. Detail of isolated and flattened bright lamellar sample as viewed by confocal microscopy. Arrows indicate oblique bundles extending across the lamella thickness.

Results. When a wet lamellar specimen is observed through its flattened cylindrical surface under a polarizing microscope, its features change in relation to the lamellar orientation with respect to the polarizing planes of the two Nicol's prisms. When the long edge of the dark lamellar specimen is oriented at 45° (0°, respectively) with the polarizing plane, collagen bundles run perpendicularly (obliquely at ±45°, respectively) to the long edge of the specimen. When the long edge of a bright lamellar specimen is oriented at 45° (0°, respectively) with the polarizing plane, collagen bundles run parallel (obliquely at ±45°, respectively) to the long edge of the specimen (FIGS. 31 and 32). The distribution of the collagen bundles appears homogeneously distributed except at some points of the oblique bundle distribution. Such discontinuities may really exist or be due to artificial removal of bundles during dissection or be due to optical elision of superimposed orthogonal bundles. Collagen bundles reveal intermediate orientations at intermediate orientations of the lamellar specimen with the polarizing plane.

Confocal Microscopy on Dark and Bright Lamellae

Dark (bright, respectively) specimens are composed of longitudinal (transverse and oblique at approximately ±45°, respectively) collagen bundle orientations. Collagen bundles that follow the osteocyte process are observed to run across layers of longitudinal collagen bundles. Confocal microscopy allowed observation of collagen orientations without overlap and of the ground substance between unidirectional areas of collagen bundles. Observation of collagen bundle direction and proximity points to the appropriateness of a biochemical analysis to quantify collagen and mucopolysaccharides in longitudinal and alternate osteons. Observations of collagen bundle direction provide information on the osteon structure. According to the invention, oblique collagen bundles of dark lamellae are observed by confocal microscopy or by polarizing microscopy.

Methods. 3 dark and 3 bright lamellar specimens were isolated as described in section 4.4 from nominal 70 μm thick transverse section. Square areas of up to 50×50 μm were scanned wet every 1 μm in the thickness direction by a Leitz confocal microscope. Since the natural fluorescence of wet bone worked well with the confocal microscope, no staining of the specimen was necessary. The photomultipliers detect light intensity and not color; red was chosen to be applied to the image.

Results. The dark lamellar specimens show a regular arrangement of collagen bundles (FIG. 31). From one border to the other, the collagen bundles are parallel to the osteon axis. Each dot is the cut radial collagen bundle that follows the osteocyte process. On bright lamellar specimens, transverse and oblique collagen bundles were evidenced with more space between bundles than in dark lamellae (FIG. 32). Such finding suggests a lower concentration of collagen. The confocal microscope allows discrimination of unidirectional areas of collagen bundles of various directions. This observation appears to be new, not elsewhere reported in the literature. The observation of collagen longitudinal and transverse bundle directions confirms Gebhardt's model. The bright lamellar specimens show ample areas of ground substance between collagen bundles, parallel and oblique to the flat lamellar borders. The larger areas of ground substance suggest a higher concentration of mucopolysaccharides in bright rather than dark lamellae. These findings support the hypothesis that, at the same degree of calcification, alternate osteons contain a greater concentration of mucopolysaccharides than longitudinal osteons. Whether the low amount (less than 1%) of mucopolysaccharides will show a significant difference between osteon types at the same degree of calcification, as predicted remains to be determined, e.g., through observation of dark lamellae by confocal microscopy.

X-Ray Diffraction on Dark and Bright Lamellae

Lamellar specimens which appear dark and bright, respectively, in cross-sections were investigated by Small- and Wide-Angle X-ray diffraction (SAXS and WAXS, respectively) for collagen and hydroxyapatite crystallite pattern orientations. Collagen bundle orientations and hydroxyapatite patterns differ between dark and bright lamellae and follow analogous patterns within the same lamellar type. These results further support Gebhardt's model. Such observations provide information on the osteon structural variables underlying the computerized osteon specimen model.

Methods. Thirteen fully calcified dark and 13 bright lamellar specimens were isolated and flattened, as described above, from 70 µm thick transverse sections. The dental drill with water cooling allowed preparation of 2 radial hemisections and 2 transverse sections. This investigation was designed to check the hypothesis of collagen and hydroxyapatite pattern differences between dark and bright lamellae. SAXS and WAXS lend themselves well to such studies because SAXS is indicative of collagen orientation through the "staining" of the collagen bundles by the hydroxyapatite crystallites while the WAXS is indicative of hydroxyapatite pattern orientation (but not the orientation of single crystals). The direction of the incident beam was chosen parallel (at 45°, respectively) to the lamellar width in dark (bright, respectively) lamellae to investigate patterns parallel (oblique at approximately ±45°, respectively) to the osteon axis (FIG. 33).

SAXS and WAXS diffraction patterns were recorded using the scanning diffractometry setup of the ID13 microfocus beamline of the European Synchrotron Radiation Facility (Grenoble, France). The beam wavelength of 0.964 Å was obtained with a Si(111) monochromator and focused to 7 µm (full-width at half-maximum) by a glass capillary. The sample was scanned through the beam by a computer controlled x/y gantry. Intact scales, as well as portions of scales were mounted on a goniometric head, with the surface of the scale orthogonal to the X-ray beam. Square areas of up to 50×50 µm were scanned with spatial resolutions of 5 µm and 10 µm. Diffraction patterns were recorded while moving the sample along the horizontal and vertical axes. Also, some horizontal and vertical linear scans were performed with spatial resolutions from 5 to 20 µm. Small and wide angle patterns were recorded sequentially on the same area by changing the sample-to-detector distance. The diffraction patterns were recorded with a MARR CCD detector with exposure times of 10 and 30 sec for wide and small angle respectively. The detector features are: 2048×2048 pixels, 64.45 µm×64.451 µm; 16 bit readout. The thin radial hemisections and transverse sections of fully calcified alternate osteons were investigated at various angles with respect to the incident beam used for verification of results.

Results. A first examination of the experimental images shows the following. The SAXS images of dark lamellae are unchanged in shape within scanned areas, evidencing one preferential orientation of collagen bundles (FIG. 34). A clear arching of the small-angle meridional reflection, which corresponds to the third-order collagen periodicity, is indicative of collagen orientation with respect to the osteon axis.

Figure 35:
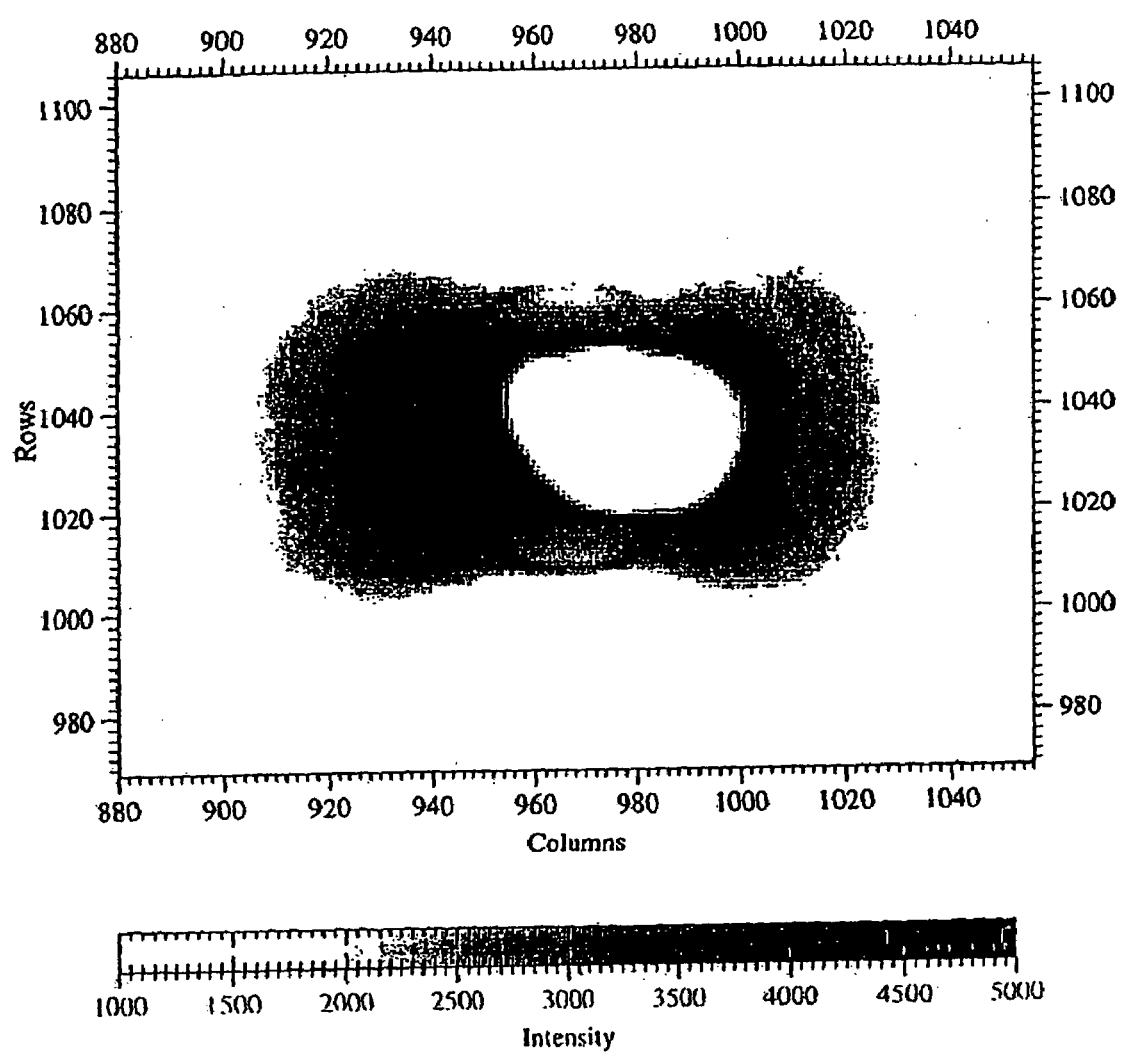
FIG. 35. Enlargement of one SAXS image from FIG. 9. Clear arching and maximum intensity orientations show single preferential collagen bundle direction perpendicular to bright lamellar width.

The arching shows no change within and across the scanned areas with intensity preferentially distributed in one direction, indicating a single preferential collagen bundle direction. Moreover, the position of the maximum intensity oriented perpendicularly to the bright lamellar width and the arching of the small-angle meridional reflection parallel to the bright lamellar width are indicative of collagen bundle orientation parallel to the osteon axis (FIG. 35).

Figure 36:
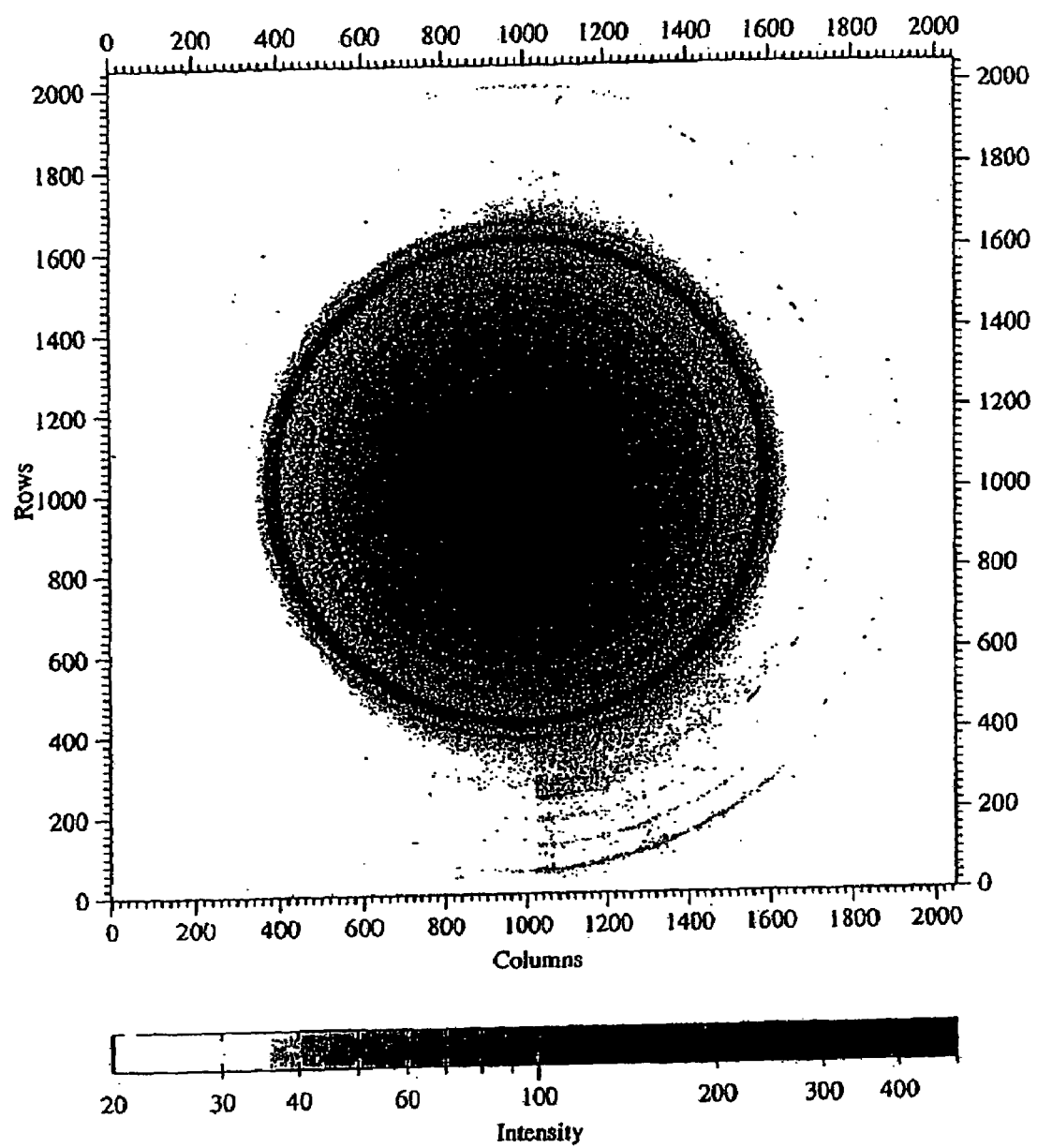
FIG. 36. WAXS image of the scanned location of the FIG. 10 SAXS image. Clear preferential orientation of the 002 reflection parallel to the dark lamella width shows single preferential collagen bundle direction perpendicular to bright lamellar width.
Figure 38:
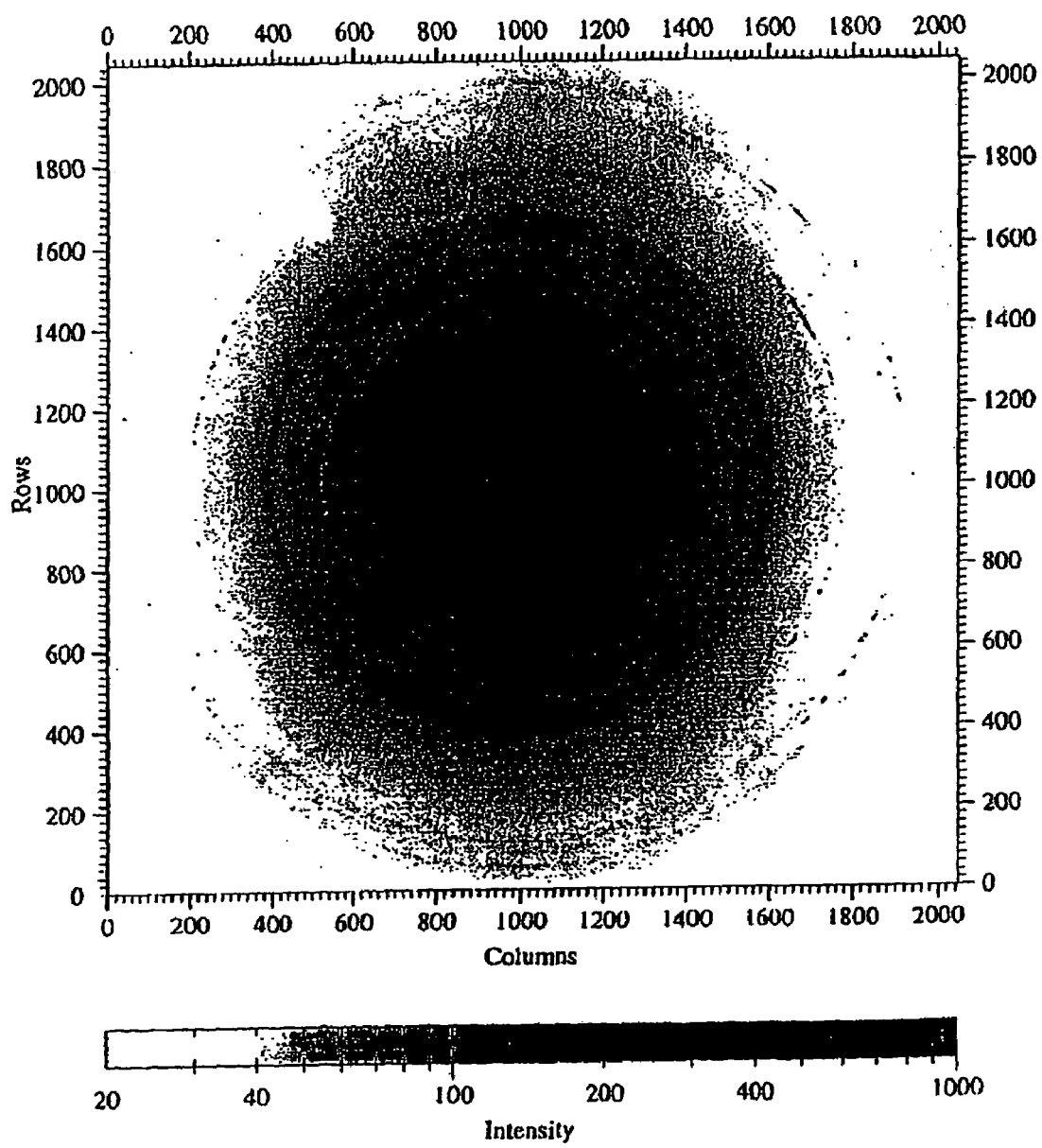
FIG. 38. WAXS image of a bright lamella scanned location, which shows lack of preferential orientation of the 002 reflection.

The WAXS images of dark lamellae show a consistent preferential orientation of the 002 reflection parallel to the bright lamellar width, which indicates one preferential orientation of hydroxyapatite patterns along the osteon axis (FIG. 36). In contrast, the SAXS images of bright lamellae change in shape (intensity and inclination) within scanned areas, evidencing one or two preferential orientations of collagen bundles at ±45° lamellar width direction (FIG. 37). Therefore, bright lamellae contain areas with oblique collagen bundles, at approximately ±45° with the osteon axis. The arching of the SAXS meridional reflection is unclear on bright lamellar specimens. It is therefore indicative of a lack of specific collagen orientation. The WAXS images on bright lamellae show a preferential orientation of the 002 reflection at 45° with respect to the lamellar width direction in only some areas (FIG. 38). This indicates the local presence of hydroxyapatite orientation oblique to the osteon axis. The lack of consistent preferential orientation of hydroxyapatite patterns suggests a higher directional disorder in comparison with dark lamellae. Note the consistency of the results for collagen bundles and hydroxyapatite patterns, which support the similarity of patterns between collagen and hydroxyapatite. Experimental images are currently being examined for differences in hydroxyapatite density between the two lamellar types.

EXAMPLE 6

Computerized Geometric/Structural Osteon Model

Similar to Example 4, this Example provides a viscoelastic model for osteons based on modeling of experimental data. Osteon specimens are prepared for subjection to dynamic torsional loading and biochemical analysis. Such tests yield viscoelastic properties and the relative percentages of collagen and mucopolysaccharides. The results obtained forms the basis for a computerized geometric/structural osteon model, that simulates the formation and propagation of fractures observed in the loaded specimens. The study is described by the following flow chart:

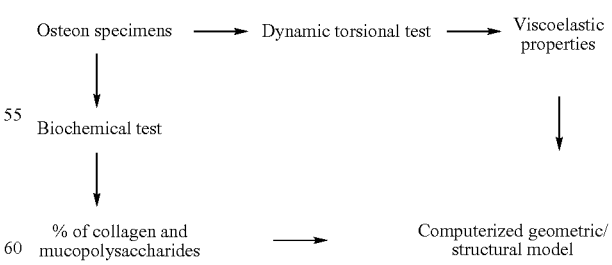

Osteon Specimen Preparation and Selection

Because of the rigorous criteria for the selection of osteon specimens (such as the haversian canal and specimen cylindrical surface being coaxial), only about 1 out of 25 specimens isolated may be eligible for mechanical testing.

For mechanical and chemical experiments, the bone material specifications and specimen preparation techniques are conducted according to the specification. Initial and final stages of calcification, as evidenced by micro-X-ray (Amprino and Engstrom, 1952), are chosen for the longitudinal and alternate osteon specimens. The type, whether longitudinal or alternate, of the specimen can be assessed only after loading by observation under polarized light a thin cross-section cut from the specimen with the dental drill. In fact, because the thickness of the transverse bone section is slightly larger than the osteon mean diameter, concentric lamellae overlap, thereby reducing or precluding the visibility of dark lamellae, and leaving open the possibility that an alternate osteon may have a bright appearance. The osteon types can be identified after mechanical testing by cutting a 100 µm cross section with the dental drill and examining it under polarizing light. Therefore, for the mechanical investigation proposed, it is necessary to prepare between 2,700 and 3,000 specimens to obtain 120 specimens (30 osteon specimens per osteon type at initial and final stages of calcification) which will satisfactorily complete the procedures adopted for loading under torsion at low and high strain rates.

For the biochemical analysis, specimens with the same geometric and structural characteristics are prepared. The procedure is considerably more expeditious but requires more specimens. The specimens for biochemical analysis are isolated from 500 µm thick transverse sections using the technique of Ascenzi A. and Bonucci (1968). In this technique, no lugs are necessary and the type of a 500 µm long osteon specimen can be easily recognized on transverse sections (FIG. 22). Osteons, whose canal of 40±3 µm runs perpendicular to the transverse section, are measured before isolation in terms of thickness of bright and dark lamellae on both sides of the section (see section entitled "Thickness Variation Within Dark and Bright Lamellae"). The number of bright and dark lamellae is counted at both sides of the section by the imaging system. Osteons whose distributions in terms of thickness and number of bright and dark lamellae match those of mechanically tested osteon specimens are selected for isolation. The dental drill is used to isolate cylindrical osteons specimens with a 210±3 µm outer diameter by cutting with an off-center tip along a circle. In fact, when the rotating axis of the needle is perpendicular to bone section surfaces, i.e. its axis coincides with the osteon axis, the tip of the needle cuts an osteon specimen of cylindrical shape with walls of uniform thickness. After isolation, the length and diameter of each specimen is checked by means of an eyepiece micrometer. Further, the Haversian canal is cleaned out by inserting a metal rod slightly (45 µm, approximately) thicker than the Haversian canal. It is necessary to isolate approximately 100 osteon specimens (FIG. 25) per osteon type at initial and final stages of calcification to have sufficient material volume for each of the two biochemical analyses.

Because of the different technical requirements of the mechanical testing and the biochemical analyses, the test specimens for each come from separately prepared groups of osteon specimens. The two groups consists of osteon specimens isolated from each region of the same mid-diaphyseal section of the femur in the same proportion. The strictness of the criteria for specimen selection and preparation ensures homogeneity between the two specimen groups.

Mechanical Testing

Once osteon specimens are prepared as described above, wet osteon specimens are tested under monotonic torsional loading. A micro-torsimeter as described above is employed, using direct visualization of the specimen with a stereo microscope during the loading sequence. The osteon specimens are loaded until rupture at constant low ($10^{-2}$) and high (10 sec$^{-1}$) strain rates.

For the proposed experiments the torsimeter is modified for attachment to an MTS 612 servohydraulic testing machine. The fixed stock of the torsimeter incorporates a reaction torque sensor (5 oz-in capacity). The drive shaft is modified to incorporate a bowstring arrangement to convert the linear actuator displacement to angle of twist. The base of the torsimeter is rigidly mounted to centralize the actuator axis with the bowstring arrangement. Ramp loadings of $10^{-2}$ mm/sec and 10 mm/sec is used to apply torque to the specimens. All the specimens are taken to failure.

The resulting output is a plot of torque versus angle-of-twist recorded in real time. A direct dependency of the torque's slope versus angle-of-twist curves is observed on the loading rate (see also previous Examples demonstrating a significant creep effect). The experimental diagrams are graphs of increasing functions of the angle-of-twist, which show a concave downward shape, regardless of the osteon type and the degree of calcification. From considerations on dynamic behavior and osteon collagen make-up, the diagrams are steeper and less concave for the high (rather than low) strain rate, independently of osteon type and degree of calcification; for low strain rate (rather than the quasi-static condition of Ascenzi A. et al., 1994), independently from the osteon type at the final degree of calcification; for the osteon specimens at the final (rather than initial) degree of calcification, independently of osteon type, for any fixed strain rate; and for the longitudinal (rather than alternate) osteon specimens, independently of degree of calcification, for any fixed strain rate.

After the mechanical testing, osteon specimens are examined under an optical microscope under both regular and fluorescent light (Huja et al., 1999) to assess fracture patterns. At low strain rates, a distortion of the lamellar structures in the areas under compression is observed (McElhaney and Byars, 1965). No cross-lamellar or cross-osteonal cracks occur because they have not been observed in macroscopic specimens. That outer lamellae are involved in the fracture process is tentatively explained by the decrease in hydroxyapatite present in the osteons as one proceeds from the vascular canal to the outer wall (Rho et al., 1999). In both osteon types the fracture agrees with the observations of Jepsen et al. (1999) that fracture in macroscopic specimens is ductile and that fracture alters bone's viscous behavior. In particular, relaxation increases with the increasing extent of fractures. Consequently, viscous effects in osteon specimens can increase with the increasing extent of fracture. The transition of the shape of our osteon specimens from a circular to a square cross-section suggests a stress concentration effect at the junction of the cylindrical portion with the rectangular lugs situated at the ends. Therefore, fractures can begin at the end of some specimens earlier during loading than would otherwise be expected.

Further, at a fixed strain rate, longitudinal and alternate osteons differ with respect to fracture patterns. This results from the following combination of general considerations on torque with previous results on osteons. On one hand, application of torque to a body can be viewed as internal tensile and compressive stresses using a judicious choice of material element orientation. The tensile and compressive stresses act approximately at a 45° angle to the longitudinal axis of the body. If a material is weaker in a longitudinal orientation than in transverse shearing, the first cracks arise from axial shearing stresses and appear in a longitudinal direction. However, if the material is weaker in tension than in shear, it usually cracks along a spiral course inclined at a 45° angle to the long axis of the body (Timoshenko and Young, 1940). On the other hand, Ascenzi A. et al. (1967 and 1972) found that at the same degree of calcification longitudinal osteons are weaker in longitudinal than in transverse shearing, while alternate osteons are weaker in tension than in shear. Therefore, in longitudinal osteons the fracture is expected to start somewhat longitudinally, between collagen bundles. Therefore, it can deviate once or twice at the beginning of the fracture and be soon followed by a smooth crack advancing rapidly across the osteon to possibly end in the vascular canal. As torque increases, collagen bundles between cracks are expected to break and cracks coalesce to create one or more predominantly longitudinal cracks. Deviations causing a dentate profile may form due to the viscoelastic, strain rate sensitive collagen and mucopolysaccharides. Such a dentate profile is therefore be more evident at low (rather than) high strain rate and at the initial stages of calcification when the osteons are richer in mucopolysaccharides. In alternate osteons, cracks spread obliquely by following the weak interfaces of lamellae. The transverse and oblique collagen bundles may break before the longitudinal ones as the osteon section enlarges. In this instance, cracks spread through lamellae less rapidly than in longitudinal osteons, as explained by the crack propagation control, characteristic of composite materials (Cook and Gordon, 1964). Once the crack breaks through transverse and oblique bundles, it propagates faster straight through the vascular canal. A long crack shows an oblique orientation between upper and lower extremities. In alternate osteons at initial stages of calcification the cracks may start at a higher value of torque and propagate more slowly than at the final stages of calcification if the percent of mucopolysaccharides is higher.

After observation of fracture patterns, the specimens are measured in length and diameter. After lug removal, the alternate osteons are sectioned and examined to assess the collagen bundle arrangements. At that point, longitudinal and alternate osteon specimens only are included in the investigation. The dark and bright lamellae of longitudinal and alternate osteons are counted and measured in thickness under polarizing light. Such values are comparable to the ones obtained by Ardizzoni (2001) by a different method. The knowledge of number and thickness of lamellae within mechanically tested specimens is necessary to prepare for the biochemical analysis sets of specimens with same distributions of lamellae.

Biochemical Analysis

A portion of the osteon specimens, prepared and selected as described above are subjected to chemical analysis. Spectroscopic techniques and video microscopy are used to study intermolecular interactions in phase transitions. These spectroscopic techniques, coupled with chromatographic separations, are critical in the biochemical analyses. Collagen (as hydroxyproline) and mucopolysaccharides (as hexosamine) is assessed on 150 µg amounts of longitudinal and alternate osteons at initial and final stages of calcification. While it is difficult to quantify small quantities precisely, the uncertainty does not affect the comparative conclusions to be made (Herring, 1972).

Osteon specimens are dried to constant weight in a vacuum desiccator over $P_2O_5$. Since decalcification of osteons is necessary to quantify hexosamine and hydroxyproline, acid hydrolysis is used. Residual HCl is removed before the assays are performed. Hydrolysis products are separated using refined chromatographic techniques as first described by Exley (1957). Hexosamine is determined spectroscopically essentially according to the procedure of Elson and Morgan, (Exley 1957) as modified by Oguchi et al. (1979). The methodology is refined to eliminate the possibility of interference from amino acids and mineral salts (Pugliarello et al., 1970). Hydroxyproline is determined, essentially according to the procedure of Serafini-Cessi and Cessi (1965), as later refined by Teerlink et al. (1989).

The biochemical analysis has been performed successfully (Pugliarello et al., 1970) on osteon specimens at initial and final stages of calcification, without regard to osteon type. Moro et al. (2000) have employed on rat bone a technique refinement that can be applied to osteons. Collagen and mucopolysaccharides percentages are significantly lower in longitudinal rather than alternate osteons. In fact, alternate osteons contain more collagen and mucopolysaccharides than longitudinal osteons at equal degrees of calcification, because alternate osteons contain bright lamellae, which are richer than dark lamellae in collagen and mucopolysaccharides. The mucopolysaccharides percentage decrease, as the degree of calcification increases, is statistically significant (non significant, respectively) in alternate (longitudinal, respectively) osteons. In fact, mucopolysaccharide percentage needs to decrease in osteons, regardless of the osteon type, for the degree of calcification to increase. The resulting collagen and mucopolysaccharides percentages for longitudinal (alternate, respectively) osteon specimens is lower (higher, respectively) than the values found by Pugliarello et al., 1970) regardless of the osteon type. The means of collagen and mucopolysaccharides percentages is combined with the mean number of dark and bright lamellae in longitudinal and alternate osteons to yield the mean percent of collagen and mucopolysaccharides within dark and bright lamellae, at initial and final stages of calcification.

The Two Way Analysis of Variance is applied to the means of the collagen and mucopolysaccharides with osteon type (longitudinal or alternate) and degree of calcification (initial or final) as factors. If normality lacks, the 2-way ANOVA is applied to the means of the logarithms. Significance is set at 0.05. The Post hoc Student-Newman-Keuls test identifies the significant factors. The biochemical analysis shows: a statistically significant higher percent of collagen and mucopolysaccharides in alternate rather than in longitudinal osteon specimens at equal stages of calcification; a statistically significant higher percent of collagen and mucopolysaccharides in bright rather than in dark lamellae at equal stages of calcification; and a statistically significant (not significant, respectively) decreasing amount of collagen and mucopolysaccharides as the degree of calcification increases in alternate (longitudinal, respectively) osteon types.

Any discrepancies or unexpected results may be of two types. Either an expected difference is an actual no difference or the difference is reversed. The actual results are examined in relation to the observed mechanical behavior through the computerized model, which is implemented with the actual chemical percentages. For instance, an actual no difference result of an elementary component percentage between two specimen group can mean that such elementary component does not contribute to a difference in mechanical behavior between such groups.

Analysis of Mechanical Diagrams

The observation of the experimental diagrams assesses elastic modulus and the ultimate strength. For each experimental diagram, the constitutive equation, which relates stress, strain and their time dependencies, is established in terms of the Ramberg-Osgood equation:

$$\theta = Tc\left(\frac{d\theta}{dt}\right)^d + aT^N\left(\frac{d\theta}{dt}\right)^b$$

where θ and T denote angle-of-twist and torque respectively; a, b, c, d, N denote constant values that depend on the material properties, with a, b, c≧0 and d≦0. This equation has accurately fitted the response set at various strain rates of a wide range of tested engineering materials (Hight and Brandeau, 1983). This is because on one hand the geometric shape of the experimental diagrams changes only moderately as the strain rate varies. On the other hand, the Ramberg-Osgood equation is a simply formulated polynomial whose coefficients are functions of the strain rate, which describes the relatively simple geometric shape of the experimental diagrams, i.e. an increasing function graph, that passes through the origin and is concave down.

The determination of the constants a, b, c, d and N follows the procedure used by Hight and Brandeau (1983) for macroscopic compact bone specimens. The Ramberg-Osgood equation suffices to produce a good fit (measured by an $r^2$ of 0.98-0.99) because the viscoelastic behavior of a single isolated osteon specimen is less complex than that of macroscopic specimens. In cases where the Ramberg-Osgood equation does not produce a good fit, increasingly more complex differential equations can be employed, starting with more complex polynomials and rational functions of T whose coefficients depend on the strain rate. Linear-viscosity is obtained (Frasca et al., 1977) at least for physiological strains. If the Ramberg-Osgood equation provides a good fit and linear-viscosity is present, the coefficients a, b, c, N equal 0, 1, 0, 0, respectively. The approximating function of each experimental diagram serves to compute the viscoelastic modulus as the derivative of the diagram approximating function at zero strain and the energy absorption capacity as the area under the approximating curve.

The 2-way ANOVA is applied to the means of the elastic and viscoelastic moduli, ultimate strength and energy absorption with osteon type (longitudinal or alternate) and degree of calcification (initial or final) as factors for each strain rate. If normality lacks, the 2-way ANOVA is applied to the means of the logarithms. Significance is set at 0.05. The Post hoc Student-Newman-Keuls test identifies the significant factors. Significant differences are obtained in elastic and viscoelastic moduli, ultimate strength, and energy absorption capacity with regard to the following: higher values at the final stages rather than at the initial stages of calcification, regardless of osteon type and the strain rates; higher values for longitudinal rather than alternate osteon specimens, regardless of degree of calcification and the strain rate; higher values for longitudinal rather than alternate osteon specimens, regardless of degree of calcification and the strain rate; smaller increase in value for longitudinal rather than alternate osteon specimens, as the strain rate increases, regardless of degree of calcification; and increase in values with increasing strain rate, regardless of osteon type and degree of calcification.

Geometric/Structural Osteon Specimen Model

The osteon specimen model fits the mechanical behavior of the osteon specimen to that of its ultrastructural components. Therefore, the model is based on the mechanical diagrams' approximating functions, angle-of twist as function of torque, and the relative percentages of the ultrastructural constituents, as obtained from the biochemical analysis. This osteon specimen computerized model allows for the concomitant incorporation of elementary component percentages and orientations, and their role during visco-elastic and plastic phases. The model allows for simulation of the fracture propagation observed in the mechanically tested specimens. In particular, the model sheds light as to the processes within the osteon specimen of micro-cracking, de-bonding, pore growth and components' breakage, which result in fracture patterns.

The model's crucial parameters are assessed from the specimens employed for mechanical and chemical analysis. Other important parameters, i.e. collagen bundle and hydroxyapatite pattern directions and bright lamellar pre-stress, have been investigated in large numbers (on the order of a few hundreds so as to cover the biological variability of osteon structures). Additional parameters, i.e. dimensions and distribution of canaliculae and lacunae, viscoelastic properties of collagen and mucopolysaccharides, collagen bundle diameter, and elastic properties and density of hydroxyapatite have not been assessed in specimens and are addressed by treating them as parameters which vary, within ranges consistent with lamellar structures, around available values from the literature. The ranging of such additional parameters accordingly serves to model different scenarios.

Material science implies that some of these parameters of a fiber reinforced laminated model have a role (perhaps minor) in the modeled comparative behavior of the two osteon types. For instance, the presence, relative distribution and density of canaliculae and lacunae affects the fracture simulation patterns, rather than the particular dimension or position of a canalicula or lacuna. Accordingly, the parametrized model of the invention allows for different values of the parameters, either exclusion of canaliculae and lacunae altogether or variation in porosity distribution. Since there is no evidence of difference in the literature between osteon types with respect to viscoelastic properties of collagen and mucopolysaccharides, and elastic properties of hydroxyapatite, their parametric values are kept constant across the two osteon model. Such parametric values are less relevant because of the comparative nature of the model. The starting parametric values of the hydroxyapatite density follow any relevant findings from a complete examination of X-diffraction results and indications from the literature. The initial parameter value for collagen bundle diameter measurement may be obtained from the literature and is kept constant across the osteon types.

The geometric model of the osteon specimens before mechanical testing consists of a hollow cylinder with coaxial lateral surfaces. Its internal diameter, external diameter, and height equal 40 μm, 210 μm, and 500 μm, respectively. Each such hollow cylinder presents pores, as shown in FIG. 26. Pores in the model will include haversian canal, canaliculae and lacunae, and the starting parametric value of the total osteon volume (Piekarski, 1970) is set equal to 20%.

The material model of each of the longitudinal and alternate osteon specimens before mechanical testing consists of a laminate whose length, width, and height correspond to the cylinder circumference, thickness, and height, respectively (FIG. 27). The layers are unidirectional fiber-reinforced laminae. The matrix represents a mixture of hydroxyapatite and mucopolysaccharides. The fibers represent collagen. The three materials that make up matrix and fibers are each treated as homogeneous and isotropic. Both matrix and fibers are considered as viscoelastoplastic. The fibers are assumed to be circular in cross-section and randomly distributed in the transverse plane. The longitudinal and alternate osteon models consist of laminae whose number and thickness will equal the mean of the lamellar number and thickness of the tested specimens. The lamina with fiber inclination γ is named γ-lamina. The values of γ will follow the results of the studies described above, so as to include and exclude, respectively, oblique fibers in the laminae modeling dark lamellae. The initial parametric value for the fiber (modeling collagen) diameter is set at 800 Å. The relative percentages of collagen and mucopolysaccharides at initial and final stages of calcification, is quantified by the biochemical analysis. The initial parametric percentage of hydroxyapatite at the highest degree of calcification is set to 40% of the lamina volume without pores (Bonfield and Li, 1967). The initial parametric hydroxyapatite volume is set 10% higher in the dark lamellar than in the bright lamellar model (Marotti et al., 1994). The initial parametric values that describe the elastic properties of the hydroxyapatite equal the findings of Katz and Ukraincik (1971). The initial parametric values that describe the viscoelastic properties of the fibers, which model collagen, equal the findings of Currey (1959) and Haut (1983). No information is available in the literature in reference to the viscoelastic properties of mucopolysaccharides. Viscoelastic parametric values are deduced from similar substances. Little information is available regarding the fluids within the pores incorporated in the microstructure. Initially, the model, by assignments of minimal material property values, disregards the structural effects of the fluid within these pores. This form of the model is then be exercised parametrically to include fluid within the pores with various bulk moduli.

The starting number of elements for the Finite Element Analysis is in the order of 618,137. This was computed by the use of brick elements of dimensions averaging 3 μm to have elements comparable to lacunae in volume. The element mesh is refined to achieve convergence of the solution. For any given value of the experimental torque, a computer program based on Montecarlo simulation is written to compute stress, strain, and phase deformation distributions. Since strain is chosen as the criterion for osteon fracture (Piekarski, 1970), the strain within each element is compared to the yield strain provided by the literature. If cracks appear to initiate at the matrix-fiber interface, an appropriate failure criterion (e.g., Von Mises, Tresca) is included. The increased probability of fracture in the neighborhood of an already fractured element is considered using the concept of stress enhancement factors. The model is verified by checking that the osteon model simulates the osteon quasi-static behavior (Ascenzi A. et al., 1994) and the specimens' dynamic fracture patterns.

The model can evidence the following experimental observations on fracture propagation by various authors. Fractures start at a weaker point of the bone structure (Carter et al., 1981). 3 to 4 small cracks form in the organic phase which yields and/or buckles and in hydroxyapatite, which pulls and makes the cracks spread at the weak interfaces between two outer lamellae (e.g. Piekarski, 1970; Simkin and Robin, 1974). Lacunae' size precludes them from acting as fracture initiators until or unless plastic deformation has created cracks at the tip and thereby extended them to the critical length for spontaneous fracture. At the front of the propagating crack, the large strains, which may be accommodated by the organic phase, contribute to the dissipation of energy. Microcracks form ahead of the advancing fracture line. The areas containing transverse and oblique collagen bundles can show slow propagation of cracks to allow for the area to absorb a large amount of energy. Slow propagation is essentially a pull-out type mechanism, that is, hydroxyapatite crystallites would be pulled out of the collagen by shear failure at the fiber-matrix interface. The rapid propagation of cracks in areas containing approximately vertical collagen bundles would allow for very low energy absorption. This should be compatible with larger areas under the experimental graphs of alternate osteons. The propagating crack avoids discontinuities (Piekarsky, 1970), hence increasing its length. Crack propagation is arrested by the presence of canaliculae and lacunae. In the case where the crack enters a discontinuity, its front is blunted, hence reducing the stress concentration factor and slowing crack propagation. When a crack is forced to enter the vascular canal, the radius at the tip of the crack becomes larger. Lacunae are more likely to act as stress concentrators than canaliculae because of their ellipsoidal cross-section. Since porosity acts as a crack arrester, porosity may contribute to increase bone's robustness (Currey, 1962) rather than increase its tendency for brittle fracture. Hydroxyapatite crystallites can be pulled out from collagen around canaliculae.

The proposed model simplifies the osteon structure; in particular: exclusion of partially calcified collagen bundles (Ascenzi A. et al., 1965) because they are not yet well understood in terms of structure; assumption of no difference in collagen mechanical properties between dark and bright lamellae because no evidence is currently available and material science points to differences in fiber bundle directions as primarily responsible for structural differences; assumption of no difference in dark and bright lamellae, separately, between longitudinal and alternate osteons because there is no evidence of difference and no lamellar isolation technique is available for longitudinal osteons; and assumption of constant lamellar thickness within any given osteon lamellae, for simplicity.

EXPERIMENTAL DESIGN OF EXAMPLES 7-14

The experiments of Examples 7-14 described herein were designed to resolve the conflicting views on the ultrastructure of bone, in particular lamellae, and to investigate whether the mechanical response of single lamellae to tensional loading can depend on the lamella's morphology with respect to as collagen bundle orientation and density distribution.

For this purpose, the following study outline was prepared:

(1) Fully calcified isolated lamellae, distinguished according to their appearance as either bright or dark under transverse polarized light, will be investigated by confocal microscopy. Domains, i.e., regions of essentially unidirectional collagen bundles, are identified. Measurements include dimensions of domains and of spaces between domains, and collagen bundle direction and density within domains.

(2) Specimens of lamellae of the same specification of those undergoing confocal examination are tested in distinct orthogonal directions to determine differences in structural response as a function of loading direction. This is accomplished using precision controlled quasi-static tensional testing.

These measurements increase the understanding of the constituent make-up of bone at the single lamella level and provide a prospective on the influence that this make-up has on the lamellar mechanical behavior. A numerical model of the fully calcified osteonic lamella that accurately reflects the characteristics of geometry, distribution and orientation of its components, yields a realistic simulation of the quasi-static tensional behavior observed experimentally.

(3) A finite element model is produced reflecting the geometry, distribution and orientation of the identified collagen bundles, as established in (1). In addition, this model incorporates porosity to properly reflect the microscopic structure of the single lamella.

(4) The model created is parametrically exercised within the limits of known property variation in literature and set to conform to the experimental results to allow for biological variations and to study biological effects. This includes variation of the experimentally measured elastic constants as well as manipulation of the load distribution and boundary conditions. Finally, the effects of these parametric manipulations on fracture and failure characteristics is investigated.

The above studies enable realistic representation of the geometry and the structure at the level of a single lamella. The representation of individual units can also be integrated to increae the accuracy of the mechanical behavior of osteons and osteon groups.

Overview of Methods and Results

To establish the microstructural differences in terms of lamellar elementary components and the impact of such differences on lamellar mechanical behavior, appropriate methodology is needed. In the experiments described herein, multiple methods of investigation were employed to shed light from different perspectives on the morphological arrangement of lamellar specimens; 1) circularly polarized light microscopy; 2) confocal microscopy; and 3) X ray diffraction methods. Confocal microscopy and small-angle X ray diffraction were employed on lamellar specimens. Other useful methodologies include combinations of confocal microscopy examinations and mechanical test procedures through mathematical analysis and computer modeling, to examine the ultrastructural variables, which regulate mechanical response to applied tension.

The studies can utilize, for example, two external lamellae of osteons at final stages of calcification obtained from donors in the 27-49 year old age. Osteons that exhibit the final stages of calcification, as evidenced by micro-X-ray (Amprino and Engström, 1952), are chosen for the alternate osteon specimens. Polarized light microscopy is used to confirm that the selected osteons are of the alternate osteon type. According to Rho et al. (1999), there is no evidence that the lamellar elastic modulus of external lamellae in fully calcified osteons depends on either osteon size or osteon lamellar number. Therefore, the degree of calcification of the external lamellae is not an important variable within and across the lamellar specimen groups.

To conduct experiments on osteonic lamellae, the availability of isolated osteonic specimens from the mid-diaphysis of the human femur of appropriate type and sufficient quantity is especially advantageous. The mid-diaphysis of long bones has been shown to contain osteons that are most consistent from a structural and morphological perspective relative to those obtained from other cortical bone locations. Osteonic lamellae vary in thickness (2-11 μm) and length (up to a few centimeters). They comprise the generally coaxial cylindrical layers of osteons, which measure 200-250 μm in diameter. The number of lamellar layers that make up an osteon range from 4-20. For a meaningful systematic study, all specimens need to have the same dimensions and structural characteristics while maintaining the characteristics of the gross entity from which they are selected as specimens. Thus, the variables can be dealt with realistically as follows:

Collagen bundle make-up: Microscopic examination of compact bone sections under polarized light reveals that all secondary osteons obtained from the mid diaphysis are composed of coaxial lamellae that appear dark and lamellae that appear bright. Examination of thousands of bone sections has revealed the following consistent observations: 1) osteons made up exclusively with bright lamellae are uncommon; osteons that are mostly dark in appearance show a thin layer of bright lamellae around the harvesian canal; and 3) among all the different combinations of dark and bright lamellae in osteons, osteons made up of essentially dark lamellae (so-called longitudinal osteons) and osteons made up of alternatively dark and bright lamellae (so-called alternate osteons) represent two ends of a spectrum, biologically and mechanically. Since the lamellar type classification, according to whether they are dark or bright, are numerous, and they appear to be independent from the osteon type to which it belongs, investigations can, at least initially, be concerned with alternate osteons only, i.e., those that reveal alternating lamellae represented by dark and light fields.

Degree of calcification: Examination of micro-X-rays of compact bone sections reveals a spectrum of intensities, ranging from dark gray to white. The X-ray intensity indicates the degree of calcification of an osteon as a whole from initial to final (Amprino and Engström, 1952). Osteons at the final stage of calcification constitute the majority, close to perhaps 90% of adult compact bone. The level of hydroxyapatite in osteons at the final stages of calcification is usually considered to remain constant within the adult age group (27 to 49 years). Several studies have indicated that the degree of calcification decreases within osteons radially from the haversian canal to the cement line (e.g., Amprino and Engstrom, 1952; Skedros, et al. 1996).

Lamellar thickness: The distribution of lamellar thickness varies among and within individual osteons. Lamellar thickness varies from lamella to lamella from the cement line to the haversian canal (Rho et al., 1999; Ardizzoni, 2001) and within the lamella along the osteon length (Ascenzi A. et al., 1982). Lamellar thickness measurements remain comparable to the values obtained on thinner sections by electron microscopy (Ascenzi A. et al., 1982) to an extent of approximately 100 μm of its length. Because of these expected normal variations, length and width of specimens need to be uniform within and across the specimen groups. The selected dimensions need to be large enough so as to provide for a good representation of the underlying lamellar structure.

To observe isolated lamellae, embedded in and isolated from the alternate osteon (the osteon that appears alternatively dark and bright in cross-section under the polarizing microscope), a novel isolation technique was applied. The novel isolation technique enabled examination of the two dissected lamellar types through and across their flattened cylindrical surface by circularly polarized microscopy, confocal microscopy and X-ray diffraction. As described in the Examples, it was evidenced that:

embedded lamellar thickness varies along the lamellar length, therefore, thickness should be measured along both lamellar specimen edges;

embedded lamellar thickness varies between dry and wet condition, hence all measurements should be taken on wet lamellar specimens;

polarized light microscopy indicates the presence of a relatively continuous orientation pattern of oblique collagen bundles within the bright lamella and of a more discrete pattern of orientations within the dark lamella;

confocal microscopy indicates morphological differences between the two lamellar types and indicates the appropriateness of a more detailed confocal microscopy study with finer scanning;

X ray diffraction supports an inference of the presence of longitudinal collagen bundles in dark lamellae and of oblique collagen bundles in bright lamellae.

Mechanical testing of specimens in tension can further support the findings listed in the last three points, and correlate to any structural differences observed in the confocal study.

Lamellar Specimen—Selection and Preparation

Lamellar specimens are prepared for tension loading and confocal microscopy analysis. Such tests yield mechanical properties and collagen orientation patterns, respectively. The results obtained will form the basis for a computerized geometric/structural osteon model, that will simulate the formation and propagation of fractures observed in the loaded specimens.

The ability to complete lamellar specimen preparation and selection is a prerequisite to conduct the described experiments. Because of the difficulty of the specimen preparation, it may be expected that only about 1 out of 3 specimens isolated are eligible for mechanical testing.

The first prerequisite to provide a uniform sample selection is to minimize variability among the specimens that will be included for evaluation. Initially transverse sections of the whole bone, 30 mm in length, is obtained from the mid-diaphysis of adult femurs (27-49 years of age) that are free of evident skeletal pathologies. These initial specimens are prepared as described above using a water cooled rotating saw blade. The experimental methodology is directed at narrowing the possible alternatives that describe the underlying structure and composition of materials that form the individual osteon lamellae.

The following are brief descriptions of the procedures that are employed. Polarized light microscopy studies have been limited to observations on the transverse sections of intact osteons and through the thickness of individual isolated lamellae. Lamellae that appear bright under these conditions indicate a preferred structural alignment of collagen bundles and hydroxyapatite in a plane perpendicular to the axis of polarization. If the alternating bright and dark fields are indicative of structural arrangement then the appearance of the layers should be reversed when the same sample is viewed from the circumferential direction in the direction of polarization. Peliminary confocal microscopy studies is optionally performed at sufficient resolution to distinguish explicit differences in structure on the order of the size of individual collagen bundles. Scanning at 0.25 mm increments enables distinguishing distinct collagen bundle arrangements that are present in the two types of lamellae. Identification through improved detail will enable reconstruction of the three dimensional nature of these constituents' geometry that would indicate a preference for resistance to directional loading.

Mechanical testing of individual lamellae have only been performed on a single type in tension and only in a single direction (equivalent to its original circumferential alignment). The loading of a single lamella type in both the circumferential and longitudinal directions will provide direct mechanical evidence of differences in mechanical behavior. It will also elucidate differences in the mechanical behavior between lamellar types. Finally, our detailed analytical modeling will enable us to parametrically exercise possible existing variations in architecture and elemental composition of the individual lamellar arrangements and the influence that these arrangements have on the mechanical response to applied loadings.

The combination of these procedures will enable us to confirm differences in structure and composition related to mechanical behavior. It will further enable us to generate refined representations of the organizational structure of individual lamellar layers and resolve many of the current discrepancies.

The lamellar specimens are isolated in the longitudinal or circumferential (anatomical) dimensions; the lamellar thickness will be always measured in the original radial direction; specimen length, width, and thickness will refer to largest, intermediate, and smallest specimen dimension. Width and length are measured at several locations for each sample using a calibrated image processing system (Image-1). The results are averaged for each dimension. The thickness of each specimen is measured using commercially available distance transducers (digital displacement inductive3 sensor, Keyence model EX 305). Several measurements are obtained of the thickness of the glass-specimen composite along the length of the specimen. Separate measurements of the glass thickness are also obtained. Subtraction of the net glass thickness from the composite measurements yields specimen thickness.

Confocal Microscopy—Samples

For confocal examination, 50 dark and 50 bright lamellar specimens are dissected from 70±3 μm transverse sections. They consist of approximately half of the lamellar circumferential length to allow for examination of the structure along the longest specimen that can be isolated. For mechanical loading, 60 dark and 60 bright lamellar specimens are prepared as follows. Dark and bright lamellar specimens are chosen on 115±3 μm and 70±3 μm transverse femoral mid-shaft sections in terms of their mean thickness along the two edges. They are measured wet inside the alternate osteon along the circumference and at the ends, as described in the studies above. Dark and bright lamellar specimens are chosen so that the wet mean thickness along each edge equals 3±1 μm and 4±1 μm, respectively. Dark and bright lamellar specimens are dissected wet as described in section 3.1 along an arc length of 70±3 μm on 115±3 μm thick transverse sections and along an arc length of 115±3 μm on 70±3 μm thick transverse sections.

The 60 specimens of each lamellar type are chosen so that the length direction of 30 of the specimens is longitudinal and the length direction of 30 specimens is transverse with respect to the osteon axis. This is to determine the mechanical response of each lamellar type with respect to loading in mutually orthogonal directions that correspond to their original longitudinal and transverse anatomical orientations. Loading is always directed along the long dimension of the specimen.

While preliminary confocal microscope observations indicate differences within lamellae of the same type with respect to pattering (e.g. domain size, number, and collagen orientation within domains), the mechanical properties within each lamellar group type are independent of the domain feature variation. This is because the mechanical response depends on the overall contributions of overlapping domains throughout the thickness dimension. This ensures enough structure homogeneity across the samples of the two lamellar type group separately. The specimen dimensions for mechanical testing set at 115 μm×70 μm are dictated by technical limitations. While the ratio of the two dimensions is smaller than the ratio recommended by engineering textbooks to avoid shear and boundary effects during tensional loading along the largest dimension, the comparative nature of the experiments make the lamellar specimen ratio acceptable. The shear and boundary effects are addressed in the numerical lamellar model. The specimens prepared for confocal microscope examination and for mechanical testing will consist of lamellar specimens isolated from each region of the same mid diaphyseal section of the femur in the same proportion to ensure homogeneity across the two groups.

All lamellar specimens are inspected with an optical microscope for micro-cracks after preparation and prior to confocal microscope analysis and mechanical loading so as to ensure integrity of the samples. Since the specimen micro dimensions make it easy to lose the specimen and the fragility of the lamellar specimens makes them prone to fracture, for the investigation proposed, it is necessary to prepare between 1,000 and 2,000 specimens to obtain a yield of about 220 specimens (110 lamellar specimens per lamellar type at final stages of calcification) which will satisfactorily complete the procedures adopted for examination under confocal microscopy and quasi static tensional loading.

Confocal Microscopy—Analysis

Dark and bright lamellar specimens are scanned every 0.25 μm through their thickness. Scanning covers the full extent of the length and width of the specimen. Collagen bundle orientation and density are measured by means of an imaging system. A weighted average of the structure is determined according to a range of orientations.

Also performed are two dimensional spatial fast Fourier transforms (2D SFFT) of the images to discretize the information into an amplitude versus frequency spectrum. The areas of domains, i.e., regions of essentially unidirectional collagen bundles, and areas between domains are measured. Collagen bundle density is computed from the distances of adjacent collagen bundles within any given domain. Means and standard deviations are computed at each scanning level across the lamellar groups, separately. Each domain is associated with a mean collagen bundle orientation by averaging the orientation of its individual collagen bundles. A finer discretization is considered if warranted. Domains are classified in terms of frequency bins of 15° range orientation intervals and in terms of mean collagen density.

Two-way Analysis of Variance (ANOVA) is applied to the means of collagen bundle orientation and density, and domain area with depth level and lamellar type (dark or bright) as factors. If normality lacks, the 2-way ANOVA is applied to the means of the logarithms. Significance is set at 0.05. The Post hoc Student Newman Keuls test identifies those factors that are significant.

Significant differences in collagen bundle orientation pattern and density, domain area and area between domain in the thickness direction between dark and bright lamellar specimens are found. Specifically, dark lamellar specimens are shown to consist almost exclusively of collagen bundles transverse to the osteon axis perhaps with additionally thin layers of oblique collagen bundles at the edges. The structure of the dark lamella along its circumferential surface should be analogous to the one of the bright lamellar specimens because bright lamellae are adjacent to dark lamellae in the alternate osteons. The bright lamellar specimens will show collagen bundles transverse to the osteon axis towards the middle thickness with oblique collagen bundles gradually increasing in angle towards the outer lateral boundaries. Collagen bundle density and area between domains values should be lower and higher, respectively, in dark rather than bright lamellar specimens because various authors (e.g., Marotti, 1990) have hypothesized that dark (bright, respectively) lamellae are collagen poor (rich, respectively). In particular, lamellae of both types consist of various domains, as indicated by Boyde (1972) by means of scanning electron microscopy.

A Leica TCS SP inverted confocal microscope with an integral computerized imaging system is used.

Mechanical Testing

Figure 49:
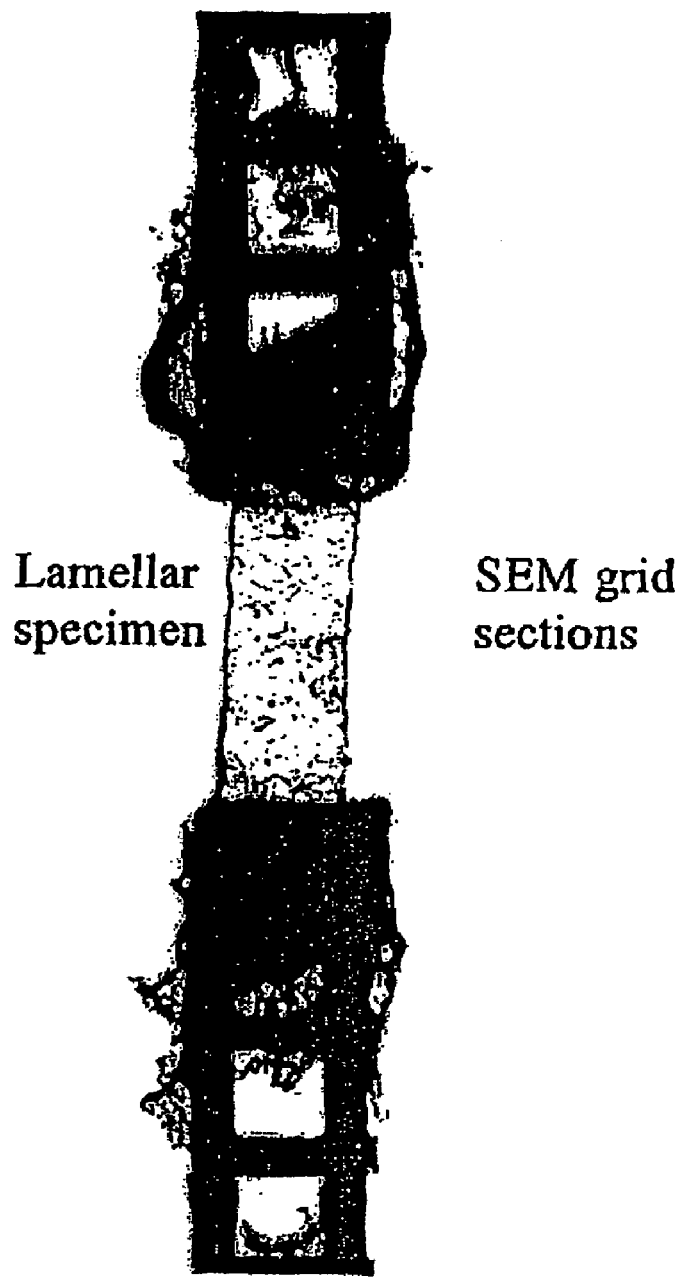
FIG. 49 Photograph of lamella specimen attached to SEM grid sections as prepared for the tensile test.

Dark and bright lamellar specimens are tested under monotonic quasi-static loading as follows. A micro-extensometer is used (Ascenzi A. et al., 1982) with direct visualization of the specimen with a stereo microscope during the specimen set up and loading sequence. The lamellar specimen is secured to the extensimeter. In particular, each end of each flattened lamellar sample is attached to the end of a support. Each 80 μm wide support is cut from a copper grid typically used in electron microscopy (FIG. 49). A very strong and quickly drying glue (Kemi Cyak CF type) is used to attach the end of each lamella to each support. Care is taken so that the glue covers a minimal portion of the lamella. Glue-free lamellar length is measured under wet conditions to ensure same length across the dark and bright lamellar specimen groups. The free ends of each support are then glued to the micro extensometer. The alignment is checked by means of the stereomicroscope. The specimens are loaded wet to rupture. For all the specimens, the mechanical loading direction is parallel to the length direction.

The resulting output is a plot of load versus deflection recorded in real time. The experimental diagrams are graphs of increasing functions of the deflection, which show a concave downward shape, regardless of the lamellar type. If confocal microscopy shows that there is no dominant collagen bundle alignment with the loading direction of specimens within a lamellar type, composite theory indicates that the plots relative to the longitudinal and transverse specimens of that lamellar type are expected to show no difference. If instead a dominant collagen alignment with the loading direction is present, then the plots relative to the longitudinal and transverse orientations of the specimens of that lamellar type are expected to show a difference. The mechanical testing results are expected to correlate with the morphological confocal microscope observations for the two lamellar types.

After the mechanical testing, lamellar specimens are examined under an optical microscope under both regular and fluorescent light (Huja et al., 1999) to assess fracture patterns. We expect microcracks to be present in the vicinity of pores (canaliculae and lacunae) and at points of material weakness and at the interface between elementary components. Evidence of significant fracture density is reflected in reduced stiffness and ultimate strength of the load vs deflection diagrams. Because of the fibered nature of the tissue, cracks are expected to progress in distinct steps with significant branching and directional changes. We will classify the complete rupturing fracture somewhat perpendicular to the loading direction in terms of number of directional changes and total length. The mechanical behavior in tension is expected to be in line with the results obtained by Ascenzi A. et al., (1998) for bright lamellae isolated by a technique different from the one used here.

After mechanical testing, the wet specimens are measured in width and thickness by the same methods used before mechanical testing because the specimens length at rupture is computed from the length before mechanical testing and the deflection at rupture is provided by the load vs. deflection plots. The specimen measurements before and after mechanical testing are necessary to prepare the computerized lamellar model.

Analysis of Mechanical Diagrams

Analysis of the experimental diagrams enables determination of the mechanical properties of the individual lamellar types. If an experimental diagram shows a decreasing portion of the graph following the expected increasing portion, it means that the specimen has experienced large strains. In that case, the specimen section perpendicular to the loading access cannot be considered as constant. Therefore, stress vs. strain diagrams cannot be obtained from the load displacement diagrams, and classical theory cannot be employed. In that case, the mechanical properties are obtained from the load displacement diagrams. If instead, an experimental diagram is always increasing, then the force vs. displacement diagrams can be converted to stress vs. strain diagrams.

In either case, the constitutive equation which represents the characteristic behavior of the curve is established in terms of a polynomial equation of degree three or four. Degree four is expected to suffice because such degree has accurately fitted the response of fully calcified osteons to loading in tension (Ascenzi A. et al., 1997), and the structure of the individual lamellae is simper than that of the osteon. If degree four does not produce a good fit, a higher degree is employed. The approximating function of each experimental diagram serves to compute the material stiffness as the derivative of the diagram, the energy absorption capacity as the area under the approximating curve. Ultimate strength (the limit of the approximating functions) is directly measured.

The 2-way ANOVA is applied to the means of the elastic modulus, ultimate strength and energy absorption with lamellar type (dark or bright) as factor. If normality lacks, the 2-way ANOVA is applied to the means of the logarithms. Significance is set at 0.05. The Post hoc Student-Newman-Keuls test will identify the significance of the factors. We expect significant differences in elastic modulus, ultimate strength, and energy absorption capacity for dark rather than bright lamellar specimens because of more collagen bundles present in dark rather than bright lamellae.

Geometric/Structural Lamellar Specimen Model

The lamellar specimen model fits the mechanical behavior of the lamellar specimen to that of its ultrastructural components. Therefore, the model is based on the approximating functions of the mechanical diagrams, deflection as function of load, and the confocal microscope observations. For the first time, this lamellar specimen computerized model allows for the incorporation of domains and their collagen bundle orientations. The model allows for simulation of the fracture propagation observed in the mechanically tested specimens. In particular, the model sheds light as to the processes within the lamellar specimen of micro-cracking, de-bonding, pore growth and elemental component breakage, which contribute to the observed fracture patterns.

The model's crucial parameters are assessed from the specimens employed for mechanical and confocal microscope analyses. Other important parameters, i.e., hydroxyapatite pattern directions and bright lamellar prestress (Ascenzi, M. G., 1999), have been investigated in large numbers (on the order of a few hundreds so as to cover the biological variability of osteon structures) of specimens as described in the preliminary studies and previously in the Ascenzi laboratory. Additional parameters, i.e., dimensions and distribution of canaliculae and lacunae, elastic properties of collagen and mucopolysaccharides, collagen bundle diameter, and elastic properties and density of hydroxyapatite have not been assessed in specimens and are addressed by treating them as parameters which vary, within ranges consistent with lamellar structures, around available values from the literature. The ranging of such additional parameters will accordingly serve to explore and discuss possible scenarios.

Material science implies that some of this fiber reinforced laminate model's inherent structure will turn out to have a minor role in the modeled comparative behavior of the two lamellar types. For instance, the presence, relative distribution and density of canaliculae and lacunae will affect the fracture simulation patterns, rather than the particular dimension or position of a canalicula or lacuna. Confirmation or refusal will derive from the parametrized model that allows, for different values of the parameters, either exclusion of canaliculae and lacunae altogether or variation in porosity distribution. Since there is no evidence of difference in the literature between osteon types with respect to elastic properties of collagen and mucopolysaccharides, and elastic properties of hydroxyapatite, their parametric values are kept constant across the two lamellar model. Such parametric values are less relevant because of the comparative nature of the model. The starting parametric values of the hydroxyapatite density will follow any relevant findings from our complete examination of our X diffraction results and indications from the literature. The initial parameter value for collagen bundle diameter measurement comes from the literature and is kept constant across the osteon types. If confocal microscope images yield new information on collagen bundle diameter, such information is incorporated in the model.

The geometric representation of the lamellar specimen consists of three stages. At the first stage, a cylindrical shell represents a wet lamella before the dissection of the specimen. The dimensions of the cylindrical shell correspond to the mean measurements of the embedded wet lamella. At the second stage, a parallelepiped represents the wet flattened lamellar specimen before mechanical testing. The length, width and thickness of the parallelepiped will equal the mean length, width and thickness measured on the wet flattened lamella. At the third stage, a parallelepiped broken into two portions will represent the wet ruptured lamellar specimen after mechanical testing. The dimensions of the parallelepiped will equal the mean measurements of the wet flattened lamella.

Figure 50:
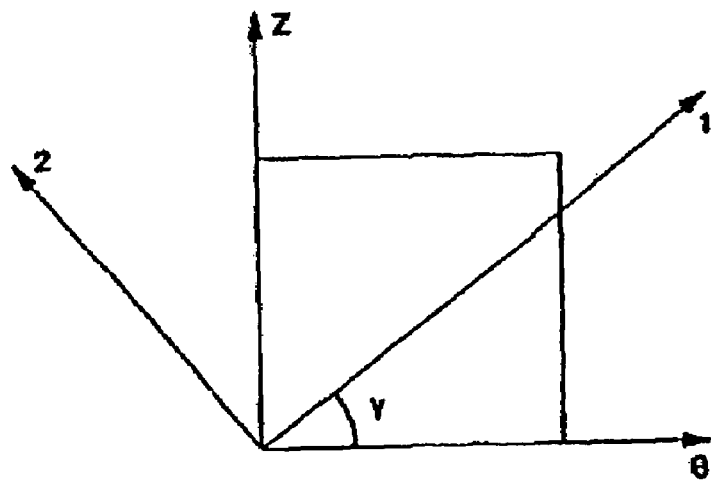
FIG. 50 On a small and thin laminar element, the principal material axes are labeled 1, 2, and 3. Direction 1 is parallel, and direction 2 perpendicular, to the fibers. Direction 3 is the radial direction, perpendicular to the plane of the diagram. circumferential and axial directions are labeled θ and z. The angle between the circumferential direction and direction 1 is denoted by γ (from Ascenzi, M.-G. (1999) A first estimation of prestress in so-called circularly fibered osteonic lamellac, J. Biomechanics, (32): 935-942).

Pores in the model will consist of a distribution of canaliculae and lacunae distributed as described in the literature (Piekarski, 1970). Each of the dark and bright lamellar specimens consists of a two phase fiber reinforced material where the fiber represents the collagen bundles and the matrix represents a mixture of hydroxyapatite and mucopolysaccharides. In this first model, the fiber orientation and density is dictated by the results of the lamellar specimen examination by confocal microscopy. The three materials that make up matrix and fibers are individually treated as homogeneous and isotropic. The elastic modulus for matrix and fibers are not available, and the values used are the best approximation available from the literature. The fibers are assumed to be circular in cross section and are distributed according to the domains observed in our confocal microscope examination. The domain with fiber inclination is named g domain (FIG. 50). The initial parametric value for the fiber diameter is set at 800 Å. The initial parametric percentage of mucopolysaccharides is set equal to 1% (Herring, 1972). For hydroxyapatite the starting percentage is set to 40% of the lamina volume without pores (Bonfield and Li, 1967). The initial parametric hydroxyapatite volume is set 10% higher in the dark lamellar than in the bright lamellar model (Marotti et al., 1994). The initial parametric values that describe the elastic properties of the hydroxyapatite will equal the findings of Katz and Ukraincik (1971). The initial parametric values that describe the elastic properties of the fibers, which model collagen, will equal the findings of Currey (1959) and Haut (1983). Since the elastic modulus of collagen, hydroxyapatite and mucopolysaccharides are not available, the starting values for the matrix and fiber properties are represented by the best approximation currently available (e.g., elastic modulus of collage from tendons). The starting values are selected from the best available approximations in the literature. Because fluid is not likely to be retained in the canaliculae and lacunae in our specimens, fluid will not be considered to have an influencing role on the structural behavior observed in our mechanical tests. Therefore, this model will not include stiffening affects during specimen loading. This is different from a lamellar model which considers the lamella as part of the intact osteon.

The starting number of elements for the Finite Element Model (FEM) is of the order of 500,000. This number was computed by the use of brick elements of dimensions averaging 1 µm, the diameter of a large canalicula. The element mesh is refined to achieve convergence of the solution. The FEM will compute the lamellar stress and strain distribution due to the deformation of the cylindrical shell portion into the parallelepiped before mechanical loading. Such distributions will take into account the prestress present in dark embedded lamellae (Ascenzi A. and Benvenuti, 1977; Ascenzi M. G., 1999). Then, for any given value of the experimental tensional load, a computer program based on Montecarlo simulation is written to compute stress, strain, and phase deformation distributions. Since strain is chosen as the criterion for osteon fracture (Piekarski, 1970), the strain within each element is compared to the yield strain provided by the literature. If cracks appear to initiate at the matrix fiber interface, an appropriate failure criterion (e.g., Von Mises, Tresca) is included. The increased probability of fracture in the neighborhood of an already fractured element is considered using the concept of stress enhancement factors.

Fractures that develop within our model are expected to start at a weaker point of the bone structure (Carter et al., 1981). Cracks are expected to initiate in the organic phase, which yields, and at hydroxyapatite crystallite boundaries, which pulls away from the organic matrix and causes the cracks to advance through the weak interfaces between domains where collagen bundles change orientation (Boyde, 1972). Cracks may also initiate at individual lacunae due to a local stress concentration in the surrounding tissue since these are relatively large with respect to the smallest dimension of the lamellar specimens. At the front of the propagating crack, the large strains, which may be accommodated by the organic phase, are expected to contribute to the dissipation of energy (Simkin and Robin, 1974; Minns, et al, 1973). Numerous microcracks are expected to form throughout the specimen. The regions containing transverse and oblique collagen bundles would tend to impede crack advancement and will slow propagation of cracks with greater energy dissipation. Slow propagation is essentially a pull out type mechanism, that is, hydroxyapatite crystallites would be pulled out of the collagen by shear failure at the fiber matrix interface. Slow propagation would be consistent with the observation of multiple directional changes in the propagated crack as well as multiple bifurcations in the crack patterns. The rapid propagation of cracks in regions containing collagen bundles somewhat perpendicular to the specimen's length would occur with very low energy absorption. Crack propagation is expected to be arrested by the presence of canaliculae and lacunae. In the case where the crack enters a discontinuity, its front is blunted, hence reducing the stress concentration factor and temporarily arresting crack propagation (Piekarsky, 1970). Lacunae are probably more likely to act as stress concentrators than canaliculae because of their ellipsoidal cross section. The orientation of the major and minor axes relative to the local stress field would determine if these structures would likely be the source of fracture initiation. Cracks will initiate sooner in the tissue surrounding the smaller radius when subjected to a local state of tension. Since porosity is expected to act as a crack arrester, porosity may contribute to increase the robustness of the bone (Currey, 1962). Hydroxyapatite crystallites may additionally be pulled out from collagen around canaliculae.

The proposed model simplifies the lamellar structure; in particular it excludes partially calcified collagen bundles (Ascenzi A. et al., 1965) because their structure is not yet well understood.

Finite Element Model

The Finite Element Method modeling technique proposed here is well established. The model is made on a SP Cluster Machine, which can handle the extraordinary number of elements. The PI has experience with two prior micro structural models. The first model consisted of a bright lamellar model (Ascenzi M.-G., 1999) which, in addition to explaining prestress, was able to explain the difference between alternate osteon and lamellar stiffness values found experimentally by independent researchers (Meunier, 1999). The second model simulated a longitudinal osteon under cyclic torsion (Ascenzi M.-G., 2000). The parametric analyses proposed in this proposed study will provide the flexibility to include lamellar details, that have not been established in the literature. If the proposed model does not reflect our test results relative to the experimentally observed fracture patterns and overall mechanical behavior, the nature of the differences are more closely analyzed in terms of the parametric values. Thus, it will explain the role of the dominating features that control the response to mechanical loading.

EXAMPLE 7

Thickness Variations Within Dark and Bright Lamellae

For this and the two experiments described below, the source of bone material consisted of adult human femoral shafts (27-49 years old), free from evident skeletal pathologies, and removed from cadavers in accordance with US regulations. The selected age range corresponds to the young age group of Kuo et al. (1998). A rotating-saw microtome with a continuous watering system to provide lubrication and prevent the material from overheating was employed to cut longitudinal segments approximately initially 30 mm long from the mid shaft of the femur. The segments were then sliced transversely into 70-120 µm thick slab sections. Micro-X-rays of these transverse slabs were prepared to allow identification (Amprino and Engström, 1952) of fully calcified osteons.

The thickness of the wet outer lamellae of alternate osteons was measured along their two ends, separately, on the thin transverse slabs. The lamellae were characterized as dark or bright by means of polarized light microscopy. Dark and bright lamellae show thickness variation between the two ends. The result points to the appropriateness of thickness measurements on lamellar specimens for the proposed investigations.

Methods. The lamellar thickness measurements were obtained on slab specimens with a height of 70±3 µm. Lamellar thickness was measured at 5 points on each of the two ends of 86 dark and 66 bright peripheral lamellar specimens while still embedded in wet alternate osteons using a Delta Sistemi IAS 2000 image analysis system.

Results. Intra-lamellar standard deviation equals 0.87 µm and 0.88 µm for dark and bright lamellar specimens, respectively. The following table shows means and standard deviations (in microns) between the two lamellar types.

TABLE 5

| Lamellar Type | Thickness On End 1 | Thickness On End 2 | Thickness Difference |
| --- | --- | --- | --- |
| Dark | 7.62 ± 1.91 | 8.58 ± 1.99 | 0.48 ± 0.47 |
| Bright | 4.27 ± 1.00 | 4.85 ± 0.96 | 0.29 ± 0.26 |

Differences between bright and dark lamellae were significant ($p<0.05$). The thickness of both dark and bright lamellar varies between lamella and within any given lamella along the osteon length as previously observed by Ascenzi A. et al. (1982) on isolated bright lamellae.

EXAMPLE 8

Thickness Variation Between Wet and Dry Lamellar Condtions

Dry and wet lamellar thicknesses were measured within the osteon samples. Whether dry or wet, dark lamellae are thicker than bright lamellae and bright lamellae expand with water to a lesser degree than the dark lamellae.

Methods. The specimens were chosen on 70±3 µm thick transverse sections. Lamellar thickness and width were measured at 5 points on each of 20 dark and 20 bright peripheral lamellar specimens in dry alternate osteon specimens by using a Delta Sistemi IAS 2000 image analysis system, and again after wetting with distilled water using a micro pipette. On each lamella, all measurements were taken consistently on one of the two transverse ends. Only thinner dark lamellae were used for comparison with bright lamellae because dark lamellae are in general thicker than bright ones (see e.g. Marotti et al., 1994), irrespective of whether they are dry or wet.

Results. The mean height ± standard deviation of the whole alternate osteon equaled 70.30±9.28 µm and 72.45±9.58 µm, under dry and wet conditions, respectively. The following table shows means and standard deviations (in microns) on which the student t test was run with significance set at 0.05.

TABLE 6

| Lamellar Type | Thickness Dry | Thickness Wet |
| --- | --- | --- |
| Dark | 4.13 ± 1.23 | 4.10 ± 1.10 |
| Bright | 3.30 ± 0.88 | 3.56 ± 0.93 |

Whether dry or wet, bright lamellae are significantly thinner than dark lamellae when enclosed in alternate osteons. Additionally, wet and dry conditions affect bright and dark lamellar thickness differently. Bright lamellae are significantly less thick when dry than wet. In contrast, dark lamellae thickness does not change significantly between wet and dry states. The thickness of bright lamellar increases from dry to wet supporting the hypothesis that bright lamellae contain a higher relative percentage of mucopolysaccarides, that tend to expand with moisture, and that the bright lamella tightly encircling dark lamella impedes expansion. The height of the whole osteon is significantly greater when wet than when measured in the dry state.

EXAMPLE 9

Isolation of Dark and Bright Lamellar Specimens

This Example describes a new technique which allows isolation of both dark and bright lamellar specimens from alternate osteons. An alternate osteon specimen is separated from the surrounding transverse bone section, and the individual coaxial lamellar layers successively separated. Previously, Ascenzi A. et al. (1982) isolated specimens of dark lamellae by a technique that cannot be reproducibly applied to isolate individual bright lamellae.

Figure 39:
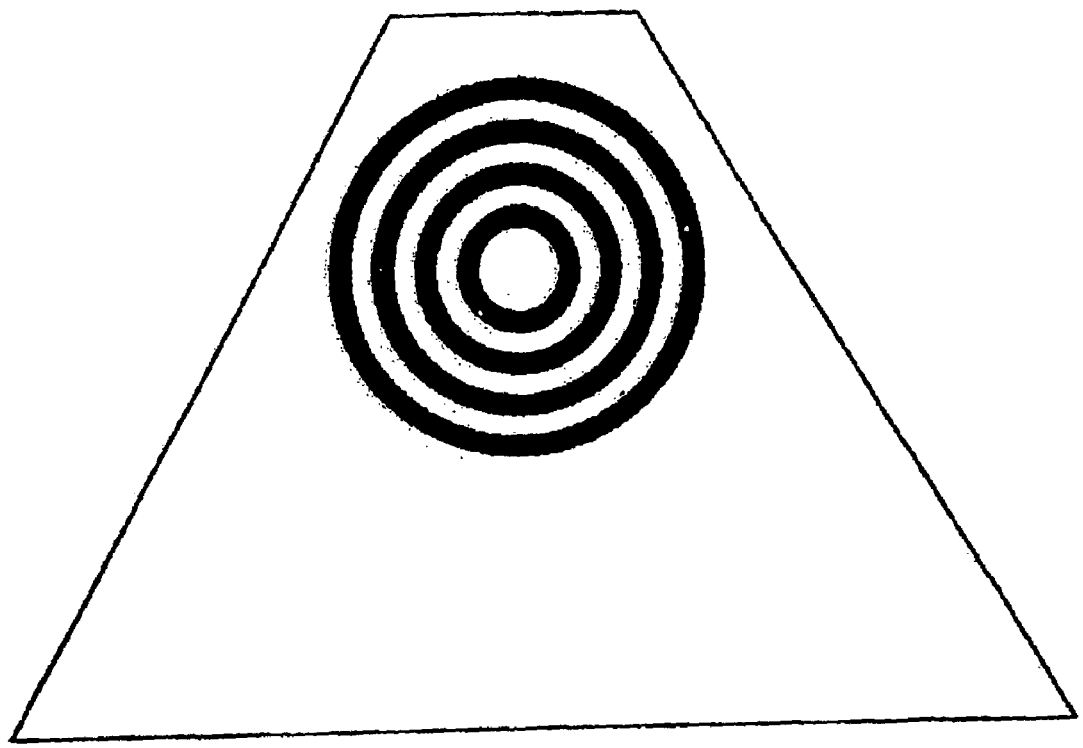
FIG. 39 Diagram showing the trapezoid cut from a thin transverse femoral section of bone that contains a chose alternate osteon (from Ascenzi, 2003).

Method. Fully calcified alternate osteons were identified on the prepared sections by means of micro X ray and polarized light microscopy. A dental drill secured to a microscope stage cut a trapezoid around each chosen osteon specimen (FIG. 39). For osteon immobilization during lamellar isolation, the base of the trapezoid away from the osteon was glued to a slide. The dark and bright lamellae at the periphery of each osteon were dissected wet with a razor sharp microtome blade, obtained by filing a steel needle. This is achieved by first separating the interstitial bone outside the alternate osteon from the outer lamella and then separating the outer lamella from the rest of the alternating osteon. The isolation of the single lamellar specimen is a very delicate operation that requires a lot of patience and accuracy. Care is taken so that remnants of interstitial bone and/or of adjacent lamella do not remain attached to the lamellar specimen. Because it is necessary to secure the bone specimen during isolation, roughly only half of the lamella can be isolated circumferentially. The lamellar specimens were then straightened in a ribbon like shape. To avoid the creation of fractures during straightening of each lamellar specimen, the operation is performed gently on wet specimens while under direct microscopic visualization. The selection of external lamellae, of lesser curvature than internal lamellae, decreases the risk of fracture formation during flattening. The difficulty of applying our free hand micro dissection technique to obtain regularly dissected and discontinuity free specimens is evidenced by the fact that approximately only 1 out 3 specimens successfully complete the procedure. This technique can be performed on transverse sections that measure 70 120 μm in thickness. The lower bound of 70 μm is chosen to ensure flatness of the section. The upper bound of 120 μm is chosen to ensure dissection reliability without indentations. The ribbon specimens are placed between two glass plates and wet with distilled water.

EXAMPLE 10

Circularly Polarized Light Microscopy on Dark and Bright Lamellae

The birefringence, that manifests itself as bright and dark annular circles when lamellae are viewed transversely under polarized light, is associated with collagen bundle arrangement. When isolated, flattened and wet lamellar specimens are viewed through the lamellar thickness, a continuous variation in patterning results as the bright lamellar specimen is gradually rotated through 90 degrees relative to the polarizing plane. A more discrete patterning variation is observed on dark lamellae examined under the same conditions. This indicated that the bundle orientation expresses some variation throughout the thickness. At selected orientations there is a clear domination of a preferred patterning arrangement.

Absence of variation would indicate an amorphous morphology of the microstructure of the specimen.

Method. 102 dark and 110 bright lamellar specimens were examined with a Laborlux Leitz equipped with polarizing light. A Zeiss laser scan microscope equipped with argon ion and helium neon lasers was used to investigate the structure and to obtain digital images of the structure, respectively. The images were archived on a hard disk and subsequently transferred to film. To increase the digital image fluorescence, structures of interest were stained with a diluted solution of eosin. For comparison purposes, a few 1-2 μm thick sections were cut at a slight angle with respect to the transverse plane from decalcified bone embedded in paraffin. The lamellae appeared better separated than in the cross section and consequently better optical resolution was obtained.

Figure 40:
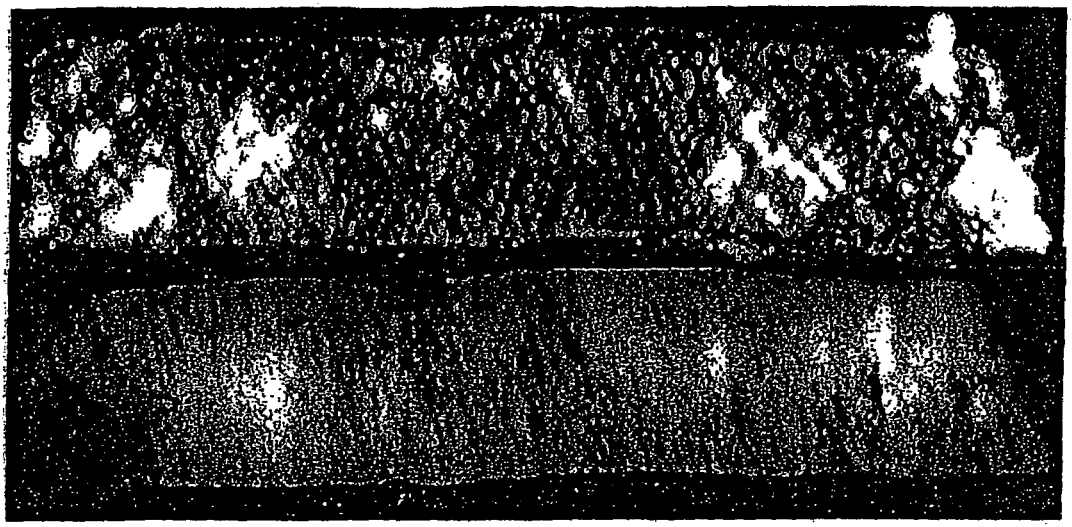
FIG. 40 Dark lamellar specimen oriented at 0° (top) and 45° (bottom) with respect to the plane of polarization.

Results. When an isolated, flattened, wet lamellar specimen is observed microscopically through its thickness under a polarized light, its features change in relation to the lamellar orientation with respect to the polarizing planes of the two Nicol's prisms. When the long edge of a dark lamellar specimen is oriented at 0° with respect to the polarizing plane, the light and dark fields align obliquely at ±45°, to the long edge of the specimen. When the long edge of a dark lamellar specimen is oriented at 45° with respect to the polarizing plane, the light and dark fields align perpendicularly to the long edge of the specimen (FIG. 40).

Figure 41:
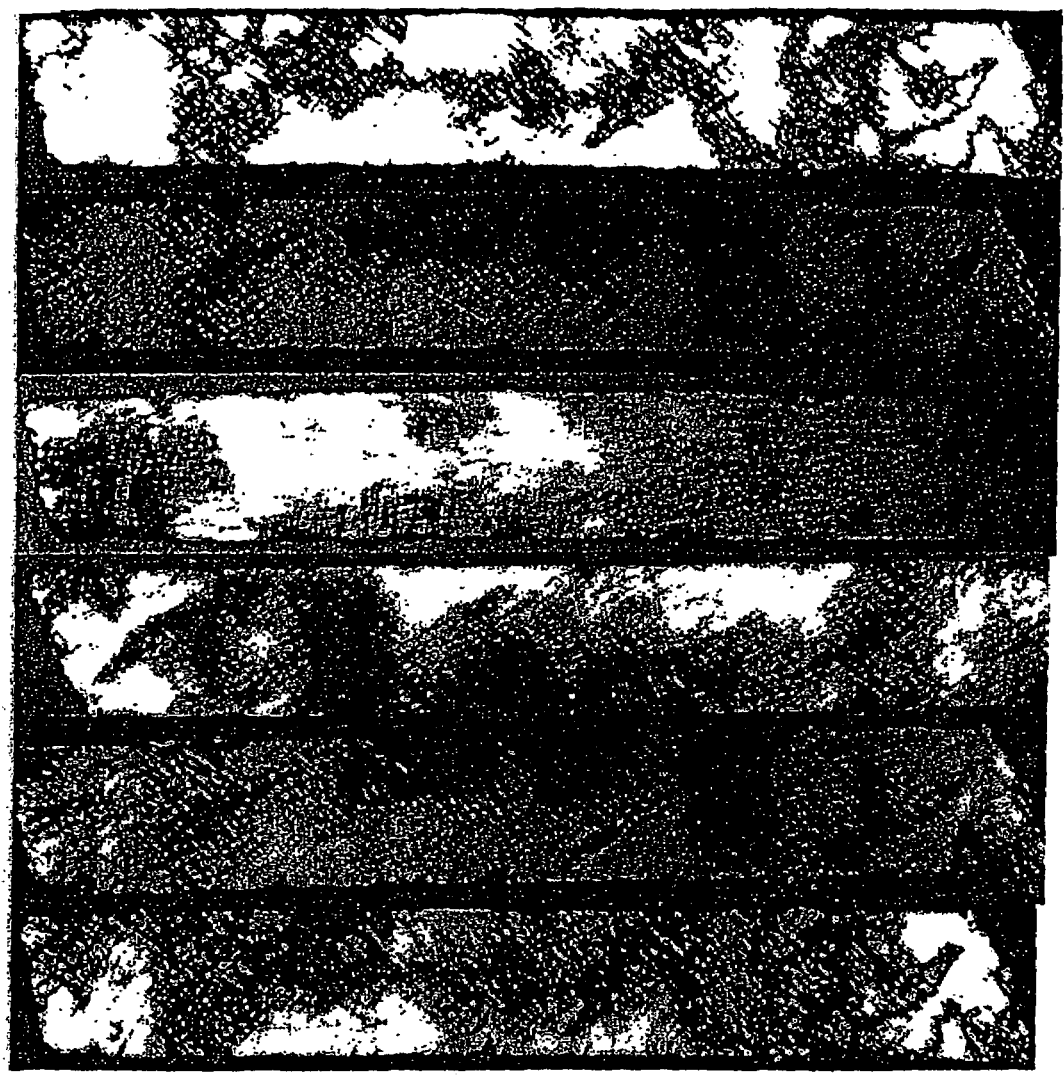
FIG. 41 From top to bottom: the orientation of the bright lamellar specimen changes in discrete steps of 0°, 39°, 45°, 80°, 84°, 90° relative to the plane of polarization.

When the long edge of a bright lamellar specimen is oriented at 45° with the polarizing plane, bright and dark fields align parallel to the long edge of the specimen (FIG. 41). When the long edge of a bright lamellar specimen is oriented at 0° with the polarizing plane, bright and dark fields align obliquely at ±45°, to the long edge of the specimen. Collagen bundles reveal intermediate orientations at intermediate orientations of the bright lamellar specimen with the polarizing plane. The collagen bundles appear homogeneously distributed along the whole lamella for both lamellar types, except at a few locations. Such discontinuities may really exist or be due to artifactual removal of bundles during dissection or be due to an optical elision of superimposed orthogonal bundles. The generalized continuous distribution of dark and bright fields as viewed under polarized light in the bright lamella affirms the expectations of various authors (e.g., Giraud-Guille, 1998) and is consistent with morphological and material science points of view.

Additional studies by confocal microscopy and X-ray diffraction suggest that oblique patterns might be minimal in bright lamellae.

EXAMPLE 11

Confocal Microscopy on Dark and Bright Lamellae

Scanning dark and bright lamellae shows differences in morphology. Since the observed morphological details leave room for several interpretations, larger specimen groups with finer scanning need to be analyzed. This confocal microscopy study was motivated by the results of the polarized light examination and was conducted to visualize collagen bundle orientation features in three dimensions, without overlap of collagen bundles of various orientation and/or ground substance.

Methods. 3 dark and 3 bright lamellar specimens were isolated as described herein. The dimension of greatest length corresponds to the circumferential direction of the layer in situ. Lamellar specimens were scanned wet every 1 μm in the thickness direction by a Leitz confocal microscope. Since the natural fluorescence of wet bone worked well with the confocal microscope, no staining of the specimen was necessary. The light detected by the photomultipliers was converted to pseudocolor in red to improve visualization of the image.

Figure 42:
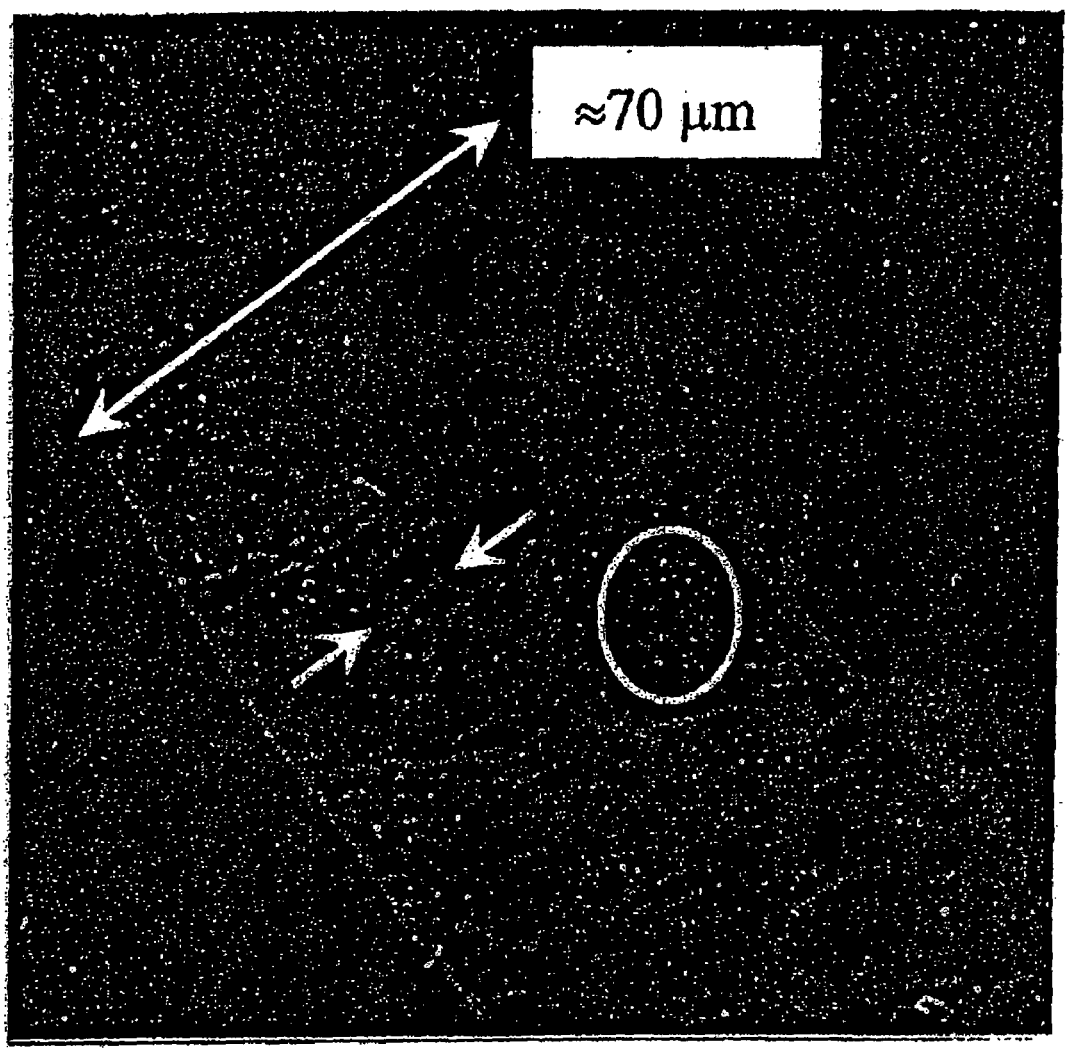
FIG. 42 Confocal microscopy detail of isolated and flattened dark lamella. Opposed arrows show the orientation of a collagen bundle arrangement ⊥ to the lamella edges. Cut radial collagen bundles appear as dots within the circle.
Figure 43:
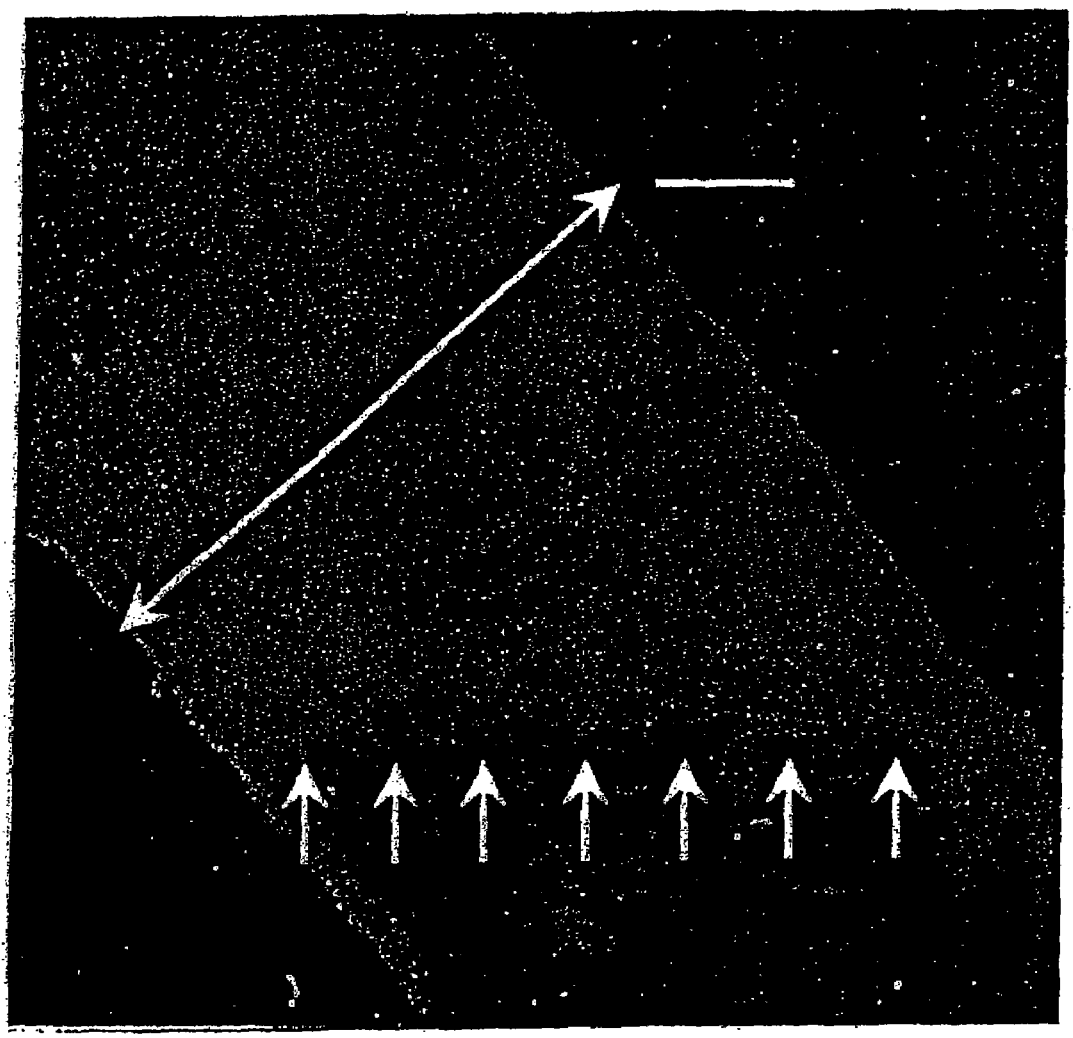
FIG. 43 Detail of isolated and flattened bright lamellar sample as viewed by confocal microscopy. Arrows indicate oblique collagen bundles extending across the lamella thickness.

Results. The dark lamellar specimens show a regular arrangement of underlying structure across the width of the specimen (FIG. 42). The bright and dark lamellae revealed different structural compositions. In the case of the dark lamellar samples discrete elements of components of the microstructure are highlighted. These consist of fibrillar elements in the plane of the image (lines) and additional elements (dots) aligned perpendicular to the same plane. There is a hint of predominant directional orientation of these fibers perpendicular to or at a slight angle to the width of the specimen that corresponds to the overall orientation of the intact osteon specimen. For the bright lamellar samples (FIG. 43) there are no such distinctly bright elements but rather there are diffuse patches of substance present that are aligned at an orientation of approximately 45° to the prepared specimen dimensions. Such patches are believed to be part of a domain. The absence of distinct fibrillar structures would support the postulate that there are differences in structural composition between the two types of lamellae. It may also be that the images were not obtained at a sufficiently high scanning resolution to be able to clearly discriminate between individual collagen bundles. The differences observed in the two types of lamellar specimens suggest that they serve distinctly different mechanical and possibly biological functions. So far we have not observed in dark lamellae by confocal microscope the oblique collagen bundles observed under polarizing microscope. As stated above, an additional explanation for the differences observed is that by scanning every 1 μm in the thickness direction, discrete structures may have been missed since the collagen bundle diameters are of the order of 0.5 0.8 μm (e.g., Herring, 1972). Examination of more lamellae by confocal microscopy in increments of 0.25 μm in the thickness direction is necessary to resolve this possible deficiency.

EXAMPLE 12

X Ray Diffraction on Dark and Bright Lamellae

Dark and bright lamellar specimens were investigated by Small- and Wide-Angle X-ray diffraction (SAXS and WAXS, respectively) for collagen and hydroxyapatite crystallite pattern orientations. These findings infer that collagen bundle orientations and hydroxyapatite patterns differ between dark and bright lamellae and follow analogous patterns within the same lamellar type. These results further support Gebhardt's theory.

Figure 44:
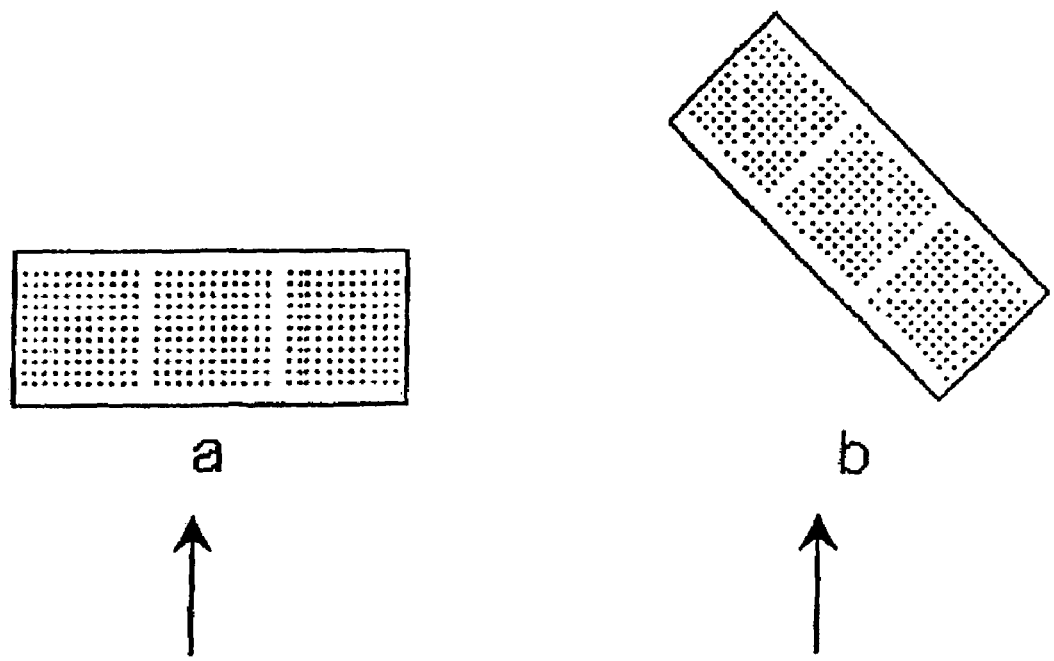
FIG. 44 Diagram of relative inclination of dark (a) and bright (b) lamellae with respect to the incident beam. Dots indicate chosen locations of scanning.

Methods. 13 fully calcified dark and 13 bright lamellar specimens were isolated from 70±3 µm transverse sections and flattened as described herein. This investigation was designed to check the hypothesis of collagen and hydroxyapatite pattern differences between dark and bright lamellae. SAXS and WAXS lend themselves well to such studies because SAXS is indicative of collagen orientation through the "staining" of the collagen bundles by the hydroxyapatite crystallites while the WAXS is indicative of hydroxyapatite pattern orientation (but not the orientation of single crystals). The direction of the incident beam was directed parallel to the lamellar plane perpendicularly to the dark lamellar specimen length direction to investigate patterns that are present and are parallel to the specimen length (FIG. 44). The bright lamellar specimen was rotated by 45° with respect to the incident beam to investigate oblique patterns. SAXS and WAXS diffraction patterns were recorded using the scanning diffractometry setup of the ID13 microfocus beamline of the European Synchrotron Radiation Facility (Grenoble, France). The beam wavelength of 0.964 Å was obtained with a Si(111) monochromator and focused to 7 µm (full width at half maximum) by a glass capillary. The sample was scanned through the beam by a computer controlled x/y gantry. Intact scales, as well as portions of scales were mounted on a goniometric head, with the surface of the scale orthogonal to the X-ray beam. Square areas of up to 50×50 µm were scanned with spatial resolutions of 5 µm and 10 µm. Diffraction patterns were recorded while moving the sample along the horizontal and vertical axes. Also, some horizontal and vertical linear scans were performed with spatial resolutions from 5 to 20 µm. Small and wide angle patterns were recorded sequentially on the same area by changing the sample-to-detector distance. The diffraction patterns were recorded with a MARR CCD detector with exposure times of 10 and 30 sec for wide and small angle respectively. The detector features are: 2048×2048 pixels, 64.45 µm×64.45 µm; 16 bit readout. The thin circumferential hemisections and transverse sections of fully calcified alternate osteons were investigated at various angles with respect to the incident beam used for verification of results.

Figure 45:
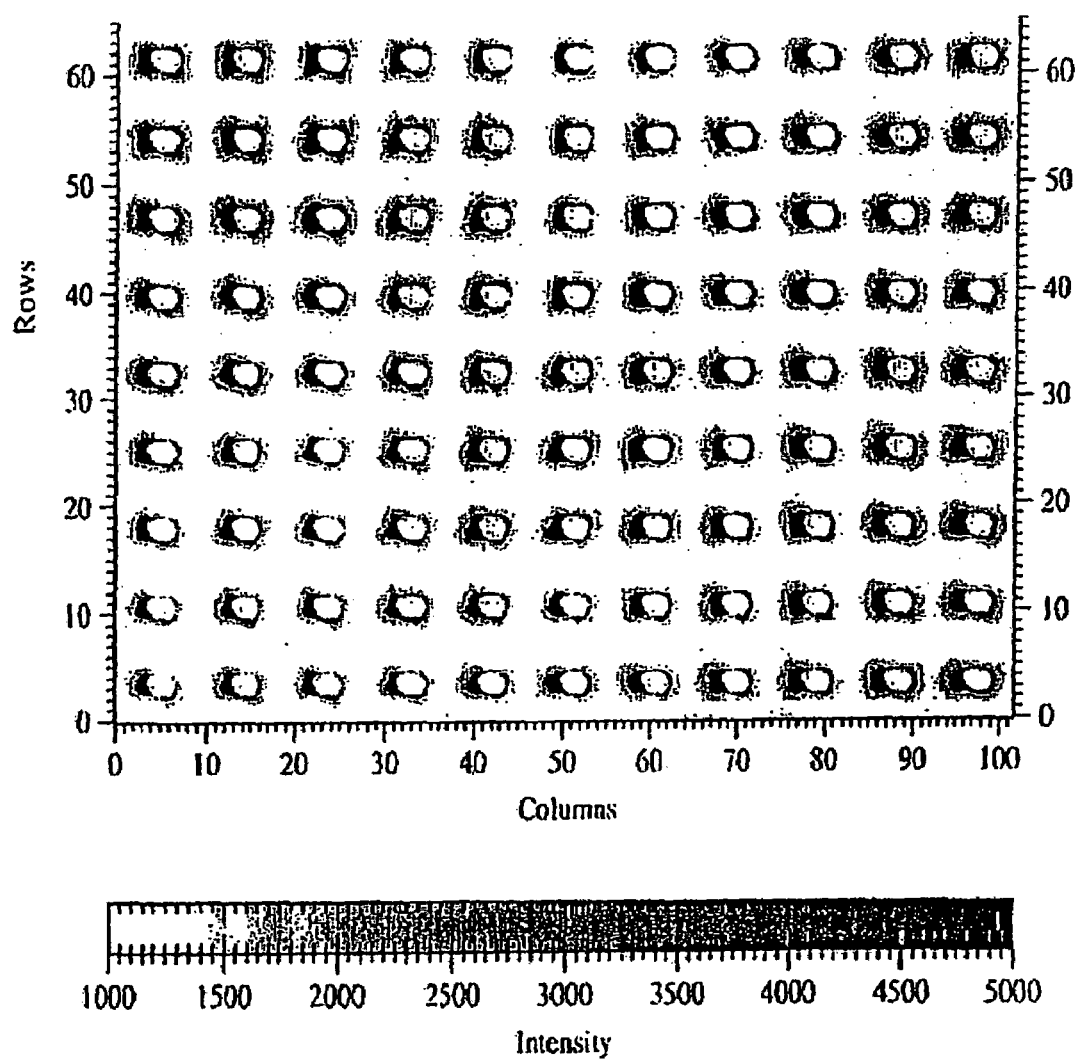
FIG. 45 SAXS images of dark lamella. The images are unchanged across the scanned area.
Figure 46:
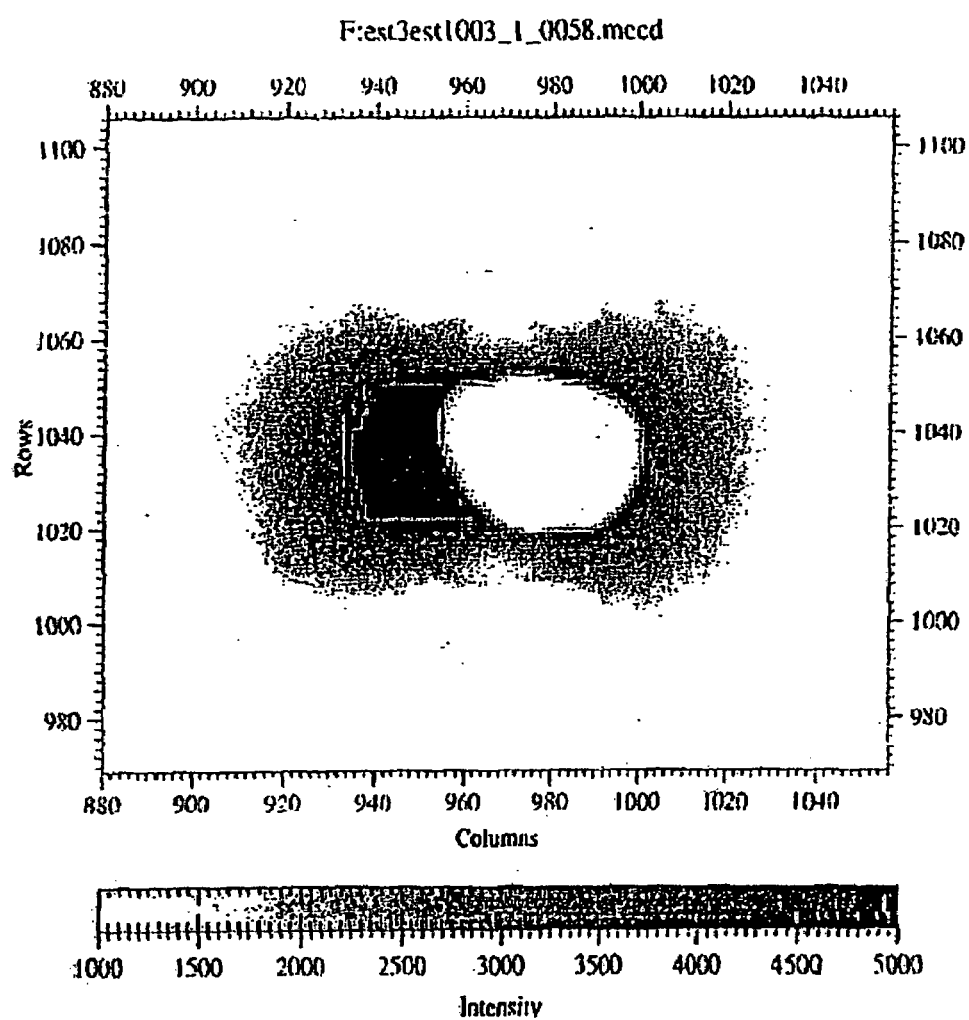
FIG. 46 Enlargement of one SAXS image from FIG. 45. Clear arching and maximum intensity orientations show single preferential collagen bundle direction perpendicular to bright lamellar width.

Results. An examination of the experimental images shows the following. The SAXS images of dark lamellae are unchanged in shape within scanned areas. This is evidence of a preferential orientation of collagen bundles (FIG. 45). A clear arching of the small-angle meridional reflection, which corresponds to the third-order collagen periodicity, is indicative of collagen orientation with respect to the osteon axis. The arching shows no change within and across the scanned areas with intensity preferentially distributed in one direction. This is interpreted as representing a single preferential collagen bundle direction. Moreover, the position of the maximum intensity oriented perpendicularly to the bright lamellar width and the arching of the small angle meridional reflection parallel to the bright lamellar width are indicative of collagen bundle orientation parallel to the osteon axis (FIG. 46). In particular, X-ray diffraction does exclude large amounts of collagen bundle and hydroxyapatite orientation oblique to the specimen length in dark lamellae.

Figure 47:
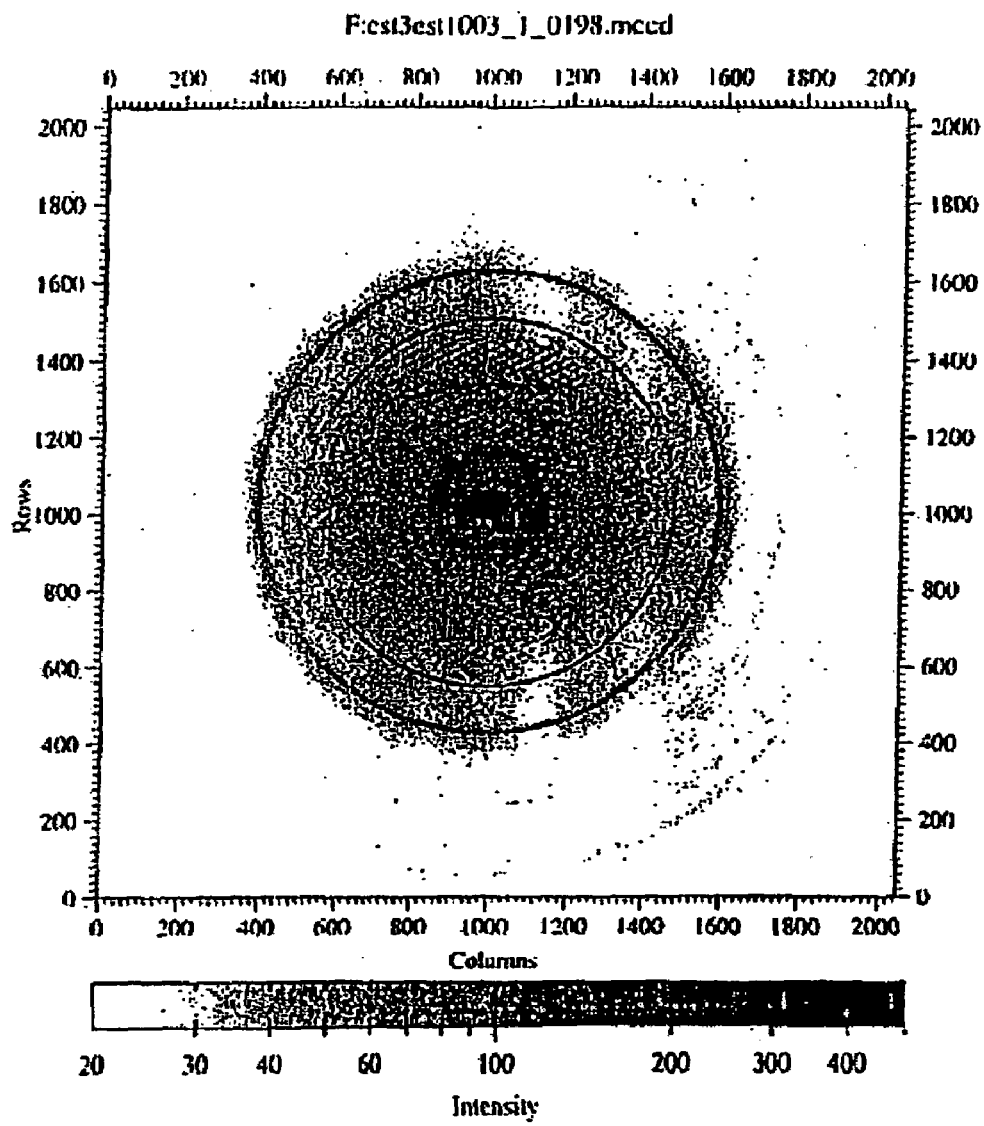
FIG. 47 WAXS image of the scanned location of the FIG. 48 SAXS image. Clear preferential orientation of the 002 reflection parallel to the dark lamellar width shows single preferential collagen bundle direction perpendicular to bright lamellar width.
Figure 48:
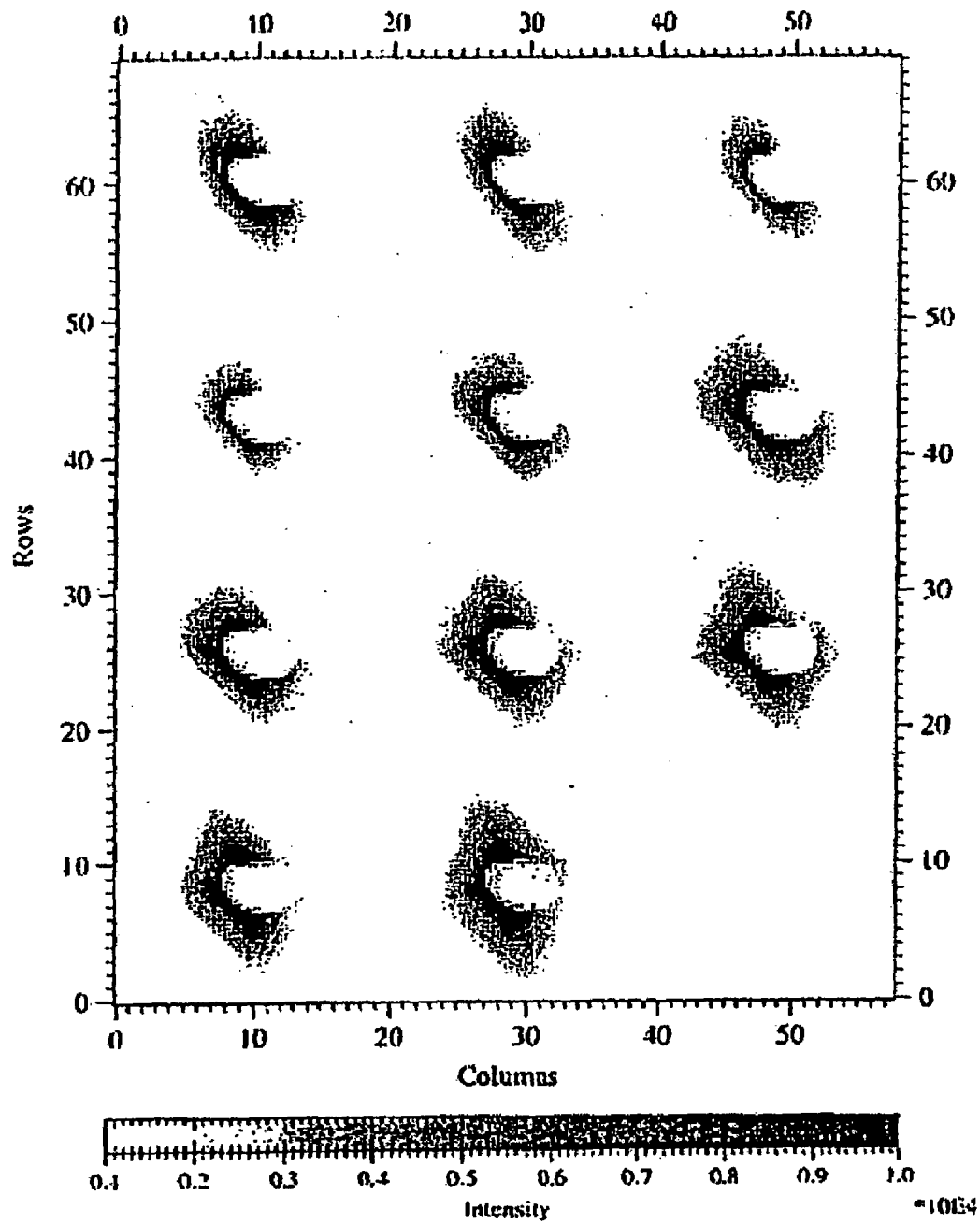
FIG. 48 SAXS images of dark lamella from a scanned area. The images change across the scanned locations.

The WAXS images of dark lamellae show a consistent preferential orientation of the 002 reflection parallel to the bright lamellar width, which indicates one preferential orientation of hydroxyapatite patterns along the osteon axis (FIG. 47). In contrast, the SAXS images of bright lamellae change in shape (intensity and inclination) within scanned areas, evidencing one or two preferential orientations of collagen bundles at ±45° lamellar width direction (FIG. 48). Therefore, bright lamellae contain areas with oblique collagen bundles, at approximately ±45° with the osteon axis. The arching of the SAXS meridional reflection is unclear on bright lamellar specimens. This is interpreted as a lack of specific collagen orientation. The WAXS images on bright lamellae show a preferential orientation of the 002 reflection at 45° with respect to the lamellar width direction in only some areas (FIG. 50). This indicates the local presence of hydroxyapatite orientation oblique to the osteon axis. The lack of consistent preferential orientation of hydroxyapatite patterns suggests a higher directional disorder in comparison with dark lamellae. Note the consistency of the results for collagen bundles and hydroxyapatite patterns, which support the similarity of patterns between collagen and hydroxyapatite. Experimental images are currently being examined for differences in hydroxyapatite density between the two lamellar types. The clarity of the result regarding the longitudinal patterns of dark lamellae, shows that the oblique patterns, if present, should be minimum so as not to create enough structural disorder. This result supports the hypothesis that oblique patterns are not present in dark lamellae.

EXAMPLE 13

Long Bones' Osteonic Lamellae, the Building Blocks of Compact Macrostructure This Example reports the assessment of the dominant orientations of collagen bundles and hydroxyapatite crystallites in dark and bright lamella.

As discussed above, bone is hierarchical, non-homogenous and anisotropic. The building blocks are entities with simple known structure, which form a pattern. Starting in the 1950's, Antonio Ascenzi's group consistently isolated microscopic units of bone and tested them mechanically. Accurate computer modeling of bone behavior allows reliable estimates of stresses applied to bone which can be applied for, e.g., to study fractures; where and how they start and spread. This Example focuses on compact bone: osteons and their coaxial layers, lamellae.

Osteons are not building blocks: even though they have a simple structure, they do not form a pattern, whereas lamellae are. Bone micromechanics finds justification in bone morphology. Back in 1930, Petersen introduced the concept that bone structures can be viewed as a four-order hierarchy arranged in decreasing size. The first order comprises the structures corresponding to gross shape and differentiation between cancellous and compact bone. The second order of compact bone includes haversian systems (or secondary osteons), cylindrical lamellar systems, and additional related structures, e.g. bone marrow. The third order consists of collagen fibrils, which lie in the ground substance. The fourth order consists of the molecular patterning between organic and inorganic phases.

Compact adult bone varies in degree of calcification and collagen bundle orientation, and these are both crucial variables in any bone model. The osteons of compact bone can be studied by micro-X-ray, using a micro-focus and a high resolution film (more than 2000 lines per millimeter), clearly revealing osteons of 220-250 micron diameters. Wet bone, for example shaft transverse sections, under circularly polarized light shows dark and bright lamellae.

Many researchers have worked on the question whether collagen bundles and/or hydroxyapatite crystallites show similar or different densities and orientations in dark and bright lamella, starting with Rauber (1873) and then Gebhardt in 1906. Some people hypothesized differences in phase orientation and other people differences in phase density (Marotti). According to the invention, we have indeed found differences in both orientation and density.

Lamellae are building blocks of the compact macrostructure. For example, in a femur sample, a 90° rotational pattern from proximal to distal third of the largest squares, which indicate dominance of bright lamellae, corresponds to the areas of maximum compression. This type of correspondence is present in all long bones, and the bright lamellar percentage increases with the compressive stress magnitude. FIG. 59 shows an example of femur analysis. In this figure, the largest squares, which indicate dominance of bright lamellae, show a clockwise rotation from upper to lower third corresponding to the concave regions of the femur. Since the femur has two curvatures, compression on the femoral head produces bending. Bending manifests itself in tension on the convex regions and compression on the concave regions. The combination of bending with axial weight-bearing gives a distribution of compression maximum on the concave regions and minimum on convex regions. Other patterns are also found that relate the lamellar type to gross geometry. Accordingly, lamellar structure is important for bone modeling.

Figure 51:
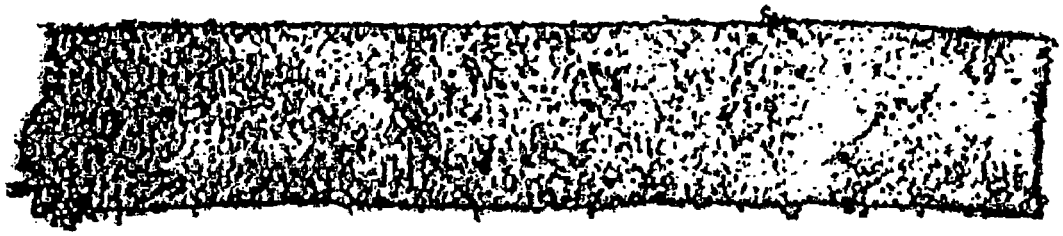
FIG. 51 Isolated flattened lamellar specimen. The breadth of this figure corresponds to the "length" of the lamellae.

As previously described, lamellae can be isolated in two ways, one of which applies to both lamellar types. In this method, a trapezoid is cut from a thin transverse section and glued to a microscope slide (FIG. 39). The outer lamella is then isolated by a free-hand technique, and the lamella is not isolated in its entirety because of the need to hold the specimen. After isolation, the lamella is gently flattened (FIG. 51). The width (i.e., breadth or length) measures approximately 70 microns.

Microscope studies using circularly polarizing light can be done by gradually rotating a wet lamellar specimen on the stage plane through 90 degrees relative to the polarizing planes of the two Nicol's prisms. FIG. 40 shows dark lamellar specimen: bidirectional close to ±45 degrees and unidirectional close to longitudinal collagen. FIG. 41 shows bright lamellar specimen: bidirectional ±45 degrees and unidirectional transverse collagen. Thus, the main difference between dark and bright lamellae is the presence of longitudinal collagen bundles in dark lamellae and of transverse bundles in bright lamellae. Differences among oblique collagen patterns are not apparent. Moreover, polarizing light does not allow for establishing thickness location of specific collagen bundle orientation.

For further studies of lamellae, X-ray diffraction in the form of SAXS and WAXS can be applied. Collagen orientation is detected through the "staining" of the collagen bundles by the hydroxyapatite crystallites. SAXS and WAX are indicative of collagen and hydroxyapatite orientation. SAXS focuses on the 64 nm collagen 3rd period (see, e.g., Hodge-Petruska (1963) model of the collagen fibril). The $3^{rd}$ period of collagen is the groove where the hydroxyapatite crystal sits. Therefore, SAXS is indicative of collagen because the collagen is tinted by the hydroxyapatite. WAXS, on the other hand, is indicative of the hydroxyapatite crystal axis because the unit c-axis coincides with the crystal long axis. WAXS focuses on the 0.688 period along the c-axis of the unit cell $Ca_{10}(PO_4)_6(OH)_2$. WAXS describes the 002 reflection, wherein 002 refers to the intersections of the plane that describes the period with the three axes of reference: In common 3D graphical representations of crystal patterns, 0 refers to the O-intercept and 2 with the ½ the intercept with the c-axis, which coincides with the axis of the crystal.

Figure 52:
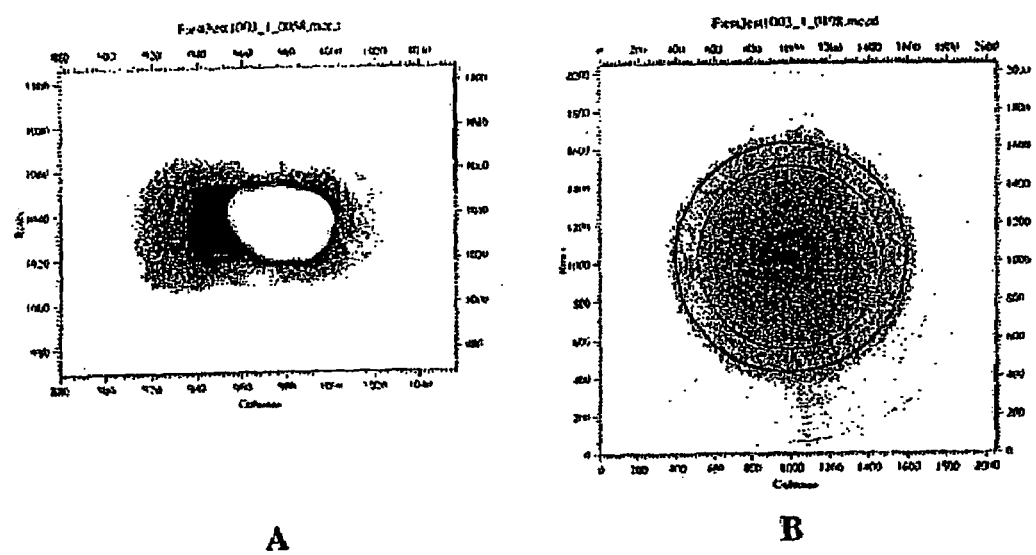
FIGS. 52A and 52B. (A) SAXS of dark lamella; (B) WAXS of dark lamella.
Figure 53:
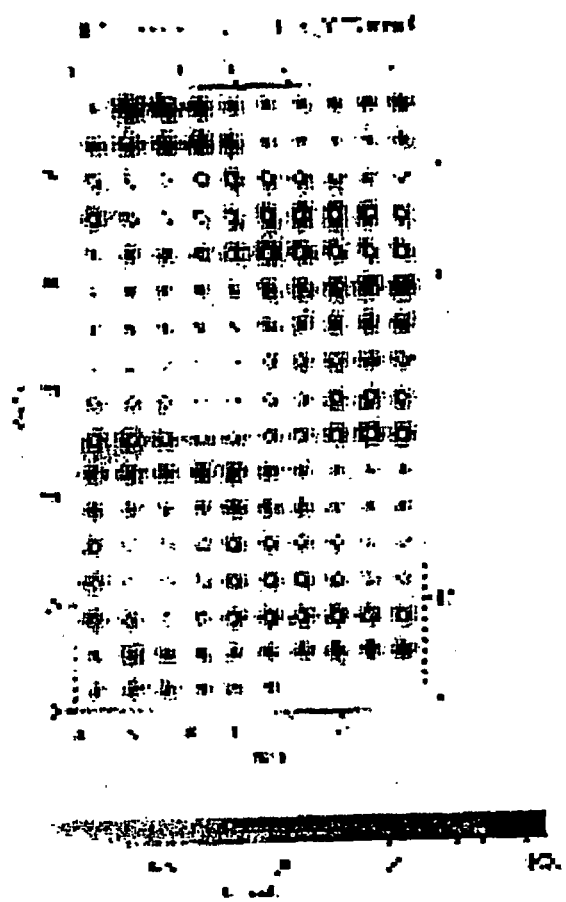
FIG. 53 SAXS of bright lamella.
Figure 54:
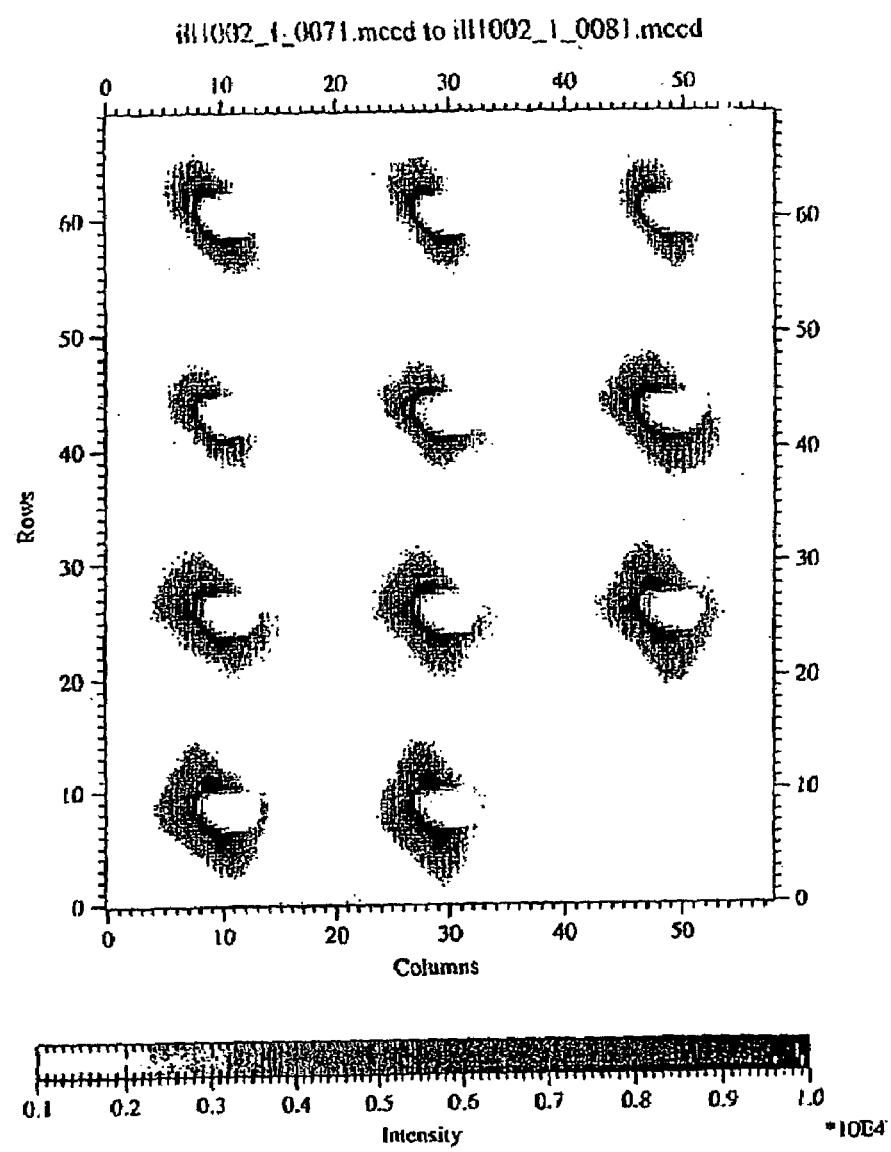
FIG. 54 SAXS of bright lamella.
Figure 55:
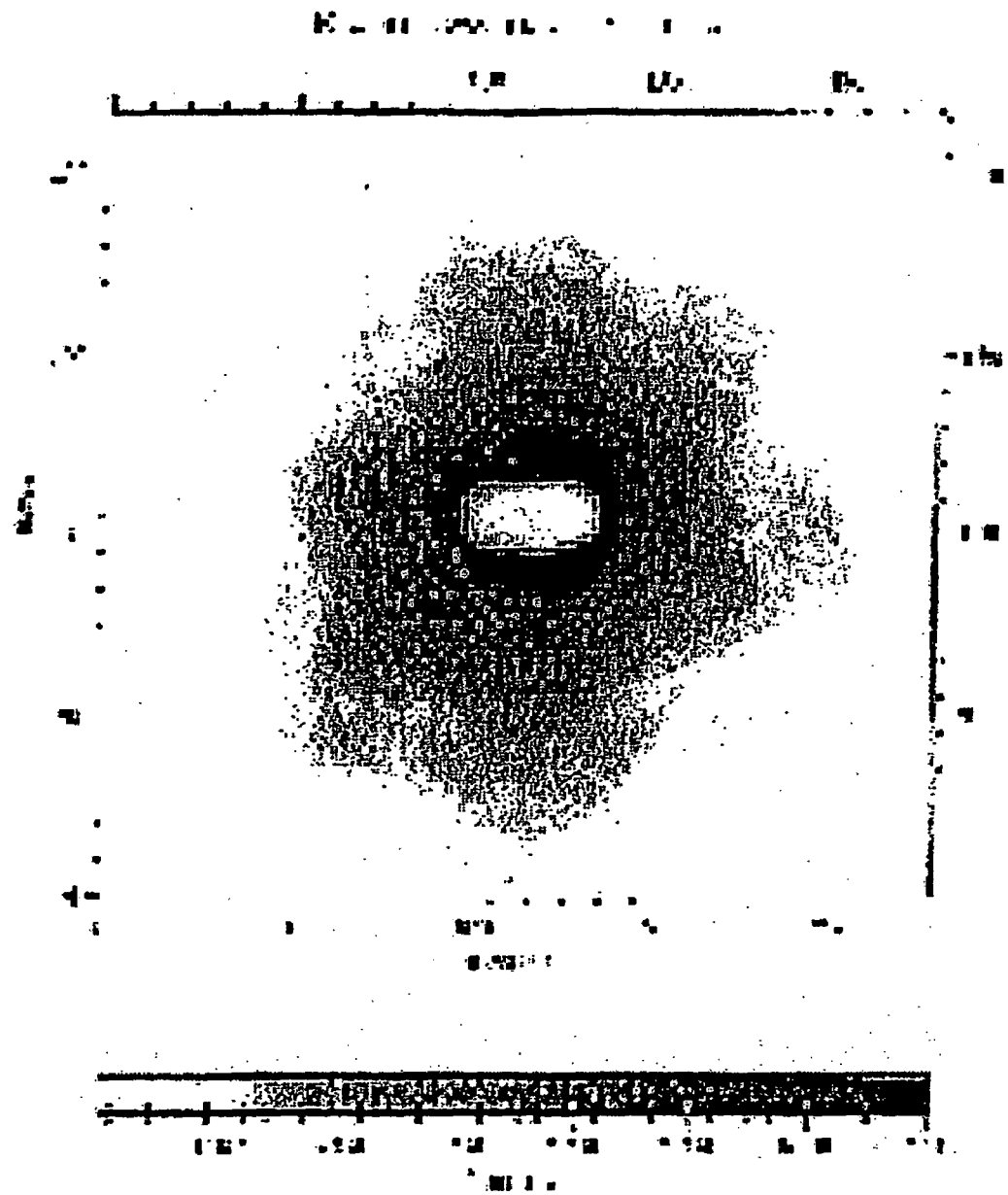
FIG. 55 SAXS of bright lamella.

Lamellar specimens, thin longitudinal hemisections and transverse sections of alternate osteons should be positioned normally to the incident beam (FIG. 44). Such sections can be used for lamellar result verification. As shown in FIG. 45, images are essentially unchanged across the scanned area. In the enlargement shown in FIG. 46, the clear arching and maximum intensity orientations show single preferential collagen bundle direction essentially parallel to dark lamellar width. Also, the diffuse inorganic phase is oriented along the lamellar width, i.e. the osteon and long bone axes. In FIG. 52, SAXS and WAXs analysis of dark lamella shows that collagen bundles and adjacent hydroxyapatite crystallites follow the same orientation. FIG. 53 shows bright lamella, wherein the images change across the scanned area (details in FIGS. 54 and 55).

Figure 56:
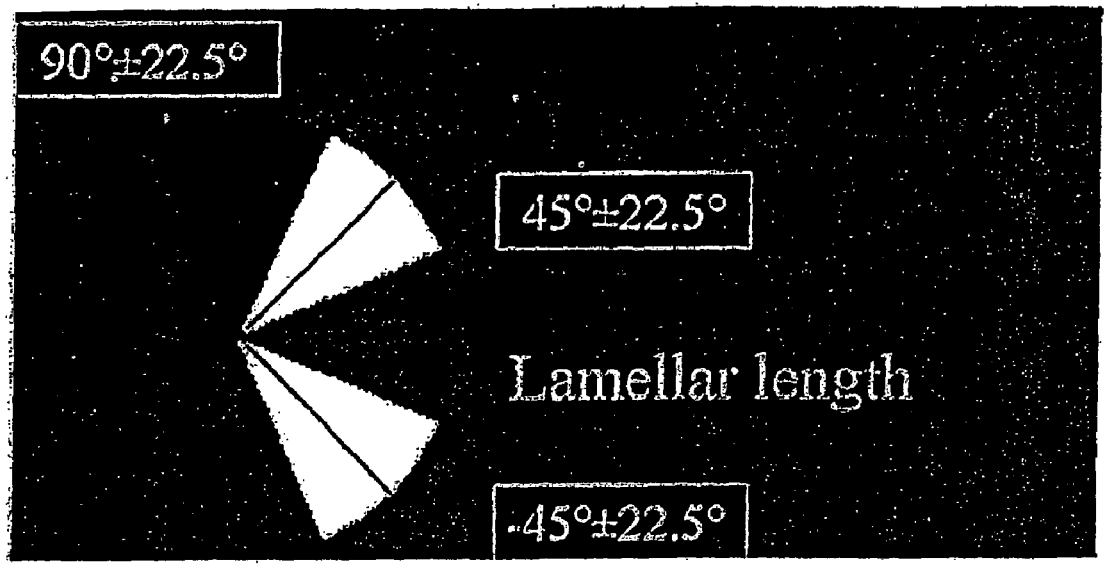
FIG. 56 Collagen and hydroxyapatite dominant directions of dark and bright lamella.

FIGS. 56 and 57 show the results of X-ray diffraction data, revealing the dominant orientations of dark and bright lamella. Specifically, the highest percentage of collagen bundle and hydroxyapatite crystallites orientation is in a single range, that between 67.5 and 112.5 (90±22.5) degrees. In bright lamella, there are two orientations, so that the collagen bundle and hydroxyapatite crystallites orientation ranges between 22.5 to 67.5 (45±22.5) degrees, and between −67.5 to −22.5 (−45±22.5) degrees, wherein the lamellar length is parallel to the x-axis. For the bone model of the invention, this means that when lamella and their collagen bundles and hydroxyapatite crystals are included in the model, the dominant percentages should average between these values.

Figure 58:
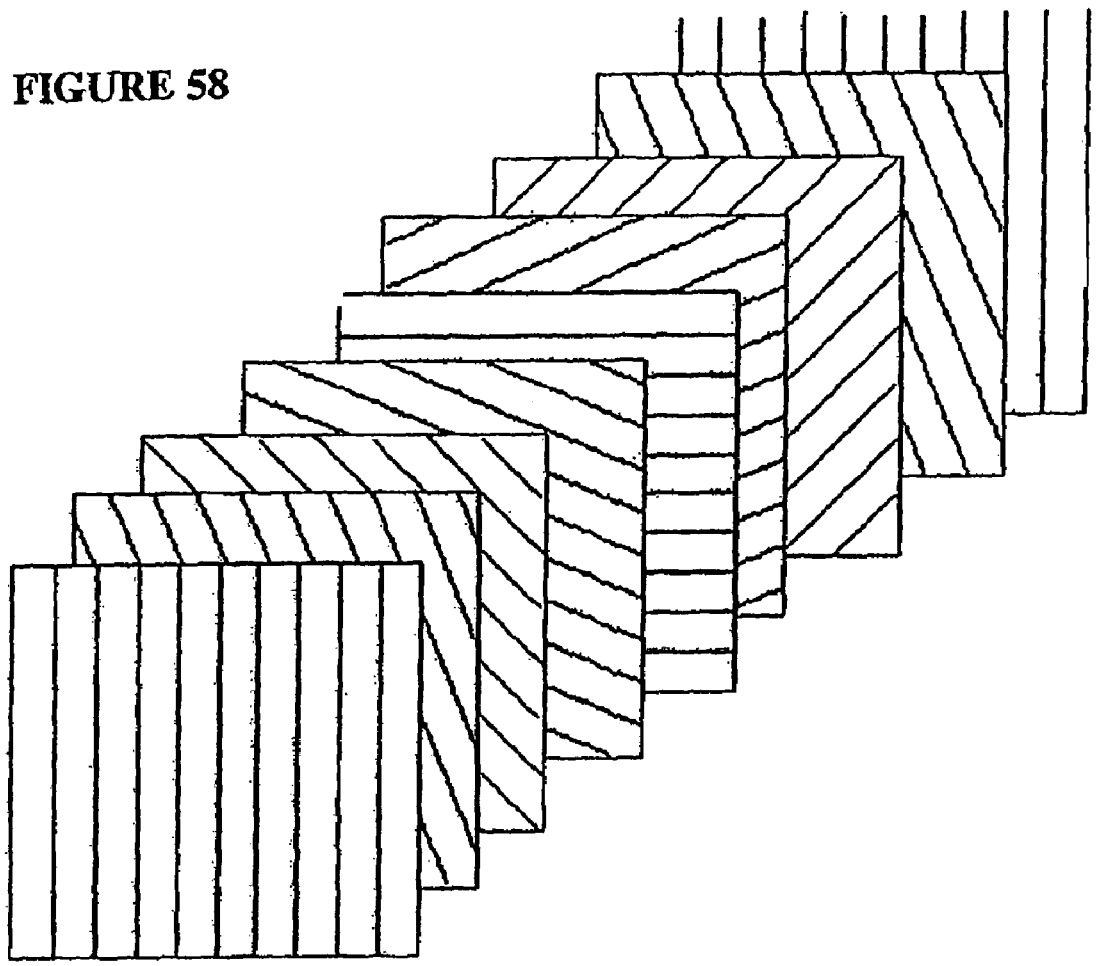
FIG. 58. Twisted plywood model of osteon.

FIG. 58 shows how the different orientations can be modeled, e.g., using a twisted plywood structure.

These above findings can all be incorporated into the bone modeling concept, as well as the dimensions of the domains, collagen density within domains (which can be studied by confocal microscopy) and the mechanical properties of lamellae (which can be studied by tensional loading with a microextensometer).

EXAMPLE 14

Structural Dimensions and Patterns Within Single Secondary Osteons

This Example explores the structural dimensions and patterns within single secondary osteons, with consideration of their biological variation. Stereometric data, combined with data from examination by regular and circularly polarized light, confocal microscopy, synchrotron X-ray diffraction and micro-focus high-resolution micro-X-ray, provide the basis for models, preferably computerized, of single osteons and single lamellae. These models provide the concurrent representation of (1) collagen-hydroxyapatite orientation, (2) relative hydroxyapatite percentage, (3) distributions of osteocytes' lacunae and canaliculae, and (4) biological variations in the dimensions of the relevant structures. The mathematical software Maple™ can be employed to implement the computerized models. While the parts of the models are preferably constructed on a personal computer, the voluminous data associated with the representation of lacunar and canalicular distributions in this Example require a supercomputer for the assembly of the models and final analysis. The programming used to define the model affords the option to randomize the dimensional specifications of osteons, lamellae, lacunae and canaliculae within the experimentally observed numeric ranges and distributions. Through this option, the program can operate so that each run of the file produces a unique random model within the observed biological variations. Further, the program can also be run to implement specific dimensional requirements. The modeling has applications in the micro-structural study of fracture propagation and remodeling, and in the simulation of mechanical testing.

This Example focuses on identifying and representing the structural patterns that are observed within a single secondary osteon, as an expression of the biological variations within the Haversian system. The comprehensive identification of the patterns comes together in a computerized modeling methodology that, within the experimentally observed biological variations, allows the structural simulation of a single osteon and/or a single lamella.

Two interconnected motivations justify the attention to osteons. First, the complexity of anisotropy and non-homogeneity in the macrostructure of compact bone can only be unraveled by descending to the osteon level and identifying the osteon's lamellae as building blocks of the macrostructure (Ascenzi A., 1988). Second, important current biological problems, such as transduction mechanism appraisal, fracture risk assessment, implant success prediction, and evaluation of new therapies for bone metabolic and remodeling disorders, depend on understanding the local microstructural properties around bone cells.

The structure of secondary osteons has remained an open question since their first microscopic observation (Leeuwenhoek, 1693). Numerous microscopic techniques (e.g. Ebner, 1875; Kölliker, 1854; Ranvier, 1887; Gebhardt, 1906; Ziegler, 1908; Weidenreich, 1930; Amprino, 1946; Ruth, 1947; Rouiller et al., 1952; Engström and Engfeldt, 1953; Frank et al., 1955; Frank, 1957; Vincent, 1957; Smith, 1960; Currey, 1964; Ascenzi A. and Bonucci, 1967, 1968; Boyde, 1969; Marotti, 1979; Reid, 1986; Giraud-Guille, 1988; Ascenzi A. et al. 1987, 1994, 1997; Ascenzi M.-G., 1999; Carter and Hays, 1977; Ascenzi M.-G. et al., 2003) have been employed towards the recognition of the relevant structural variables and the generation of appropriate models. Collagen fibril orientation, degree of calcification, and distribution of osteocyte lacunae and canaliculae are relevant variables. The range of collagen density variability and its relevance remain unclear. The most recent theory on osteon's lamellar structure (Ascenzi M.-G. et al., 2003) differentiates the lamellar types in terms of collagen bundle and hydroxyapatite orientation and is based on findings by regular and circularly polarized light, confocal microscopy, synchrotron X-ray diffraction and micro-focus high-resolution micro-X-ray on isolated osteon lamellae.

The methodology of this Example starts with the expression of the geometry of a single osteon or a single lamella by means of thick hollow cylinders, cylindrical shells, ellipsoids and thin long cylinders (Andreuzzi, 2003). It expands the existing structural theory regarding the collagen-hydroxyapatite distribution within the osteon to include lacunar and canalicular distributions. The methodology is checked through comparison of the generated model with an actual specimen. New information emerges on the coexisting distributions of lamellar, lacunar and canalicular distributions across the spectrum of osteon types.

Method

Figure 60:
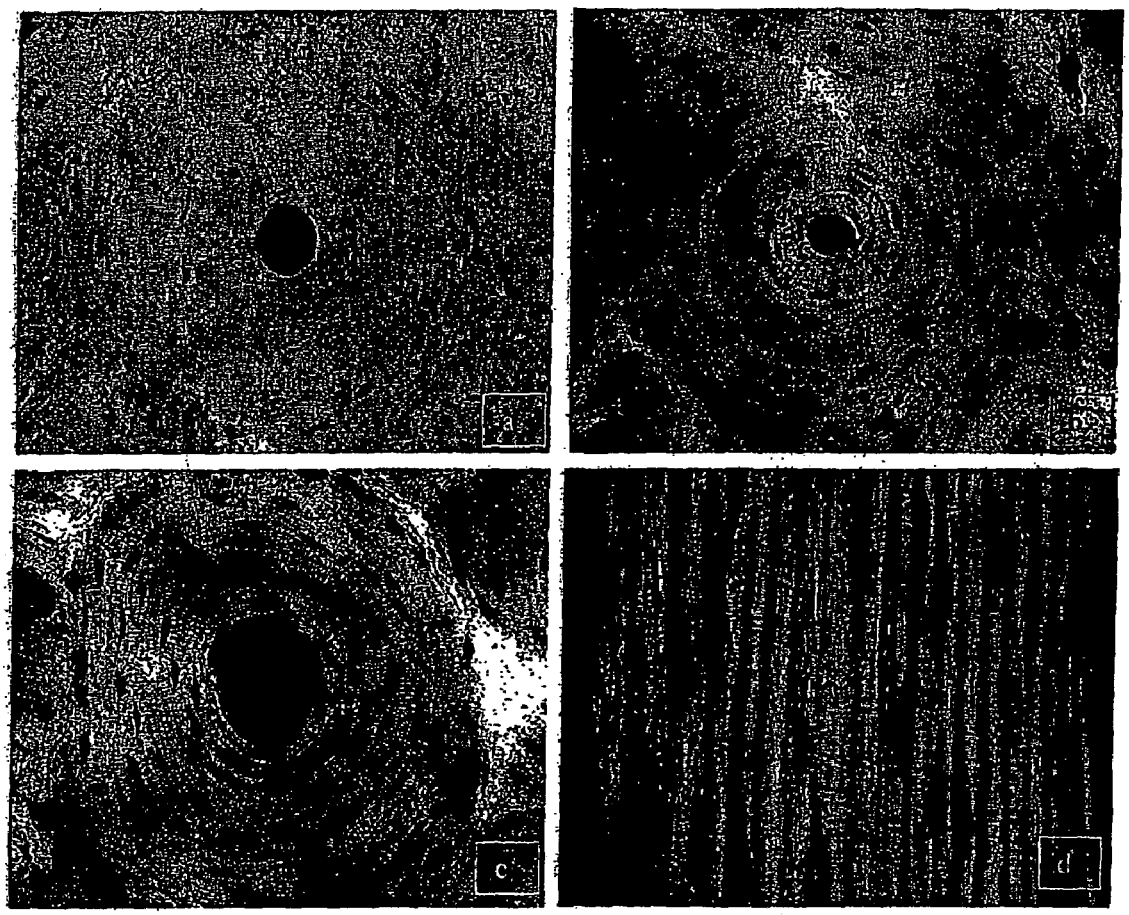
FIG. 60(a)-(d). Examples of biological variations within transverse (a-c) and longitudinal (d) osteon sections viewed by transmission microscopy. (a) Extinct osteon #551 (×281); (b) alternate osteon #311 (×281); (c) bright # 381 (×281); and (d) alternate osteon #361 (×637).

This Example presents a new methodology to model the biological variability of compact bone microstructures. FIG. 60 shows examples of such variability. The new methodology is based on the identification of experimentally observed structural patterns. It is independent of the particular experimental data that is employed to define the ranges of variability in the model. Experimental data on osteons presented here is employed to verify the model.

Experimental Data

The osteon data is obtained from the observation and measurement of photographs taken under regular and circularly polarized light microscopy of 124 transverse sections and of 54 longitudinal sections of femoral osteons at magnifications ranging between 190 and 600. Such photographs were prepared by Antonio Ascenzi and Alessandro Benvenuti at the University of Rome "La Sapienza" during their decades of research on osteons.

The photographic material was prepared as follows. Post mortem femoral shafts, free of evident bone pathology, of male humans aged 19-40, provided the bone material. The middle shaft of each femur was removed, defleshed and air-dried. A rotating saw microtome equipped with a continuous water lavage to prevent heating of the material was used to section the material. The middle-shafts were first cut into 3 cm long transverse sections. The 3 cm long transverse sections were cut into 50-100 μm thick either transverse or longitudinal sections. All the sections were micro-X-rayed (Amprino and Engström, 1952) to assess the degree of calcification of the osteons. The micro-X-rays were examined under regular light to select osteons that were mostly cylindrical in shape and at either the beginning (70%) or final stages (100%) of calcification. The sections were then examined under circular polarizing light to choose the subset of osteons, which are representative of the spectrum of all possible lamellar arrangements. Such osteons are those that under circularly polarizing light in transverse section appear predominantly dark (extinct osteons), alternatively dark and bright (alternate osteons), and predominantly bright (bright osteons). The longitudinal sections were then used to prepare osteon specimens by latheing. A Leitz camera was used to photograph each of the osteons chosen on the transverse and longitudinal sections, perpendicularly to either the section's transverse cut or the osteon lathed surface. The focus of the camera was adjusted so only the generally longitudinally oriented lacunae appear on the longitudinal section.

A precision scale was used to measure the details of the osteon structure shown on the photographs. The dimensions of larger entities, such as osteon radii, were measured in triplicate, while the dimensions of smaller entities, such as lacunae and canaliculae, were measured twice by two different technicians to ensure measurement consistency. The error was at most on the order of ±1.31 μm. Osteon radii, number of lacunae, lacunar dimensions and relative distances, and canalicular length were measured on photographs of transverse sections. Lacunar dimensions and relative distances were measured on photographs of osteon specimens obtained from longitudinal sections. Tables 7 and 8 present the ranges and averages of each measured entity across the five osteon groups: extinct osteons at final stages of calcification, alternate osteons at either initial or final stages of calcification, and bright osteons at final stages of calcification. The extinct osteons at initial stages of calcifications were too few to be included.

Structural Patterns

The following patterns emerged from observation of the photographs:
I. The lacunae closer to the cement line, that is the osteon outer lateral boundary, lie on the outer-most one or two lamellae and are among the largest present in the osteon section.
II. The lacunae closer to the Haversian canal lie on the inner-most one or two lamellae.
III. Any three adjacent lacunae on a transverse section are located at a staggered distance from the Haversian canal and can be visualized as located at the vertices of a triangle.
IV. The lacunar cross section is rounder and less elongated in extinct osteons than in alternate and bright osteons.
V. The canaliculae are mostly generally radially distributed on planes transverse to the osteon axis. They appear to spread as their distance from the lacuna where they initiated increases. This is especially pronounced for the canaliculae running towards the cement line.

Mathematical Model

The model is developed from the above-identified patterns and from results as to collagen bundle and hydroxyapatite orientation (Ascenzi, M.-G. et al., 2003) as explained below.

The construction of the model is realized with a computer program containing procedures of Maple™ (Waterloo Maple Inc., Waterloo, Ontario, Canada;) syntax. The program provides for the construction of a three-dimensional model. The program begins with the option to build either a random or a specific model or a combination of the two. If the random model is chosen, at any time during the model's construction when an entity dimension needs to be entered, the program chooses a random value within the entity's range (from Tables 7 and 8) and along its observed distribution. The tabular data can be replaced by any other experimental data set of osteons on transverse and on longitudinal sections. If the specific model is chosen, the user specifies the desired dimensional choices. This second option was introduced to test the program's flexibility and ability to reproduce the photographic images of osteon specimens. The third option combines the previous two to allow certain dimensions to be chosen randomly while others are specified. This option serves to build models of specimens where only some of the constituent dimensions are known. The following explanation refers to the random model because it is more general and any random choice can be replaced by a user's choice.

Once the osteon type (extinct, alternate or bright) is chosen, the program builds the model's geometry, which is differentiated between global (model of single osteon with lamellae or single lamella) and local (model of lacunae and canaliculae). The global geometry consists of thick cylinders and cylindrical shells, which model osteons and lamellae (Ascenzi M.-G., 1999), respectively. Within the global geometry, the description of the collagen and hydroxyapatite orientation is specified. The local geometry consists of ellipsoids that model lacunae (Ebner, 1875) and thin cylinders that model canaliculae. Both the global and local geometry are specified in terms of equations obtained by appropriate translations, rotations and intersections of cylinders and ellipsoids initially centered at the origin of a reference system. Because the lamellar model is obtained from the osteon model by a mathematical process that simulates the experimental isolation of a single lamella portion from an alternate osteon (Ascenzi, M.-G. et al., 2003), the osteon model is presented first.

Global Geometry

The random choices of external and internal diameters and height for the osteon model specify the global geometry's hollow cylinder. The sequence of the osteon's lamellae is then modeled in dependence of the osteon type (extinct, alternate or bright). If the alternate osteon type is chosen, either the program chooses randomly, or the user specifies, whether the lamella adjacent to the Haversian canal is extinct or bright. The thickness of the thin coaxial cylinders that model the lamellae are then chosen randomly or by the user within the ranges observed experimentally under circularly polarized light during the years of experience with lamellar isolation: 3-15 μm for extinct and 2-12 μm for bright lamellae. Such values can be replaced by the user's desired values. The procedure for selecting the random lamellar thickness values stops as soon as the osteon model thickness is achieved or exceeded. If exceeded, the last lamellar thickness is excluded and the difference between the osteon model thickness and the sum of the lamellar models' thickness values is randomly divided and distributed among the lamellar models.

Figure 61:
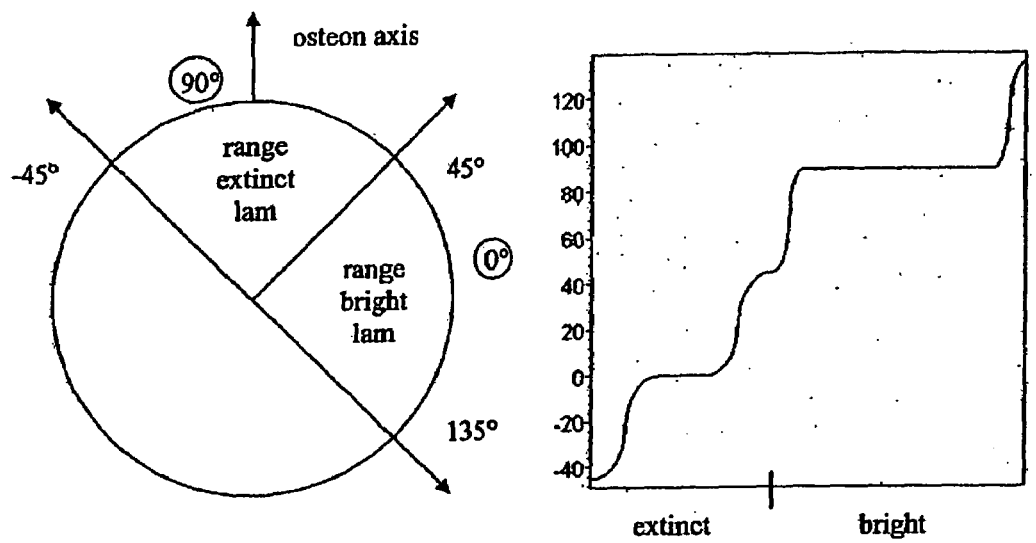
FIG. 61(a)-(b). (a) Angle ranges of collagen-hydroxyapatite orientation for extinct (−45°, 45°) and bright (45°, 135°) with respect to the osteon axis. The circled values 90° and 0° are the dominant orientations. (b) Collagen-hydroxyapatite orientation angle within two adjacent extinct and bright lamellae of alternate osteon within lamellar thickness of 6.25 and 10 µm respectively. The horizontal segments show a dominant orientation at 0° for the extinct lamella and minor orientation at 90° for the bright lamella.

Each extinct and bright lamellar representation in the model is then associated to a function that represents the collagen and hydroxyapatite orientation distribution with respect to the osteon model axis. The unidirectional dominance at 0 degrees within a [−45,45] degree range for the extinct lamella and a bi-directional dominance at ±45 degrees within a [45,135] degree range for the bright lamella (FIG. 61a) by X-ray diffraction is translated mathematically as follows. The collagen-hydroxyapatite orientation is modeled by continuous and smooth functions in agreement with the continuous and smooth variations (FIG. 61b) observed by polarized light on lamellar flattened specimens. Because X-ray diffraction does not quantify the "dominance", in first approximation dominance is translated into 75% of the lamellar thickness for both lamellar types. Since the "dominance" location is still experimentally unclear within the lamellar thickness, the dominant orientation is placed in the middle of the extinct lamella and towards the edges of the bright lamella for simplicity. A more precise and sophisticated model of collagen-hydroxyapatite orientation awaits further information from a confocal microscopy study, which is currently underway. FIG. 61 shows the collagen-hydroxyapatite orientation on two adjacent lamellae of an example of alternate osteon model.

Local Geometry: Ellipsoids

Figure 62:
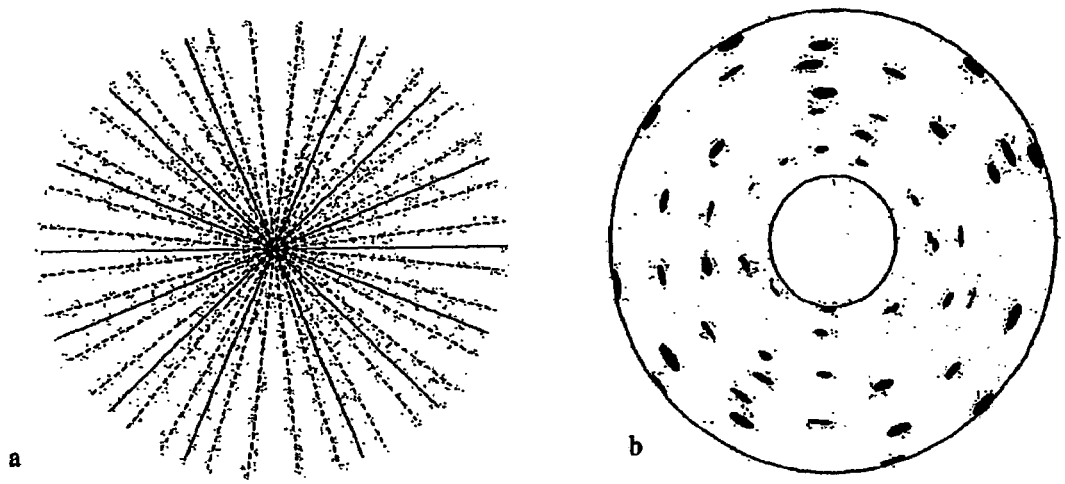
FIG. 62(a)-(b). (a) The centers of the ellipsoids which model the lacunae are first distributed randomly along n solid rays (in this model, n=16) and then moved circumferentially randomly within the region bracketed by the adjacent dashed rays. (b) The generated ellipsoids that model the lacunae within the two cylindrical surfaces that lie next to the Haversian canal and cement line.

The first step is assignment of the distribution of the centers of the ellipsoids. In accordance with the fact that the osteon tissue is generated starting from the cement line inward, the centers of the ellipsoids are chosen from the osteon model outer boundary inward. Because of pattern I the distances of the centers of the ellipsoids modeling the outermost lacunae are chosen randomly so that the centers fall within the two most-outer thin coaxial cylinders modeling the lamellae. By drawing rays from each outer lacuna to an estimated center of the Haversian canal on the photographs, it is observed that each ray intersected some lacunae and a few more lacunae lay at a relatively small distance from each ray. Therefore, a random number of rays (see solid rays in FIG. 62a) are chosen corresponding to a fixed angle (22.5° in the figure). The ellipsoid centers were placed along rays at a randomly chosen fixed radial distance from each other within the measured range starting with one within the two most external thin cylinders and finishing with one within the two most internal thin cylinders (in agreement with pattern II). Finally, the ellipsoid centers were translated a random distance from the ray circumferentially within an ad hoc angular range to create disorder (FIG. 62b). Unwanted intersections between any two ellipsoids are avoided in two ways: first, by choosing an angular range smaller than the angle between two successive black rays by the angle corresponding to the maximum value of the ellipsoid axis; and secondly, by choosing alternatively on any other ray the first ellipsoid's center to be located within the first-second thin cylinders closer to the model's inner cylindrical surface or within the second-third thin cylinders closer to the model's inner cylindrical surface.

Pattern III was satisfied as the centers of the ellipsoids are placed randomly along the rays. A random value is chosen for the ellipsoid major axis within the range of the major axis of the lacunar longitudinal section in Table 8 because the exact orientation of the almost longitudinally oriented lacunae on the photographs is unknown. The medium and minor axis of the ellipsoid are computed by multiplying the value of the major axis by a random value within the ranges for the medium-major and minor-medium ratios, respectively. If the found value is not in the appropriate range, the range value closer to it will be assigned. Such ratio ranges equal [3/4,1] and [1/10,1/2], respectively, and they were found through the process of reproducing osteon images with the presented method. The program allows selection of the orientation of the ellipsoid along the collagen-hydroxyapatite orientation at the center of the ellipsoid or along the osteon axis. This option was introduced to check which is more realistic in the reproduction of osteon photographs by this method. The program allows the choice of generating ellipsoids whose transverse section consistently increases with the center's distance from the model's internal boundary (Ardizzoni, 2001) or not (the existence of such pattern has not yet been checked).

From Whole Transverse Section to Sector

The generation of canaliculae relative to the 360° transverse section, even if the height of the model is kept small, would create an unmanageably large file impossible to import into a finite element program. The maximum file size limit is on the order of 15 Mb. To limit the size of the model's file, the modeling was restricted to a sector of the 360° transverse section. To generate the 360° model of desired height, the modeled sector is rotated and translated relative to its axis after importing it into a supercomputer. To define the local geometry at the boundaries of the model's sector, symmetries that do not exist in reality are introduced in the model so that the details of the local geometry can recombine and provide continuity within the final model.

The osteon sector to be modeled will be a cylindrical sector (see e.g. FIG. 63) corresponding to the angle ϕ subtended by the minimum circumferential distance between adjacent, more external lacunae. For the experimental data presented here, such angle is on the order of 22.5°. The sector will contain three families of ellipsoids whose centers are initially placed along the initial, middle, and final ray of the angle ϕ. Since the rotated sector will need to recombine with the initial one, the centers along the initial and final rays will need to be positioned at corresponding distances from the model's inner boundary. Afterwards the ellipsoids will be moved randomly circumferentially as in the 360° case, except that here the corresponding ellipsoid on the initial and final ray of the sector will need to move by the same amount. In particular, only portions of the ellipsoids on the initial and final rays which fall within the sector are modeled.

Local Geometry: Canaliculae

The radii of canaliculae are not part of the experimental data. The minimum and maximum values for the canalicular radius are 0.3 and 0.6 microns, respectively (Piekarski, 1976), and the random choices are assumed to follow a uniform distribution for lack of further information.

To generate the thin cylinders that model the generally radially oriented canaliculae (pattern V), the coordinates of the points distributed at the vertices of a grid of side d are identified in the ellipsoid on the plane spanned by the major and medium axes of the ellipsoids. The value of d is chosen larger than twice the maximum diameter of a canalicula to avoid non empty intersections of adjacent thin cylinders. The program offers the option of chosing a random a random subset of such points. For each ellipsoid, the thin cylinders starting at each of the points are then differentiated between the ones that run from the ellipsoid towards either the outer or inner curved boundary of the model. For both types, the angle between the thin cylinder axis with the initial axis of ϕ is a random value that increases with the distance of the initial point from the center of the ellipsoid. This is to allow the spread of the thin cylinders exiting the same ellipsoid. A range between ±34° yields realistic orientations. The program has the option to interrupt the thin cylinders from running for their random length if they intersect ellipsoids different from the ellipsoid at which they initiated. When a thin cylinder starts at a point located along the initial or final ray of the sector only the half of the thin cylinder that lies in the sector is drawn so that boundaries match when the sector is replicated.

While photographs indicate that the majority of canaliculae are generally oriented radially and perpendicularly to the osteon canal (perhaps 85%), the rest of the canaliculae that initiate or end at lacunae are modeled as oriented either along the collagen-hydroxyapatite orientation or along the osteon axis or transversely, as is sometimes observed on photographs. Further, only the canaliculae that initiate at lacunae are modelled here because a criteria to establish the position of others is not formulated.

Lamellar Isolation Simulation

Figure 65:
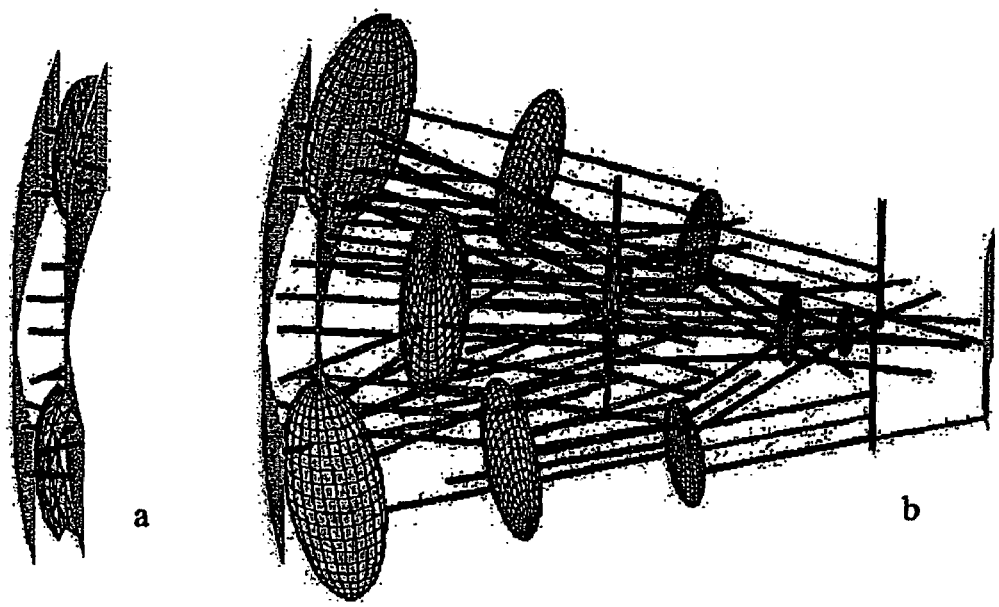
FIG. 65(a)-(b). Example of lamellar isolation simulation. (a) Lamellar model obtained from (b) alternate osteon model by intersection.

The whole outermost lamellar portion simulated in the osteon model by a thin cylindrical layer is "isolated" from the model (FIG. 65) to simulate experimental isolation of outermost lamella from alternate osteon. The ellipsoids and canaliculae of the alternate osteon model (FIG. 65a) are intersected with the boundaries of the thin layer (FIG. 65b). Since intersection of geometrical objects is a time-consuming computer process, the number of geometric objects to be intersected is decreased by a program procedure that shortens the thin cylinder representing the canalicula to the thin layer representing the lamellar portion by means of diminishing the size of parameters' ranges.

Comparison Between Methodology Result and Experimental Findings

The flexibility and validity of the methodology were evaluated by using it to reproduce osteon section photographs. For any transverse or longitudinal osteon section that was modeled by the described method, good agreement was found between photograph and model. That is, if the model is printed on transparency film at the same magnification of the photograph, superimposition of model with photograph shows coincidence of structural entities.

Figure 64:
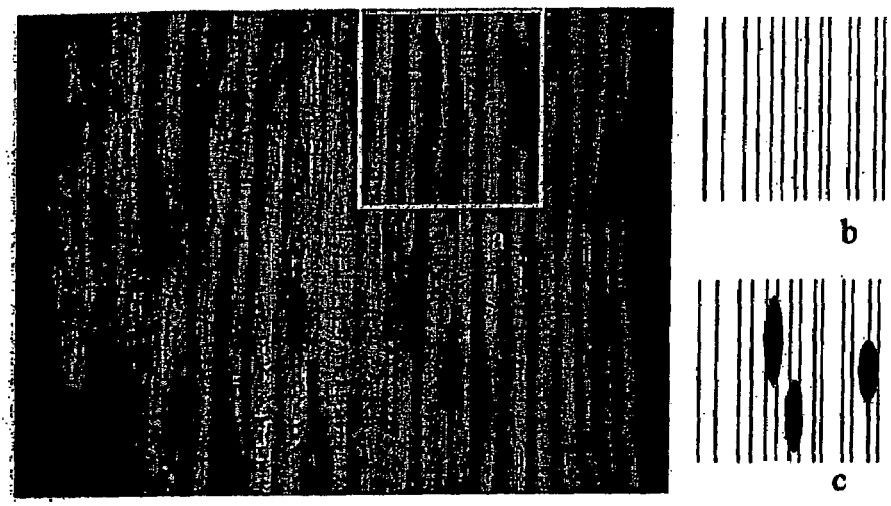
FIG. 64(a)-(c). Alternate osteon specimen #361 viewed longitudinally (×637): (a) photograph; (b) model of extinct and bright lamellae only; and (b) model of extinct and bright lamellae with lacunae. (c) A lamella-lacunar model in providing a representation of the three lacunae inside the square.

FIGS. 63 and 64 illustrate examples of modeling. FIG. 63a shows a portion of bright osteon viewed transversely under polarizing light. FIG. 63b shows the lacunar-canalicular model of an osteon sector. FIG. 63c shows a three-dimensional detail of the sector model with a plane indicating the section represented in FIG. 63b. The (two) lacunae and their canaliculae that intersect the plane appear also in FIG. 63b while the rest of the structure is randomly generated.

FIG. 64a is the photograph of a portion of alternating osteon viewed longitudinally under polarizing light. The alternating extinct and bright lamellae and lacunae are visible. The structure delimited by the square is simulated is FIGS. 64b and 64c. Because the program models the lamellae without their wobbling (Ascenzi A. et al, 1982), the lamellae and their model coincide only at the base of the square. The lamella-lacunar model in FIG. 64c provides a representation of the three lacunae inside the square.

Application of the Mode 1

This Example addresses the question of structural patterns and biological variation within extinct, alternate, and bright osteons in relation to collagen orientation, degree of calcification, and distribution of lamellae, canaliculae and lacunae. The comprehensive representation of these osteon features obtained by the methodology presented allows the elucidation of hypotheses regarding the long-standing questions as to osteon structure.

Parameters for the preferred method are the exclusion of (a) fine porosity below canalicular size, (b) interface specification between collagen and hydroxyapatite crystallites and (c) domains smaller than lamellar size. Further, the canalicular axis is modeled as a line and not a curve as it actually is. Such limitations may be removed at a later date. The accuracy of the method was checked by creating models of specific configurations within and at the extremes of the measurement ranges. This was made possible by the flexibility of the method, which by means of parameters allows the user to change the properties of the model locally. The process of checking the accuracy has proven itself valuable in the determination of parameter value ranges to be used in the preparation of random models, such as density and orientation of canaliculae. Because the precision of the model depends on how well the measurements obtained for the microstructural elements and patterns represent the biological variation, currently available photographs of microstructures are being observed and additional ones will be taken to identify possible additional patterns or dependencies.

Secondary osteon three-dimensional modeling has been viewed in the context of the compact bone macrostructure (see e.g. Katz, 1981; Hogan, 1992; Aoubiza et al., 1996) or as a self-contained structure (Pidaparti and Burr, 1992; Ascenzi, M.-G., 1999; Andreuzzi, 2003). In the context of the compact bone macrostructure, the osteon as been modeled as a two-phase collagen/hydroxyapatite fiber reinforced composite and then homogenized into a homogeneous unit with isotropic, orthotropic or transversely isotropic mechanical properties. Pidaparti and Burr (1992) and Aoubiza et al. (1996) have modeled the osteonic lamellae at a fixed collagen orientation to estimate the mechanical properties of the osteon. Ascenzi, M.-G. (1999) introduced the variability of collagen orientation through the lamellar thickness in a three-dimensional model of a single bright lamella for prestress estimate. The same approach was then extended in Andreuzzi (2003) to a single osteon model of extinct and bright type. Various authors have investigated the effect of the presence of Haversian canals, lacunae and canaliculae on osteon tissue's elastic properties (e.g. Cowin, 1999; Sevostianov and Kachanov, 2000). The present example includes both (i) a more realistic continuously variable orientation distribution of collagen across the lamellar thickness in accordance with the lamellar type as viewed under circularly polarized microscopy and (2) a geometrical representation of lacunae and canaliculae.

Figure 66:
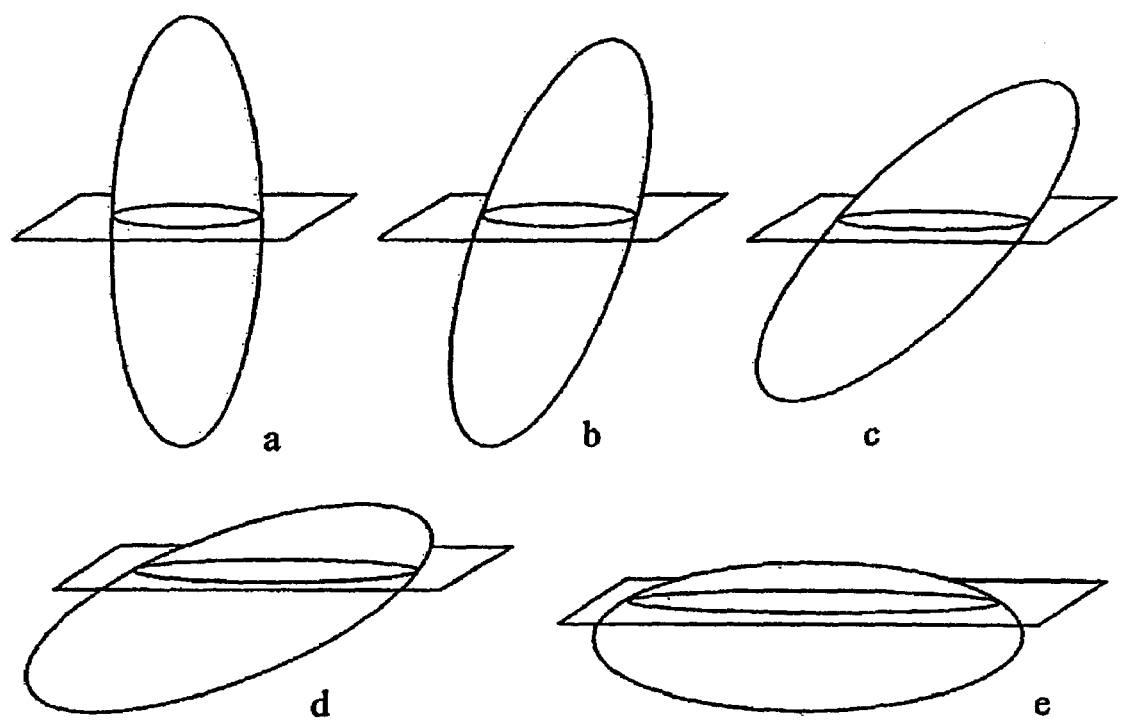
FIG. 66(a)-(e). Ellipses obtained by intersecting ellipsoids (which represent lacunae not to scale) with transverse planes at a constant vertical distance from the centers of the ellipsoids. The area of the ellipse increases with the angle between the major axis of the ellipsoid and the vertical direction. The angle equals (a) 0°; (b) 22.5°; (c) 45°; (d) 67.5°; and (e) 90°.

The data collected to check the methodology is part of an expanding database. The number of specimens for each osteon group needs to increase before comparison among the measurements of the various osteon groups is made. Nevertheless, the current findings are within the ranges reported in the literature. The measurements for the major and minor axes of the lacunar transverse sections are consistent with the collagen-hydroxyapatite simulation angle in the model. That is, the extinct osteons, whose collagen-hydroxyapatite orientation has been hypothesized (Ascenzi, M.-G. et al., 2003) as dominantly oriented along the osteon axis, show a smaller minimum value of the angle range than alternate and bright osteons where the collagen-hydoxyapatite orientation is hypothesized to be dominant transversely with respect to the osteon axis. FIG. 66 shows how the transverse section of an ellipsoid varies with the inclination of the major axis of the ellipsoid with respect to the transverse plane. The ellipse intersection is smaller and rounder at 90 degrees and it looses the roundness and elongates as the angle decreases to 0 degrees. This fact and the ability of our methodology to reproduce lacunae in photographic images by means of ellipsoids whose major axis is aligned with the collagen-hydroxyapatite orientation is consistent with the assumption that lacunae elongation parallels the direction of collagen orientation. The microstructural patterns identified in this example have been partially observed previously by already cited authors. In particular, the larger size of the most external lacunae has been previously explained in terms of the higher deposition rate of the relative bone cell at that location (Boyde, 1969). Further, it should be noted here that the photographs of both transverse and longitudinal osteon sections show canaliculae that suddenly stop. Such stopping could be due either to the fact that the canaliculae at that point where they appear to stop continue to proceed in the structure out of the plane of focus or that they thin down and become invisible for the current magnification. Such feature is replicated by the modeling method.

The strength of the proposed methodology lies in its flexibility. First, any of the methodology procedures can be rendered more sophisticated and adjusted to future findings. Second, the methodology relies on parameters that can be varied to match future biological observation of specimens. The efficiency of the method in terms of computer time, which averages a few minutes on a PC for a sector of approximately 15 µm height, relies on a balance between the use of functions and sequences. Employment of functions or sequences exclusively maximizes computational time. Therefore, function evaluations are computed as numeric lists periodically in the program to improve the efficiency of the computations. Further, mathematical elegance and computer efficiency are often at odds in the execution of the program. In fact, mathematical conciseness and simplicity may cost extra computer time, which is unaffordable in this program in view of the voluminous data treated.

An application in progress employs the model's geometry and the estimation of prestress in the bright lamella (Ascenzi, M.-G., 1999) to simulate osteon cyclic torsional loading by finite element analysis. The Maple™ image of an alternate osteon sector that contains the information of collagen and hydroxyapatite orientation and porosity is exported from Maple™ as a dxf file. The dxf file format was chosen because it retains the list of the points' coordinates that specify the geometry. The dxf file was then converted into an igs file, which can be imported into the finite element software Abaqus™. Abaqus™ is used to rotate and translate the sector to build a portion of model of an osteon or lamellar specimen. In order to maintain the total number of elements within the limitations of the software, it is necessary to work on a homogeneous model and then refine the mesh locally to represent lacunae and canaliculae only in the model's portion of interest by means of the modeling methodology presented here.

A further application of the models is in the investigation of modeling the mechanism by which fractures initiate and propagate. In fact, material science posits that (1) a fracture initiator is an 8-10 μm long micro-crack; (2) the orientation of the microcrack has an effect on the minimum stress necessary to elongate the crack at its weakest point, the tip; and (3) discontinuity in the structure as small as a micron can act as crack arresters. Therefore, because of the size match, lacunae are the obvious candidates as fracture initiators and both lacunae and canaliculae may act as crack arresters. Since the osteon models generated by the presented methodology include the representation of collagen, hydroxyapatite, lacunae and canaliculae, such models are suitable to be used to explain the process of fracture initiation, coalescence, and spread. Further, the orientation of the lacuna with respect to the osteon axis and the osteon's degree of calcification would affect the minimum stress necessary to initiate fracture of the lacunae at one of its apices. In particular, since the methodology of the invention supports the hypothesis that the lacunar orientation follows the collagen-hydroxyapatite orientation, the simulated fracture patterns would be expected to differ among osteons with different collagen-hydroxyapatite orientation distributions, as have been observed experimentally (see e.g. Ascenzi A. et al., 1994). A deeper understanding of the factors that control fracture initiation and spread would then shed light on the process of fracture propagation in the bone macrostructure.

TABLE 7

Dimensional measurements of osteons, lacunae, and canaliculae on transverse osteon sections.

| | Osteon type (% calcification): | | | | |
|---|---|---|---|---|---|
| | Extinct (100%) | Alternate (70%) | Alternate (100%) | Bright (70%) | Bright (100%) |
| | | | Number of specimens | | |
| Entity measured | 36 Range (mean ± sd) | 24 Range (mean ± sd) | 31 Range (mean ± sd) | 20 Range (mean ± sd) | 13 Range (mean ± sd) |
| osteon external radius, μm | 84.27-206.38 (121.56 ± 23.50) | 106.45-163.33 (137.42 ± 14.44) | 93.75-163.21 (123.82 ± 16.09) | 102.35-153.71 (128.27 ± 13.24) | 127.95-178.57 (147.88 ± 15.72) |
| osteon internal radius, μm | 14.11-37.82 (25.18 ± 6.31) | 25.00-56.31 (39.00 ± 6.97) | 10.84-41.02 (25.18 ± 8.49) | 24.33-57.42 (42.31 ± 8.63) | 10.77-46.77 (28.42 ± 12.94) |
| number lacunae | 8-56 (27 ± 11) | 13-49 (29 ± 9) | 14-49 (29 ± 9) | 18-54 (36 ± 11) | 29-69 (51 ± 13) |
| major axis lacunar section, μm | 1.85-29.79 (11.29 ± 1.01) | 3.27-29.80 (12.81 ± 1.80) | 3.03-19.09 (11.20 ± 1.41) | 3.19-31.80 (12.91 ± 1.63) | 3.37-30.77 (14.83 ± 20.74) |
| minor axis lacunar section, μm | 1.87-12..31 (5.83 ± 1.10) | 1.63-10.68 (5.61 ± 1.32) | 1.04-9.19 (6.31 ± 1.31) | 3.13-11.28 (5.74 ± 0.84) | 3.08-10.87 (5.43 ± 0.83) |
| minimum radial distance between lacunae, μm | 3.08-13.33 (4.81 ± 2.55) | 3.23-17.06 (5.84 ± 3.64) | 3.03-10.60 (6.27 ± 2.89) | 3.13-10.07 (4.96 ± 2.43) | 3.03-10.60 (6.02 ± 2.48) |
| minimum circumferential distance between lacunae, μm | 3.08-18.45 (7.26 ± 4.13) | 3.23-17.06 (7.04 ± 3.79) | 1.64-32.97 (8.21 ± 7.17) | 3.19-14.13 (6.07 ± 3.37) | 3.51-14.49 (6.54 ± 2.99) |
| maximum canalicular length, μm | 9.46-51.06 (26.61 ± 10.75) | 16.13-86.81 (31.29 ± 20.36) | 12.99-51.81 (27.22 ± 12.05) | 16.45-48.87 (27.56 ± 10.40) | 10.10-53.38 (25.94 ± 12.40) |

TABLE 8

Dimensional measurements relative to lacunae on longitudinal osteon sections.
Alternate osteon at 100% calcification on longitudinal sections

| Number of specimens | 54 |
|---|---|
| Entity measured | Range (mean ± sd) |
| major axis lacunar section, μm | 6.07-25.00 (20.03 ± 9.01) |
| minor axis lacunar section, μm | 1.57-5.31 (1.99 ± 0.82) |
| minimum distance between lacunae, μm | 3.66-36.40 (20.43 ± 8.60) |

EXAMPLE 15

Confocal Microscopy Experiments

A. Distribution of Collagen Bundle Orientation in Human Secondary Osteons

Circularly polarized light microscopy, micro-X-ray and confocal microscopy allow observation of distribution of domains throughout isolated lamellar specimens of fully calcified secondary osteons. (Domains are 3D regions of essentially unidirectional collagen orientation. (Boyd (1972)). This approach is novel in its assessment of domain characteristics along lamellar thickness direction, i.e., the radial direction, in embedding osteons prior to specimen isolation. Differences in domain distribution are found between the two building blocks of osteons: lamellae that appear extinct and lamellae that appear bright in cross-sections under circularly polarized light.

Material: 70±3 µm thick cross-sections were prepared from femoral mid-shafts, aged 19-40, free of skeletal pathologies. Sections were micro-X-rayed with resolution of 2000 lines per millimeter. Fully calcified osteons that appear alternatively extinct and bright under circularly polarized light were identified for lamellar specimen isolation. 18 extinct and 13 bright lamellar specimens adjacent to the cement lines were isolated, Ascenzi et al. (2003), and gently flattened along specimen thickness direction.

Methods: Specimens were scanned every 0.5 µm by a Leica TCS-SP confocal microscope (Heidelberg, Germany) with krypton laser (568 nm excitation) and 63×Planapochromat lens. The 0.51 µm interval is chosen in relation to plane of focus thickness to avoid either missing, or replicating, structures. Natural fluorescence of wet bone provides good contrast between tissue components. Light detected by photomultipliers converts to pseudo-color for good visualization. Images were digitally memorized and further magnified and analyzed using Image-I (Sun Microsystems Inc) at 1575× life size (FIG. 1). Bright elements are interpreted as collagen bundles on a background interpreted as a mix of mucopolysaccharides and glycoproteins. Collagen bundle orientation was measured relative to the specimen length, i.e., relative to a plane perpendicular to original osteon axis. Domains were identified as continuous regions of at least 3 or 4 unidirectional collagen bundles whose orientation varies up to ±7.5° both on the plane of focus and across adjacent images.

Figure 67:
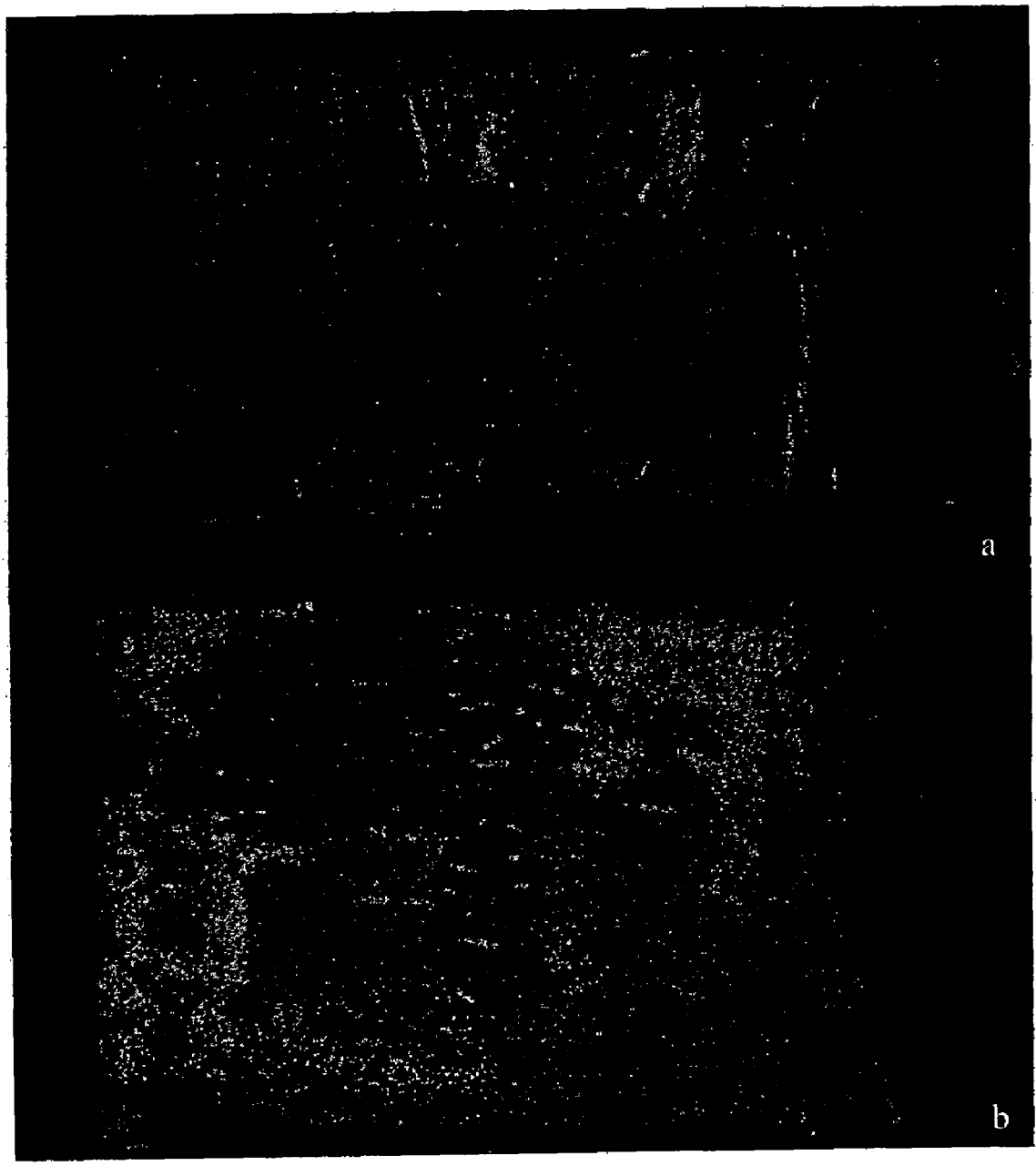
FIG. 67(a)-(b). Confocal microscopy images of (a) an extinct lamella specimen, and (b) a bright lamella specimen with characteristic bundles somewhat paralle to specimen length.

Results: The bright lamellar specimens show higher variation in collagen bundle orientation distribution in terms of higher number and smaller size of domains and higher number of distinct domain orientations. While extinct specimens may show only a domain orientation per area of focus, the bright specimens can show up to 4 domains per area of focus. The domain dimensions range between 7.61 and 175.251 µm for extinct and 9.27-163.40 µm for bright specimens on the plane of focus. The depth of the domain perpendicular to the plane of focus is smaller than lamellar thickness. Depth range is estimated as 1.33-4.38 µm for extinct and 1.67-5.00 µm for bright specimens. The measured domain dimensions are larger than values relative to domains observed by scanning electron microscopy near the Haversian canal (Boyde (1972)). The difference is explained in terms of local stress concentration effects around the canal which increase collagen orientation variability. The range of domain orientations per lamellar type is smaller (12°-158°) for extinct than (1°-179°) for bright specimens. Consequently, collagen that parallels specimen length is characteristic of bright specimens. FIG. 67(b). The results agree with observations by polarized light and synchrotron X-ray diffraction (Ascenzi et al. (2003)). Dots on images of both specimen types are portions of collagen cut during lamellar isolation from radially oriented collagen in original osteons. FIG. 67 (a, b). The findings are in line with the mechanical significance of collagen orientations in long bone shafts, Ascenzi (1988), and the skeletal adaptation to mechanical function, Frost (1987).

B. Collagen Bundle Distribution Along Human Secondary Osteons' Radial Direction

Collagen orientation distribution within so-called bright and extinct lamellae, the building blocks of secondary osteons, is observed along the previously unexplored osteon radial direction.

Figure 68:
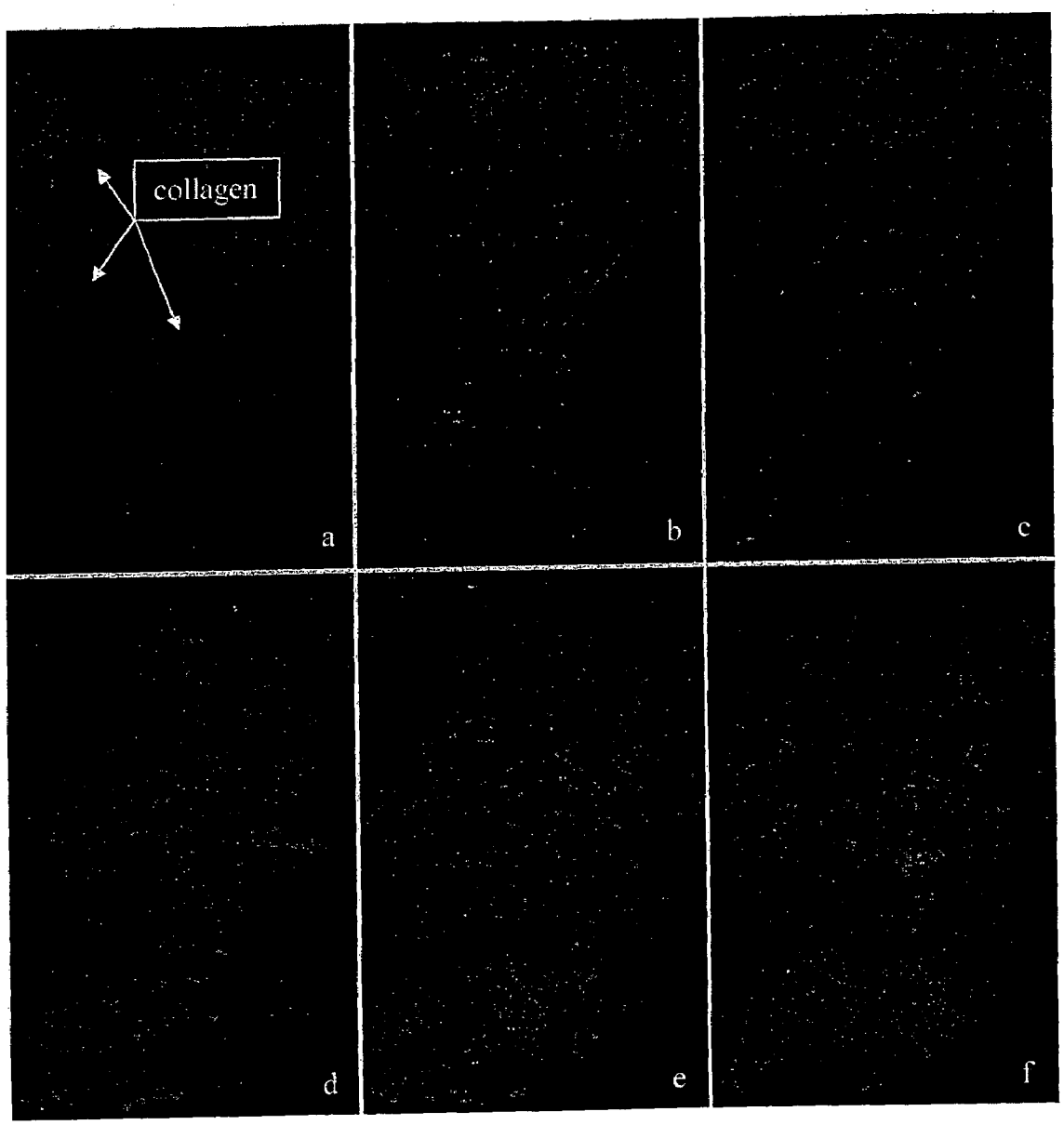
FIG. 68(a)-(f). Confocal microscopy images of bright lamellae, showing collagen orientation.

70±3 µm thick cross-sections were cut from femoral mid-shafts, aged 19-40, pathology-free. 22 fully-calcified lamellar specimens, 11 per type identified as bright or extinct on transverse section under circularly polarized light, were then isolated and gently flattened. Ascenzi, M-G (2003). A Leica TCS-SP confocal microscope (krypton laser, 63× Planapochromat lens) scanned wet specimens each 0.5 µm through thickness. Natural fluorescence shows as green pseudo-color at 1575× and 3000× magnification with Image-I and Xarax-X. Collagen bundles appear as bright elements on dark background of mucopolysaccharides and glycoproteins. FIG. 68(a). Long portions of canaliculae appear to follow local collagen orientation. Domains were identified as 3D regions whose collagen bundle orientation varies to ±7.5° within and across adjacent scans. Collagen orientation within domain was measured relative to original osteon axis.

Figure 69:
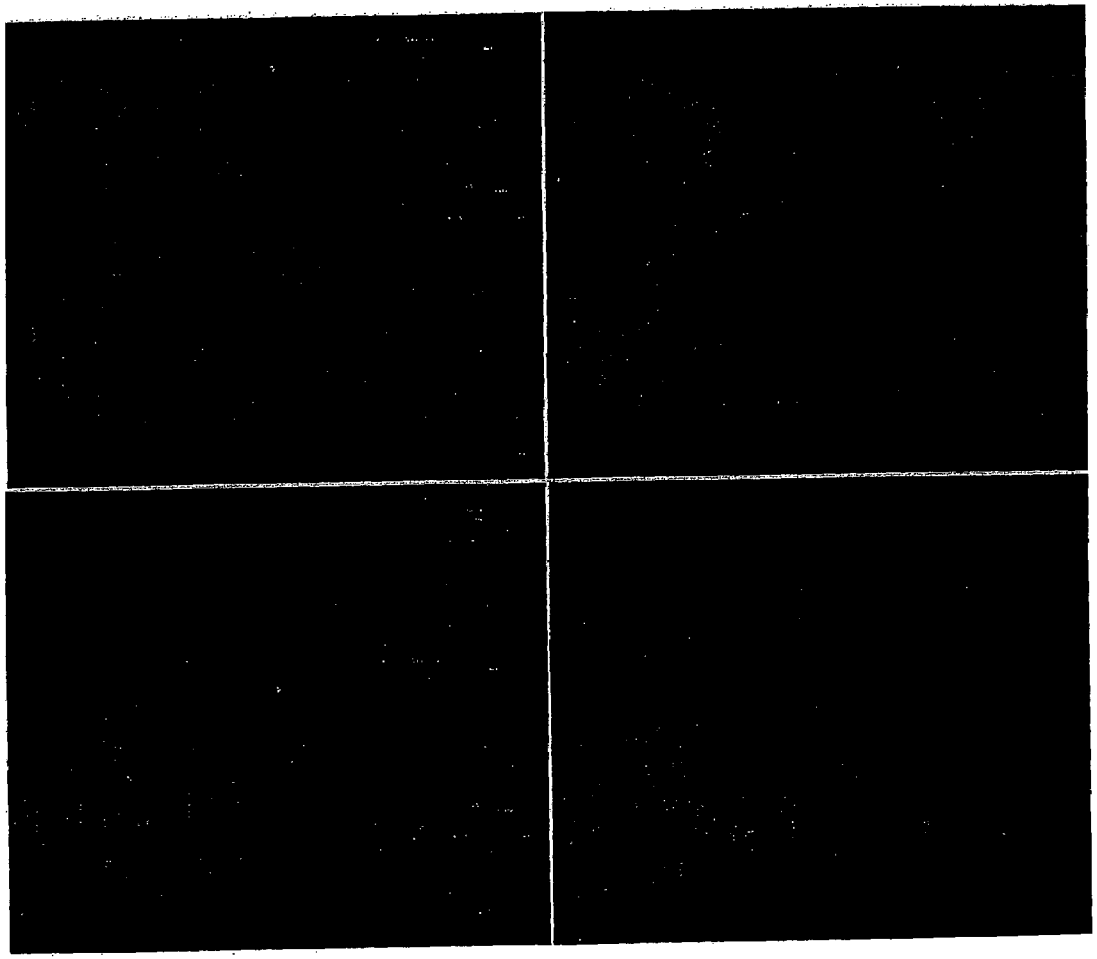
FIG. 69. Confocal microscopy images of extinct lamellae, showing collagen orientation.

Bright lamellae show characteristic collagen distribution somewhat transverse to the original osteon axis within the middle thickness, FIG. 68(d), becoming gradually oblique towards approximately ±45° relative to the osteon axis. FIG. 68(b), (c) (d). Extinct lamellae show a characteristic collagen distribution whose orientation makes up to a ±22.5° angle relative to the original osteon longitudinal axis. FIG. 69.

Results conform to findings by different methods. Ascenzi M-G (2003). These include mechanical significance of bone shaft collagen orientations, Ascenzi A (1988), and skeletal adaptation to mechanical function, Frost (1987). Results may be integrated in high-accuracy, super-computer hierarchical bone models, Ascenzi M-G (2004), e.g. to test hip prostheses virtually.

The patents, applications, test methods, and publications mentioned herein are hereby incorporated by reference in their entirety.

Many variations of the present invention will suggest themselves to those skilled in the art in light of the above detailed description. All such obvious variations are within the full intended scope of the appended claims.

BIBLIOGRAPHY

Amprino, R. and Engström, A. (1952) Studies on X-ray absorption and diffraction of bone tissue. Acta Anat, 15, 1-22.

Ampirino, R: Reported in Levi G, Istologia, (3rd ed.) Unione Tipografico Editrice Torinese, Turin, 511 (1946).

Andreuzzi M (2003) Modelli di microstruttura ossea (compatta e umana) a variazione biologica. Tesi di Laurea in Matematica, Rome, Italy.

Aoubiza B, Crolet J M and Meunier A (1996) On the mechanical characterization of compact bone structure using homogeneization theory. J. Biomech. 29, 1539-1547.

Antman, S. (1995) Nonlinear Problems of Elasticity. Springer. New York.

Ardizzoni A. (2001) Osteocyte lacunar size—lamellar thickness relationships in human secondary osteons. Bone, 25:215.

Ascenzi, A. (1988) The micromechanics versus the macromechanics of cortical bone—A comprehensive presentation. J. Biomech. Eng., 110, 357-363.

Ascenzi, A., Ascenzi M. G., Benvenuti, A., and Mango, F. (1997) Pinching in longitudinal and alternate osteons during cyclic loading. J. Biomechanics, 30, 689-695.

Ascenzi, A., Baschieri P., and Benvenuti, A. (1994) The torsional properties of single selected osteons. J. Biomech., 27, 875-884.

Ascenzi, A., Baschieri P., and Benvenuti, A. (1990) The bending properties of single osteons. J. Biomech., 23, 763771.

Ascenzi, A. and Benvenuti, A. (1980), Evidence of a state of initial stress in osteonic lamellae, Acta Orthop. Belg., 46, 580.

Ascenzi, A. and Benvenuti, A. (1977) Evidence of a state of initial stress in osteonic lamellae, J. Biomech., 10:447.

Ascenzi, A., Benvenuti, A., and Bonucci, E. (1982) The tensile properties of single osteonic lamellae: technical problems and preliminary results. J. Biomech., 15:29.

Ascenzi, A., Benvenuti, A., Mango, F. and Simili, R. (1985) Mechanical hysteresis loops from single osteons: Technical devices and preliminary results. J. Biomech., 18, 391-398.

Ascenzi, A., Benvenuti, A., Bigi, A., Foresti, E., Koch, M. H. J., Mango, F., Ripamonti, A., and Roveri, N. (1998) X-ray diffraction on cyclically loaded osteons. Calc. Tissue Int., 62, 266-273.

Ascenzi, A. and Bonucci, E. (1972) The shearing properties of single osteons. Anat. Rec., 172, 499-510.

Ascenzi, A. and Bonucci, E. (1968) The compressive properties of single osteons. Anat. Rec., 161, 377-392.

Ascenzi, A. and Bonucci, E. (1967) The tensile properties of single osteons. Anat. Rec., 158, 375-386.

Ascenzi, A. and Bonucci, E. (1964) The ultimate tensile strength of single osteons. Acta Anat., 58, 160-183.

Ascenzi, A., Bonucci, E., Bocciarelli, S. (1965) An electron microscope study of osteon calcification. J. Ultr. Research., 12, 287-303.

Ascenzi, A., Boyde, A., Portigliatti-Barbos, M. and Carando, S. (1987a) Micro-biomechanics vs Macrobiomechanics in cortical bone. A micromechanical investigation of femurs deformed by bending. J. Biomech., 20, 1045-1053.

Ascenzi, A., Improta, S., Portigliatti-Barbos, M. and Carando, S. and Boyde, A. (1987b) Distribution of lamellae in human femoral shafts deformed by bending with inferences on mechanical properties. Bone, 8, 319-325.

Ascenzi, M.-G. (2001 a) Antonio Ascenzi (1915-2000), J. Biomechanics, 34:4.

Ascenzi, M.-G. (2001b) Antonio Ascenzi (1915-2000) Calcified Tissue International, 68:2.

Ascenzi, M.-G. (2000) Cyclic torsional loading of longitudinal and alternate osteons. National Science Foundation grant n. 0075055.

Ascenzi, M.-G. (2000) National Science Foundation grant description.

Ascenzi, M.-G. (1999a.) Evidence of macroscopic prestress in human femoral shaft, Abstracts of the XVIIth conference of the International Society of Biomechanics, Calgary.

Ascenzi, M.-G. (1999b) A first estimation of prestress in so-called circularly fibered osteonic lamellae, J. Biomech., 32, 935.

Ascenzi, M.-G. (1998a) A first estimate of prestress in so-called circularly fibered osteonic lamellae, Abstracts of the 11th conference of the European Society of Biomechanics, J. Biomech., 31, Suppl. 1, 22.

Ascenzi, M.-G, Ascenzi, A., Burghammer, M., Panzavolta, S., Benvenuti, A. and Bigi, A. (2003) Structural differences between "dark" and "bright" isolated human osteonic lamellae. Journal of Structural Biology, 141, 22-33.

Ascenzi, M.-G., Benvenuti, A., and Ascenzi, A. (2000) Single osteon micromechanical testing. In: Mechanical testing of bone (An Y. and Draughn R. eds), CRC Press, Boca Raton, Fla.

Ascenzi M-G, et al. (2004) Distribution of collagen bundle orientation in human secondary osteons, Scanning, 26, 2, 90-91.

Bell, G. H. (1956) Bone as a mechanical engineering problem. In: The Biochemestry and Physiology of Bone (Boume G. H. ed) Academic Press, New York.

Birkenhäger-Frenkel, D. H., Courpon, P., Hüpscher, E. A. et al. (1988) Age related changes in cancellous bone structure. A two-dimensional study in the transiliac and iliac crest biopsy sites. Bone Miner., 4, 197-.

Bloom, W. and Fawcetts D. (1986) A Textbook of Histology. W. B. Saunders, Philadelphia.

Bonfield, W. and Li, C. H. (1967) Anisotropy of nonelastic flow in bone. J. Appl. Phys., 38:2450.

Bonucci, E. (2000) Basic composition and structure of bone. In: Mechanical testing of bone (An Y. and Draughn R. eds), CRC Press, Boca Raton, Fla.

Bourne, G. H. (1971) The Biochemistry and Physiology of Bone, Academic Press, New York.

Boyde, A. (1972) Scanning electron microscope studies of bone. In: Bourne, G. (Ed.), The Biochemistry and Physiology of Bone. Academic Press, London, 259.

Boyde, A., Bianco, P., Portigliatti-Barbos, M. and Ascenzi, A. (1984) Collagen Orientation in compact bone: 1. A new method for the determination of the proportion of collagen parallel to the plane of compact bone sections. Metab. Bone Dis. & Rel. Res., 5, 299-307.

Boyde A, Hobdell M H: Scanning electron microscopy of lamellar bone. Z. Zellforsch 93, 213-231 (1969)

Burr, D. B., Schaffler, M. B. and Frederickson, R. G. (1988) Composition of the cement line and its possible mechanical role as a local interface in human compact bone. J. Biomech., 21, 939-945.

Carando, S., Portigliatti-Barbos, M., Ascenzi, A. and Boyde, A. (1989) Orientation of collagen in human tibial and fibular shaft and possible correlation with mechanical properties. Bone, 10, 139-142.

Carando, S., Portigliatti-Barbos, M., Ascenzi, A., Riggs, C., and Boyde, A. (1991) Macroscopic shape of, and lamellar distribution within, the upper limb shafts, allowing inferences about mechanical properties. Bone, 12, 265-269.

Carter, D. R., Cater, W. E., Spengler, D. M., and Frankel, V. H. (1981) Fatigue behavior of adult cortical bone: the influence of mean strain and strain range. Acta Orthop. Scand., 52:481.

Carter, D. R. and Hayes, W. C. (1977) Compact bone fatigue damage—I. Residual strength and stiffness. J. Biomech., 10, 325-337.

Carter, D. R. and Hayes, W. C. (1976) Fatigue life of compact bone—I. Effects of stress amplitude, temperature and density. J. Biomech., 9, 27-34.

Carter, D. R., Hayes, W. C. and Schurman, D. J. (1976) Fatigue life of compact bone—II Effects of microstructure and density. J. Biomech., 9, 211-218.

Carter D. and Hays W C (1977) The compressive behavior of bone as a two-phase porous structure. J. Bone Joint Surg. 59, 954-962.

Carter, D. R. and Spengler, D. M. (1978) Mechanical properties and composition of cortical bone. Clin. Orthop., 135,192-217.

Cook, J. and Gordon, J. E. (1964) A mechanism for the control of crack propagation in all brittle systems. Proc. R. Soc. Lond., Ser. A, 282, 508-520.

Couteau, B., Payan, Y., Lavallee, S. (2000) The mesh-matching algorithm: an automatic 3D mesh generator for finite element structures. J. Biomech., 33, 1005-1009.

Cowin, S C (1999) Bone poroelasticity. J. Biomech. 32, 217-238.

Crolet J.-M., Aoubiza, B. and Meunier, A. (1993) Compact bone: numerical simulation of mechanical characteristics. J. Biomech., 26, 677-687.

Currey, J. D. (1969) The relationship between the stiffness and the mineral content of bone. J. Biomech., 2, 477-480.

Currey, J. D. (1964) Three analogies to explain the mechanical properties of bone. Biorheology, 2, 1-10.

Currey, J. D. (1962) Stress concentrations in bone. Quart. J. Microscop. Sci., 103, 111-113.

Currey, J. D. (1959) Differences in tensile strength of bone of different hystological types. J. Anat., 93, 87-95.

Ebner, V. (v) (1887) Sind die Fibrillen des Knochengewebes verkalktoder nicht? Arch. Mikr. Anat., 29:213.

Ebner (v) V (1875) Ueber den feineren Bauder Knochensubstanz. Sitzber. Akad. Wiss. Wien 111/72, 49-138.

Engström A, Engfeldt B: Lamellar structure of osteons demonstrated by microradiography. Experientia 9, 19 (1953).

Evans, F. G. and Vincentelli, R. (1969) Relation of collagen fiber orientation to some mechanical properties of human cortical bone. J. Biomech., 2, 63-71.

Evans, P. (1978) Relations between torsion properties and histology of adult human compact bone. J. Biomech., 11, 157-165.

Frank R, Frank P, Klein M, Fontaine R (1955) L'os compact humain normal au microscope electronique. Arch. Anat. Microsc. Morphol. Exp. 44, 191-206.

Frank R (1957) Contributions à l'étude au microscope electronique des tissues calcifies normaux etpathologiques. Thèse de Doctorat en Médecine, Strasbourg, France.

Frasca, P., Harper, R. and Katz, J. (1977) Collagen fiber orientation in human secondary osteons. Acta Anat., 98, 1-13.Frasca, P., Harper, R. and Katz, J. (1981) Strain and frequency dependence of shear storage modulus for human single osteons and cortical bone microsamples-size and hydration effects. J. Biomech, 14, 679-690.

Frasca, P., Harper, R. and Katz, J. (1976) Isolation of single ostesons and osteons lamellae. Acta Anat., 95, 122-129.

Frost, H M (1987) Vital biomechanics. Proposed general concept for skeletal adaptation to mechanical usage, Calc Tissue Int, 45: 145-156.

Gebhardt, W., (1906) Ueber funktionell wichtige Anordnungsweisen der feineren und gröberen Bauelemente des Wirbeltierknochens. II. Spezieller Teil. 1. Der Bau der Haverssohen Lamellensysteme und seine funktionelle Bedeutung. Arch. Entwickl. Mech Org., 20, 187-322.

Giraud-Guille, M. M. (1988) Twisted plywood architecture of collagen fibrils in human compact bone osteons. Calc. Tissue Int., 42, 167-180.

Gupta, V., and Bergström, J. S. (1998) Compressive failure of rocks by shear faulting. J. of Geoph. Res. 103, 23, 875-23,895.

Hazama, H. (1956) Study on torsional strength of the compact substance of human being. J. Kyoto Pref. Med. Univ., 60, 167-184 (Japanese text).

Hert J., Fiala P. and Petrtyl M. (1994) Osteon orientation of the diaphysis of the long bones in man. Bone, 15, 269-277.

Haut, R. C. (1983) Age-dependent influence of strain rate on the tensile failure of rat-tail tendon. Trans. ASME, 105:296.

Hayes, W. and Carter, D. (1979) Biomechanics of Bone. In: Skeleton Research: An Experimental Approach (D. Simmons and A. Kunin, eds.), Academic Press Inc., New York, 1, 263-299.

Herring, G. M. (1972) The organic matrix of bone. In: The Biochemistry and Physiology of Bone (G. H. Bourne, ed), Academic Press, New York, 128.

Hogan H A (!992) Micromechanics modeling of Haversian cortical bone properties. J. Biomech. 25, 549-556.

Hohling, H. J., Barckhaus, R. H., Krefting, E. R., Althoff, J. and Quint, P. (1990) Collagen mineralization: aspects of the structural relationship between collagen and apatite cristallites. In: Ultrastructure of Skeletal Tissues: Bone and Cartilage in Health and Disease (E. Bonucci and P. M. Morra, eds.), Kluwer Academic Publishers, Boston, 41-62.

Huja, S. S., Hasan, M. S., Pidaparti, R., Turner, C. H., Garetto, L. P. and Burr, D. (1999) Development of a fluorescent light technique for evaluating microdamage in done subjected to fatigue loading. J. Biomech., 32, 1243-1249.

Jepsen, K. J. and Davy, D. T. (1997) Comparison of damage accumulation measures in human cortical bone. J. Biomech., 30, 891-894.

Jepsen, K. J., Davy, D. T. and Krzypow, D. J. (1999) The role of the lamellar interface during torsional yielding of human cortical bone. J. Biomech., 32, 303-310.

Jones, R. M. (1975) Mechanics of Composite Materials. McGraw-Hill, New York.

Katz J L (1981) Composite material models for cortical bone. In Mechanical Properties of Bone (Edited by Cowin, S C), AMD, 45,171-184. American Society of Mechanical Engineers, New York.

Katz, J. L. and Meunier, A. (1987) The elastic anisotropy of bone. J. Biomech., 20, 1063-1070.

Katz, J. L. and Ukraincik, K. (1971) On the anisotropic elastic properties of hydroxyapatite. J. Biomech., 4, 221-227.

Kleerekoper, M., Villanueva, A. R., Stanciu, J., et al. (1985) The role of three-dimensional trabecular microstructure in the pathogenesis of vertebral compression fractures. Calc. Tissue. Int., 37, 594-597.

Knets, I., Pfafrod, G., Saulgozis, Y., Laizan, Y. and Yanson, K. (1973) Degree of deformation and strength of compact bone tissue during torsion. Polymer Mech., 5, 91 1-918. (Russian text).

Koch, J. C. (1917) The laws of bone architecture. Am. J. Anat., 21, 177-293.

Kölliker A (1854) Manual of Man Microscopical Anatomy. Lippincott,

Grambo and Co., Philadelphia. Kuo, T. Y., Skedros, J. G. and Bloebaum R. D. (1998) Comparison of human, primate, and canine femora: Implications for biomaterials testing in total hip replacement, J. Biomed. Mater. Res., 40:475.

Lakes, R. (1995) On the torsional properties of single osteons, J. Biomech., 28, 1409-1410.

van Leeuwenhoek A (1693) An extract of a letter from Mr. Anth. Van. Leeuwenhoek containing several observations on the texture of the bones of animals compared with that of wood: on the bark of trees: on the little scales found on the cuticula, etc. Philos. Trans. R. Soc. London 202, 838-843.

Mah, J. and Hatcher, D. (2000) Imagining trends and applications for the millenium. Orthod. Prod., 1, 14-18.

Maj, G. and Toajari, E. (1937) Osservazioni sperimentali sul meccanismo di resistenza del tessulo osseo lamellare compatto alle azioni meccaniche. Chir. Irgani. Mov., 22, 541-557.

Marotti G (1979) Osteocyte orientation in human lamellar bone and its relevance to the morphometry of periosteocytic lacunae. Metab. Bone Dis & Rel. Res. 1, 325-333.

Marotti, G. (1993) A new theory of bone lamellation. Calc. Tissue Int., 53, suppl. 1:S47.

Marotti, G. (1990) The original contributions of the scanning electron microscope to the knowledge of bone structure. In: Bonucci E. and Motta, P. M. (Eds.). Ultrastructure of Skeletal Tissue. Kluwer Academic Publishers, 19.

Marotti, G., Muglia, M. A., Palumbo, C., and Zoffe, D. (1994) The microscopic determinants of bone mechanical properties. Ital. J. Miner. Electrolyte Metab., 8, 167-175.

Martens, M., van Audekercke, R., de Meester, P. and Mulier, J. (1980) The mechanical characteristics of the long bones of the lower extremity in torsional loading. J. Biomech., 13, 667-676.

McElhancy, J. H. and Byars E. F. (1965) Dynamic response of biological materials. ASME, 65 WA/HUF 9.Mente P. L. (2000) Micromechanical testing of single trabeculae. In: Mechanical testing of bone (An Y. and Draughn R. eds), CRC Press, Boca Raton, Fla.

Meunier, A. (1999) Personal communication.

Michel, M., Guo, X. D., Gibson, L., McMahon, T. and Hayes, W. (1993) Compressive fatigue behavior of bovine trabecular bone. J. Biomech, 26, 453-463.

Miller, G. and Piotrowski, G. (1974) A brief note on the variability of the torsional strength of paired bones. J. Biomechanics, 7, 247-248.

Minns, R. J., Soden, P. D. and Jackson, D. S. (1973) The role of the fibrous components and ground substance on the mechanical properties of biological tissues: A preliminary investigation. J. Biomech., 6:153.

Moore D. and McCabe G. (1989) Introduction to the practice of statistics. W. H. Freeman and Co., New York.

Moreland, M. (1980) Morphological effects of torsion applied to growing bone. J. Bone Jt. Surg., 62-B, 230-237.

Narayanan R. and Roberts T. (1991) Structures Subjected to Repeated Loading. Stability and Strength, Elsevier, London.

Petersen, H. (1930) Die Organe des Skeletsystems. In: Handhuch der mikroskopischen Anatomie des Menshen (Mollendorff (v.), W. ed.), Springer, Berlin, 521-678.

Pfafrod, G., Knets, I., Saulgozis, Y., Kregers, A. and Yanson, K. (1975) Age-related changes in the strength of compact bone tissue under torsion. Polymer Mech., 3, 493-503. (Russian text).

Pfafrod, G., Saulgozis, Y., Knets, I., Saulgozis, Y. and Yanson, K. (1972) Experimental determination of the shear modulus of compact bone. Polymer Mech., 4, 697-705. (Russian text).

Philipson, B. (1965) Composition of cement lines in bone. J. Histochem. Cytochem., 13, 270-281.

Pidaparti, R. and Burr D. (1992) Collagen fiber orientation and geometry effects on the mechanical properties of secondary osteons. J. Biomech., 25, 869-880.

Piekarski, K. (1970) Fracture of bone. J. of Appl. Physics, 41, 215-223.

Portigliatti-Barbos, M., Bianco, P. and Ascenzi, A. (1983) Distribution of osteonic and interstitial components in the human femoral shaft with reference to structure, calcification, and mechanical properties. Acta Anat., 15, 178-186.

Portigliatti-Barbos, M., Bianco, P., Ascenzi, A. and Boyde, A. (1984) Collagen orientation in compact bone: II. Distribution of lamellae in the whole of the human femoral shaft with reference to its mechanical properties. Metab. Bone Dis. & Rel. Res., 5, 309-315.

Portigliatti-Barbos, M., Carando, S., Ascenzi, A. and Boyde, A. (1987) On the structural symmetry of human femurs, Bone, 8, 165-169.

Ranvier, L. (1887) Traité Technique d'Histologie, F. Savy, Paris.

Rauber, A. (1873) Elasticitat and Festigkeit der Knochen. Leipzig, Wilhelm Engelmann.

Reid S A (1986) A study of lamellar organization in juvenile and adult human bone. Anat. Embryol. 174, 329-338.

Rho, J. Y., Zioupos, P., Currey, J. D., and Pharr, G. M. (1999) Variations in the individual thick lamellar properties within osteons by nanoindentation, Bone, 25, 295-300.

Rokey, K. C. (1983) The Finite Element Method: a basic introduction. New York, Wiley.

Rouillier C-H, Huber L, Kellenberger E-D, Rutishauser E (1952) La structure lamellaire de l'ostéone. Acta Anat. 14, 9-22.

Ruth E B (1947) Bone studies. I. Fibrillar structure of adult human bone. Am. J. Anat. 80, 35-53.

Rybicki, E. F., Simonen, F. A., and Weis, E. B. (1972) On the mathematical analysis of stress in the human femor. J. Biomech., 5, 203-215.

Riggs, C. M., Lanyon, L. E., and Boyde, A. (1993a) Functional associations between collagen fibre orientation and locomotor strain direction in cortical bone of the equine radius, Anat. Embryol., 187, 231-238.

Riggs, C. M., Vaughan, L. C., Evans, G. P., Lanyon, L. E. and Boyde, A. (1993b) Mechanical implications of collagen fibre orientation in cortical bone of the equine radius, Anat. Embryol., 187, 239-248.

Rouillier C.-H., Huber, L., Kellenberger, E.-D. and Rutishauser, E. (1952) La structure lamellaire de l' ostéone. Acta Anat., 14:19.

Rouillier, C.-H. (1956) Collagen fibers of connective tissue. In: The Biochemistry and Physiology of Bone (G. H. Bourne, ed), 107-147, Academic Press, London/New York.

Ruth, E. B. (1947) Bone studies. 1. Fibrillar structure of adult human bone. Amer. J. Anat., 80:35.

Saatcioglu, M. (1991) Modeling hysteretic force-deformation relationship for reinforced concrete elements. In: Earthquake-Resistant Concrete Structures, Inelastic Response and Design (S. K. Ghosh, ed.), American Concrete Institute (ACI-SP 127), Detroit, 153-198.

Sasaki N. (2000) Viscoelastic properties of bone and testing methods. In: Mechanical testing of bone (An Y. and Draughn R. eds), CRC Press, Boca Raton, Fla.

Sammarco, G., Burstein, A., Davis, W. and Frankel, V. (1971) The biomechanics of torsional fractures; the effect of loading rate on ultimate properties. J. Biomech., 4, 113-117.

Schaffler, M., Burr, D. B. and Frederickson, R. G. (1987) Morphology of the osteonal cement line in human bone. Anat. Rec., 217, 223-228.

Schaffler, M. B., Radin E. L. and Burr, D. B. (1989) Mechanical and morphological effects of strain rate on fatigue of compact bone. Bone, 10, 207-214.

Schaffler, M. B., Radin, E. L. and Burr, D. B. (1990) Long-term fatigue behavior of compact bone at low strain magnitude and rate. Bone, 11, 321-326

Seireg, A. and Kempke, W. (1969) Behavior of in vivo bone under cyclic loading. J. Biomech., 2, 455-461.

Sevostianov I, Kachanov M (2000) Impact of the porous microstructure on the overall elastic properties of the osteonal cortical bone. J. Biomech. 33, 881-888.

Shiga, T., Ogawa, J., Shibata, A. and Shibuya, J. (1970) The dynamic properties of reinforced concrete frames.

Simkin, A., and Robin, G. (1974) Fracture formation in differing collagen fiber pattern of compact bone. J. Biomech., 7, 183-188.

Skedros J. G., Mason M. W., Nelson M. C., and Bloebaum R. D. (1996) Evidence of structural and material adaptation to specific strain features in cortical bone. The Anatomical Record, 246:47-63.

Smith J W (1960) The arrangement of collagen bundles in human secondary osteons. J. Bone Joint Surg. 42B, 588-605.

Timoshenko, S., and Young, D. H. (1962) Elements of Strength of Materials. Van Nostrand, Princeton.

Vincent J (1957) Corrélation entre la microradiographie et l'image en lumiére polarisée de l'os secondaire. Exp. Cell. Res. 13, 422-424.

Vincentelli, R. and Evans, F. G. (1971) Relations among mechanical properties, collagen fibers, and calcification in adult human cortical bone. J. Biomech., 4, 193-201.

Vinson, J. R. (1993) The Behavior of Shells Composed of Isotropic and Composite Materials. Kluwer Academic Publishers, Boston.

Wakabayasashi, M. (1986) Design of Earthquake-Resistant Buldings. McGraw-Hill, New York.

Weindenreich F (1930) Das Knochengewebe. In: von Mollendor, (Ed.),

Handbuch der mikroskopischen Anatomie des Menschen. Springer, Berlin, 391-520.

Wickramasinghe, S. N. (1975) Human Bone Marrow. Blackwell Scientific Publications, Philadelphia.

Ziegler D (1908) Studien über die feinere Struktur des Röhrenknochens und dessen Polarization. Dtsch. Z. Chir. 85, 248-262.

Ziv, V., Wagner, M. D., and Weiner, S. (1996) Microstructure-microhardness relations in parallel-fibered and lamellar bone. Bone, 19, 417-428.

Zysset, P. K., Guo X. E., Hoffler C. E., Moore K. E., and Goldstein S. (1999) Elastic modulus and hardness of cortical and trabecular bone lamellae measured by nanoindentation in the human femur. J. Biomech., 32, 1005-1012.

We claim:

1. A method of predicting a mechanical response of a region of a subject bone to an applied force comprising the steps of:
(a) identifying a subject bone;
(b) selecting at least one database comprising empirical data representative of the subject bone, wherein the empirical data is based on recorded observations of at least one cadaveric bone corresponding to the subject bone, wherein recording the observations comprises:
  (1) selecting a three-dimensional macrostructural sample from the cadaveric bone in which microstructural elements are present;
  (2) identifying at least one individual microstructural element in the selected macrostructural sample; and
  (3) generating viscoelastic data comprising at least one mechanical property of the identified microstructural element obtained by subjecting the identified microstructural element to at least one force;
(c) using the database with a computer program to generate a simulated region of the subject bone, the simulated region comprising at least one simulated microstructural element, wherein the computer program performs the steps of:
  (1) defining a simulated three-dimensional region corresponding to the simulated microstructural element of the simulated region of the subject bone;
  (2) creating a finite element mesh defining a finite number of three-dimensional elements filling the simulated three-dimensional region; and
  (3) assigning at least one property to each of a plurality of the elements in the finite element mesh using viscoelastic data from the database;
(d) using a computer program to predict a mechanical response of the region of the subject bone to an applied force, wherein the computer program performs the steps of:
  (1) generating a simulated force applied to the simulated three-dimensional region;
  (2) calculating a response to the simulated force for each of a plurality of elements in the finite element mesh using the at least one assigned property for each element;
  (3) computing a response of the simulated three-dimensional region to the simulated force using the calculated responses of the plurality of elements in the finite element mesh;
  (4) computing the mechanical response of the simulated region of the subject bone from the computed response of the simulated three-dimensional region to the simulated force; and
  (5) outputting the computed mechanical response of the region of the subject bone to the simulated force.

2. The method of claim 1, wherein
the database further comprises at least one of empirically collected dimensional data and distributional data from at least one ultrastructural component from the sample, and
elements in the finite element mesh are defined at least in part using the ultrastructural data.

3. The method of claim 2, wherein the ultrastructural component is at least one of a lacuna and a canalicula from the sample.

4. The method of claim 2, wherein elements in the finite element mesh are representative of an ultrastructural component.

5. The method of claim 4, wherein the ultrastructural component is at least one of a lacuna and a canalicula from the sample.

6. The method of claim 1, wherein the region of the subject bone corresponds to a lamella.

7. The method of claim 1, wherein the region of the subject bone corresponds to an osteon.

8. The method of claim 1, wherein the region of subject bone corresponds to a macrostructural region comprising a plurality of micro structural elements.

9. The method of claim 1, wherein at least one force is selected from tension, compression, shear, bending, and torsion.

10. The method of claim 1, wherein the microstructural elements identified from the sample are lamellae.

11. The method of claim 10, wherein the mechanical properties are selected from tension, compression, shear, bending, torsion, prestress, pinching, cement line slippage, stress distribution, and strain distribution.

12. The method of claim 10, wherein the lamellae are one or both of bright and dark lamellae.

13. The method of claim 1, wherein the microstructural elements identified from the sample are osteons.

14. The method of claim 13, wherein the osteons are one or both of longitudinal and alternate osteons.

15. The method of claim 13, wherein the osteon mechanical properties are selected from angle-of-twist as a function of torque per unit force, strain rate, and time.

16. The method of claim 1, wherein
the viscoelastic data further comprises empirically observed orientations of collagen bundles within micro structural elements, and
the orientation data is used in assigning properties to elements.

17. The method of claim 16, wherein the orientation data corresponds to lamellae organized within an osteon having an osteon axis, and wherein at least one dark lamella within the osteon is oriented at an angle ranging from 0 degrees to substantially less than ±45 degrees with respect to the osteon axis.

18. The method of claim 16, wherein the orientation data corresponds to lamellae organized within an osteon having an osteon axis, and wherein at least one bright lamella within the osteon is oriented at an angle ranging from a midpoint orientation with respect to the osteon axis to an angle of about ±45 degrees with respect to the midpoint orientation.

19. The method of claim 16, wherein the orientation data corresponds to lamellae organized within an osteon having an osteon axis, and wherein at least one dark lamella within the osteon is oriented at an angle of up to ±23 degrees with respect to the osteon axis.

20. The method of claim 16, wherein the orientation data corresponds to lamellae organized within an osteon having an osteon axis, and wherein at least one bright lamella within the osteon is oriented at an angle ranging from a midpoint orientation with respect to the osteon axis to an angle of about ±23 degrees with respect to the midpoint orientation.

21. The method of claim 1, wherein the simulated three-dimensional region corresponding to a selected region of the subject bone is determined from an in vivo scan of the subject bone.

22. The method of claim 8, wherein
the database further comprises empirical data recording the spatial distribution of microstructural elements within a cadaveric sample, and
the step of generating a simulated region of the subject bone further comprises defining a spatial configuration of simulated microstructural elements in the simulated region using data from the database.

23. The method of claim 8, wherein
the database further comprises empirical data recording the spatial distribution of microstructural elements within the subject bone, and
the step of generating a simulated region of the subject bone further comprises defining a spatial configuration of simulated microstructural elements in the simulated region using data from the database.

24. The method of claim 23, wherein the spatial configuration of simulated microstructural elements is observed using an in vivo scan of the subject bone to obtain microstructure distribution in the subject bone.

25. The method of claim 1, wherein at least steps (d)(2) and d(3) are repeated for each of a plurality of simulated forces.

26. The method of claim 25, wherein the simulated force is applied incrementally.

27. The method of claim 1, wherein the mechanical response comprises fracture initiation, wherein fracture initiation comprises microcracking, debonding, breakage, void growth, or combinations thereof.

28. The method of claim 1, wherein the mechanical response comprises fracture propagation.

29. The method of claim 1, wherein the step of calculating a response to the simulated force accounts for a prestress distribution in the simulated region of the subject bone.

30. The method of claim 1, wherein the cadaveric bone is compact bone.

31. The method of claim 1, wherein the cadaveric bone is obtained from a human.

32. The method of claim 1, further comprising the steps of:
generating at least one distribution function corresponding to the distribution of empirically observed values for a measurement recorded in the database;
using the distribution function to assign values for at least one property of the elements in the finite element mesh.

33. The method of claim 1, wherein
the subject bone corresponds to a bone attached to a prosthesis, and
the applied force corresponds to forces acting on the bone as a consequence of the attached prosthesis.

34. A computerized bone model stored on one or more computer readable media for predicting a mechanical response of a region of a subject bone to an applied force, comprising:
(a) a database comprising empirical data representative of a subject bone, wherein the empirical data comprises recorded observations of at least one microstructural element from a cadaveric bone corresponding to the subject bone; and
(b) a set of computer readable instructions for use with the database comprising:
(1) instructions for generating a simulated region of the subject bone wherein the simulated region comprises at least one simulated microstructural element;
(2) instructions for defining a simulated three-dimensional region corresponding to the simulated microstructural element of the simulated region of the subject bone;
(3) instructions for creating a finite element mesh defining a finite number of three-dimensional elements filling the simulated three-dimensional region;
(4) instructions for assigning at least one material property to each of a plurality of the elements in the finite element mesh using data from the database;
(5) instructions for applying a simulated force to the simulated three-dimensional region;
(6) instructions for calculating a response to the simulated force for each of the plurality of elements in the finite element mesh using the assigned at least one property for each element;
(7) instructions for computing a response of the simulated three-dimensional region to the simulated force using the calculated responses of the plurality of elements in the finite element mesh;
(8) instructions for computing the mechanical response of the simulated region of the subject bone from the computed response of the simulated three-dimensional region to the simulated force; and
(9) instructions for outputting the computed mechanical response of the region of the subject bone to the simulated force.

35. The computerized bone model of claim 34 wherein
the database further comprises at least one of empirically collected dimensional data and distributional data from at least one ultrastructural component, and
elements in the finite element mesh are defined at least in part using the ultrastructural data.

36. The computerized bone model of claim 35, wherein the ultrastructural component is at least one of a lacuna and a canalicula.

37. The computerized bone model of claim 35, wherein elements in the finite element mesh are representative of an ultrastructural component.

38. The computerized bone model of claim 37, wherein the ultrastructural component is at least one of a lacuna and a canalicula.

39. The computerized bone model of claim 34, wherein the region of the subject bone corresponds to a lamella.

40. The computerized bone model of claim 34, wherein the region of the subject bone corresponds to an osteon.

41. The computerized bone model of claim 34, wherein the region of subject bone corresponds to a macrostructural region comprising a plurality of microstructural elements.

42. The computerized bone model of claim 34, wherein the microstructural elements identified from the sample are lamellae.

43. The computerized bone model of claim 42, wherein the mechanical properties are selected from tension, compression, shear, bending, torsion, prestress, pinching, cement line slippage, stress distribution, and strain distribution.

44. The computerized bone model of claim 42, wherein the lamellae are one or both of bright and dark lamellae.

45. The computerized bone model of claim 34, wherein the microstructural elements identified from the sample are osteons.

46. The computerized bone model of claim 45, wherein the osteons are one or both of longitudinal and alternate osteons.

47. The computerized bone model of claim 45, wherein the osteon mechanical properties are selected from angle-of-twist as a function of torque per unit force, strain rate, and time.

48. The computerized bone model of claim 34, wherein
the viscoelastic data further comprises empirically observed orientations of collagen bundles within microstructural elements, and
the orientation data is used in assigning properties to elements.

49. The computerized bone model of claim 48, wherein the orientation data corresponds to lamellae organized within an osteon having an osteon axis, and wherein at least one dark lamella within the osteon is oriented at an angle ranging from 0 degrees to substantially less than ±45 degrees with respect to the osteon axis.

50. The computerized bone model of claim 48, wherein the orientation data corresponds to lamellae organized within an osteon having an osteon axis, and wherein at least one bright lamella within the osteon is oriented at an angle ranging from a midpoint orientation with respect to the osteon axis to an angle of about ±45 degrees with respect to the midpoint orientation.

51. The computerized bone model of claim 48, wherein the orientation data corresponds to lamellae organized within an osteon having an osteon axis, and wherein at least one dark lamella within the osteon is oriented at an angle of up to ±23 degrees with respect to the osteon axis.

52. The computerized bone model of claim 48, wherein the orientation data corresponds to lamellae organized within an osteon having an osteon axis, and wherein at least one bright lamella within the osteon is oriented at an angle ranging from a midpoint orientation with respect to the osteon axis to an angle of about ±23 degrees with respect to the midpoint orientation.

53. The computerized bone model of claim 34, wherein the simulated three-dimensional region corresponding to a selected region of the subject bone is determined from an in vivo scan of the subject bone.

54. The computerized bone model of claim 41, wherein
the database further comprises empirical data recording the spatial distribution of microstructural elements within a cadaveric sample, and
the set of computer readable instructions further comprises instructions for defining a spatial configuration of simulated microstructural elements in the simulated region using data from the database.

55. The computerized bone model of claim 41, wherein
the database further comprises empirical data recording the spatial distribution of microstructural elements within the subject bone, and
the set of computer readable instructions further comprises instructions for defining a spatial configuration of simulated microstructural elements in the simulated region using data from the database.

56. The computerized bone model of claim 55, wherein the spatial configuration of simulated microstructural elements is observed using an in vivo scan of the subject bone to obtain microstructure distribution in the subject bone.

57. The computerized bone model of claim 34, wherein the cadaveric bone is compact bone.

58. The computerized bone model of claim 34, wherein the cadaveric bone is obtained from a human.

59. The computerized bone model of claim 34, wherein the set of computer readable instructions further comprises:
instructions for generating at least one distribution function corresponding to the distribution of empirically observed values for a measurement recorded in the database;
instructions for using the distribution function to assign values for at least one property of elements in the computerized model.

* * * * *

UNITED STATES PATENT AND TRADEMARK OFFICE
CERTIFICATE OF CORRECTION

| | |
|---|---|
| PATENT NO. | : 7,353,153 B2 |
| APPLICATION NO. | : 10/844051 |
| DATED | : April 1, 2008 |
| INVENTOR(S) | : Maria-Grazia Ascenzi et al. |

It is certified that error appears in the above-identified patent and that said Letters Patent is hereby corrected as shown below:

On the Title Page Item (63)

Please delete "Continuation-in-part of application No. 10/429,491, filed on May 5, 2003, now Pat. No. 7,212,958, which is a continuation-in-part of application No. 10/357,090, filed on Feb. 3, 2003, now Pat. No. 7,283,940, which is continuation-in-part of application No. 10/066,293, filed on Jan. 31, 2002, now Pat. No. 7,127,383, which is a continuation-in-part of application No. 09/981,684, filed on Oct. 17, 2001, now pat. No. 7,124,067" and;

insert --Continuation-in-part of U.S. Patent Application Serial No. 10/429,491 now U.S. Patent No. 7,212,958, filed May 5, 2003, which is a continuation-in-part of U.S. Patent Application Serial No. 10/357,090, filed February 3, 2003. Continuation-in-part of U.S. Patent Application Serial No. 10/066,293 now U.S. Patent No. 7,127,383, filed January 31, 2002, which is a continuation-in-part of U.S. Patent Application Serial No. 09/981,684 now U.S. Patent No. 7,124,067, filed October 17, 2001--

Signed and Sealed this

Fifteenth Day of July, 2008

JON W. DUDAS
*Director of the United States Patent and Trademark Office*